(12) United States Patent
Glinka et al.

(10) Patent No.: US 8,906,868 B2
(45) Date of Patent: Dec. 9, 2014

(54) AMINOGLYCOSIDE DERIVATIVES

(75) Inventors: Tomasz W. Glinka, Cupertino, CA (US); Olga Rodny, Mill Valley, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/697,302

(22) PCT Filed: May 12, 2011

(86) PCT No.: PCT/US2011/036344
§ 371 (c)(1),
(2), (4) Date: Nov. 9, 2012

(87) PCT Pub. No.: WO2011/143497
PCT Pub. Date: Nov. 17, 2011

(65) Prior Publication Data
US 2013/0059808 A1    Mar. 7, 2013

Related U.S. Application Data

(60) Provisional application No. 61/334,088, filed on May 12, 2010, provisional application No. 61/392,258, filed on Oct. 12, 2010.

(51) Int. Cl.
| | | |
|---|---|---|
| A61K 31/70 | (2006.01) |
| C07H 15/00 | (2006.01) |
| C07H 17/02 | (2006.01) |
| C07H 15/06 | (2006.01) |
| C07H 15/236 | (2006.01) |

(52) U.S. Cl.
CPC .................................. *C07H 15/236* (2013.01)
USPC ............. 514/40; 514/41; 536/16.8; 536/17.9; 536/18.2

(58) Field of Classification Search
None
See application file for complete search history.

(56) References Cited

U.S. PATENT DOCUMENTS

| 2012/0135946 A1* | 5/2012 | Goldblum et al. ............... 514/40 |
| 2012/0208781 A1* | 8/2012 | Bruss et al. ...................... 514/41 |

FOREIGN PATENT DOCUMENTS

WO    WO 87/05297    9/1987

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Ali, B. H., Agents Ameliorating or Augmenting Experimental Gentamicin Nephrotoxicity: Some Recent Research., Food Chern Toxicol (2003), 41(11), 1447-52.
Aminocyclitol Antibiotics, ACS Symposium Series 125, Jun. 1980, K. L. Rhinehart, T. Suami (Editors).
Kotra, L. P. et al., "Aminoglycoside: perspectives on mechanisms of action and resistance and strategies to counter resistance", Antimicrob. Agents Chemother., (2000),44(12),3249-3256.
Magnet S., et al., "Molecular insights into aminoglycoside action and resistance", Chern. Rev., (2005), 105(2), 477-498.
Mingeot-Leclercq, M. P. et al., "Aminoglycosides: activity and resistance", Antimicrob. Agents Chemother. (1999), 43(4), 727-737.
Mingeot-Leclercq, M. P.; Tulkens, P. M., Aminoglycosides: nephrotoxicity, Antimicrob Agents Chemother (1999),43,(5), 1003-12.
Nagai, J.; et al., Molecular aspects of renal handling of aminoglycosides and strategies for preventing the nephrotoxicity, Drug Metab Pharmacokinet. Jun. 2004;19(3):159-70.
Price KE, Godfrey JC, Kawaguchi H. Effect of structural modifications on the biological properties of aminoglycoside antibiotics containing 2-deoxystreptamine, in: Perlman D, editor. "Structure-activity relationships among the semisynthetic antibiotics." New York: Academic Press; 1977. p. 239-375.
Rougier, F. et al., Aminoglycoside dosages and nephrotoxicity: quantitative relationships. Clin Pharmacokinet (2003), 42,(5), 493-500.
Rougier, F. et al., Aminoglycoside nephrotoxicity. CUff Drug Targets Infect Disord (2004), 4,(2), 153-62.
Schacht, J., Antioxidant therapy attenuates aminoglycoside-induced hearing loss. Ann N Y Acad Sci (1999), 884, 125-30.
Song, B. B.; et al., Iron Chelators Protect from Aminoglycoside-Induced Cochleo- and Vestibulo-Toxicity. Free Radic Biol Med (1998), 25,(2), 189-95.
Vakulenko, S. B.; and Mobashery, S., "Versatility of Aminoglycosides and Prospects for Their Future" Clin. Microbiol. Rev., (2003), 16, 430-450.
Wang, J.; Chang, C.-W. T. in "Aminoglycoside Antibiotics: From Chemical Biology to Drug Discovery" Arya, D. P., Eds.; Wiley, 2007; pp. 141-177.
Wright, G. D. et al., Aminoglycoside antibiotics. Structures, functions, and resistance. Adv Exp Med Biol 1998, 456, 27-69.
Boxler, et al., Semisynthetic aminoglycoside antibacterials. Part 9. Synthesis of novel 1- and 3-ept-substituted derivatives of sisomicin and gentamincin from the 1- and 3-oxo-derivatives, Journal of the Chemical Society, Perkin Transactions 1, Jan. 1, 1981, 2168-2185.
Hiraiwa, et al., Effect of varying the 4"-position of arbekacin derivatives on antibacterial activity against MRSA and *Pseudomonas aeruginosa*, Bioorg Med Chem Lett. Nov. 15, 2007;17(22):6369-72. Epub Aug 28, 2007.
Hiraiwa, et al., Synthesis and antibacterial activity of 5-deoxy-5-episubstituted arbekacin derivatives, Bioorg Med Chem Lett. Jul. 1, 2007;17(13):3540-3. Epub Apr. 25, 2007.
Umezawa, et al., Synthesis of 1-N_ACYL Derivatives of 3', 4'-Dideoxy-6'-N-Methylkanamycin B and their antibacterial activities, J Antibiot (Tokyo). Apr. 1975;28(4):340-3.

* cited by examiner

*Primary Examiner* — Traviss C McIntosh, III
(74) *Attorney, Agent, or Firm* — Knobbe Martens Olson & Bear LLP

(57) ABSTRACT

The present invention relates to antimicrobial agents. Some embodiments include compounds, compositions, methods of preparation, and methods of treatment using new aminoglycosides and aminoglycoside derivatives.

32 Claims, No Drawings

AMINOGLYCOSIDE DERIVATIVES

RELATED APPLICATIONS

This application is the U.S. National Phase Application No. PCT/US2011/036344 entitled "AMINOGLYCOSIDE DERIVATIVES" filed May 12, 2011 and published in English on Nov. 17, 2011 as WO2011/143497 which claims the benefit of U.S. Provisional Application No. 61/334,088 filed on May 12, 2010 and U.S. Provisional Application No. 61/392,258 filed on Oct. 12, 2010, both of which are incorporated by reference in their entirety.

FIELD OF THE INVENTION

The present invention relates to antimicrobial agents. Some embodiments include compounds, compositions, methods of preparation, and methods of treatment relating to aminoglycosides and aminoglycoside derivatives.

BACKGROUND

Antibiotics are an effective tool in the treatment of infectious diseases. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Extensive use of antibiotics, including some aminoglycosides such as streptomycin and kanamycin, began in the 1950's. As the problem of global antibiotic resistance has continued to increase, antibiotics, have assumed increasing importance in clinical practice. For some aminoglycosides, their broad antimicrobial spectrum, rapid bactericidal action, and synergistic action with other drugs made them especially useful in the treatment of serious nosocomial infections (Umezawa, H.; Hooper, I. R., Aminoglycoside Antibiotics, Publisher: Springer Verlag 1982; Price K E, Godfrey J C, Kawaguchi H. Effect of structural modifications on the biological properties of aminoglycoside antibiotics containing 2-deoxystreptamine. In: Perlman D, editor. Structure-activity relationships among the semisynthetic antibiotics. New York: Academic Press; 1977. p. 239-375; Aminocyclitol Antibiotics, ACS Symposium Series 125, June 1980, K. L. Rhinehart, T. Suami (Editors); and Wright, G. D. et al., Aminoglycoside antibiotics. Structures, functions, and resistance. Adv Exp Med Biol 1998, 456, 27-69).

However, the usefulness of certain aminoglycosides in medicine has been impaired by several factors. For example, the development of microbial resistance has reduced the effectiveness of some aminoglycoside antibiotics. In some cases, microbial resistance is mediated by bacterial enzymes modifying the structure of the aminoglycoside (Mingeot-Leclercq, M. P. et al., "Aminoglycosides: activity and resistance", Antimicrob. Agents Chemother. (1999), 43(4), 727-737; Magnet S., Blanchard, J. S., "Molecular insights into aminoglycoside action and resistance", Chem. Rev., (2005), 105(2), 477-498; Vakulenko, S. B.; and Mobashery, S., "Versatility of Aminoglycosides and Prospects for Their Future" Clin. Microbiol. Rev., (2003), 16, 430-450; and Kotra, L. P. et al., "Aminoglycoside: perspectives on mechanisms of action and resistance and strategies to counter resistance", Antimicrob. Agents Chemother., (2000), 44(12), 3249-3256).

In addition, the use of some aminoglycoside antibiotics, such as amikacin, netilmicin, arbekacin, and etimicin, is limited due to toxicity considerations (Rougier, F. et al., Aminoglycoside dosages and nephrotoxicity: quantitative relationships. Clin Pharmacokinet (2003), 42, (5), 493-500; and Rougier, F. et al., Aminoglycoside nephrotoxicity. Curr Drug Targets Infect Disord (2004), 4, (2), 153-62).

Thus, there is a need for new aminoglycoside antibiotics.

SUMMARY OF THE INVENTION

The present invention relates to antimicrobial agents. Some embodiments include compounds, compositions, methods of preparation, and methods of treatment relating to aminoglycosides and aminoglycoside derivatives. In some embodiments, there is provided a compound of general formula (I) or a pharmaceutically acceptable salt or pro-drug thereof:

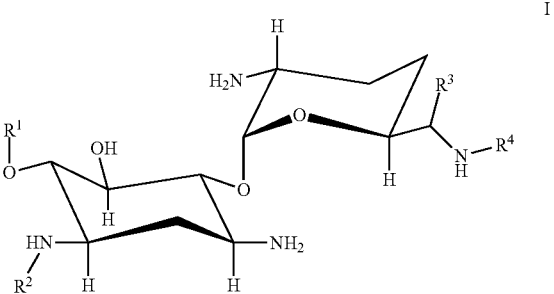

wherein,
$R^1$ is selected from the group consisting of

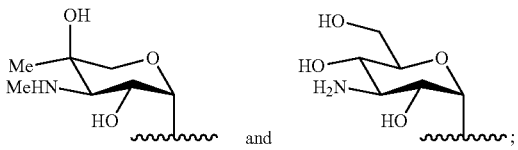

$R^2$ is selected from the group consisting of $-(CR^5R^6)_nR^7$, $-C(=X)NR^{10}(CR^5R^6)_nR^7$ and $-C(=X)(CR^5R^6)_nR^7$;

$R^3$ is selected from the group consisting of H and Me;

$R^4$ is selected from the group consisting of unsubstituted carbocyclyl, substituted or unsubstituted heterocyclyl, $-C(=NR^8)R^{14}$, $-(CR^5R^6)_nR^7$ and $-C(=NR^8)(CR^5R^6)_nR^7$;

each $R^5$ is independently selected from the group consisting of H, F, amino, aminoC$_{1-6}$alkyl, OH, $-C_{1-6}$alkylOR$^{12}$ and C$_{1-6}$alkyl;

each $R^6$ is independently selected from the group consisting of H, F, aminoC$_{1-6}$alkyl, $-C_{1-6}$alkylOR$^{12}$ and C$_{1-6}$alkyl, provided that each CR$^5$R$^6$ unit does not comprise two OH, two NH$_2$, one OH and one NH$_2$, one F and one NH$_2$, or one F and one OH;

each $R^7$ is selected from the group consisting of H, OR$^{12}$, NR$^9$R$^{10}$ and $-$NHC($=$NR$^8$)R$^{14}$;

alternatively $R^5$ and $R^7$ or $R^6$ and $R^7$ are taken together with the atom or atoms to which they are attached to form a four, five or six membered substituted or unsubstituted heterocyclyl ring;

alternatively $R^5$ and $R^6$ are taken together with the atom or atoms to which they are attached to form a three, four, five or six membered substituted or unsubstituted carbocyclyl or a substituted or unsubstituted heterocyclyl ring;

each $R^8$ is independently selected from the group consisting of H, $OR^{12}$, CN and $C_{1-6}$alkyl;

with the proviso that at least one of $R^5$, $R^6$, $R^7$ and $R^8$ is not H;

each $R^9$ is independently selected from the group consisting of H and $-(CR^5R^6)_nR^{13}$;

each $R^{10}$ is independently selected from the group consisting of H and $-(CR^5R^6)_mR^{13}$;

each $R^{12}$ is independently selected from the group consisting of H, $C_{1-6}$alkyl, $C_{2-6}$alkylOH and $C_{2-6}$alkylamino;

each $R^{13}$ is independently selected from the group consisting of OH and $NH_2$;

each $R^{14}$ is independently selected from the group consisting of H and $NR^9R^{10}$;

each X is independently selected from O and $NR^8$;

each m is independently an integer from 0 to 5; and each n is independently an integer from 1 to 5.

In some embodiments, there is provided a compound of general formula (I) or pharmaceutically acceptable salt or pro-drug thereof:

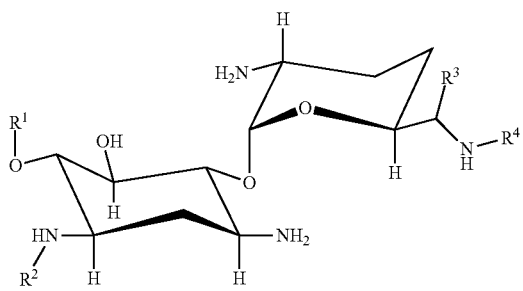

I wherein, $R^1$ is selected from a group consisting of

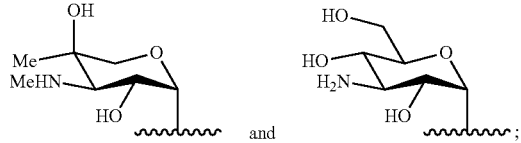

and $R^2$ is selected from the group consisting of $-C(=NR^8)NR^{10}(CR^5R^6)_nR^7$ and $-C(=NR^8)(CR^5R^6)_nR^7$;

$R^3$ is selected from the group consisting of H and Me;

$R^4$ is selected from the group consisting of H and Me;

each $R^5$ is independently selected from the group consisting of H, F, amino, amino$C_{1-6}$alkyl, OH, $-C_{1-6}$alkyl$OR^{12}$ and $C_{1-6}$alkyl;

each $R^6$ is independently selected from the group consisting of H, F, amino$C_{1-6}$alkyl, $-C_{1-6}$alkyl$OR^{12}$ and $C_{1-6}$alkyl, provided that each $CR^5R^6$ unit does not comprise two OH, two $NH_2$, one OH and one $NH_2$, one F and one $NH_2$, or one F and one OH;

each $R^7$ is selected from the group consisting of H, $OR^{12}$, $NR^9R^{10}$, $-NHC(=NR^8)R^{14}$, and $-NHNH_2$;

alternatively $R^5$ and $R^7$ or $R^6$ and $R^7$ are taken together with the atom or atoms to which they are attached to form a four, five or six membered substituted or unsubstituted heterocyclyl ring;

alternatively $R^5$ and $R^6$ are taken together with the atom or atoms to which they are attached to form a three, four, five or six membered substituted or unsubstituted carbocyclyl or a substituted or unsubstituted heterocyclyl ring;

each $R^8$ is independently selected from the group consisting of H, $OR^{12}$, CN and $C_{1-6}$alkyl;

each $R^9$ is independently selected from the group consisting of H and $-(CR^5R^6)_nR^{13}$;

each $R^{10}$ is independently selected from the group consisting of H and $-(CR^5R^6)_mR^{13}$;

each $R^{12}$ is independently selected from the group consisting of H, $C_{1-6}$alkyl, $C_{2-6}$alkylOH and $C_{2-6}$alkylamino;

each $R^{13}$ is independently selected from the group consisting of OH and $NH_2$;

each $R^{14}$ is independently selected from the group consisting of H and $NR^9R^{10}$;

each m is independently an integer from 0 to 5; and each n is independently an integer from 1 to 5.

Some embodiments include stereoisomers, pro-drugs, and pharmaceutically acceptable salts of a compound of general formula (I).

Some embodiments of the present invention include pharmaceutical compositions comprising any one of the foregoing compounds and a pharmaceutically acceptable carrier.

Some embodiments of the present invention include methods for treating or preventing a bacterial infection. Some such embodiments include administering to a subject in need thereof an effective amount of any one of the foregoing compounds or compositions. In some embodiments, the subject is a mammal. In some embodiments, the mammal is a human.

Some embodiments of the present invention include use of any one of the foregoing compounds or compositions in the preparation of a medicament for treating a bacterial infection. More embodiments include any one of the foregoing compounds or compositions to treat a bacterial infection.

In some embodiments, the bacteria infection comprises a bacteria selected from *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae,*

Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, or Staphylococcus saccharolyticus.

In particular embodiments, the bacteria is selected from Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii, or Bacteroides splanchnicus.

Some embodiments of the present invention include methods to prepare any one of the foregoing compounds or compositions.

DETAILED DESCRIPTION

The present invention relates to antimicrobial agents. Some embodiments include compounds, compositions, methods of preparation, and methods of treatment relating to aminoglycosides and aminoglycoside derivatives. In some embodiments, modifications to the N1 and N6' positions of gentamicin C1a have improved activity against bacterial strains possessing aminoglycoside modifying enzymes. Some embodiments include aminoglycosides and aminoglycoside derivatives with improved antimicrobial activity and reduced toxicity.

Some embodiments relate to structures such as gentamicin C1a, C2 and C2a, micronomicin and dibekacin. Some embodiments include N1- and N6'-modified derivatives of gentamicin C1a, C2 and C2a, micronomicin and dibekacin. In some embodiments, carbon atom numbering is as follows in (A):

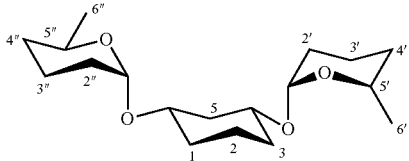

Some embodiments of the present invention include compounds of formula (I) or salts, pharmaceutically acceptable salts or pro-drugs thereof:

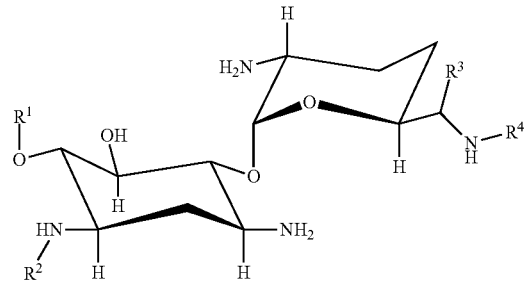

In some embodiments, $R^1$ is selected from the group consisting of

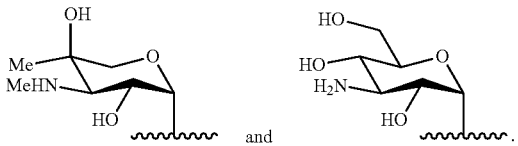

In some embodiments, $R^2$ is selected from the group consisting of $-(CR^5R^6)_nR^7$, $-C(=X)NR^{10}(CR^5R^6)_nR^7$ and $-C(=X)(CR^5R^6)_nR^7$.

In some embodiments, $R^3$ is selected from the group consisting of H and Me.

In some embodiments, $R^4$ is selected from the group consisting unsubstituted carbocyclyl, substituted or unsubstituted heterocyclyl, $-C(=NR^8)R^{14}$, $(CR^5R^6)_nR^7$ and $-C(=NR^8)(CR^5R^6)_nR^7$.

In some embodiments, each $R^5$ is independently selected from the group consisting of H, F, amino, amino$C_{1-6}$alkyl, OH, $-C_{1-6}$alkylOR$^{12}$ and $C_{1-6}$alkyl.

In some embodiments, each $R^6$ is independently selected from the group consisting of H, F, amino$C_{1-6}$alkyl, $-C_{1-6}$alkyl OR$^{12}$ and $C_{1-6}$alkyl, provided that each $CR^5R^6$ unit does not comprise two OH, two $NH_2$, one OH and one $NH_2$, one F and one $NH_2$, or one F and one OH.

In some embodiments, each $R^7$ is selected from the group consisting of H, OR$^{12}$, NR$^9$R$^{10}$ and $-NHC(=NR^8)R^{14}$.

In some embodiments, alternatively $R^5$ and $R^7$ or $R^6$ and $R^7$ together with the atom or atoms to which they are attached to form a four, five or six membered substituted or unsubstituted heterocyclyl ring.

In some embodiments, alternatively $R^5$ and $R^6$ together with the atom or atoms to which they are attached to form a three, four, five or six membered substituted or unsubstituted carbocyclyl or a substituted or unsubstituted heterocyclyl ring.

In some embodiments, each $R^8$ is independently selected from the group consisting of H, OR$^{12}$, CN and $C_{1-6}$alkyl.

In some embodiments, each $R^5$, $R^6$, $R^7$ and $R^8$ are not all simultaneously H;

In some embodiments, each $R^9$ is independently selected from the group consisting of H and $-(CR^5R^6)_nR^{13}$.

In some embodiments, each $R^{10}$ is independently selected from the group consisting of H and $-(CR^5R^6)_mR^{13}$.

In some embodiments, each $R^{12}$ is independently selected from the group consisting of H, $C_{1-6}$alkyl, $C_{2-6}$alkylOH and $C_{2-6}$alkylamino.

In some embodiments, each $R^{13}$ is independently selected from the group consisting of OH and $NH_2$.

In some embodiments, each $R^{14}$ is independently selected from the group consisting of H and $NR^9R^{10}$.

In some embodiments, each X is independently selected from O and $NR^8$.

In some embodiments, each m is independently an integer from 0 to 5.

In some embodiments, each n is independently an integer from 1 to 5.

In some embodiments, $R^1$ is

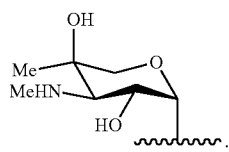

In some embodiments, $R^1$ is

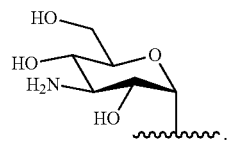

In some embodiments, $R^2$ is $-(CR^5R^6)_nR^7$.
In some embodiments, $R^2$ is $-C(=X)(CR^5R^6)_nR^7$.
In some embodiments, $R^2$ is $-C(=X)NR^{10}(CR^6R^6)_nR^7$.
In some embodiments, X is O; n is an integer from 2 to 3; $R^{10}$ is $-(CR^5R6)_mR^{13}$; m is 0; $R^{13}$ is OH.
In some embodiments, X is O.
In some embodiments, X is NH.
In some embodiments, $R^7$ is OH.
In some embodiments, $R^7$ is $NH_2$.
In some embodiments, $R^7$ is $-NHNH_2$.
In some embodiments, $R^7$ is $-NHC(=NH)NH_2$.
In some embodiments, $R^2$ selected from the group consisting of:

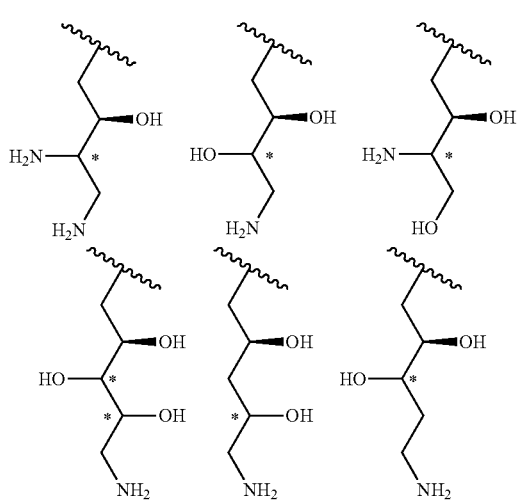

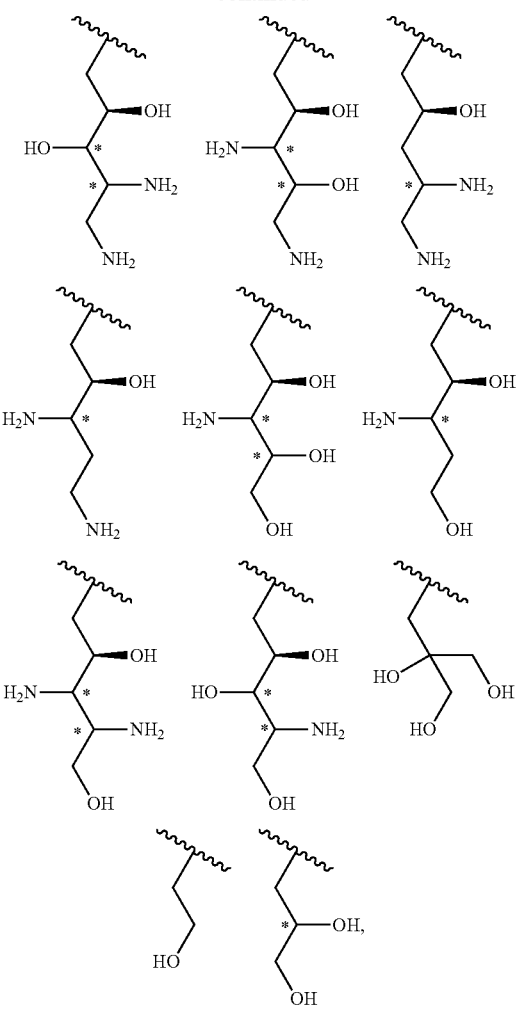

wherein * is a stereogenic center of R or S configuration.

In some embodiments, $R^2$ selected from the group consisting of:

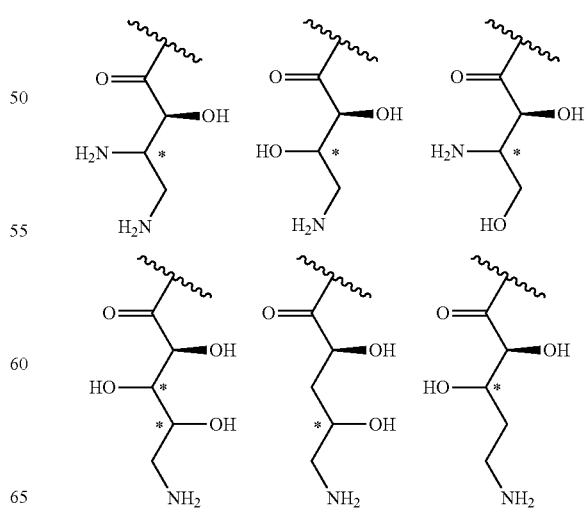

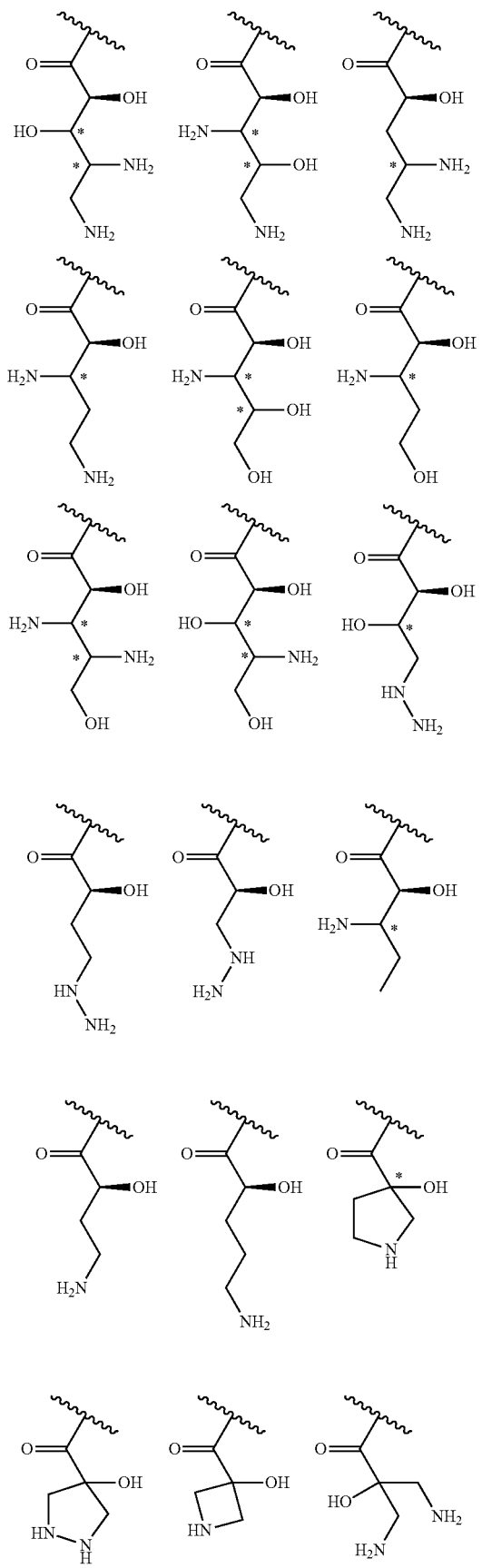
-continued
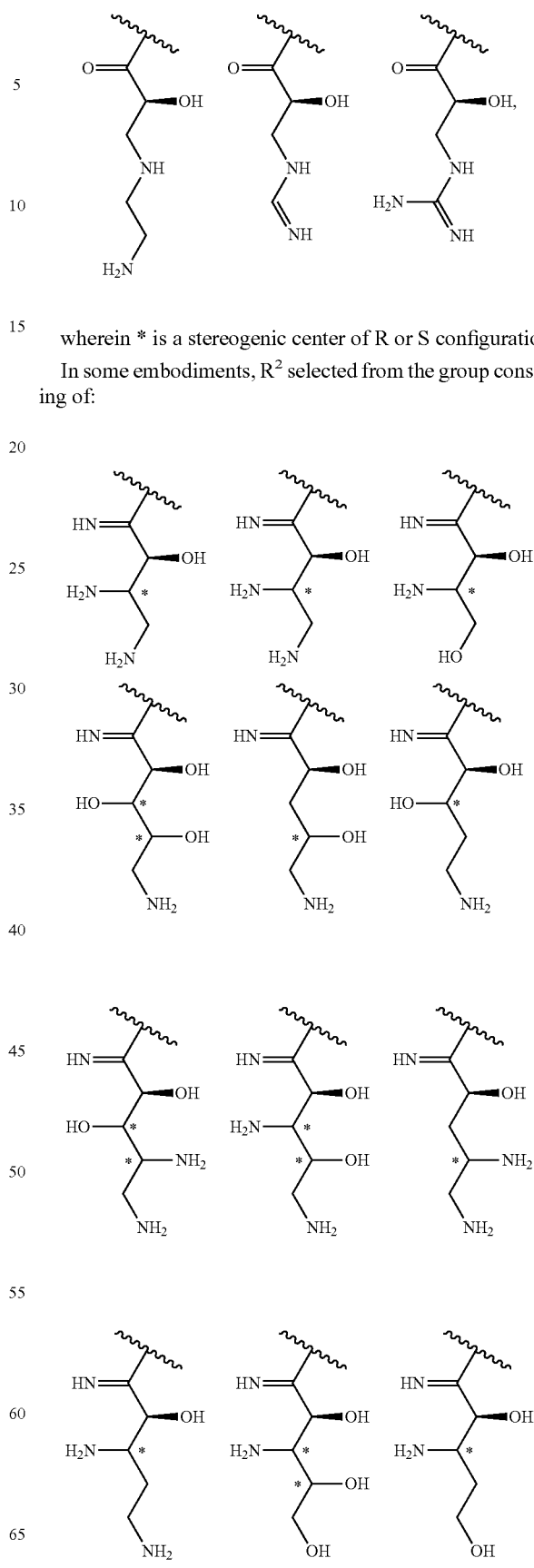
-continued
wherein * is a stereogenic center of R or S configuration.
In some embodiments, $R^2$ selected from the group consisting of:

-continued

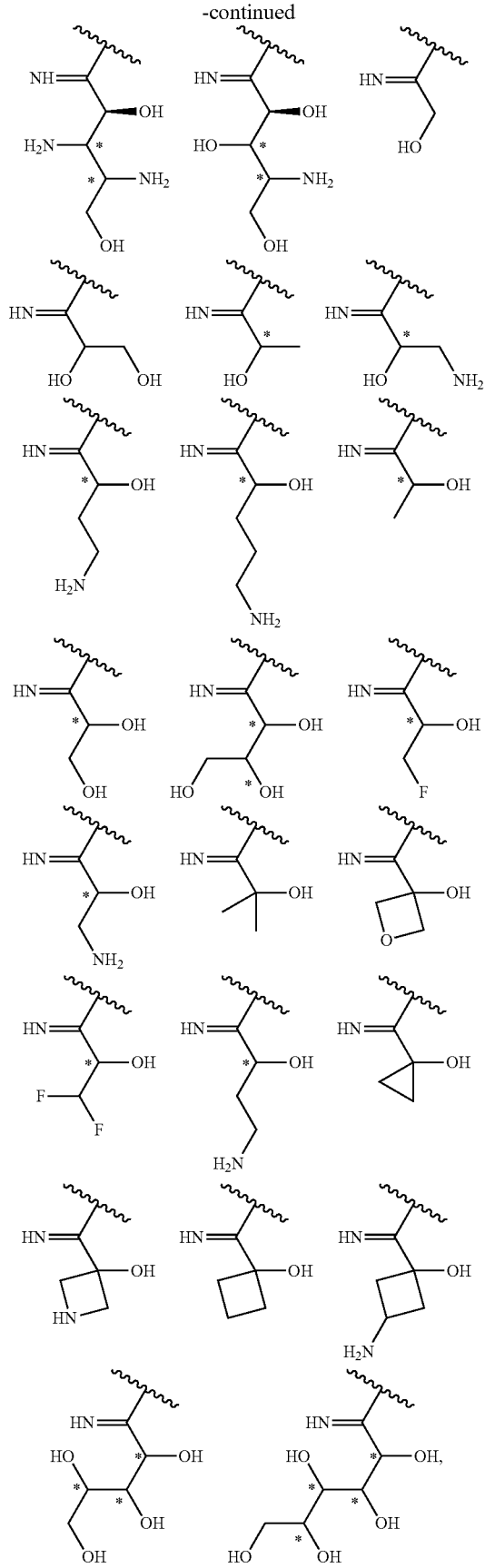

wherein * is a stereogenic center of R or S configuration.

In some embodiments, $R^2$ selected from the group consisting of:

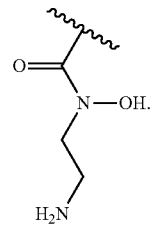

In some embodiments, $R^3$ is H.
In some embodiments, $R^4$ is $-C(=NR^8)R^{14}$.
In some embodiments, $R^8$ is H and $R^{14}$ is $-NR^9R^{10}$.
In some embodiments, $R^4$ is $-(CR^5R^6)_nR^7$.
In some embodiments, n is an integer from 2 to 3 and $R^7$ is OH.
In some embodiments, $R^4$ selected from the group consisting of:

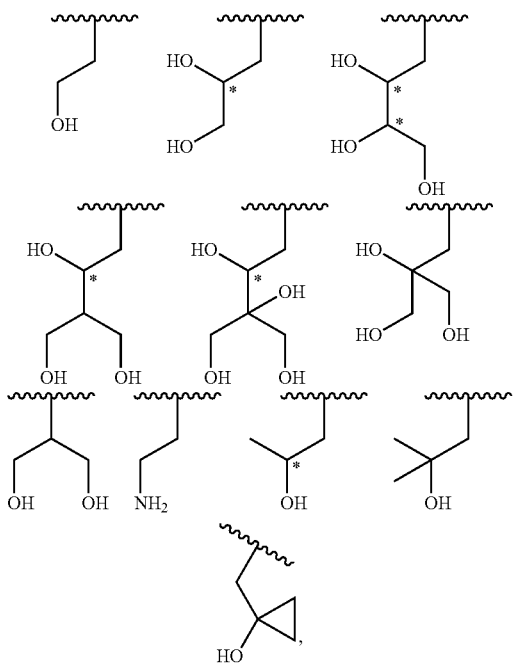

wherein * is a stereogenic center of R or S configuration.
In some embodiments, $R^4$ is $-C(=NR^8)(CR^5R^6)_nR^7$.
In some embodiments, $R^8$ is H; n is an integer from 1 to 3 and $R^7$ is selected from the group consisting of OH and $NH_2$.
In some embodiments, $R^4$ selected from the group consisting of:

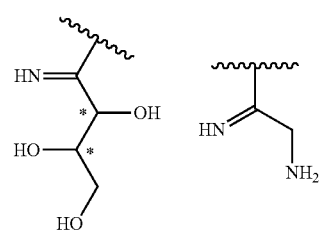

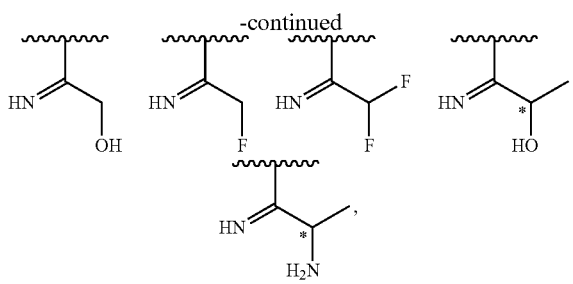

wherein * is a stereogenic center of R or S configuration.

Some embodiments of the present invention include compounds of formula (I) or salts, pharmaceutically acceptable salts or pro-drugs thereof:

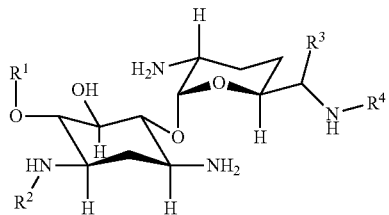

In some embodiments, $R^1$ is selected from the group consisting of

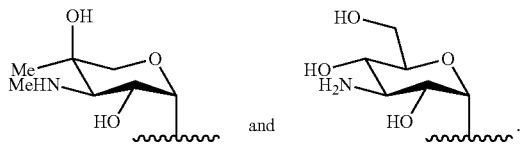

In some embodiments, $R^2$ is selected from the group consisting of $C(=NR^8)NR^{10}(CR^5R^6)_nR^7$ and $-C(=NR^8)(CR^5R^6)_nR^7$.

In some embodiments, $R^3$ is selected from the group consisting of H and Me.

In some embodiments, $R^4$ is selected from the group consisting of H and Me.

In some embodiments, each $R^5$ is independently selected from the group consisting of H, F, amino, aminoC$_{1-6}$alkyl, OH, $-C_{1-6}$alkylOR$^{12}$ and C$_{1-6}$alkyl.

In some embodiments, each $R^6$ is independently selected from the group consisting of H, F, aminoC$_{1-6}$alkyl, $-C_{1-6}$alkylOR$^{12}$ and C$_{1-6}$alkyl, provided that each CR$^5$R$^6$ unit does not comprise two OH, two NH$_2$, one OH and one NH$_2$, one F and one NH$_2$, or one F and one OH.

In some embodiments, each $R^7$ is selected from the group consisting of H, OR$^{12}$, NR$^9$R$^{10}$, $-$NHC($=$NR$^8$)R$^{14}$, and $-$NHNH$_2$.

In some embodiments, alternatively $R^5$ and $R^7$ or $R^6$ and $R^7$ are taken together with the atom or atoms to which they are attached to form a four, five or six membered substituted or unsubstituted heterocyclyl ring.

In some embodiments, alternatively $R^5$ and $R^6$ are taken together with the atom or atoms to which they are attached to form a three, four, five or six membered substituted or unsubstituted carbocyclyl or a substituted or unsubstituted heterocyclyl ring.

In some embodiments, each $R^8$ is independently selected from the group consisting of H, OR$^{12}$, CN and C$_{1-6}$alkyl.

In some embodiments, each $R^9$ is independently selected from the group consisting of H and $-(CR^5R^6)_nR^{13}$.

In some embodiments, each $R^{10}$ is independently selected from the group consisting of H and $-(CR^5R^6)_mR^{13}$.

In some embodiments, each $R^{12}$ is independently selected from the group consisting of H, C$_{1-6}$alkyl, C$_{2-6}$alkylOH and C$_{2-6}$alkylamino.

In some embodiments, each $R^{13}$ is independently selected from the group consisting of OH and NH$_2$.

In some embodiments, each $R^{14}$ is independently selected from the group consisting of H and NR$^9$R$^{10}$.

In some embodiments, each m is independently an integer from 0 to 5.

In some embodiments, each n is independently an integer from 1 to 5.

In some embodiments, $R^1$ is

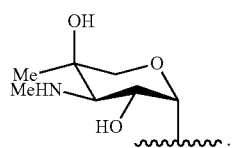

In some embodiments, $R^1$ is

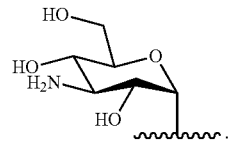

In some embodiments, $R^2$ is $-C(=NH)(CR^5R^6)_nR^7$; $R^7$ is selected from the group consisting of OH and NH$_2$.

In some embodiments, $R^2$ is selected from the group consisting of:

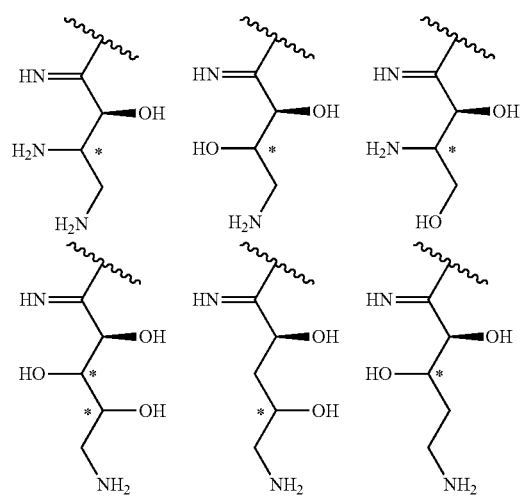

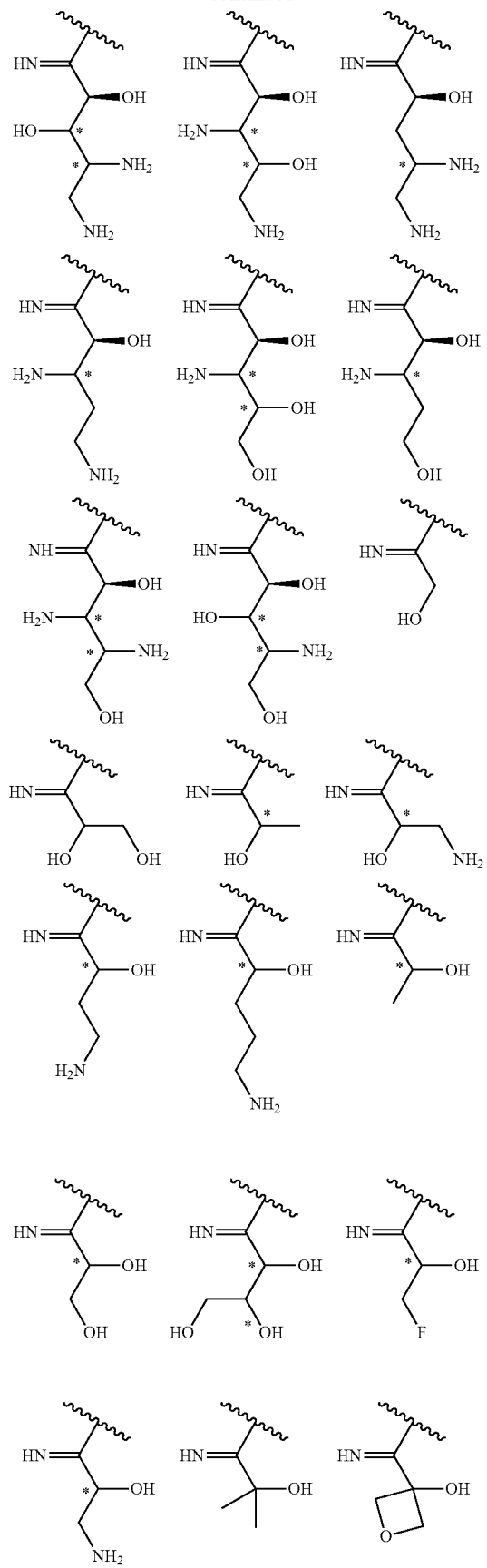
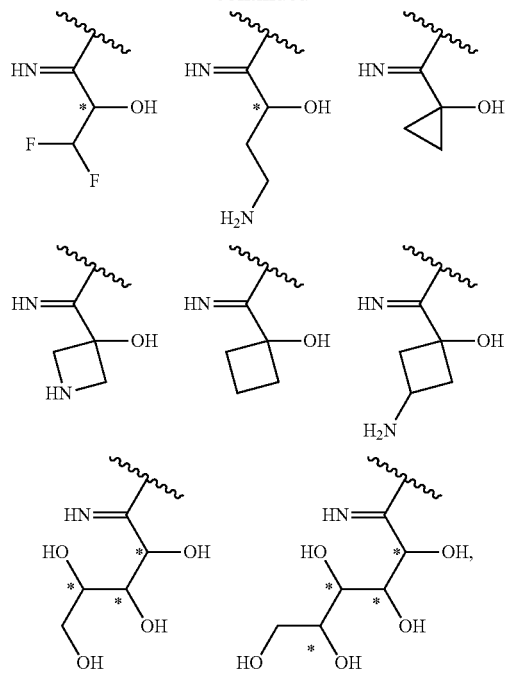
wherein * is a stereogenic center of R or S configuration.
In some embodiments, $R^4$ is Me.
In some embodiments, compounds of formula (I) do not include the compounds selected from the group consisting of:
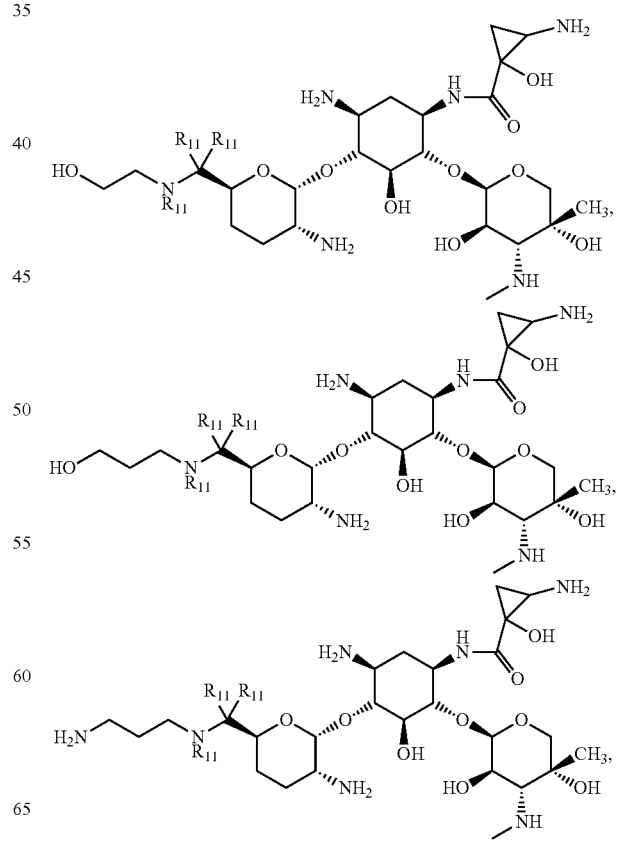

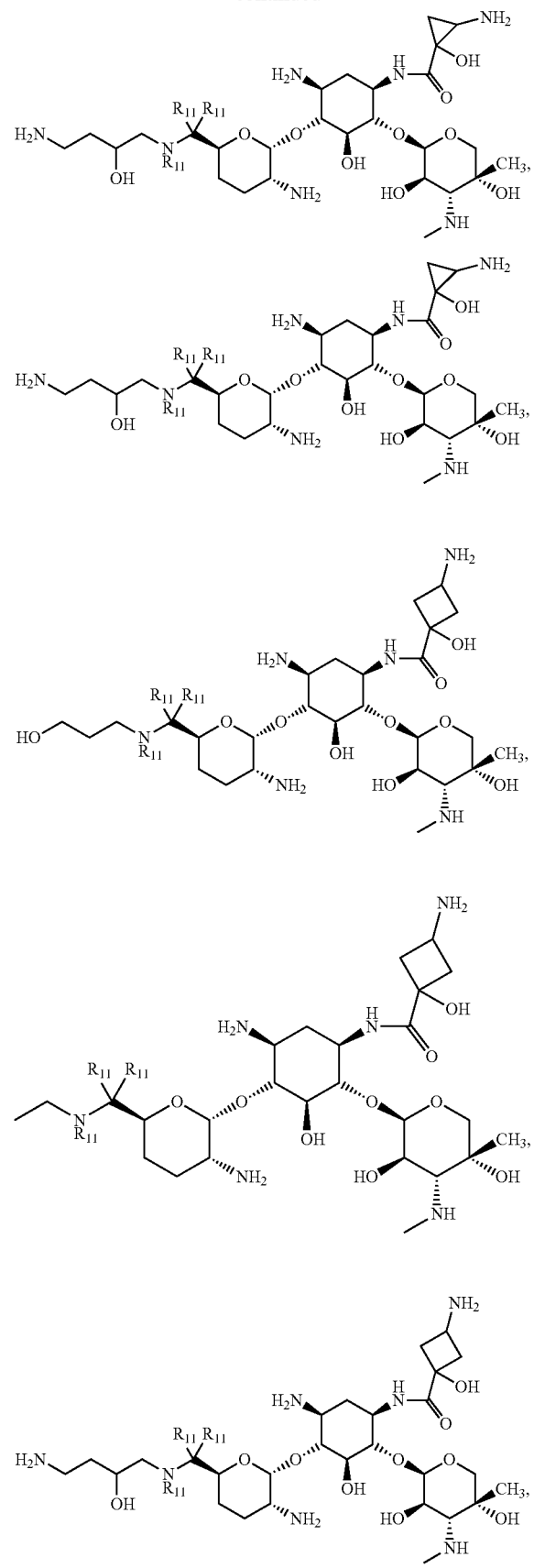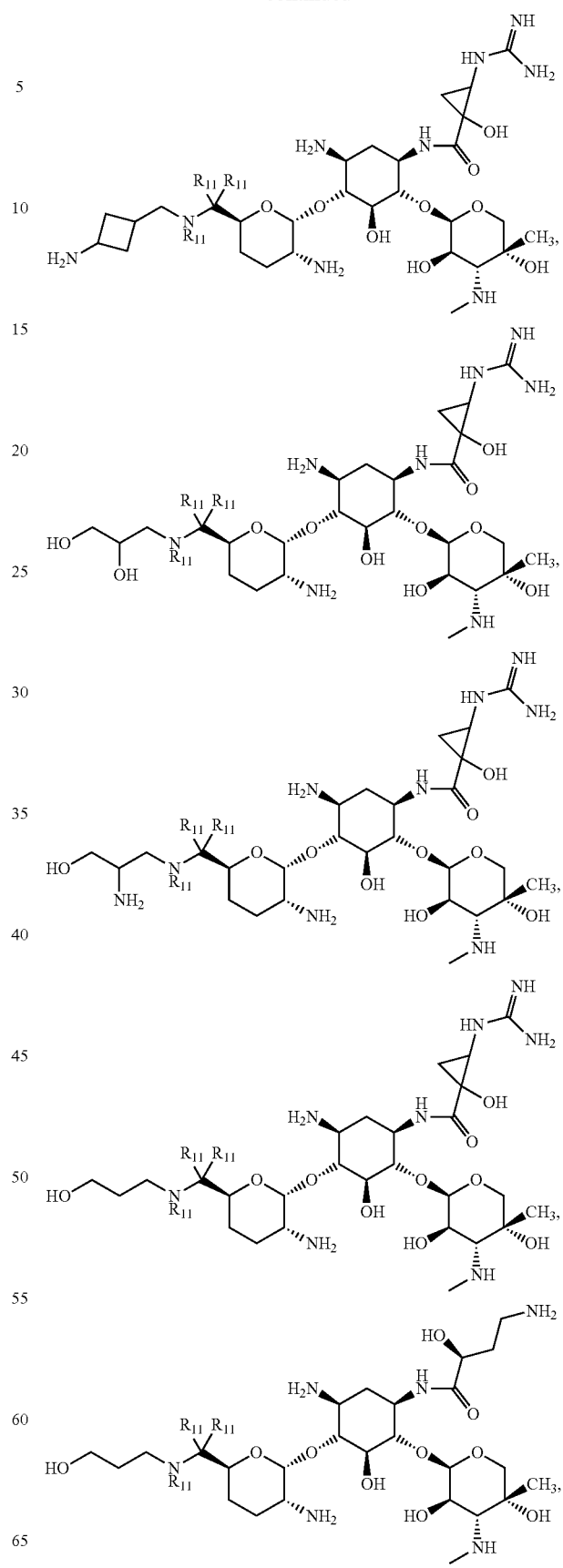

19
-continued
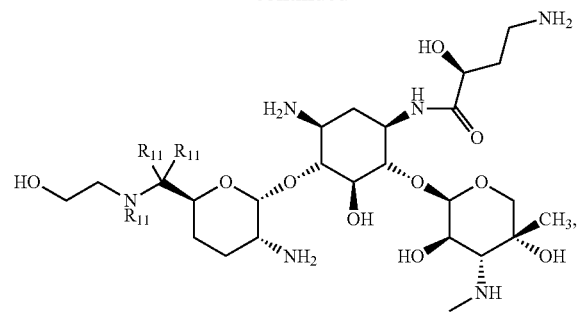
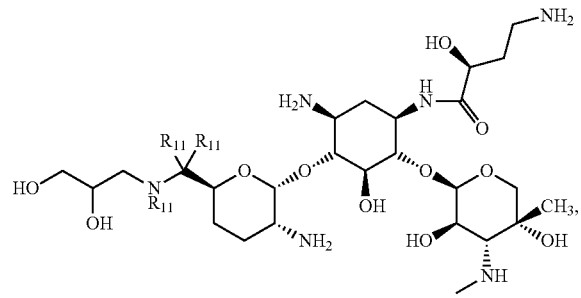
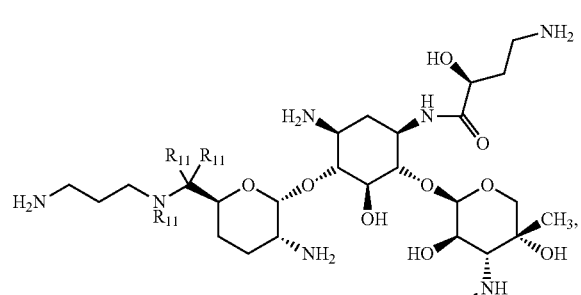
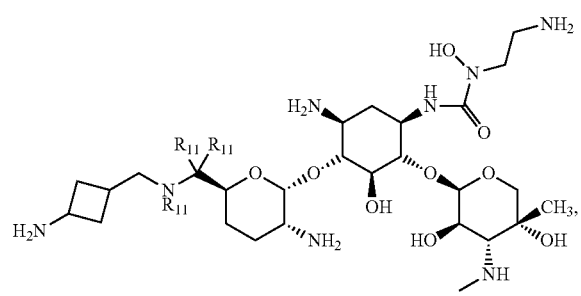
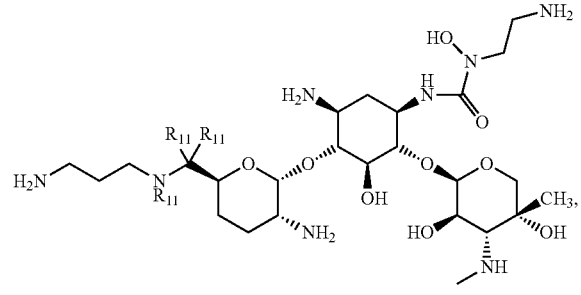
20
-continued
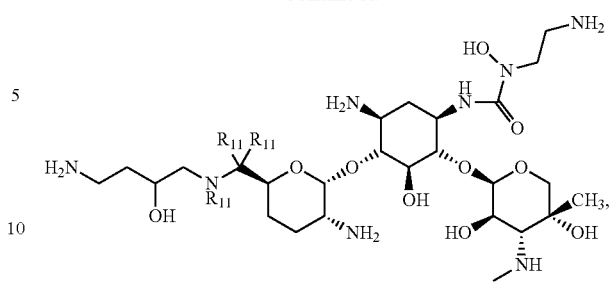
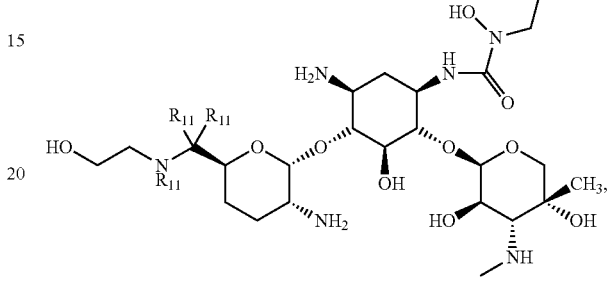
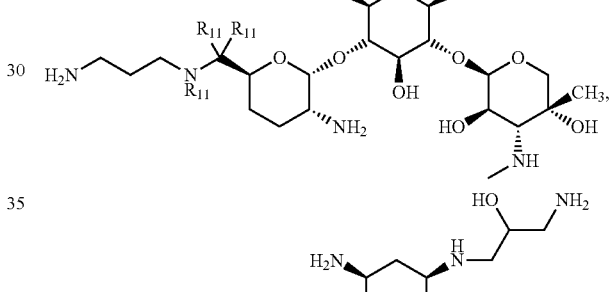
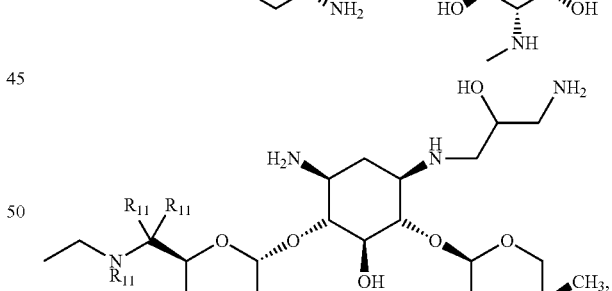
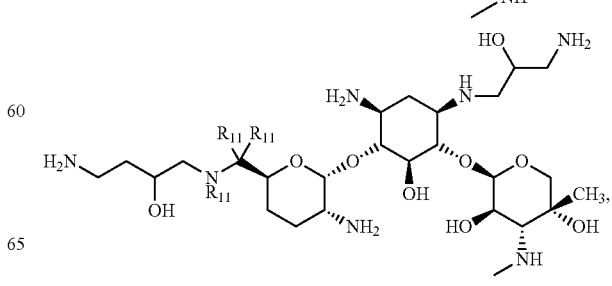

21
-continued
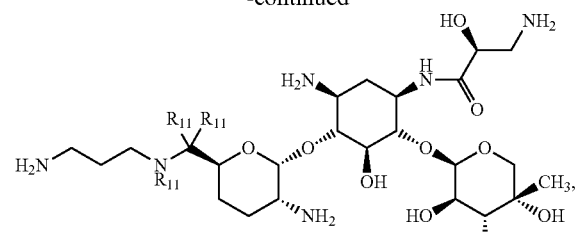
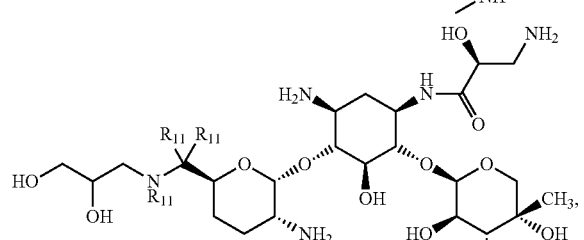
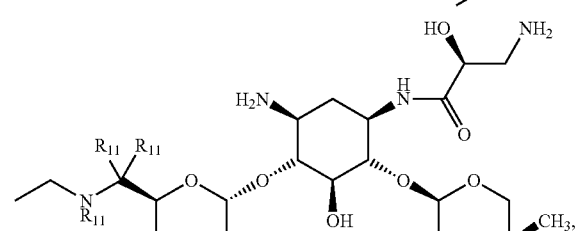
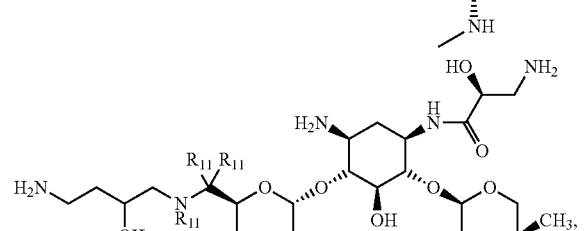
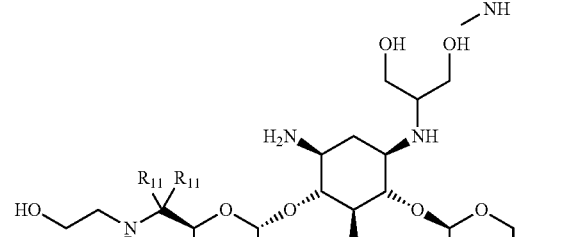
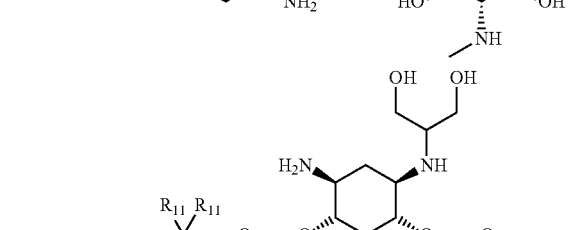
22
-continued
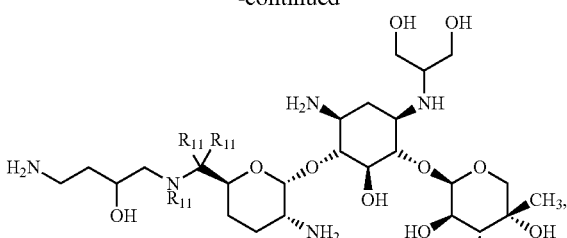
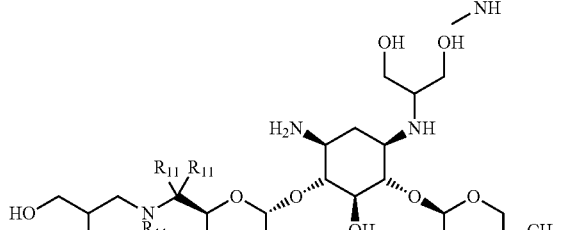
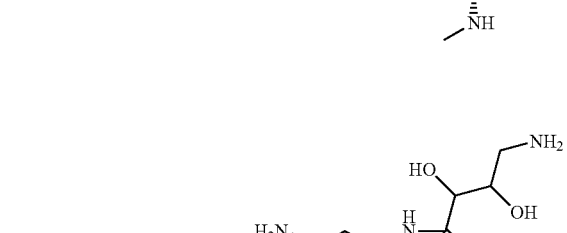
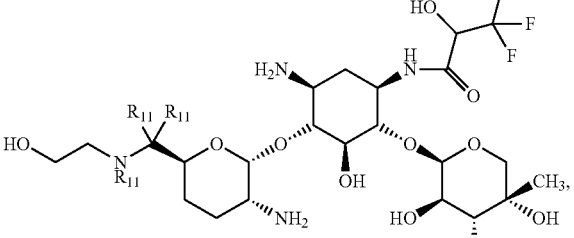
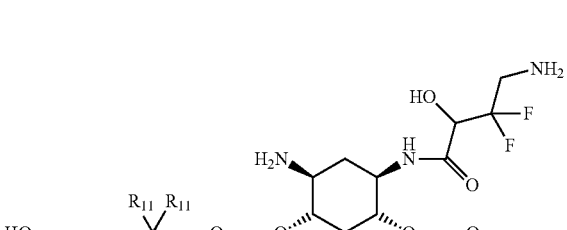

23
-continued
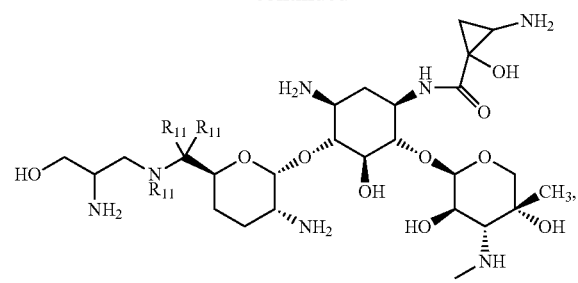
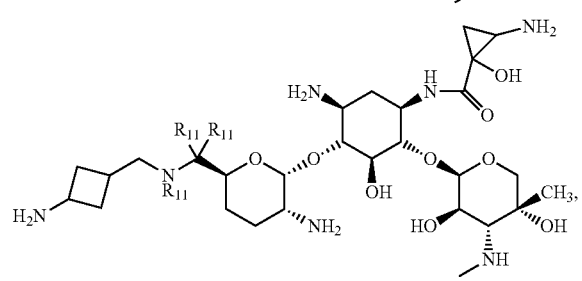
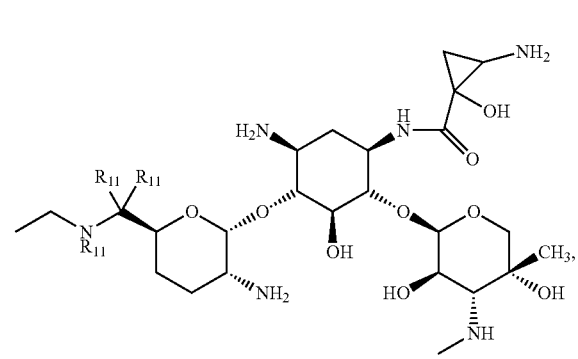
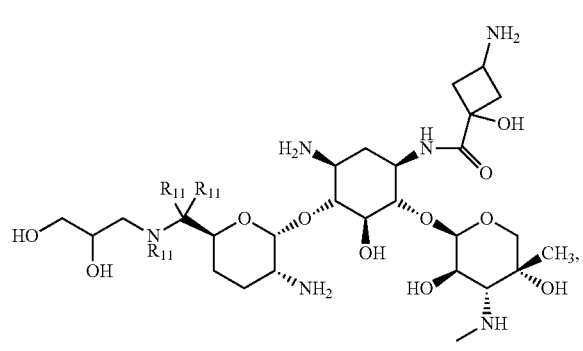
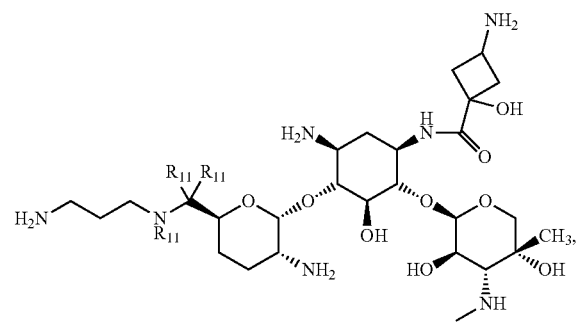
24
-continued
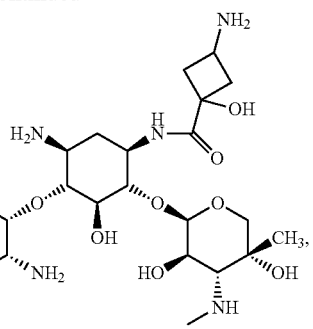
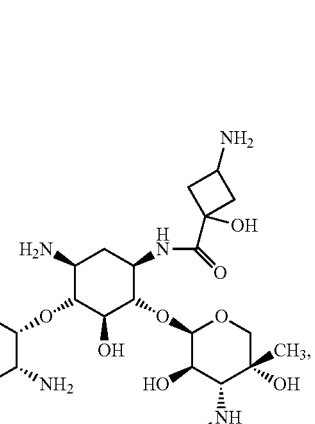
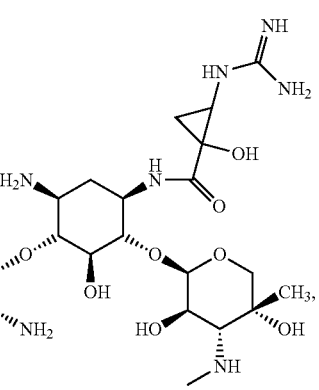
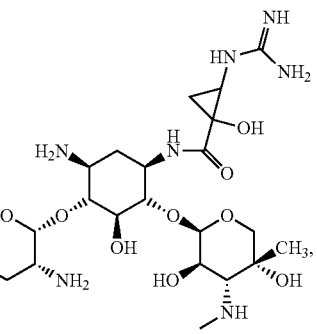

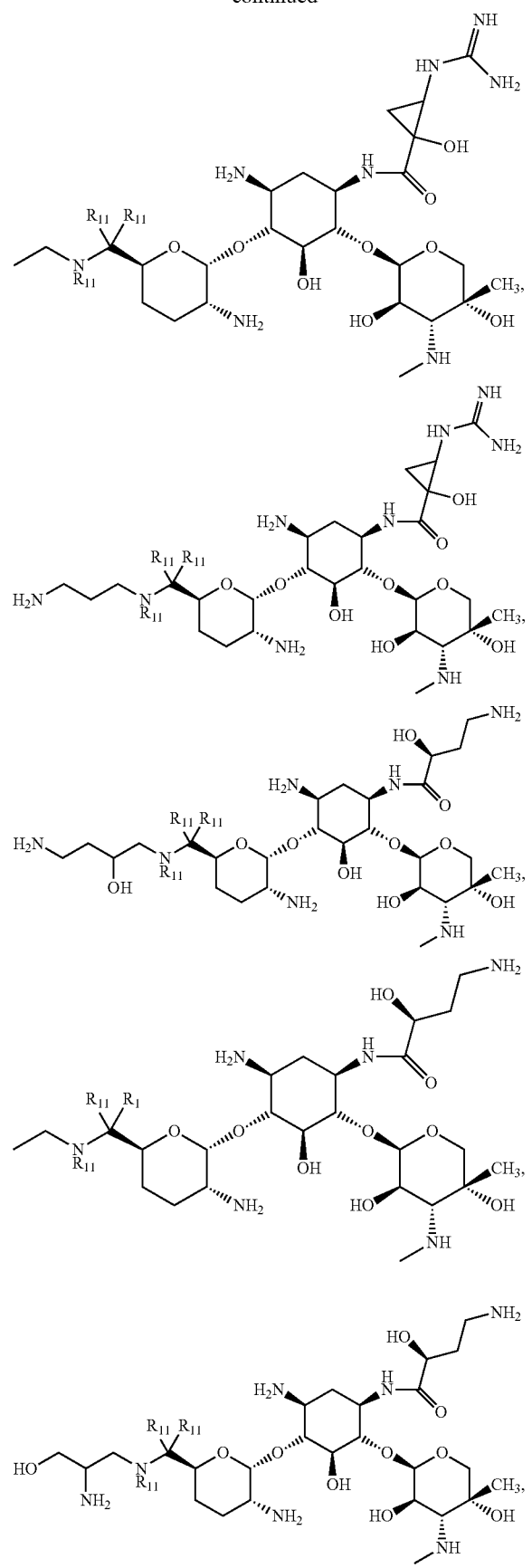
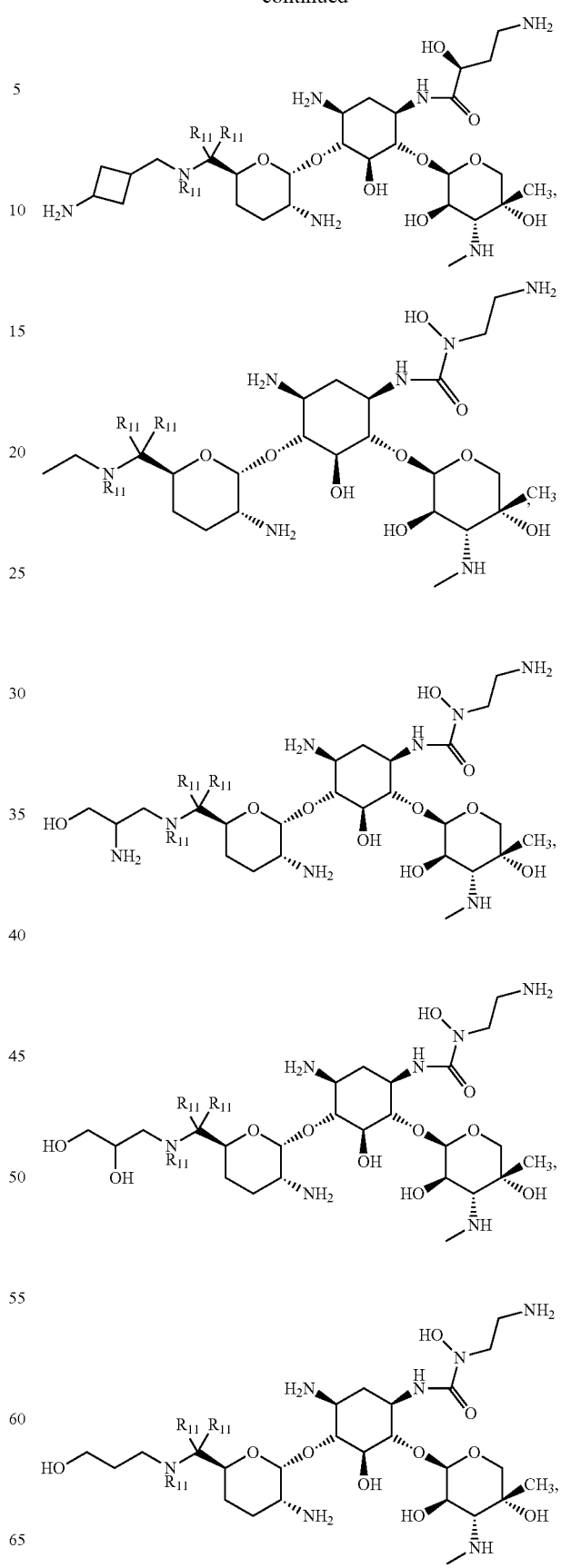

27
-continued
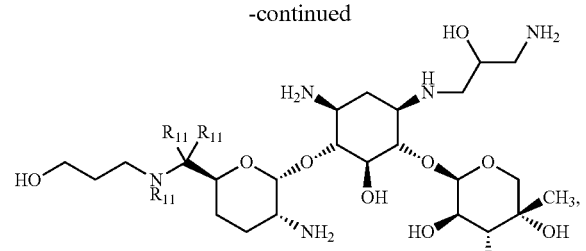
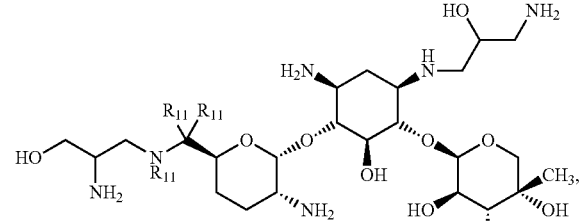
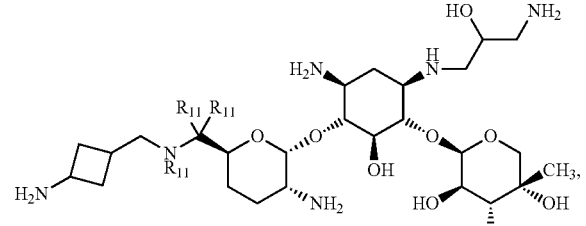
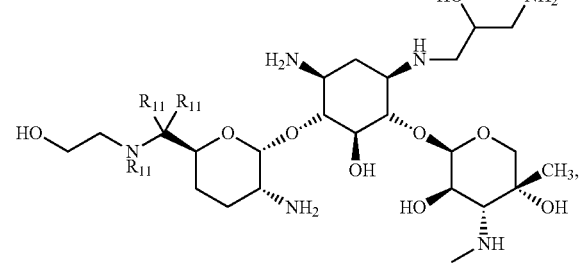
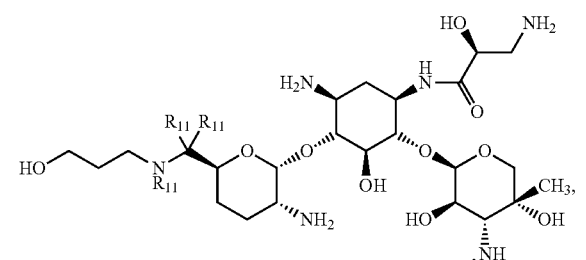
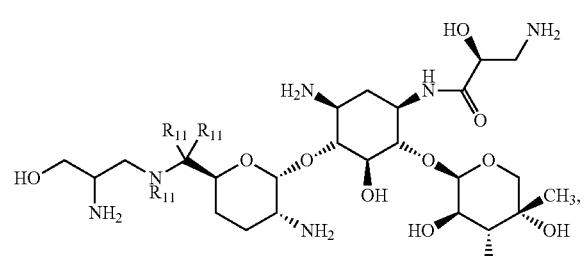
28
-continued
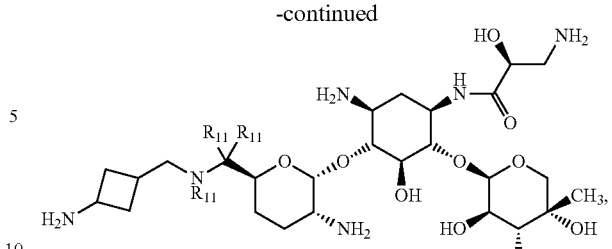
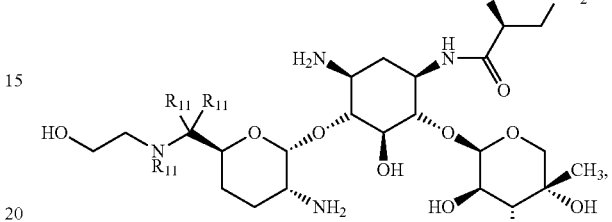
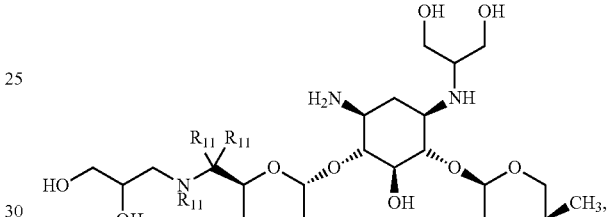
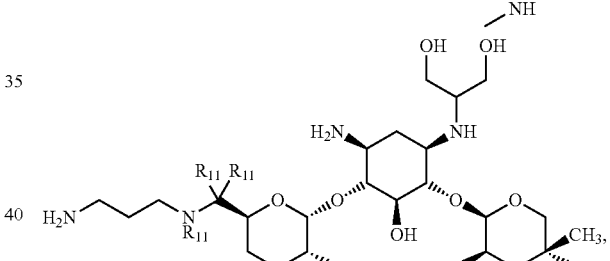
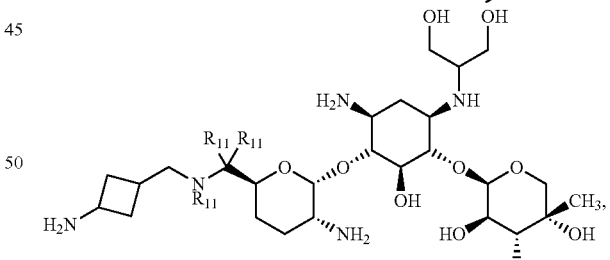
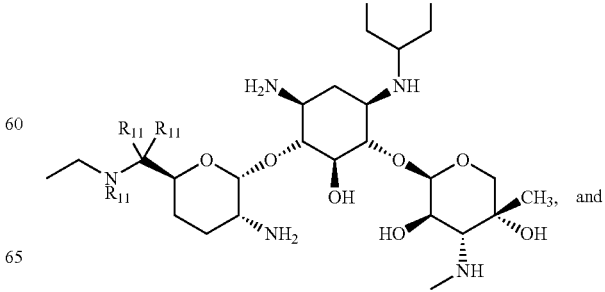
and -continued

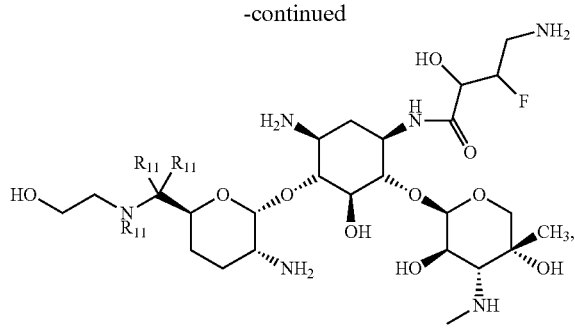

wherein each $R_{11}$ is independently hydrogen or methyl.

Aminoglycosides

Aminoglycosides are potent, bactericidal compounds. Examples of aminoglycosides include amikacin, arbekacin, gentamicin, kanamycin, neomycin, netilmicin, paromomycin, streptomycin, tobramycin, and apramycin.

Some aminoglycosides are particularly active against aerobic, gram-negative bacteria and act synergistically with beta-lactams against certain Gram-positive organisms. Some aminoglycosides are used in the treatment of severe infections, including, for example, infections of the abdomen and urinary tract, bacteremia, and endocarditis. They are also used for prophylaxis, especially against endocarditis.

Aminoglycosides include an aminocyclitol ring saturated with amine and hydroxyl substitutions. In some clinically useful aminoglycosides, the aminocyclitol moiety is streptamine or 2-deoxystreptamine. In streptomycin, the aminocyclitol moiety includes a streptidine moiety. The aminocyclitol nucleus is connected through glycosidic linkages to various amino sugars (aminoglycosides).

The aminoglycosides can be conveniently divided into three structural types based on the position of their glycosidic linkages. Aminoglycosides are basic, strongly polar compounds that are positively charged (cationic). They are highly soluble in water, relatively insoluble in lipids, and have enhanced antimicrobial activity in alkaline rather than acidic environments. As a result, aminoglycosides are minimally absorbed from the gut and penetrate the blood brain barrier poorly. Aminoglycosides are metabolically stable compounds that are excreted unchanged in the urine. The cationic nature of the aminoglycosides contributes to their antimicrobial activity. Because of their positive charge, they are able to bind negatively charged lipopolysaccharide of the bacterial cell wall and a variety of intracellular and cell membrane anionic molecules such as DNA, RNA, and phospholipids. Cellular uptake process is self-promoted involving the drug-induced disruption of $Mg^{2+}$ bridges between adjacent lipopolysaccharide molecules.

Without wishing to be bound by any one theory, the bactericidal action of some aminoglycosides is believed to be mediated by the compound binding to the bacterial 30S or 50S ribosomal subunit to disrupt RNA translation and protein synthesis. Such disruption produces abnormal transmembrane proteins that compromise the barrier properties of the bacterial membrane.

Many aminoglycosides are toxic. Types of toxicity include acute toxicity, nephrotoxicity, and ototoxicity. Various molecular mechanisms for aminoglycoside chronic toxicity have been suggested (Mingeot-Leclercq, M. P.; Tulkens, P. M., Aminoglycosides: nephrotoxicity. Antimicrob Agents Chemother (1999), 43, (5), 1003-12.). In some cases, for example, reversible nephrotoxicity in proximal tubule of nephrons, and irreversible ototoxicity in auditory hair cells, the toxic effects of aminoglycosides may be due in part to the active accumulation of aminoglycosides in the cells of these organs (Nagai, J.; Takano, M., Molecular aspects of renal handling of aminoglycosides and strategies for preventing the nephrotoxicity), and also to the generation of radical oxygen species (ROS) mediated by iron-aminoglycoside complexes (Ali, B. H., Agents Ameliorating or Augmenting Experimental Gentamicin Nephrotoxicity Some Recent Research. Food Chem Toxicol (2003), 41(11), 1447-52., Schacht, J., Antioxidant therapy attenuates aminoglycoside-induced hearing loss. Ann N Y Acad Sci (1999), 884, 125-30; Song, B. B.; et al., Iron Chelators Protect from Aminoglycoside-Induced Cochleo- and Vestibulo-Toxicity. Free Radic Biol Med (1998), 25, (2), 189-95.). Moreover, many modifications to the aminoglycoside structure result in modified aminoglycosides with a reduced antibacterial activity (Wang, J.; Chang, C.-W. T. In Aminoglycoside Antibiotics From Chemical Biology to Drug Discovery, Arya, D. P., Eds.; Wiley, 2007; pp 141-177).

Some embodiments of the present invention include compounds and compositions comprising aminoglycosides and aminoglycoside derivatives with improved antimicrobial activity and reduced toxicity.

DEFINITIONS

Terms and substituents are given their ordinary meaning unless defined otherwise, and may be defined when introduced and retain their definitions throughout unless otherwise specified, and retain their definitions whether alone or as part of another group unless otherwise specified.

As used herein, "alkyl" means a branched, or straight chain chemical group containing only carbon and hydrogen, such as methyl, isopropyl, isobutyl, sec-butyl and pentyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 9 carbon atoms, preferably 1 to 6, and more preferably 1 to 5 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "amido" means a H—CON— or alkyl-CON—, carbocyclyl-CON—, aryl-CON—, heteroaryl-CON— or heterocyclyl-CON group wherein the alkyl, carbocyclyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" includes both $RNR^8CO$— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, carbocyclyl-CO—, aryl-CO—, heteroaryl-CO— or heterocyclyl-CO— group wherein the alkyl, carbocyclyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro and fluoro are preferred halides. The term "halo" also contemplates terms sometimes referred to as "halogen", or "halide".

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of O, N or S, and wherein when the heterocycle is five membered, preferably it has one or two heteroatoms selected from O, N, or S.

As used herein, "substituted amino" means an amino radical which is substituted by one or two alkyl, cycloalkyl, aryl, heteroaryl or heterocyclyl groups, wherein the alkyl, aryl, heteroaryl or heterocyclyl are defined herein.

As used herein, "substituted hydroxyl" means RO— group wherein R is an alkyl, an aryl, heteroaryl or a heterocyclyl group, wherein the alkyl, cycloalkyl, aryl, heteroaryl or heterocyclyl are defined herein.

As used herein, "substituted thiol" means RS— group wherein R is an alkyl, an aryl, heteroaryl or a heterocyclyl group, wherein the alkyl, cycloalkyl, aryl, heteroaryl or heterocyclyl are defined herein.

As used herein, "sulfonyl" means an $alkylSO_2$, $arylSO_2$, $heteroarylSO_2$, $carbocyclylSO_2$, or $heterocyclyl-SO_2$ group wherein the alkyl, carbocyclyl, aryl, heteroaryl or heterocyclyl are defined herein.

As used herein, "sulfamido" means an alkyl-N—$S(O)_2N$—, aryl-$NS(O)_2N$—, heteroaryl-$NS(O)_2N$—, carbocyclyl-$NS(O)_2N$ or heterocyclyl-$NS(O)_2N$— group wherein the alkyl, carbocyclyl, aryl, heteroaryl or heterocyclyl group is as herein described.

As used herein, "sulfonamido" means an alkyl-$S(O)_2N$—, aryl-$S(O)_2N$—, heteroaryl-$S(O)_2N$—, carbocyclyl-$S(O)_2N$— or heterocyclyl-$S(O)_2N$— group wherein the alkyl, carbocyclyl, aryl, heteroaryl or heterocyclyl group is as herein described.

As used herein, "ureido" means an alkyl-NCON—, aryl-NCON—, heteroaryl-NCON—, carbocyclyl-NCON— or heterocyclyl-NCON— group wherein the alkyl, carbocyclyl, aryl, heteroaryl or heterocyclyl group is as herein described.

As used herein, "guanidino" means an alkyl-NC(=NR')N—, aryl-NC(=NR')N—, heteroaryl-NC(=NR')N—, carbocyclyl-NC(=NR')N— or heterocyclyl-NC(=NR')N— group wherein R is an H, substituted or unsubstituted hydroxyl, CN, alkyl, aryl, heteroaryl or a heterocyclyl group, wherein the alkyl, carbocyclyl, aryl, heteroaryl or heterocyclyl group is as herein described.

The skilled artisan will recognize that some structures described herein may be resonance forms or tautomers of compounds that may be fairly represented by other chemical structures, even when kinetically; the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "agent" or "test agent" includes any substance, molecule, element, compound, entity, or a combination thereof. An agent includes, but is not limited to, e.g., protein, polypeptide, peptide or mimetic, small organic molecule, polysaccharide, polynucleotide, and the like. An agent can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

Compounds and compositions herein also specifically contemplate pharmaceutically acceptable salts, whether cationic or anionic. A "pharmaceutically-acceptable salt" is an anionic salt formed at any acidic (e.g., carboxyl) group, or a cationic salt formed at any basic (e.g., amino) group. Many such salts are known in the art, as described in WO 87/05297, Johnston et al., published Sep. 11, 1987 (incorporated by reference herein). Preferred counter-ions of salts formable at acidic groups can include cations of salts, such as the alkali metal salts (such as sodium and potassium), and alkaline earth metal salts (such as magnesium and calcium) and organic salts. Preferred salts formable at basic sites include anions such as the halides (such as chloride salts). Of course, the skilled artisan is aware that a great number and variation of salts may be used, and examples exist in the literature of either organic or inorganic salts useful in this manner.

It is also clearly contemplated that compounds of the invention can be provided as biohydrolyzable prodrugs, as they are understood in the art. "Prodrug", as used herein is any compound wherein when it is exposed to the biological processes in an organism, is hydrolyzed, metabolized, derivatized or the like, to yield an active substance having the desired activity. The skilled artisan will recognize that prodrugs may or may not have any activity as prodrugs. It is the intent that the prodrugs described herein have no deleterious effect on the subject to be treated when dosed in safe and effective amounts. These include for example, biohydrolyzable amides and esters. A "biohydrolyzable amide" is an amide compound which does not essentially interfere with the activity of the compound, or that is readily converted in vivo by a cell, tissue, or human, mammal, or animal subject to yield an active compound of the invention. A "biohydrolyzable ester" refers to an ester compound of the invention that does not interfere with the activity of these compounds or that is readily converted by an animal to yield an active formula (I) compound. Such biohydrolyzable prodrugs are understood by the skilled artisan and are embodied in regulatory guidelines.

The term "mammal" is used in its usual biological sense, and includes humans, cattle, horses, dogs, and cats, and many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population (s) is damaging the cells or other tissue of a mammal. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, incorporated by reference in its entirety.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO87/05297, Johnston et al., published Sep. 11, 1987 (incorporated by reference herein).

"Solvate" refers to the compound formed by the interaction of a solvent and an EPI, a metabolite, or salt thereof. Suitable solvates are pharmaceutically acceptable solvates including hydrates.

"Subject" as used herein, means a human or other mammal, e.g., a dog, a cat, a mouse, a rat, a cow, a sheep, a pig, a goat, a non-human primate or a bird, e.g., a chicken, as well as any other vertebrate or invertebrate.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection, whereby the treatment reduces the likelihood that the patient will develop an infection. The term "therapeutic treatment" refers to administering treatment to a patient already suffering from an infection.

Administration and Pharmaceutical Compositions

Some embodiments include pharmaceutical compositions comprising: (a) a safe and therapeutically effective amount of the aminoglycoside, or its corresponding enantiomer, diastereoisomer or tautomer, or pharmaceutically acceptable salt; and (b) a pharmaceutically acceptable carrier.

The novel aminoglycoside derivatives are administered at a therapeutically effective dosage, e.g., a dosage sufficient to provide treatment for the disease states previously described. While human dosage levels have yet to be optimized for the compounds of the preferred embodiments, generally, a daily dose for most of the aminoglycosides described herein is from about 0.5 mg/kg or less to about 20 mg/kg or more of body weight, preferably from about 1.0 mg/kg to 15.0 mg/kg of body weight, and most preferably from about 1.5 mg/kg to 10.0 mg/kg of body weight. Thus, for administration to a 70 kg person, the dosage range would be about 35 mg per day or less to about 1400 mg per day or more, preferably from about 70 mg per day to 1050 mg per day, and most preferably from about 105 mg per day to 700.0 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the preferred embodiments.

The compounds useful as described above can be formulated into pharmaceutical compositions for use in treatment of these conditions. Standard pharmaceutical formulation techniques are used, such as those disclosed in *Remington's The Science and Practice of Pharmacy*, 21$^{st}$ Ed., Lippincott Williams & Wilkins (2005), incorporated by reference in its entirety.

In addition to the selected compound useful as described above, the compositions of the present invention contain a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent. In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parental administration include propylene glycol, ethyl oleate, pyrrolidone, ethanol, and sesame oil.

The compositions of this invention are preferably provided in unit dosage form. As used herein, a "unit dosage form" is a composition of this invention containing an amount of a compound that is suitable for administration to an animal, preferably mammal subject, in a single dose, according to good medical practice. (The preparation of a single or unit dosage form however, does not imply that the dosage form is administered once per day or once per course of therapy. Such dosage forms are contemplated to be administered once, twice, thrice or more per day, and are expected to be given more than once during a course of therapy, though a single administration is not specifically excluded. The skilled artisan will recognize that the formulation does not specifically contemplate the entire course of therapy and such decisions are left for those skilled in the art of treatment rather than formulation.)

The compositions useful as described above may be in any of a variety of forms, suitable (for example) for oral, nasal, rectal, topical (including transdermal), ocular, intracerebral, intracranial, intrathecal, intra-arterial, intravenous, intramuscular, or other parental route of administration. (The skilled artisan will appreciate that oral and nasal compositions comprise compositions that are administered by inhalation, and made using available methodologies.) Depending upon the particular route of administration desired, a variety of pharmaceutically-acceptable carriers well-known in the art may be used. These include solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: Modern Pharmaceutics, 4$^{th}$ Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. These oral forms comprise a safe and effective amount, usually at least about 5%, with a maximum of about 90%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising aminoglycosides and aminoglycoside derivatives described herein. Some methods include administering a compound, composition, pharmaceutical composition described herein to a subject in need thereof. In some embodiments, a subject can be an animal, e.g., a mammal, a human. In some embodiments, the bacterial infection comprises a bacteria described herein. As will be appreciated from the foregoing, methods of treating a bacterial infection include methods for preventing bacterial infection in a subject at risk thereof.

Further embodiments include administering a combination of compounds to a subject in need thereof. A combination can include a compound, composition, pharmaceutical composition described herein with an additional medicament. Examples of additional medicaments include an antibacterial agent, antifungal agent, an antiviral agent, an anti-inflammatory agent and an anti-allergic agent.

Examples of additional antibacterial agents include chloramphenicol, tetracyclines, synthetic and semi-synthetic penicillins, beta-lactams, quinolones, fluoroquinolnes, macrolide antibiotics, peptide antibiotics, and cyclosporines. Examples of antifungal agents include azoles, diazoles, triazoles, miconazole, fluconazole, ketoconazole, clotrimazole, itraconazole griseofulvin, ciclopirox, amorolfine, terbinafine, amphotericin B, potassium iodide, and flucytosine (5FC). Examples of antifungal agents include vidarabine, acyclovir, gancyclovir, nucleoside-analog reverse transcriptase inhibitors, AZT (zidovudine), ddI (didanosine), ddC (zalcitabine), d4T (stavudine), 3TC (lamivudine), non-nucleoside reverse transcriptase inhibitors, nevirapine, delavirdine, protease Inhibitors, saquinavir, ritonavir, indinavir, nelfinavir, ribavirin, amantadine, rimantadine and interferon Examples of anti-inflammatory and/or anti-allergic agents include corticosteroids, non-steroidal antiinflammatory drugs, anti-histamines, immunomodulating agents, and immunosuppressants.

Indications

The compounds and compositions comprising aminoglycosides and aminoglycoside derivatives described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples further describe the present invention, and are used for the purposes of illustration only, and should not be considered as limiting.

EXAMPLES

General Procedures

Materials used in preparing the aminoglycosides described herein may be made by known methods or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March *Advanced Organic Chemistry* (Wiley), Carey and Sundberg, *Advanced Organic Chemistry* (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, 4$^{th}$ Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

[1]H nuclear magnetic resonance spectra (NMR) were measured in the indicated solvents on either a Bruker NMR spectrometer (Avance™ DRX500, 500 MHz for 1H) or Varian NMR spectrometer (Mercury 400BB, 400 MHz for 1H). Peak positions are expressed in parts per million (ppm) downfield from tetramethylsilane. The peak multiplicities are denoted as follows, s, singlet; d, doublet; t, triplet; m, multiplet.

Analytical HPLC was performed according to one of the following methods:

Method 1: Thermo Finnigan LCQ LC/MS/MS system; Agilent Eclipse Plus C18 4.6×150 mm column (5 µm), gradient (Mobile Phases, A—Water with 0.01% NH$_4$OH and B—Acetonitrile with 0.01% NH$_4$OH): 2 minutes at 0% Acetonitrile, then 0-90% over 6.4 minutes, then 90% for 1.4 minutes at a flow of 2 mL/min with detection by mass spectrum TIC.

Method 2: Applied Biosystems 3200 Q LC/MS/MS system; Supelco Discovery HS F5 15 cm×2.1 mm column (5 µm), gradient (Mobile Phases, A—Water with 0.1% TFA and B—Acetonitrile with 0.1% TFA): 0.01 min at 5% Acetonitrile, then 5-95% over 9 minutes at a flow rate of 0.4 mL/min with detection by mass spectrum TIC.

The following abbreviations have the indicated meanings:
AMG=aminoglycoside
Boc$_2$O=di-tert-butyldicarbonate
Brine=saturated aqueous sodium chloride
CBz-OSu=N-(benzyloxycarbonyloxy)succinimide
DBU=1,8-diazabicyclo[5.4.0]undec-7-ene
DCC=dicyclohexylcarbodiimide
DCM=dichloromethane
DMAP=4-(dimethylamino)-pyridine
DMF=dimethylformamide
DMSO=dimethylsulfoxide
ESIMS=electron spray mass spectrometry
EtOAc=ethyl acetate
EtOH=ethyl alcohol
HONB-pNZ=N-(4-nitrobenzylcarbonate)bicyclo[2.2.1]hept-5-ene-2,3-dicarboxylic acid imide
HOSu=N-hydroxysuccinimide
iPrOH=iso-propanol
MeCN=acetonitrile
MeOH=methanol
MsCl=methanesulfonyl chloride
NMR=nuclear magnetic resonance
Nos=2-nitrobenzenesulfonyl
pNZ=p-nitrobenzyloxycarbonyl
p-TsOH=p-toluenesulfonic acid
py=pyridine
RP HPLC=reverse phase high performance liquid chromatography
TBAB=tetra-n-butylammonium bromide
TFA=trifluoroacetic acid
THF=tetrahydrofuran
THP=tetrahydropyranyl
TMSCN=trimethylsilyl cyanide
Z=benzyloxy-carbonyl The following example schemes are provided for the guidance of the reader, and collectively represent an example method for making the compounds provided herein. This method is not limiting, and it will be apparent that other routes may be employed to prepare these compounds.

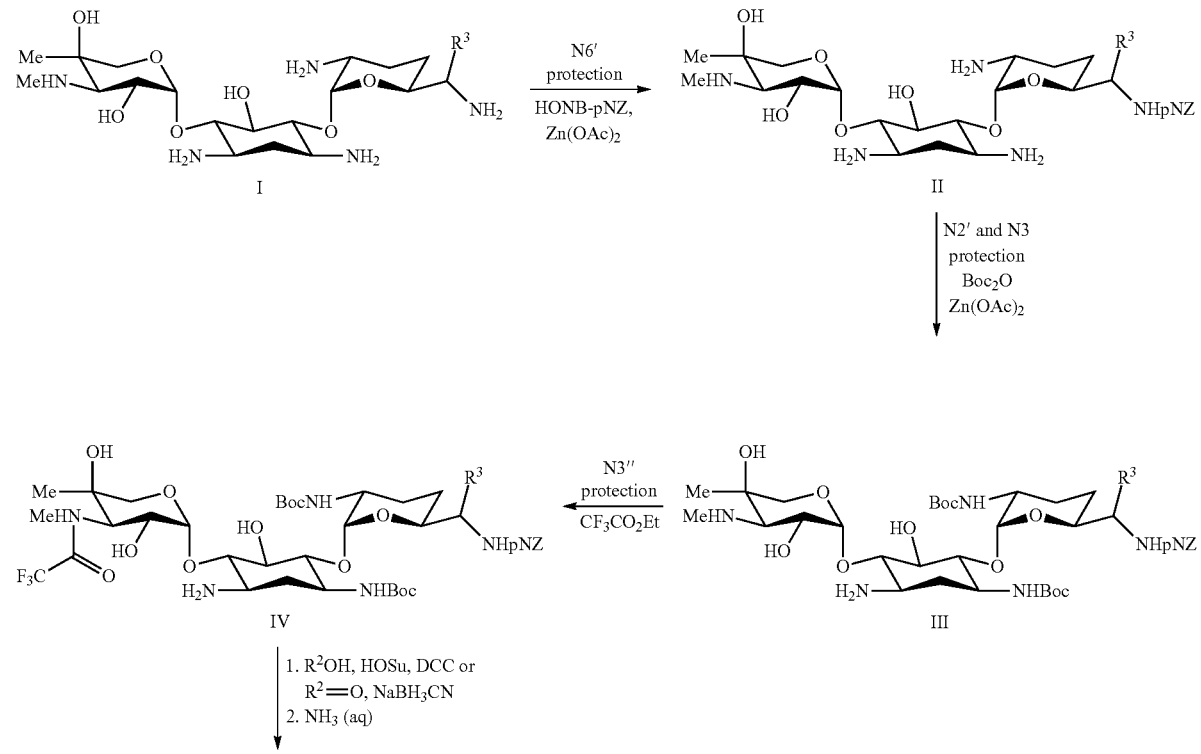

Scheme 1a.

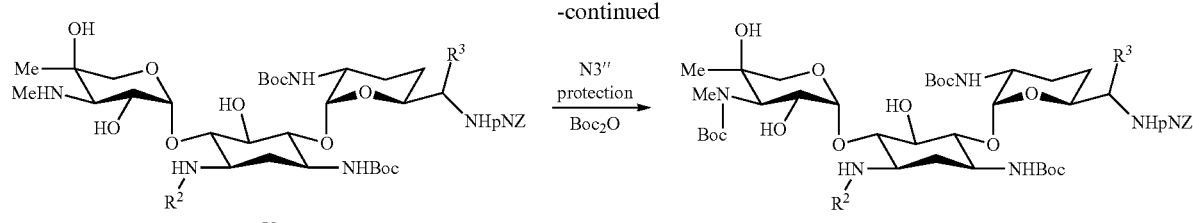

Scheme 1a describes a method for preparation of aminoglycoside derivatives (XI) by first reacting gentamicin C1a or a derivative (I) with N-(4-nitrobenzylcarbonate)bicyclo[2.2.1]hept-5-ene-2,3-dicarboxylic acid imide (HONB-pNZ) in the presence of zinc acetate to protect N6'. R group definitions are as provided above. AMG (II) was further protected at N2' and N3 with di-tert-butyl dicarbonate in the presence of zinc acetate and then with ethyl trifluoroacetate to protect N'' producing AMG (VI). Reaction of AMG (VI) with the acid or the aldehyde/ketone of $R^2$ followed by ammonia deprotection of N'' produces the desired N1 substituted AMG (V). Reprotection of N3'' with di-tert-butyl dicarbonate followed by removal of the p-nitrobenzyloxycarbonyl group from N6' yields AMG (VII). Activation of N6' with 2-nitrobenzenesulfonyl chloride followed by treatment of N6' with the alkyl halide of $R^4$ produces AMG (IX). Final deprotection of all the amines yields the desired AMG derivatives (XI).

Scheme 1b.

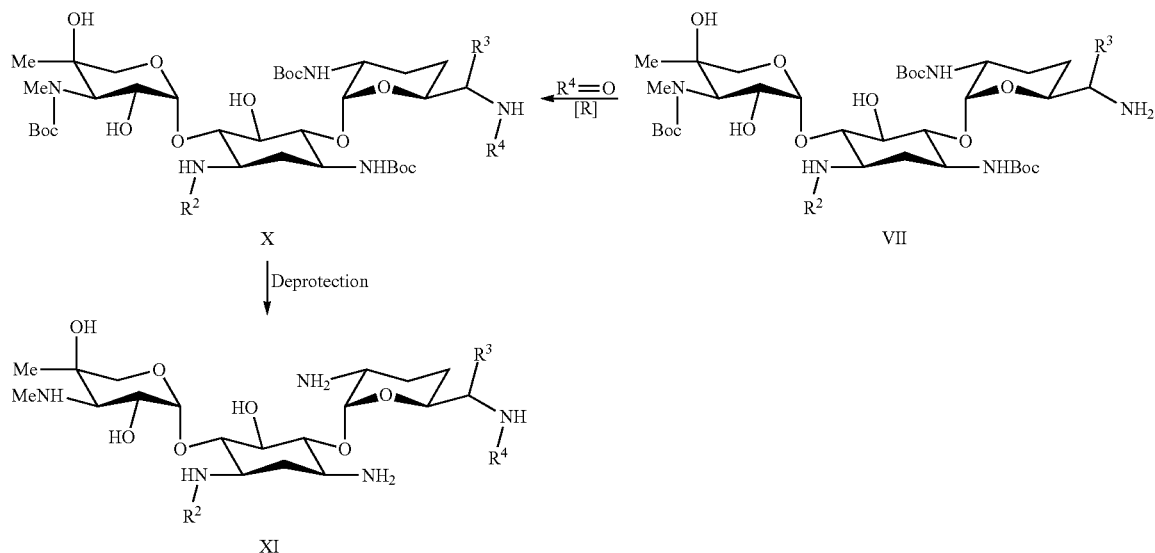

Scheme 1b describes an alternative method for preparation of aminoglycoside derivatives (XI). R group definitions are as provided above. Taking AMG (VII) from Scheme 1a and performing a reductive amination with the aldehyde of $R^4$ produces the N1, N6' substituted protected AMG (X). Final deprotection of all the amines yields the desired AMG derivatives (XI).

Scheme 2.

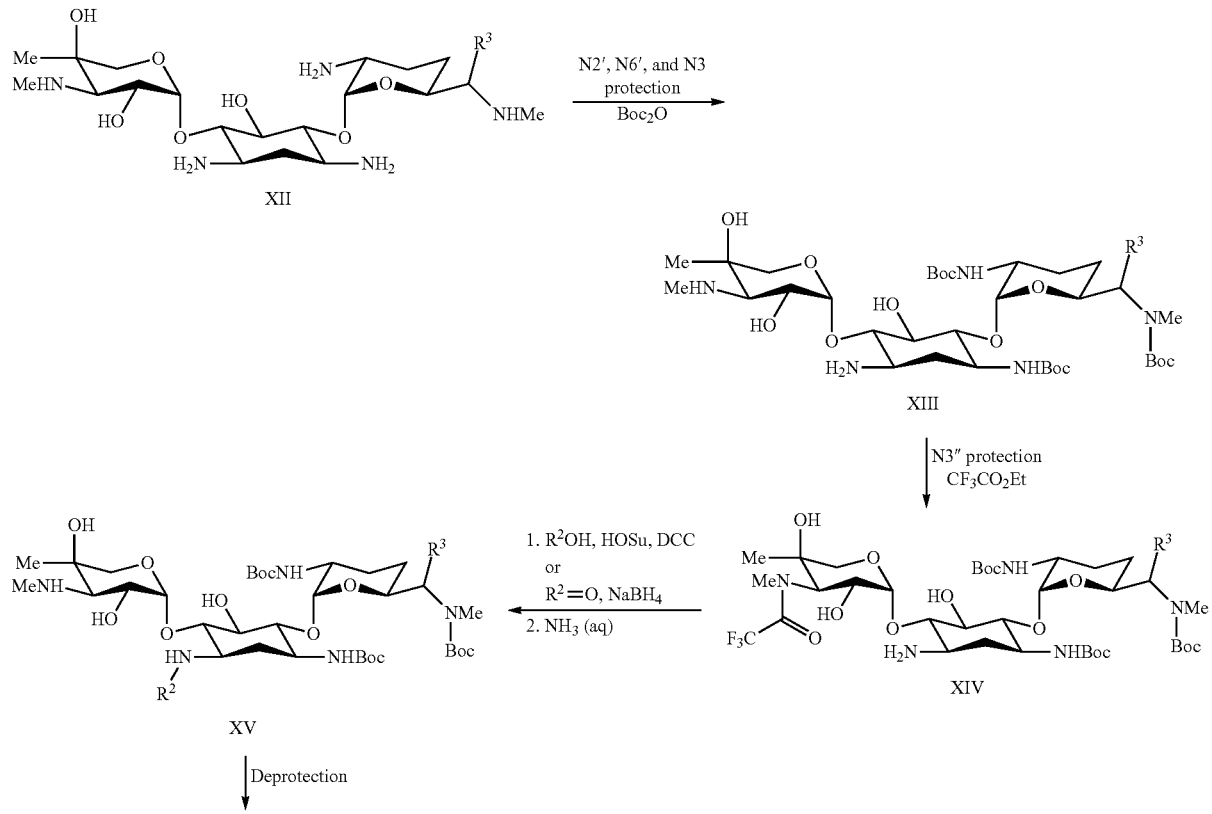

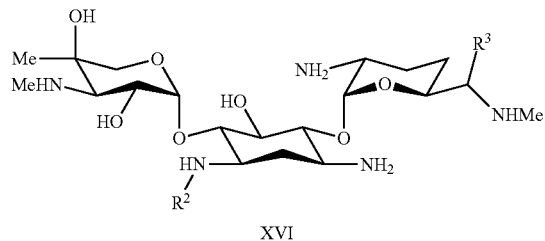

XVI

Scheme 2 describes a method for preparation of aminoglycoside derivatives (XVI) by first reacting micronomicin or a derivative (XII) with di-tert-butyl dicarbonate in the presence of zinc acetate to protect N2', N6' and N3 to produce AMG (XIII). R group definitions are as provided above. N3" protection with ethyl trifluoroacetate yields AMG (XIV). Reaction of AMG (XIV) with the acid or the aldehyde/ketone of $R^2$ followed by ammonia deprotection of N3" produces the desired N1 substituted AMG (XV). Final deprotection of all the amines yields the desired AMG derivatives (XVI).

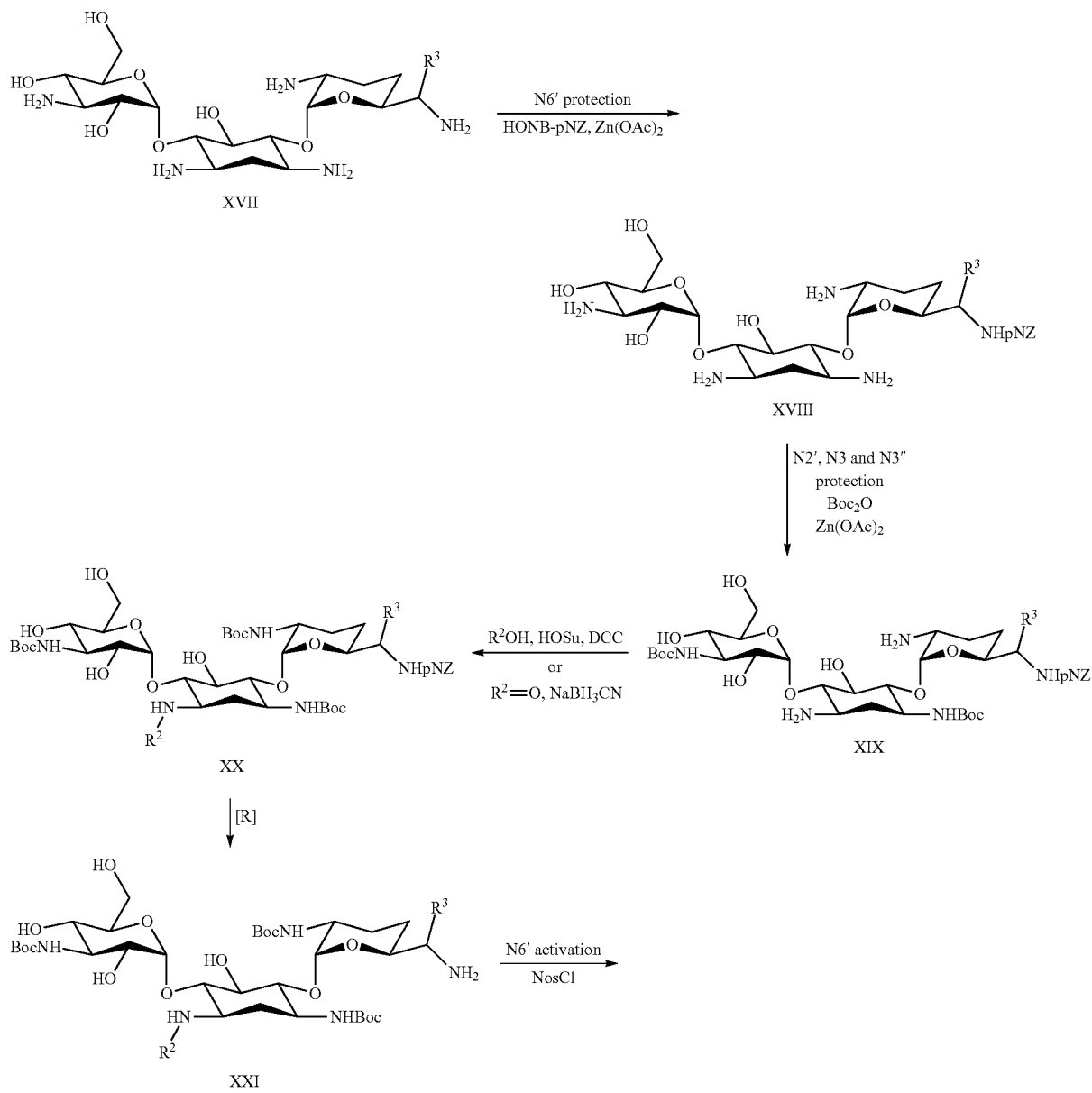

-continued

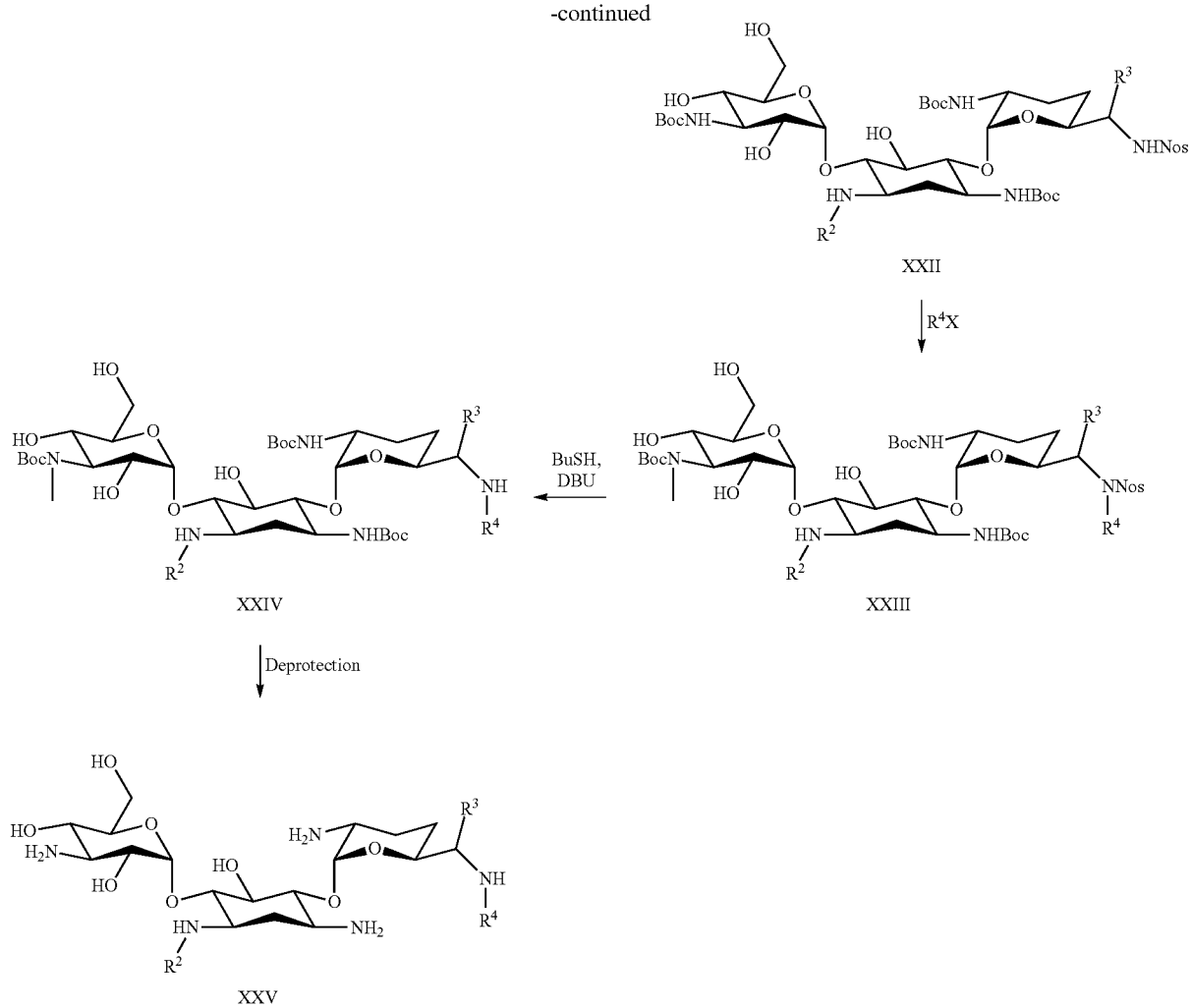

Scheme 3 describes a method for preparation of aminoglycoside derivatives (XXV) by first reacting dibekacin or a derivative (XVII) with HONB-pNZ in the presence of zinc acetate to protect N6'. R group definitions are as provided above. AMG (XVIII) was further protected at N2', N3 and N3" with di-tert-butyl dicarbonate and zinc acetate followed by reaction with the acid or the aldehyde/ketone of $R^2$ to produce the desired N1 substituted AMG (XX). Removal of the p-nitrobenzyloxycarbonyl group from N6' yields AMG (XXI). Activation of N6' with 2-nitrobenzenesulfonyl chloride followed by treatment of N6' with the alkyl halide of $R^4$ produces AMG (XXIII). Final deprotection of all the amines yields the desired AMG derivatives (XXV).

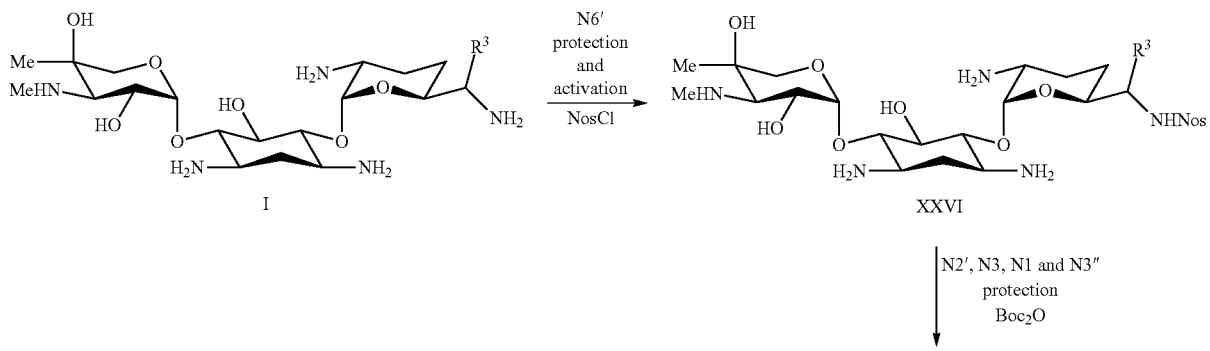

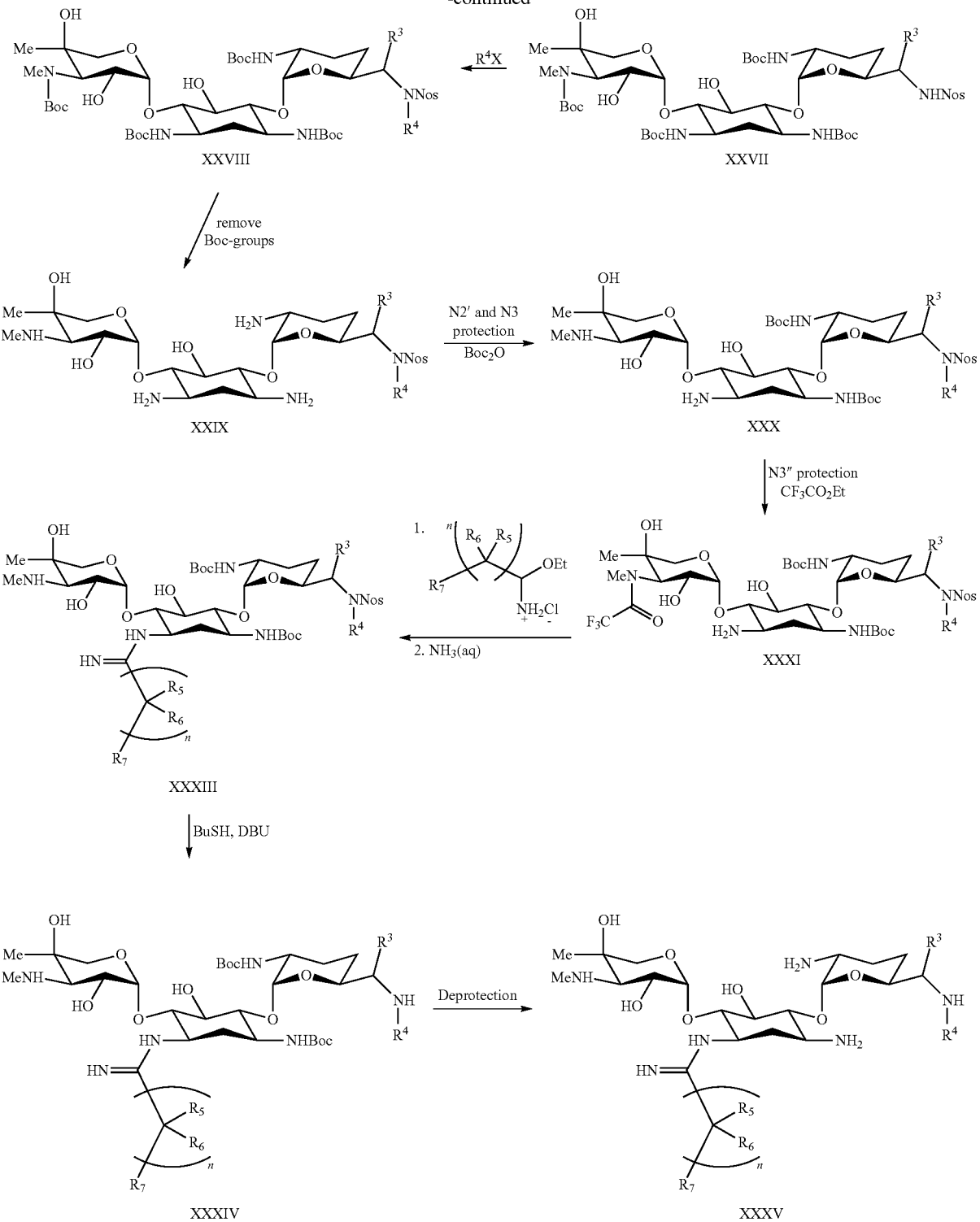

Scheme 4 describes a method for preparation of aminoglycoside derivatives (XXXV) by first reacting gentamicin C1a or a derivative (I) with 2-nitrobenzenesulfonyl chloride to activate N6'. R group definitions are as provided above. AMG (XXVI) was further protected at N2', N3, N1 and N3" with di-tert-butyl dicarbonate followed by reaction with the alkyl halide of $R^4$ produces AMG (XXVIII). Removal of all four Boc-group yields AMG (XXIX). Selective protection of N2' and N3 with di-tert-butyl dicarbonate in the presence of zinc acetate produces AMG (XXX). N3" protection with ethyl trifluoroacetate followed by reaction with the ethyl acetimidate (XXXII) gives AMG (XXXIII). Final deprotection of all the amines yields the desired AMG derivatives (XXXV).

Illustrative Intermediate Compound Examples

Synthesis of (4R,5S)-4-(azidomethyl)-3-(tert-butoxycarbonyl)-2,2-dimethyloxazolidine-5-carboxylic acid XXXIX Synthesis of XXXIX is depicted in Scheme 5 and Example 1.

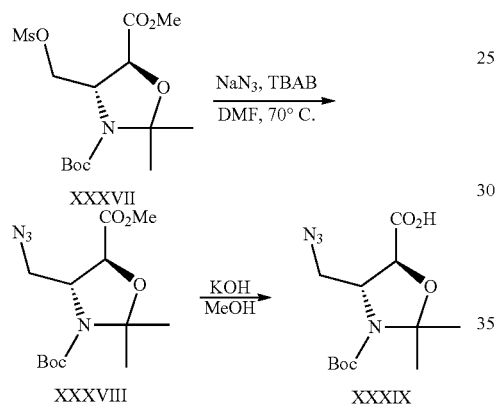

Example 1

Step 1

Compound XXXVI (0.23 g, 0.81 mmol) was dissolved in mixture of DCM (20 mL) and Et$_3$N (0.12 g, 1.2 mmol) before cooling to −10° C. MsCl (0.13 g, 1.15 mmol) was added in portions during 10 min and the mixture was stirred for additional 4 h. Cold DCM (20 mL) was added followed by water (20 mL) and 1N HCl (20 mL). The organic phase was separated, dried over Na$_2$SO$_4$ and evaporated producing crude (4R,5S)-3-tert-butyl 5-methyl 2,2-dimethyl-4-((methylsulfonyloxy)methyl)oxazolidine-3,5-dicarboxylate XXXVII (0.30 g, 0.80 mmol, quant) which was used in the next step. ESIMS found for C$_{14}$H$_{25}$NO$_8$S m/z 390 (M+Na).

Step 2

Compound XXXVII (0.30 g, 0.80 mmol) was dissolved in DMF (10 mL) followed by the addition of NBu$_4$Br (0.092 g, 0.28 mmol) and then NaN$_3$ (0.15 g, 2.32 mmol). The mixture was heated at 70° C. for 7 h. Water (30 mL) was added to the cooled reaction mixture and it was extracted with EtOAc (3×20 mL). The organic phase was separated, dried over Na$_2$SO$_4$ and evaporated. The residue was purified on a silica gel column (3:1 hexane/EtOAc→1:1 hexane/EtOAc) to yield (4R,5S)-3-tert-butyl 5-methyl 4-(azidomethyl)-2,2-dimethyloxazolidine-3,5-dicarboxylate XXXVIII (0.078 g, 0.25 mmol, 31%). ESIMS found for C$_{13}$H$_{22}$N$_4$O$_5$ m/z 337 (M+Na).

Step 3

Compound XXXVIII (0.064 g, 0.21 mmol) was dissolved in MeOH (1 mL) and a solution of 2M KOH (0.15 mL, 0.3 mmol) was added. The solution was stirred for 2 h at room temperature. The solvent was evaporated under reduced pressure and the resulting residue was treated with water and extracted with diethyl ether. The aqueous phase was separated, acidified with 1N HCl (pH=2) and extracted with EtOAc (3×15 mL). The organic phase was dried over Na$_2$SO$_4$ and evaporated producing (4R,5S)-4-(azidomethyl)-3-(tert-butoxycarbonyl)-2,2-dimethyloxazolidine-5-carboxylic acid XXXIX (0.057 g, 0.19 mmol, 92%). ESIMS found for C$_{12}$H$_{20}$N$_4$O$_5$ m/z 301 (M+H).

Synthesis of (4S,5R)-5-(tert-butoxycarbonylamino)-2,2-dimethyl-1,3-dioxane-4-carboxylic acid XLIII Synthesis of XLIII is depicted in Scheme 6 and Example 2.

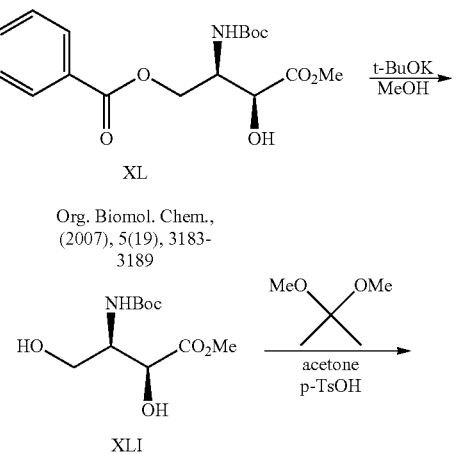

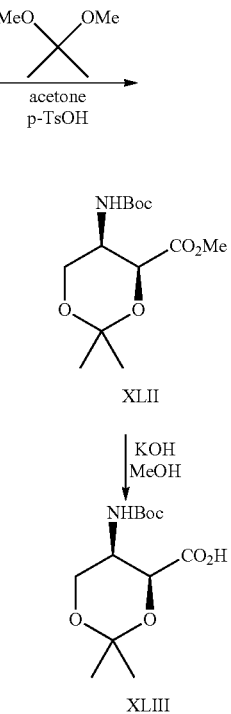

Example 2

Step 1

Compound XL (1.11 g, 2.90 mmol) was dissolved in MeOH (80 mL) and potassium t-butoxide (100 mg, 1 mmol) was added and the mixture was left stirring overnight at room temperature. The mixture was treated with $NH_4Cl$ (0.5 g) and was evaporated to dryness. The residue was purified on a silica gel column (20:1 DCM/MeOH) to produce (2S,3R)-methyl 3-(tert-butoxycarbonylamino)-2,4-dihydroxybutanoate XLI (0.42 g, 1.68 mmol, 58%). ESIMS found for $C_{10}H_{19}NO_6$ m/z 272 (M+Na).

Step 2

Compound XLI (0.17 g, 0.69 mmol) was dissolved in acetone (10 mL) with 2,2-dimethoxypropane (2 mL) and p-toluenesulfonic acid (10 mg). The mixture was stirred at room temperature for 1 h and was quenched with $Et_3N$ (3 drops). It was evaporated to dryness and the residue was purified on a silica gel column (4:1 hexane/EtOAc) to yield (4S,5R)-methyl 5-(tert-butoxycarbonylamino)-2,2-dimethyl-1,3-dioxane-4-carboxylate XLII (0.15 g, 0.50 mmol, 73%). ESIMS found for $C_{13}H_{23}NO_6$ m/z 312 (M+Na).

Step 3

Compound XLII (0.15 g, 0.50 mmol) was dissolved in a mixture of $THF/H_2O/MeOH$ (10/5/5 vol, 20 mL) and $LiOH \times H_2O$ (50 mg, 1.20 mmol) was added and the mixture and it was left stirring at room temperature overnight. The reaction mixture was diluted with water (10 mL) and acidified with 10% citric acid until pH=3. The mixture was extracted with chloroform. Organic phase was dried over $Na_2SO_4$ and evaporated to dryness producing (4S,5R)-5-(tert-butoxycarbonylamino)-2,2-dimethyl-1,3-dioxane-4-carboxylic acid XLIII (0.12 g, 0.43 mmol, 90%). ESIMS found for $C_{12}H_{21}NO_6$ m/z 274 (M–H).

Synthesis of (4S,5R)-5-(azidomethyl)-2,2-dimethyl-1,3-dioxolane-4-carboxylic acid XLVII Synthesis of XLVII is depicted in Scheme 7 and Example 3.

Scheme 7

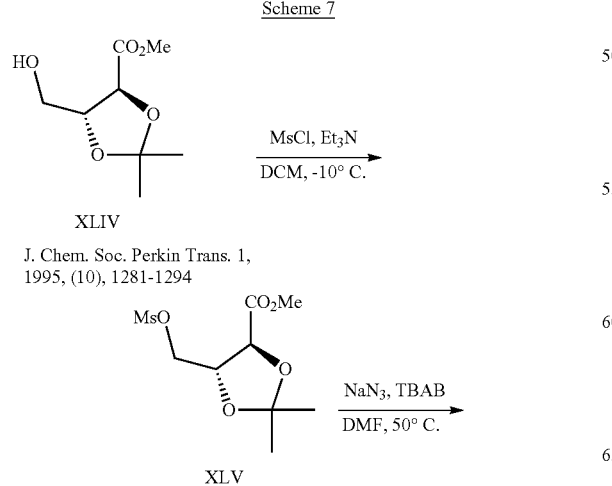

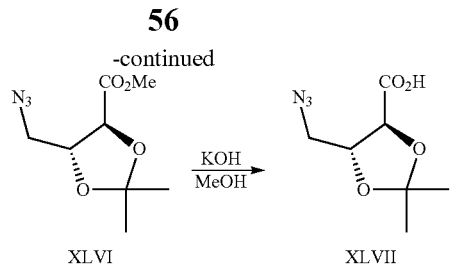

Example 3

Step 1-3

Procedures can be found in example 1. The final compound XLVII was isolated as a solid. ESIMS found for $C_7H_{11}N_3O_5$ m/z 224 (M+H).

Synthesis of (S)-5-(1,3-dioxoisoindolin-2-yl)-2-hydroxypentanoic acid LI

Synthesis of LI is depicted in Scheme 8 and Example 4.

Scheme 8

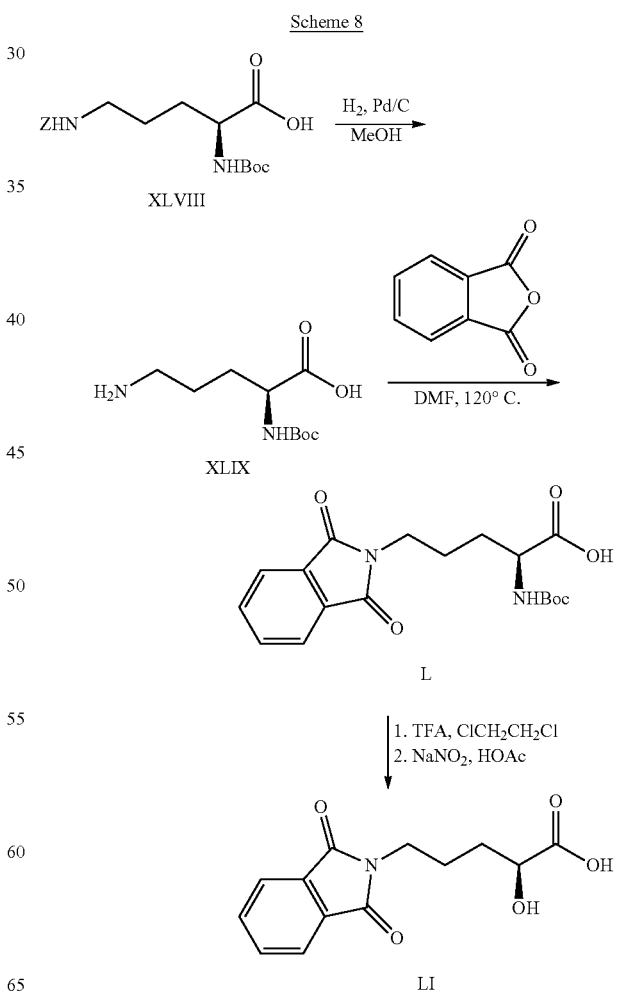

Example 4

Step 1

A solution of (S)-12,12-dimethyl-3,10-dioxo-1-phenyl-2,11-dioxa-4,9-diazamidecane-8-carboxylic acid XLVIII (7.60 g, 20.7 mmol) in MeOH (200 mL) was purged with argon before adding 10% Pd/C catalyst (0.15 g). The flask was purged with hydrogen and the reaction mixture was stirred under atmospheric pressure at room temperature for 18 h. The mixture was filtered through Celite, and the filtrate was concentrated to dryness to obtain (S)-5-amino-2-(tert-butoxycarbonylamino)pentanoic acid XLIX (4.48 g, 19.3 mmol, 93%) which was used in the next step without purification.

Step 2

To a solution of (S)-5-amino-2-(tert-butoxycarbonylamino)pentanoic acid XLIX (6.64 g, 28.6 mmol) in DMF (150 mL) was added phthalic anhydride (4.3 g, 29.0 mmol). The mixture was placed in a tightly closed ampule and heated at 120° C. for 24 h. After the reaction was complete, the solvent was evaporated under vacuum and the residue was subjected to column chromatography on silica gel (100:1 DCM:MeOH→10:1 DCM:MeOH) affording (S)-2-(tert-butoxycarbonylamino)-5-(1,3-dioxoisoindolin-2-yl)pentanoic acid L (8.92 g, 24.6 mmol, 86%). ESIMS found for $C_{18}H_{22}N_2O_6$ m/z 361 (M–H)$^-$.

Step 3

A solution of (S)-2-(tert-butoxycarbonylamino)-5-(1,3-dioxoisoindolin-2-yl)pentanoic acid L (1.45 g, 4.0 mmol) in dichloroethane (25 mL) was cooled to 0° C. Trifluoroacetic acid was added in one portion and the mixture was allowed to warm to room temperature and stir for 2 h. The mixture was concentrated to dryness mixed with water (18.5 mL), HOAc (9.5 mL) and aqueous NaNO$_2$ (1.2 g in 25 mL H$_2$O). After 15 min another portion of HOAc (14 mL) was added and the mixture was stirred at room temperature for 18 h. The reaction mixture was concentrated to dryness. The residue was dissolved in water (100 mL), the pH was adjusted to 1 by addition of 10% aqueous HCl, and the solution was extracted with diethyl ether (5×100 mL). The organic phase was dried over Na$_2$SO$_4$ and concentrated to dryness under reduced pressure afford (S)-5-(1,3-dioxoisoindolin-2-yl)-2-hydroxypentanoic acid LI (0.98 g, 3.73 mmol, 93%). ESIMS found for $C_{13}H_{13}NO_5$ m/z 262 (M–H)$^-$.

Synthesis of 1-(tert-butoxycarbonyl)-3-hydroxyazetidine-3-carboxylic acid LIII

Synthesis of LIII is depicted in Scheme 9 and Example 5.

Scheme 9

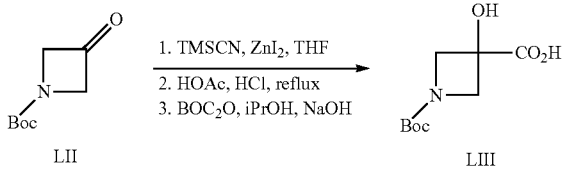

Example 5

Step 1-3

To a solution of tert-butyl 3-oxoazetidine-1-carboxylate LII (2.0 g, 11.7 mmol) in THF (50 mL) under an argon atmosphere was added ZnI$_2$ (0.11 mg, cat) followed by TMSCN (1.62 g, 16.4 mmol). The mixture was stirred at room temperature for 18 h, and was concentrated to dryness under reduced pressure. The residue was dissolved in EtOAc (100 mL), washed with aqueous NaHCO$_3$ and water and then concentrated to dryness. The residue was dissolved in HOAc (25 mL) and treated with concentrated aqueous HCl (25 mL). The mixture was heated at reflux for 3 h and was concentrated to dryness. The residue was dissolved in iPrOH (20 mL) and 2 M aqueous NaOH (20 mL) followed by Boc$_2$O (1.66 g, 8.0 mmol) were added. The iPrOH was removed with a rotary evaporator, water (30 mL) was then added to the residue and the mixture was extracted with Et$_2$O (2×30 mL). The aqueous phase was acidified with 1 N aqueous HCl to pH=2 and extracted with EtOAc (3×30 mL). The organic phase was dried over Na$_2$SO$_4$, filtered and concentrated under reduced pressure. The crude product was purified by column chromatography on silica gel (100% EtOAc→1:1 EtOAc:MeOH) affording 1-(tert-butoxycarbonyl)-3-hydroxyazetidine-3-carboxylic acid LIII (0.17 g, 0.79 mmol, 7%). ESIMS found for $C_9H_{15}NO_5$ m/z 216 (M–H)$^-$.

Synthesis of (S)-(2,2-dimethyl-1,3-dioxolan-4-yl)methyl 4-methylbenzenesulfonate LV Synthesis of LV is depicted in Scheme 10 and Example 6.

Scheme 10

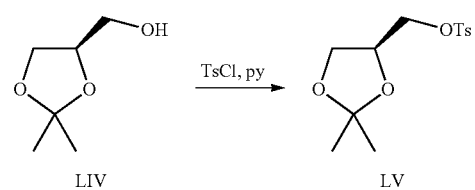

Example 6

Step 1

To a solution of (R)-(2,2-dimethyl-1,3-dioxolan-4-yl)methanol LIV (23.1 g, 0.175 mol) in pyridine (150 mL) at 0° C. was added tosyl chloride (44.5 g, 0.23 mol) in portions. The mixture was stirred for 7 h at 0° C. and was placed in a refrigerator for 18 h. Et$_2$O (150 mL) was added and the mixture was washed with 1 N aqueous HCl (5×150 mL). The organic layer was washed with aqueous NaHCO$_3$ (150 mL) and water (150 mL). The organic phase was dried over Na$_2$SO$_4$, filtered, concentrated and dried under vacuum. The crude product was purified by column chromatography on silica gel (1:1 Et$_2$O:hexane) to afford (S)-(2,2-dimethyl-1,3-dioxolan-4-yl)methyl 4-methylbenzenesulfonate LV (42.1 g, 0.15 mol, 84%).

Synthesis of 2-fluoroethyl 2,4-dinitrobenzenesulfonate LVII

Synthesis of LVII is depicted in Scheme 11 and Example 7.

Scheme 11

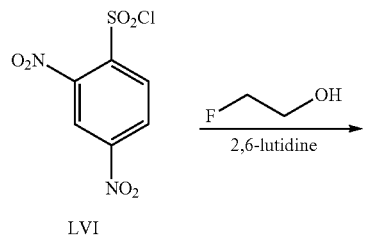

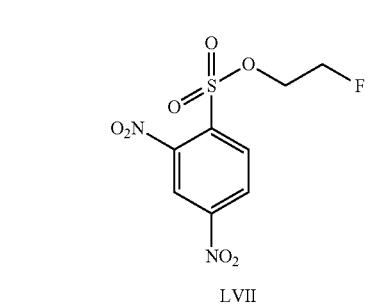

Example 7

Step 1

To a solution of 2-fluoroethanol (1.28 g, 20 mmol) in 2,6-lutidine (20 mL) at −10° C. was added 2,4-dinitrobenzene-1-sulfonyl chloride LVI (4.91 g, 18.7 mmol) in portions. A precipitate formed so CHCl₃ (50 mL) was added to the reaction mixture in order to ensure efficient stirring. After 10 min, the mixture was washed with cold 10% aqueous HCl (150 mL) and water (2×50 mL). The organic phase was dried over Na₂SO₄, filtered and concentrated under reduced pressure. The crude product was purified by column chromatography on silica gel (1:2 EtOAc:hexane) to afford 2-fluoroethyl 2,4-dinitrobenzenesulfonate LVII (1.44 g, 4.90 mmol, 24%).

Synthesis of (S)-3-(1,2-bis(tert-butoxycarbonyl)hydrazinyl)-2-hydroxypropanoic acid LX Synthesis of LX is depicted in Scheme 12 and Example 8.

Scheme 12

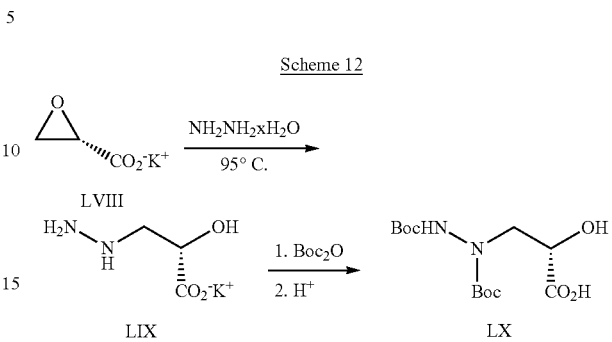

Example 8

Step 1

Potassium (S)-oxirane-2-carboxylate LVIII (0.63 g, 5 mmol) and hydrazine hydrate (2.57 g, 51 mmol) were heated at 95° C. for 3 days. Hydrazine and water were removed and the residue was dried at 40° C. under vacuum to produce potassium (S)-3-hydrazinyl-2-hydroxypropanoate LIX (0.75 g), which was used without purification in the next step. ESIMS found for C₃H₇N₂O₃K m/z 119 (M)⁻.

Step 1

To a solution of potassium (S)-3-hydrazinyl-2-hydroxypropanoate LIX (0.74 g, 4.7 mmol) in methanol (10 mL) was added dropwise a solution of Boc₂O (3.2 g, 14.6 mmol) in MeOH (5 mL) at room temperature. After 30 min, the pH was adjusted to 9 with KOH and the mixture was stirred for 18 hours. It was evaporated to dryness and partitioned between water (10 mL) and diethyl ether (10 mL). The aqueous phase was additionally extracted with diethyl ether (10 mL) and EtOAc (10 mL) and then acidified with 1 N HCl until pH=2. It was extracted with EtOAc (3×10 mL). The combined organic extracts were washed with water, dried over Na₂SO₄ and concentrated to produce (S)-3-(1,2-bis(tert-butoxycarbonyl)hydrazinyl)-2-hydroxypropanoic acid LX (0.99 g, 3.1 mmol, 66% over the two steps). ESIMS found for C₁₃H₂₄N₂O₇ m/z 319 (M−H)⁻.

Illustrative Compound Examples

Synthesis of (2S)-4-amino-N-((1R,2S,3S,4R,5S)-5-amino-4-((2R,3R,6S)-3-amino-6-((2-hydroxyethylamino)methyl)tetrahydro-2H-pyran-2-yloxy)-2-((2R,3R,5R)-3,5-dihydroxy-5-methyl-4-(methylamino)tetrahydro-2H-pyran-2-yloxy)-3-hydroxycyclohexyl)-2-hydroxybutanamide 1

An example synthesis of 1 is depicted in Scheme 13 and Example 9.

Scheme 13

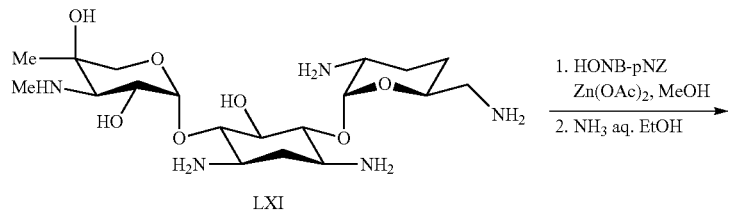

-continued
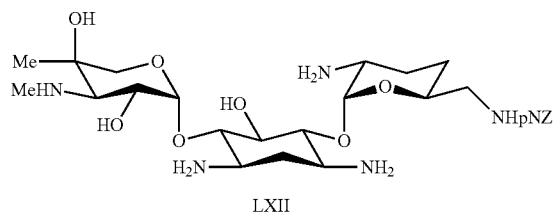
LXII
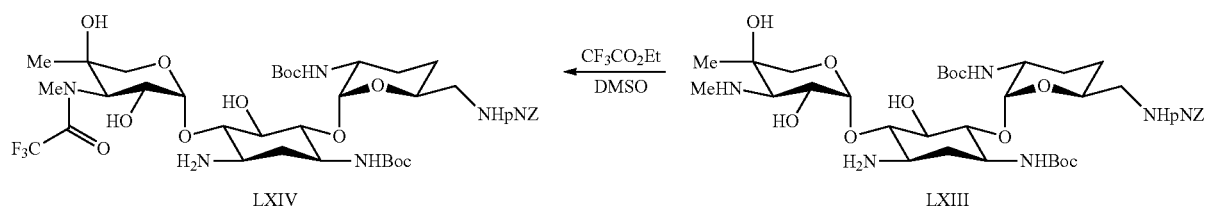
LXIV ← LXIII
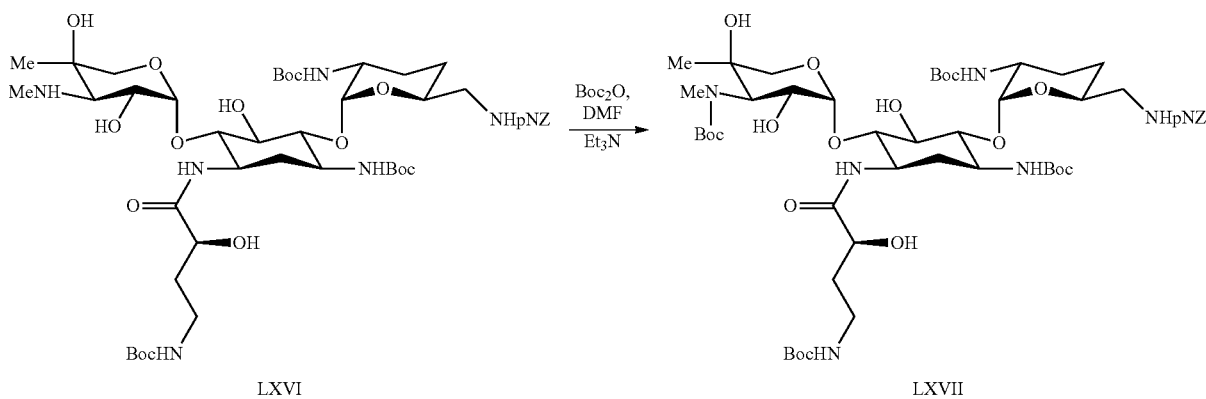
LXVI → LXVII

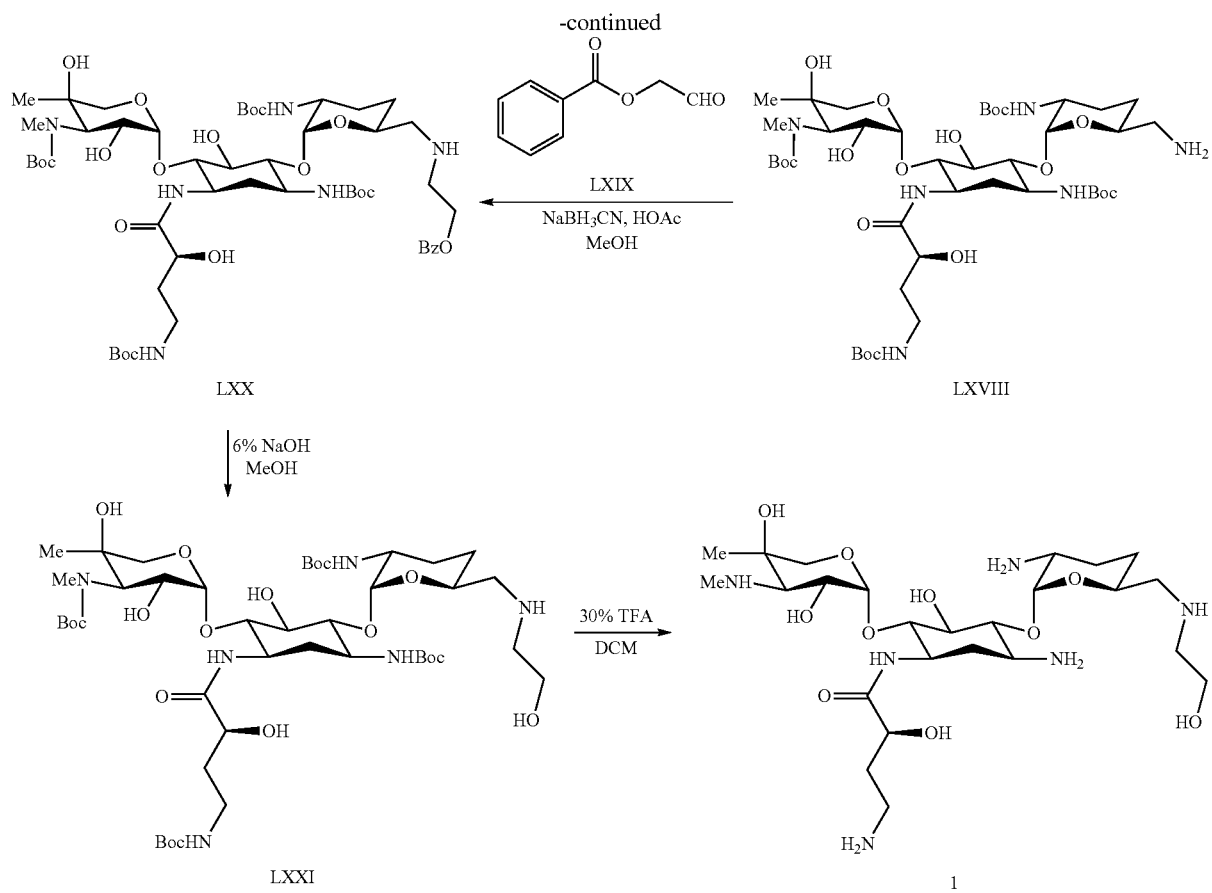

Example 9

Step 1

Gentamicin C1a (LXI) (100.0 g, 90% content, 0.20 mol) was dissolved in methanol (1.0 L). Zn(OAc)$_2$×2 H$_2$O (145 g, 0.66 mol) was added at room temperature and the mixture was stirred for 18 h after which time a solution of HONB-pNZ (71.6 g, 0.20 mol) in DCM (0.5 L) was added dropwise. It was stirred at room temperature for 18 h. The mixture was concentrated under reduced pressure. The residue was treated with a mixture of ammonia (2.4 L) and DCM (0.9 L) and stirred for 0.5 h. The organic phase was discarded while the aqueous phase was saturated with sodium chloride and extracted with a mixture of DCM:iPrOH (7:3) (8×0.8 L, the process was controlled by TLC monitoring). The organic extract was concentrated to dryness and the residue was purified on a silica gel column (5:1 DCM:MeOH→20:1 MeOH/NH$_3$) to give 4-nitrobenzyl((2S,5R,6R)-5-amino-6-((1R,2S,3S,4R,6S)-4,6-diamino-3-((2R,3R,4R,5R)-3,5-dihydroxy-5-methyl-4-(methylamino)tetrahydro-2H-pyran-2-yloxy)-2-hydroxycyclohexyloxy)tetrahydro-2H-pyran-2-yl)methylcarbamate LXII (51.6 g, 82 mmol, 41% yield). ESIMS found for C$_{27}$H$_{44}$N$_6$O$_{11}$ m/z 629 (M+H).

Step 2

Compound LXII (10.43 g, 16.6 mmol) was dissolved in MeOH (200 mL). Zn(OAc)$_2$×2 H$_2$O (11.0 g, 50 mmol) was added at room temperature and the mixture was stirred for 18 h after which time a solution of Boc$_2$O (8.63 g, 41.5 mmol) and DMAP (100 mg) in THF (80 mL) was prepared and was added dropwise to the above reaction mixture. The reaction was stirred at room temperature for 18 h. The mixture was concentrated under reduced pressure. The residue was treated with ethanol (50 mL) and ammonia (25 mL) and stirred for 0.5 h. The mixture was evaporated to dryness, treated with water (100 mL) and extracted with DCM (3×100 mL). The organic extract was dried over Na$_2$SO$_4$, concentrated and the residue was purified on a silica gel column (100% MeOH→10:1 MeOH/NH$_3$) to produce 4-nitrobenzyl((2S,5R,6R)-6-((1R,2R,3S,4R,6S)-4-amino-3-((2R,3R,4R,5R)-3,5-dihydroxy-5-methyl-4-(methylamino)tetrahydro-2H-pyran-2-yloxy)-6-(tert-butoxycarbonylamino)-2-hydroxycyclohexyloxy)-5-(tert-butoxycarbonylamino)tetrahydro-2H-pyran-2-yl)methylcarbamate LXIII (9.62 g, 11.6 mmole, 70% yield). ESIMS found for C$_{37}$H$_{60}$N$_6$O$_{15}$ m/z 829 (M+H).

Step 3

Compound LXIII (26.9 g, 32.5 mmol) was dissolved in DMSO (160 mL) and CF$_3$CO$_2$Et (5.10 g, 35.7 mmol) was added. The mixture was stirred at room temperature for 1 h. The reaction mixture was poured into water (350 mL) and brine (30 mL). The mixture was extracted with EtOAc (5×100 mL). The organic extract was washed with 5% aq. NaCl, dried over Na$_2$SO$_4$ and concentrated to dryness to obtain crude 4-nitrobenzyl((2S,5R,6R)-6-((1R,2R,3S,4R,6S)-4-amino-3-((2R,3R,4R,5R)-3,5-dihydroxy-5-methyl-4-(2,2,2-trifluoro-N-methylacetamido)tetrahydro-2H-pyran-2-yloxy)-6-(tert-butoxycarbonylamino)-2-hydroxycyclohexyloxy)-5-(tert-butoxycarbonylamino)tetrahydro-2H-pyran-2-yl)methylcarbamate LXIV (28.5 g). ESIMS found for C$_{39}$H$_{59}$N$_6$O$_{16}$F$_3$ m/z 925 (M+H).

Steps 4-5

Compound LXIV (1.36 g, 6.2 mmol) and N-hydroxysuccinimide (0.71 g, 6.2 mmol) were dissolved in THF (50 mL). The solution was treated with DCC (1.28 g, 6.1 mmol) at room temperature and stirred for 1.5 h while a precipitate formed. The solid was filtered off and the clear solution was added to the solution of (S)-4-(tert-butoxycarbonylamino)-2-hydroxybutanoic acid LXV (2.53 g, 2.74 mmol) [*Tetrahedron Letters* (2002), 43(48), 8693-8696] dissolved in pyridine (65 mL). The mixture was left stirring at room temperature for 18 h before concentrating to dryness. The resultant yellow foam was dissolved in MeOH (25 mL), treated with ammonia (25 mL) and stirred for 4 h. The mixture was concentrated to dryness and the solid residue LXVI was dissolved in DMF (15 mL). The solution was treated with Et$_3$N (0.42 g, 4.2 mmol) and a solution of Boc$_2$O (1.20 g, 5.5 mmol) in DMF (2 mL) was added. The mixture was stirred at room temperature for 18 h. Water (20 mL) and NaCl was added until saturation. The mixture was extracted with EtOAc (3×30 mL) and subsequently with DCM (2×20 mL). The combined organic extracts were dried over Na$_2$SO$_4$ and evaporated to dryness. The residue was purified on a silica gel column (100% CHCl$_3$→9:1 CHCl$_3$/EtOH) to obtain 4-nitrobenzyl((2S,5R,6R)-6-((1R,2S,3S,4R,6S)-3-((2R,3R,4R,5R)-3,5-dihydroxy-5-methyl-4-((methyl)tert-butoxycarbonylamino)tetrahydro-2H-pyran-2-yloxy)-6-(tert-butoxycarbonylamino)-2-hydroxy-4-((S)-2-hydroxy-4-(tert-butoxycarbonylamino)butanamido)cyclohexyloxy)-5-(tert-butoxycarbonylamino)tetrahydro-2H-pyran-2-yl)methylcarbamate LXVII (1.75 g, 1.55 mmol, 56% yield). ESIMS found for C$_{51}$H$_{83}$N$_7$O$_{21}$ m/z 1152 (M+Na).

Step 6

Compound LXVII (1.86 g, 1.65 mmol) was dissolved in a mixture of EtOH (40 mL) and water (24 mL) and Na$_2$S$_2$O$_4$ (1.0 g, 6.0 mmol) was added followed by a solution of NaOH (0.35 g, 8.7 mmol) in water (8.0 mL). The mixture was heated at 70° C. for 2 h. EtOH was evaporated, more water (25 mL) was added and the mixture was extracted with EtOAc (3×25 mL), combined organic extracts were washed with 5% aq. NaOH and water. The solution was dried over Na$_2$SO$_4$ and evaporated to dryness to yield crude tert-butyl (2R,3R,6S)-6-(aminomethyl)-2-((1R,2S,3S,4R,6S)-3-((2R,3R,4R,5R)-4-((methyl)tert-butoxycarbonylamino)-3,5-dihydroxy-5-methyltetrahydro-2H-pyran-2-yloxy)-6-(tert-butoxycarbonylamino)-4-((S)-4-(tert-butoxycarbonylamino)-2-hydroxy butanamido)-2-hydroxycyclohexyloxy)tetrahydro-2H-pyran-3-ylcarbamate LXVIII (1.34 g). ESIMS found for C$_{43}$H$_{78}$N$_6$O$_{17}$ m/z 951 (M+H).

Step 7

Compound LXVIII (0.56 g, 0.59 mmol) was dissolved in MeOH (20 mL) with HOAc (0.1 mL). 2-Oxoethyl benzoate LXIX [*Tetrahedron* (2009), 65(11), 2344-2350](0.077 g, 0.47 mmol) dissolved in MeOH (5 mL) was added followed by NaBH$_3$CN (0.06 g, 0.94 mmol). The mixture was left stirring at room temperature for 3 h and then evaporated to dryness. The residue was treated with EtOAc (15 mL) and the solution was washed with NaHCO$_3$ aq. (10 mL). The organic phase was dried over Na$_2$SO$_4$ and concentrated. Crude LXX was purified by RP HPLC on a Titan 150×50 mm 10 um column with a 0-90% Water (0.1% formic acid)/MeOH (0.1% formic acid) gradient producing 2-(((2S,5R,6R)-5-(tert-butoxycarbonylamino)-6-((1R,2S,3S,4R,6S)-3-((2R,3R,4R,5R)-4-((methyl)tert-butoxycarbonylamino)-3,5-dihydroxy-5-methyltetrahydro-2H-pyran-2-yloxy)-6-(tert-butoxycarbonylamino)-4-((S)-4-(tert-butoxycarbonylamino)-2-hydroxybutanamido)-2-hydroxycyclohexyloxy)tetrahydro-2H-pyran-2-yl)methylamino)ethyl benzoate LXX (58.3 mg, 0.053 mmol, 9% yield). ESIMS found for C$_{52}$H$_{86}$N$_6$O$_{19}$ m/z 1099.4 (M+H).

Step 8

Compound LXX (58.3 mg, 0.053 mmol) was dissolved in 6% NaOH in MeOH (4 mL) and stirred for 30 min at room temperature. The solution was adjusted to pH 7 using 1 N HCl before adding brine (5 mL). This solution was extracted with DCM (3×), dried over MgSO$_4$, evaporated to dryness under vacuum and purified on a silica gel column (100% DCM→5:1 DCM/MeOH) to produce tert-butyl (2R,3R,6S)-2-((1R,2S,3S,4R,6S)-3-((2R,3R,4R,5R)-4-((methyl)tert-butoxycarbonylamino)-3,5-dihydroxy-5-methyltetrahydro-2H-pyran-2-yloxy)-6-(tert-butoxycarbonylamino)-4-((S)-4-(tert-butoxycarbonylamino)-2-hydroxybutanamido)-2-hydroxycyclohexyloxy)-6-((2-hydroxyethylamino)methyl)tetrahydro-2H-pyran-3-ylcarbamate LXXI (27.9 mg, 0.03 mmol, 52.9% yield). ESIMS found for C$_{45}$H$_{82}$N$_6$O$_{18}$ m/z 995.4 (M+H).

Step 9

To compound LXXI (27.9 mg, 0.03 mmol) was added 30% TFA/DCM (2 mL) and the mixture was stirred for 3 h. The solvent was removed under vacuum and the resulting solid was lyophilized from water/acetonitrile to produce (S)-4-amino-N-((1R,2S,3S,4R,5S)-5-amino-4-((2R,3R,6S)-3-amino-6-((2-hydroxyethylamino) methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxy butanamide 1 (22.2 mg, 0.02 mmol, 70% yield). ESIMS found for C$_{25}$H$_{50}$N$_6$O$_{10}$ m/z 595.2 (M+H). HPLC retention time 5.22 min (Method 1).

Synthesis of (S)-3-amino-N-((1R,2S,3S,4R,5S)-5-amino-4-((2R,3R,6S)-3-amino-6-((2-hydroxyethylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxypropanamide 2

An example synthesis of 2 is depicted in Scheme 14 and Example 10.

Scheme 14

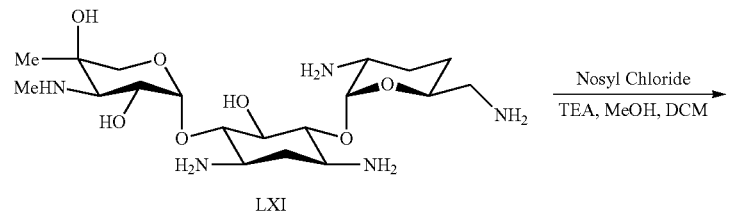

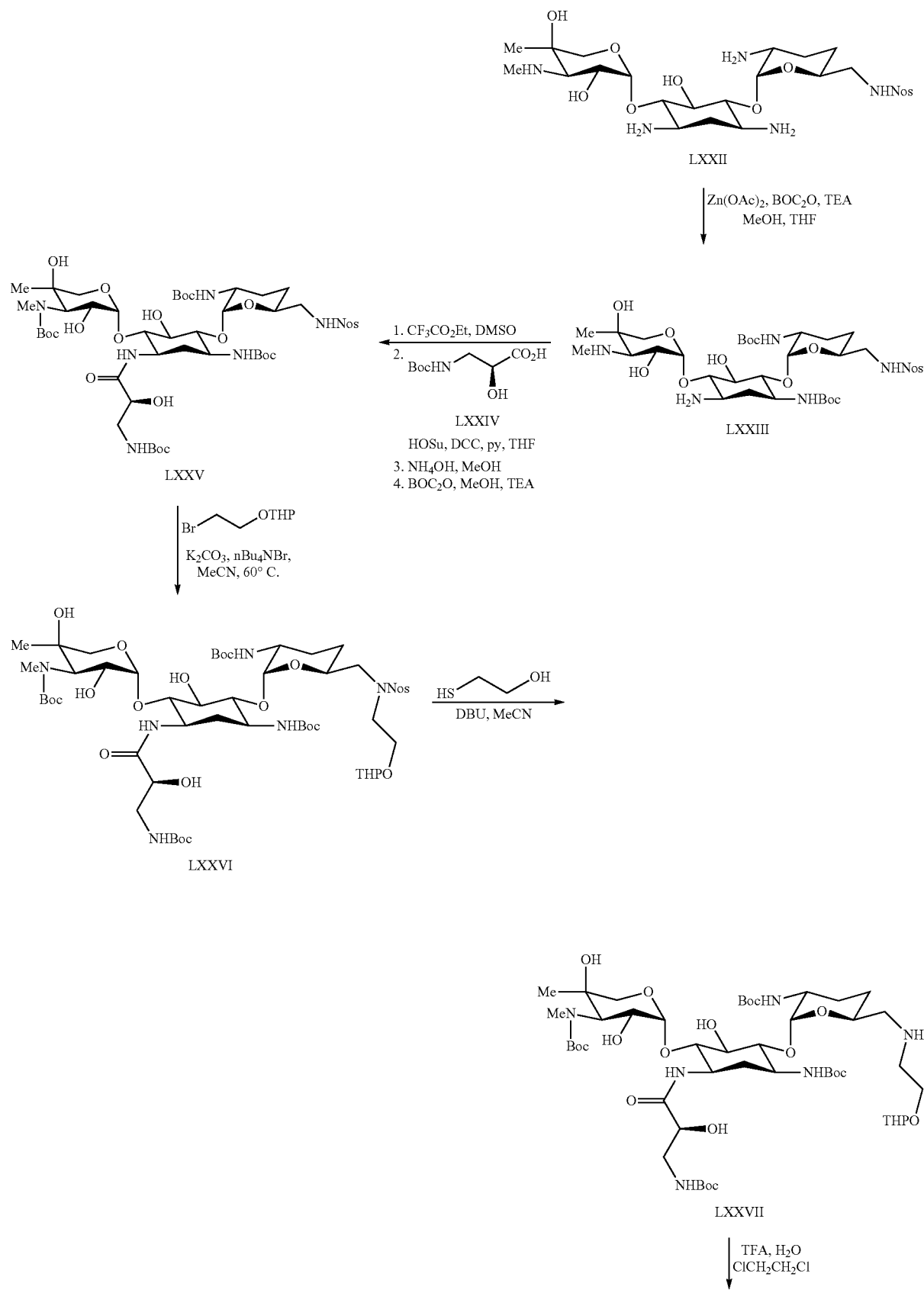

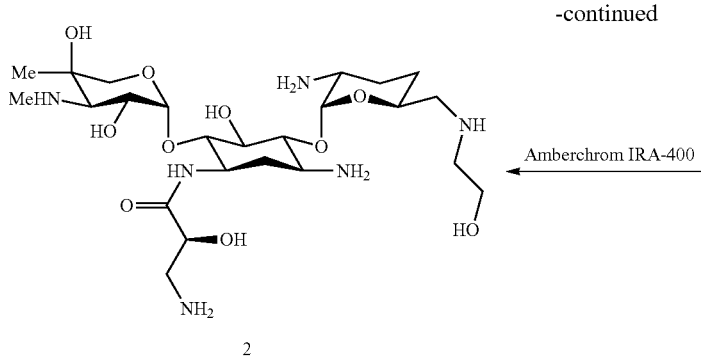 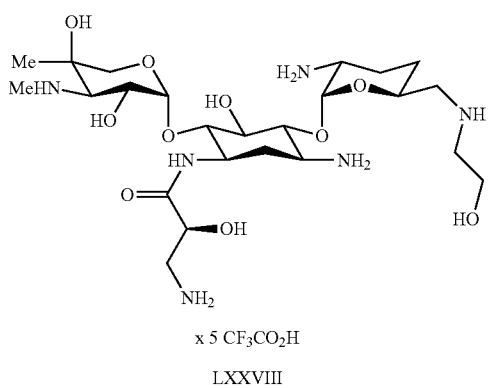

Example 10

Step 1

To a solution of Gentamicin C1a (LXI) (20.0 g, 90% content, 0.04 mol) in MeOH (400 mL) was added Et₃N (4.5 g, 0.045 mol) and the mixture was cooled to −60° C. Nosyl chloride (9.9 g, 0.045 mol) in DCM (80 mL) was added dropwise. The mixture was stirred at room temperature for 18 h after which time it was concentrated under reduced pressure. The residue was chromatographed on a silica gel column (5:1 DCM:MeOH→10:1 MeOH:NH₃) to produce N-(((2S,5R,6R)-5-amino-6-((1R,2S,3S,4R,6S)-4,6-diamino-3-((2R,3R,4R,5R)-3,5-dihydroxy-5-methyl-4-(methylamino)tetrahydro-2H-pyran-2-yloxy)-2-hydroxycyclohexyloxy)tetrahydro-2H-pyran-2-yl)methyl)-2-nitrobenzenesulfonamide LXXII (10.1 g, 0.015 mol, 40% yield). ESIMS found for $C_{25}H_{42}N_6O_{11}S$ m/z 635 (M+H).

Step 2

To a solution of compound LXXII (17.4 g, 27.5. mmol) in MeOH (350 mL) was added Zn(OAc)₂×2 H₂O (15.1 g, 68.8 mmol) at room temperature. The mixture was stirred for 1 h after which time a solution of Boc₂O (12.5 g, 57.5 mmol) in THF (100 mL) was added dropwise to the reaction mixture. The reaction was stirred at room temperature for 18 h. The mixture was concentrated under reduced pressure, dissolved in DCM (500 mL), treated with 10% ammonia (100 mL) and stirred for 0.5 h. The organic phase was separated and extracted with 10% ammonia (4×100 mL) and water (100 mL). The organic phase was dried over Na₂SO₄, filtered and evaporated to dryness to yield tert-butyl (2R,3R,6S)-2-((1R,2R,3S,4R,6S)-4-amino-3-((2R,3R,4R,5R)-3,5-dihydroxy-5-methyl-4-(methylamino)tetrahydro-2H-pyran-2-yloxy)-2-hydroxy-6-tert-butoxycarbonylamino cyclohexyloxy)-6-((2-nitrophenylsulfonamido)methyl)tetrahydro-2H-pyran-3-ylcarbamate LXXIII (14.6 g, 17.5 mmol, 63% yield). ESIMS found for $C_{35}H_{58}N_6O_{15}S$ m/z 835 (M+H).

Step 3

To a solution of compound LXXIII (20.2 g, 24.2 mmol) in DMSO (100 mL) was added CF₃COOEt (2.85 mL, 24.0 mmol). The mixture was stirred at room temperature for 1.5 h. The reaction mixture was poured into water (300 mL) and brine (30 mL) and then extracted with EtOAc (5×100 mL). The organic extract was washed with 5% aq. NaCl, dried over Na₂SO₄ and concentrated to dryness. The residue was dissolved in pyridine (150 mL). (S)-3-(tert-Butoxycarbonylamino)-2-hydroxypropanoic acid LXXIV (8.43 g, 41.1 mmol) and N-hydroxysuccinimide (4.73 g, 41.1 mmol) were dissolved in THF (150 mL) and cooled to 0° C. The solution was treated with DCC (8.47 g, 41.1 mmol), warmed up to room temperature and stirred for 3 h while a precipitate formed. The solid was filtered off and the clear solution of active ester was added to the above pyridine solution. The mixture was stirred at room temperature for 3 h and then concentrated to dryness. The resultant yellow foam was dissolved in methanol (120 mL), treated with ammonia (50 mL) and stirred for 1 h. The mixture was concentrated to dryness and the residue was dissolved in EtOAc (300 mL), washed with brine, dried over Na₂SO₄, filtered and evaporated under vacuum. The residue was then dissolved in MeOH (120 mL). Et₃N (5 mL, 36.0 mmol) was added followed by Boc₂O (7.5 g, 34.4 mmol). The mixture was left stirring at room temperature for 18 h. The mixture was evaporated to dryness, the residue was washed with water and the organic phase was dried over Na₂SO₄, filtered and concentrated. The crude product was purified on a silica gel column (50:1 DCM:MeOH→15:1 DCM:MeOH) to produce tert-butyl (2R,3R,6S)-2-((1R,2S,3S,4R,6S)-3-((2R,3R,4R,5R)-3,5-dihydroxy-5-methyl-4-(N-methyl-tert-butoxycarbonylamino) tetrahydro-2H-pyran-2-yloxy)-2-hydroxy-4-((S)-2-hydroxy-3-tert-butoxycarbonylaminopropanamido)-6-tert-butoxycarbonylamino cyclohexyloxy)-6-((2-nitrophenylsulfonamido)methyl)tetrahydro-2H-pyran-3-ylcarbamate LXXV (18.1 g, 16.1 mmol, 66% yield). ESIMS found for $C_{48}H_{79}N_7O_{21}S$ m/z 1122 (M+H).

Step 4

To a solution of compound LXXV (18.0 g, 16.0 mmol) in MeCN (100 mL) was added 2-(2-bromoethoxy)tetrahydro-2H-pyran (16.9 g, 81.2 mmol), K₂CO₃ (11.4 g, 82.6 mmol) and nBu₄NBr (0.85 g, 2.6 mmol). The mixture was heated at 60° C. for 24 h. After the reaction was complete, the solvent was evaporated and the residue was dissolved in EtOAc and washed with water. The organic phase was dried over Na₂SO₄, filtered and concentrated. The residue was chromatographed on silica gel (2:1 EtOAc:DCM→20:1 EtOAc:MeOH) to afford tert-butyl (2R,3R,6S)-2-((1R,2S,3S,4R,6S)-3-((2R,3R,4R,5R)-3,5-dihydroxy-5-methyl-4-(N-methyl-tert-butoxycarbonylamino)tetrahydro-2H-pyran-2-yloxy)-2-hydroxy-4-((S)-2-hydroxy-3-tert-butoxycarbonylaminopropanamido)-6-tert-butoxy carbonylaminocyclohexyloxy)-6-((2-nitro-N-(2-(tetrahydro-2H-pyran-2-yloxy)ethyl)phenylsulfonamido)methyl) tetrahydro-2H-pyran-3-ylcarbamate LXXVI (10.2 g, 8.16 mmol, 50% yield). ESIMS found for $C_{55}H_{91}N_7O_{23}S$ m/z 1250 (M+H).

Step 5

To a solution of compound LXXVI (14.5 g, 11.6 mmol) in MeCN (230 mL) was added 2-mercaptoethanol (4.57 g, 63.0 mmol) followed by DBU (3.97 g, 26 mmol). The mixture was stirred at room temperature for 2.5 h. The solvent was evaporated and the residue was partitioned between water (60 mL) and EtOAc (200 mL). The organic phase was dried over $Na_2SO_4$, filtered and concentrated. The residue was chromatographed on silica gel (9:1 EtOAc:MeOH→4:1 EtOAc:MeOH) to afford tert-butyl (2R,3R,6S)-2-((1R,2S,3S,4R,6S)-3-((2R,3R,4R,5R)-3,5-dihydroxy-5-methyl-4-(N-methyl-tert-butoxycarbonylamino)tetrahydro-2H-pyran-2-yloxy)-2-hydroxy-4-((S)-2-hydroxy-3-tert-butoxycarbonylaminopropanamido)-6-tert-butoxycarbonylaminocyclohexyloxy)-6-((2-(tetrahydro-2H-pyran-2-yloxy)ethylamino)methyl)tetrahydro-2H-pyran-3-ylcarbamate LXXVII (8.9 g, 8.36 mmol, 72% yield). ESIMS found for $C_{49}H_{88}N_6O_{19}$ m/z 1065 (M+H).

Step 6

Compound LXXVII (9.86 g, 9.27 mmol) was dissolved in 30% TFA/DCM (500 mL) and stirred for 2 h. The solvent was removed under vacuum and the residue was triturated with ether and filtered to give the TFA salt LXXVIII. The resulting solid was neutralized by passing the aqueous solution through an Amberlite IRA 400 (hydroxide form) resin column. The solvent was removed under reduced pressure and the solid was lyophilized from water/acetonitrile to produce (S)-3-amino-N-((1R,2S,3S,4R,5S)-5-amino-4-((2R,3R,6S)-3-amino-6-((2-hydroxyethylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxypropanamide 2 (4.73 g, 8.16 mmol, 88% yield). ESIMS found for $C_{24}H_{48}N_6O_{10}$ m/z 581.2 (M+H). HPLC retention time 4.36 min (Method 2).

Synthesis of (2S,3R)-3,4-diamino-N-((1R,2S,3S,4R,5S)-5-amino-4-((2R,3R,6S)-3-amino-6-(aminomethyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxybutanamide 3

An example synthesis of 3 is provided in Scheme 15 and Example 11.

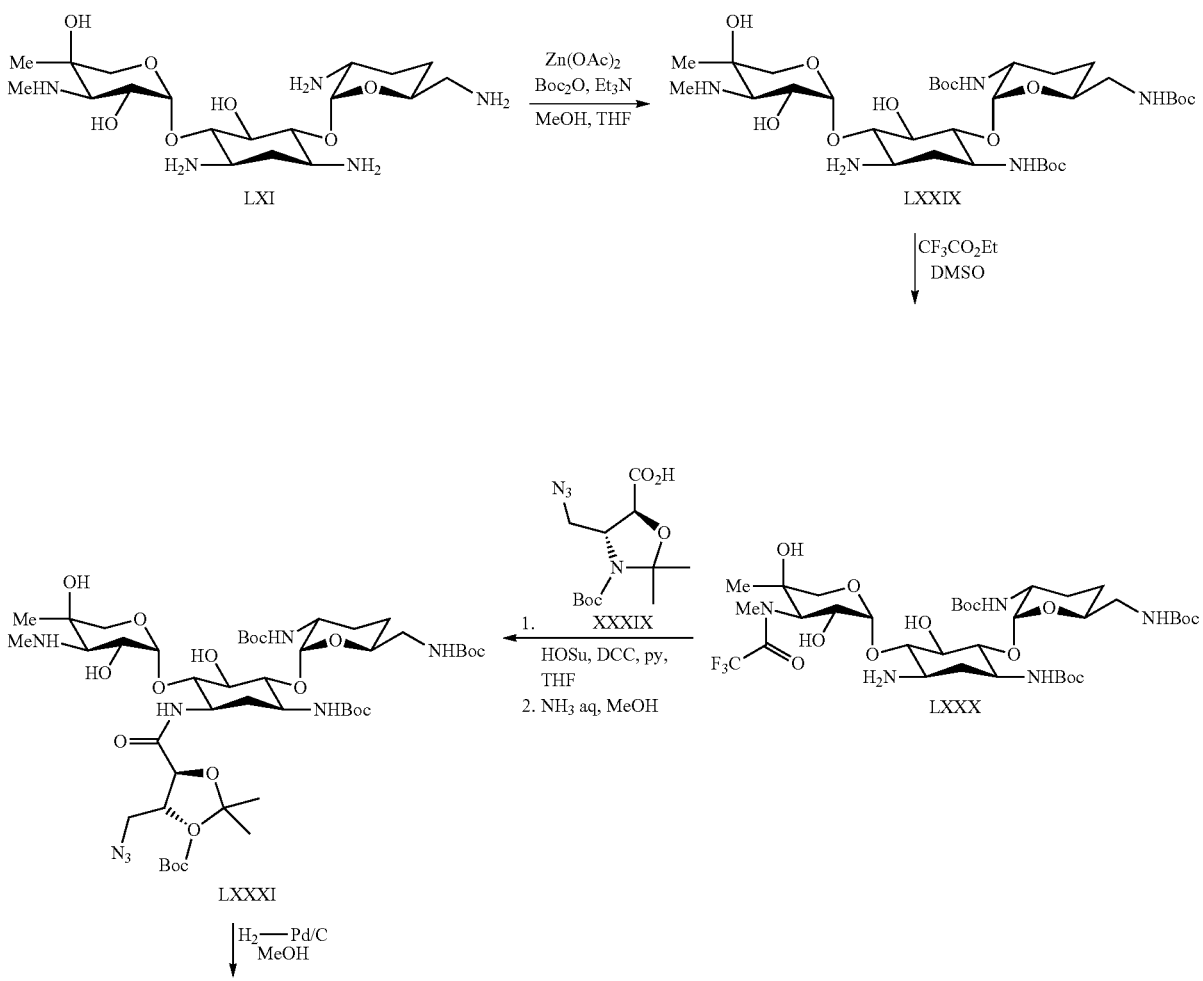

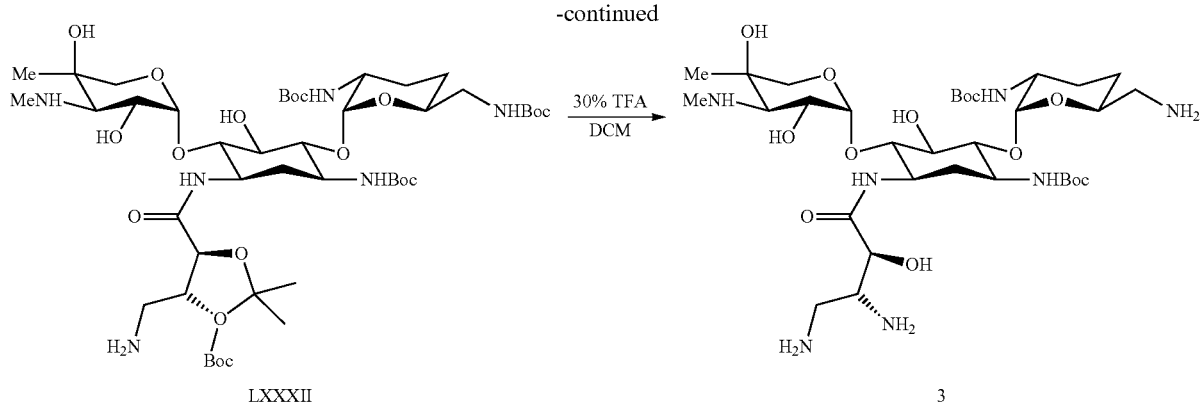

LXXXII → 3

Example 11

Steps 1-3

Procedures can be found in example 9.

Step 4

Compound LXXXI (0.034 g, 0.033 mmol) was dissolved in MeOH (10 mL) followed by addition of 5% Pd/C catalyst (10 mg) under argon. The flask was flushed with $H_2$ and the reaction mixture was stirred overnight at room temperature. The catalyst was removed by filtration through a Celite pad and the filtrate was concentrated. The residue was purified on a silica gel column (2:1 hexane/EtOAc→100% EtOAc) to produce (4R,5S)-tert-butyl 4-(aminomethyl)-5-((1R,2S,3S,4R,5S)-2-((2R,3R,4R,5R)-3,5-dihydroxy-5-methyl-4-(methylamino)tetrahydro-2H-pyran-2-yloxy)-3-hydroxy-5-(tert-butoxycarbonylamino)-4-((2R,3R,6S)-3-(tert-butoxycarbonylamino)-6- ((tert-butoxycarbonylamino) methyl)tetrahydro-2H-pyran-2-yloxy) cyclohexylcarbamoyl)-2,2-dimethyloxazolidine-3-carboxylate LXXXII (0.016 g, 0.015 mmol, 48% yield). ESIMS found for $C_{46}H_{83}N_7O_{17}$ m/z 1006 (M+H).

Step 5

Procedure can be found in example 9. The final compound 3 was isolated as the trifluoroacetic acid salt. ESIMS found for $C_{23}H_{47}N_7O_9$ m/z 566 (M+H). HPLC retention time 4.95 min (Method 1).

Synthesis of (2S)-4-amino-N-((1R,2S,3S,4R,5S)-5-amino-4-((2R,3R,6S)-3-amino-6-((2,3-dihydroxypropylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxybutanamide 8

An example synthesis of 8 is provided in Scheme 16 and Example 12.

Scheme 16

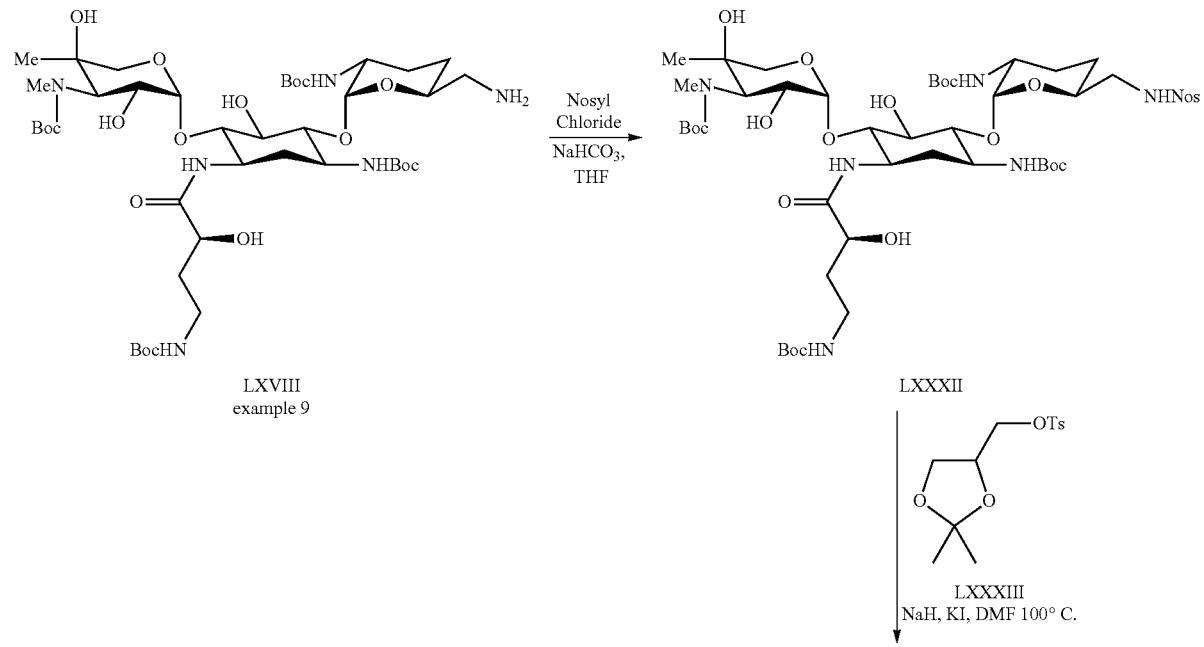

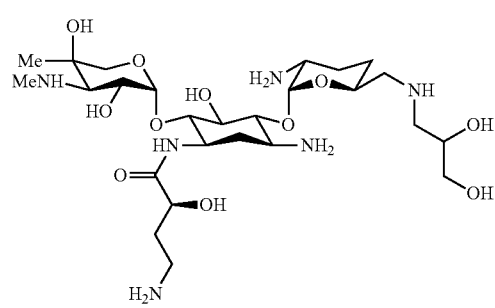 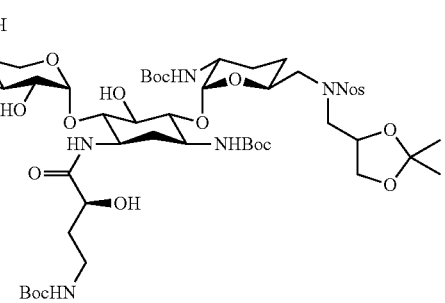

Example 12

Step 1

To a solution of compound LXVIII from example 9 (12.9 g, 15.3 mmol) in THF (50 mL) was added NaHCO$_3$ (5.8 g, 68.8 mmol). The mixture was cooled to 0° C. and a solution of nosyl chloride (3.9 g, 17.6 mmol) in THF (30 mL) was added dropwise. The mixture was stirred at room temperature for 18 h. The mixture was concentrated, dissolved in EtOAc (200 mL) and washed with water. The organic phase was dried over Na$_2$SO$_4$, filtered and concentrated. The residue was purified by column chromatography on silica gel (100% DCM→1:1 DCM:MeOH) to produce tert-butyl (2R,3R,6S)-2-((1R,2S,3S,4R,6S)-3-((2R,3R,4R,5R)-3,5-dihydroxy-5-methyl-4-(N-methyl-tert-butoxycarbonylamino)tetrahydro-2H-pyran-2-yloxy)-2-hydroxy-4-((S)-2-hydroxy-4-tert-butoxycarbonylaminobutanamido)-6-tert-butoxycarbonylaminocyclohexyloxy)-6-((2-nitrophenylsulfonamido)methyl)tetrahydro-2H-pyran-3-ylcarbamate LXXXII (12.6 g, 11.1 mmol, 73% yield). ESIMS found for C$_{49}$H$_{81}$N$_7$O$_{21}$S m/z 1136 (M+H).

Step 2

To a solution of compound LXXXII (1.13 g, 1.0 mmol) in DMF (5 mL) cooled to −60° C. was added NaH (0.044 g, 1.1 mmol). The cooling bath was removed and the mixture was allowed to warm to room temperature. After the mixture became homogeneous, (2,2-dimethyl-1,3-dioxolan-4-yl)methyl 4-methylbenzenesulfonate LXXXIII (0.71 g, 2.5 mmol) was added followed by KI (cat). The mixture was heated at 100° C. for 3 days. The mixture was concentrated and purified by column chromatography on silica gel (50:1 DCM:MeOH→30:1 DCM:MeOH) to give tert-butyl (2R,3R,6S)-2-((1R,2S,3S,4R,6S)-3-((2R,3R,4R,5R)-3,5-dihydroxy-5-methyl-4-(N-methyl-tert-butoxycarbonylamino)tetrahydro-2H-pyran-2-yloxy)-2-hydroxy-4-((S)-2-hydroxy-4-tert-butoxycarbonylaminobutanamido)-6-tert-butoxycarbonylaminocyclohexyloxy)-6-((N-((2,2-dimethyl-1,3-dioxolan-4-yl)methyl)-2-nitrophenylsulfonamido)methyl)tetrahydro-2H-pyran-3-ylcarbamate LXXXIV (0.48 g, 0.38 mmol, 38% yield). ESIMS found for C$_{55}$H$_{91}$N$_7$O$_{23}$S m/z 1250 (M+H).

Step 3-4

Procedures can be found in example 10. The final compound 8 was isolated as the trifluoroacetic acid salt (0.13 g, 0.11 mmol, 29.5% yield for 2 steps). ESIMS found for C$_{26}$H$_{52}$N$_6$O$_{11}$ m/z 625 (M+H). HPLC retention time 4.10 min (Method 2).

Synthesis of (2S,3R)-3-amino-N-((1R,2S,3S,4R,5S)-5-amino-4-((2R,3R,6S)-3-amino-6-(aminomethyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxy cyclohexyl)-2,4-dihydroxybutanamide 20

An example synthesis of 20 is provided in Scheme 17 and Example 13.

Scheme 17

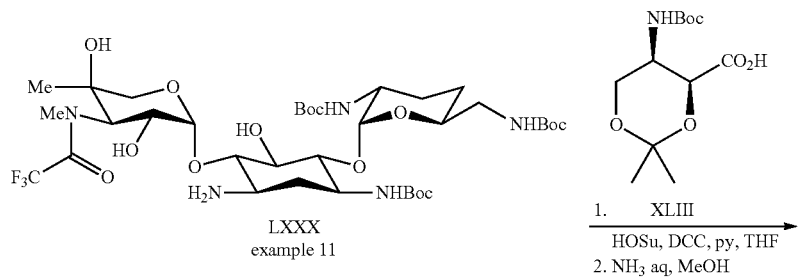

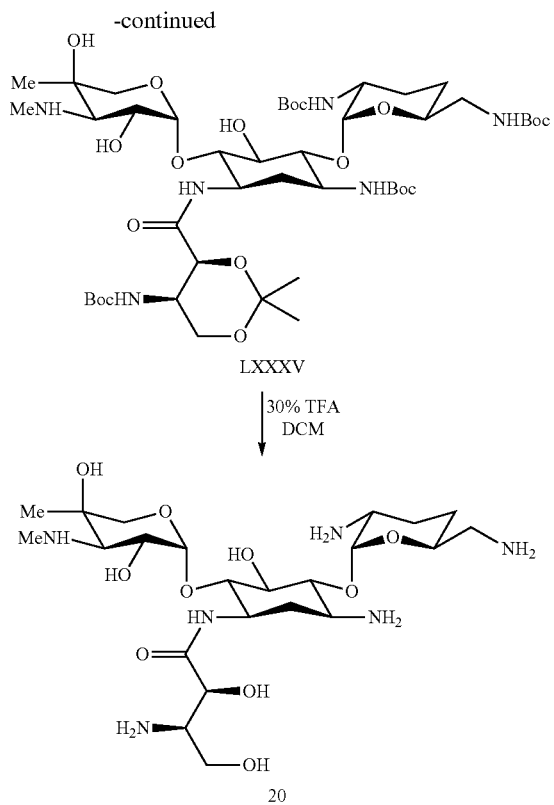

Procedures can be found in example 9. The final compound 20 was isolated as the trifluoroacetic acid salt. ESIMS found for $C_{23}H_{46}N_6O_{10}$ m/z 567 (M+H). HPLC retention time 5.01 min (Method 1).

Synthesis of (2S,3R)-4-amino-N-((1R,2S,3S,4R,5S)-5-amino-4-((2R,3R,6S)-3-amino-6-(aminomethyl)tetrahydro-2H-pyran-2-vyloxy)-2-((2R,3R,4R,5R)-3,5-dihydroxy-5-methyl-4-(methylamino)tetrahydro-2H-pyran-2-yloxy)-3-hydroxycyclohexyl)-2,3-dihydroxybutanamide 21

An example synthesis of 21 is depicted in Scheme 18 and Example 14.

Scheme 18

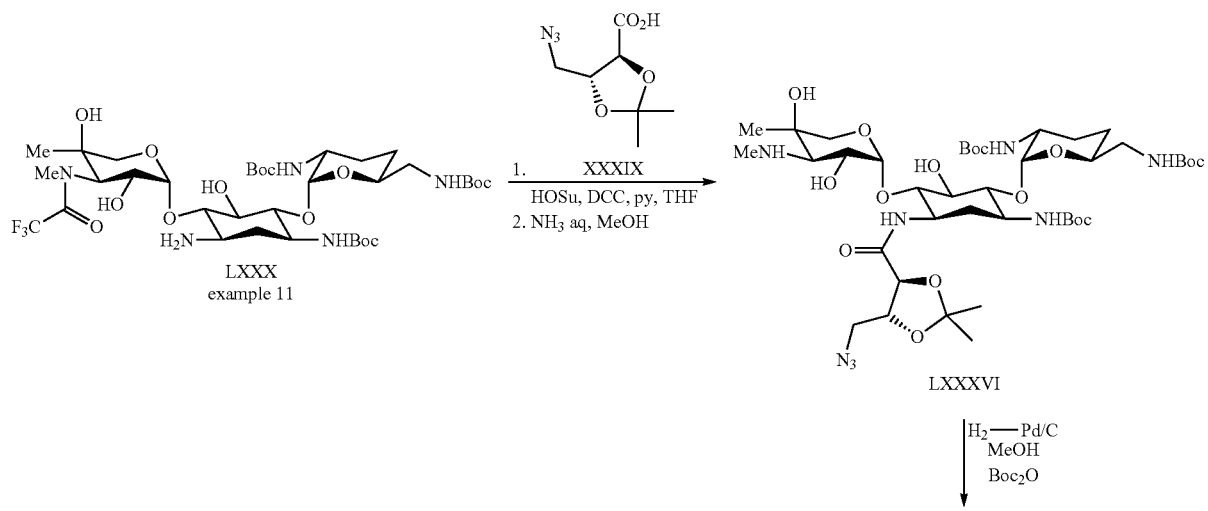

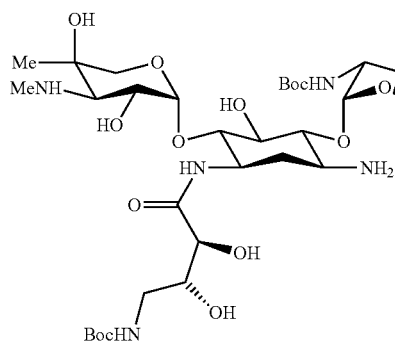
21

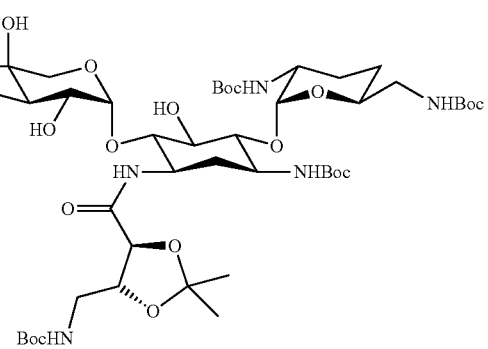
LXXXVII

Example 14

Step 1-2

Procedure can be found in example 9.

Step 3

Compound LXXXVI (0.30 g, 0.32 mmol) was dissolved in MeOH (20 mL), and 5% Pd/C catalyst (25 mg) was added under argon. Boc$_2$O (0.15 g, 0.70 mmol) was added and the flask was flushed with H$_2$ and the reaction mixture was stirred overnight at room temperature. The catalyst was removed by filtration through a Celite pad and the filtrate was concentrated. The residue was purified on a silica gel column (2:1 hexane/EtOAc→100% EtOAc) to obtain tert-butyl((2S,5R,6R)-6-((1R,2S,3S,4R,6S)-3-((2R,3R,4R,5R)-3,5-dihydroxy-5-methyl-4-(methylamino)tetrahydro-2H-pyran-2-yloxy)-4-((4S,5R)-2,2-dimethyl-5-((tert-butoxycarbonylamino)methyl)-1,3-dioxolane-4-carboxamido)-2-hydroxy-6-(tert-butoxycarbonylamino)cyclohexyloxy)-5-(tert-butoxycarbonylamino)tetrahydro-2H-pyran-2-yl)methylcarbamate LXXXVI (0.27 g, 0.24 mmol, 75% yield). ESIMS found for C$_{51}$H$_{90}$N$_6$O$_{20}$ m/z 1130 (M+Na).

Step 4

Procedure can be found in examples 9. The final compound 21 was isolated as the trifluoroacetic acid salt. ESIMS found for C$_{23}$H$_{46}$N$_6$O$_{10}$ m/z 567 (M+Na). HPLC retention time 4.82 min (Method 1).

The following compound is prepared in accordance with the procedure described in the above example 6.

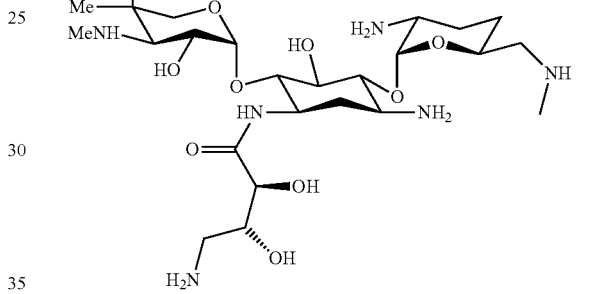
23

(2S,3R)-4-amino-N-((1R,2S,3S,4R,5S)-5-amino-4-((2R,3R,6S)-3-amino-6-((methylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxy cyclohexyl)-2,3-dihydroxybutanamide 23. ESIMS found for C$_{24}$H$_{48}$N$_6$O$_{10}$ m/z 581 (M+H). HPLC retention time 5.28 min (Method 1).

Synthesis of N-((1R,2S,3S,4R,5S)-5-amino-4-((2R,3R,6S)-3-amino-6-(aminomethyl)tetrahydro-2H-pyran-2-vlxy)-2-((2R,3R,4R,5R)-3,5-dihydroxy-5-methyl-4-(methylamino)tetrahydro-2H-pyran-2-yloxy)-3-hydroxycyclohexyl)-2-hydroxy acetimidamide 22

An example synthesis of 22 is depicted in Scheme 19 and Example 15.

Scheme 19

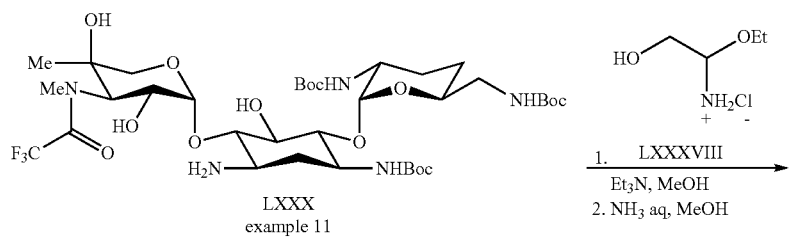
LXXX
example 11

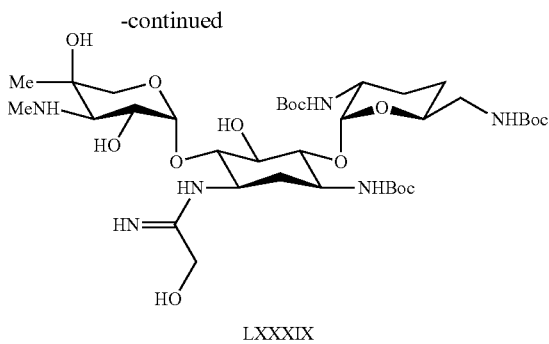

LXXXIX

↓ 30% TFA
DCM

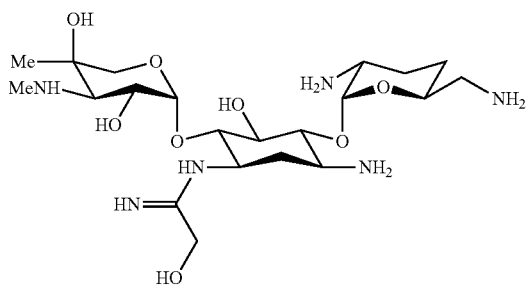

22

Example 15

Step 1-2

Compound LXXX (0.50 g, 0.59 mmol) was dissolved in MeOH (15 mL) and treated with $Et_3N$ (0.30 g, 2.95 mmol) followed by ethyl 2-hydroxyacetimidate LXXXVIII [*Archiv der Pharmazie* (1998), 321, 45-49, incorporated by reference in its entirety](0.42 g, 2.95 mmol). The mixture was stirred at room temperature for 3 days. Ammonia (10 mL) was added and the mixture was stirred for 4 h. The mixture was concentrated to dryness and the residue was purified on a silica gel column (20:1 EtOAc/MeOH→4:1 EtOAc/MeOH). A fraction, which contained LXXXIX (0.34 g) was further purified by dissolving in DCM (10 mL) and extracting with water. The organic phase was dried over $Na_2SO_4$ and concentrated. The solid was treated with diethyl ether, filtered and dried producing tert-butyl((2S,5R,6R)-6-((1R,2S,3S,4R,6S)-3-((2R,3R,4R,5R)-3,5-dihydroxy-5- methyl-4-(methylamino)tetrahydro-2H-pyran-2-yloxy)-2-hydroxy-4-(2-hydroxyacetimidamido)-6-(tert-butoxycarbonylamino)cyclohexyloxy)-5-(tert-butoxycarbonylamino)tetrahydro-2H-pyran-2-yl)methylcarbamate LXXXIX (0.17 g, 0.21 mmol, 36% yield).

Step 3

Procedure can be found in example 9. The final compound 22 was isolated as the trifluoroacetic acid salt. ESIMS found for $C_{21}H_{42}N_6O_8$ m/z 507 (M+H).

Synthesis of (S)-5-amino-N-((1R,2S,3S,4R,5S)-5-amino-4-((2R,3R,6S)-3-amino-6-((2-hydroxyethylamino)methyl)tetrahydro-2H-pyran-2-yloxy)-2-((2R,3R,4R,5R)-3,5-dihydroy-1-methyl-4-(methylamino)tetrahydro-2H-pyran-2-yloxy)-3-hydroxycyclohexyl)-2-hydroxypentanamide 40

An example synthesis of 40 is depicted in Scheme 20 and Example 16.

Scheme 20

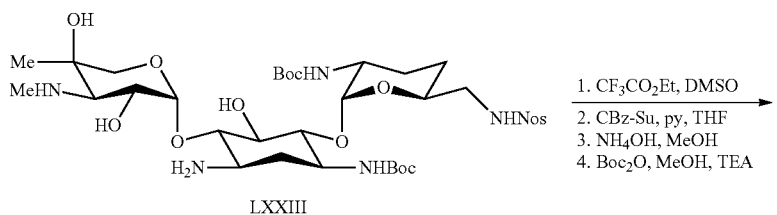

LXXIII

-continued
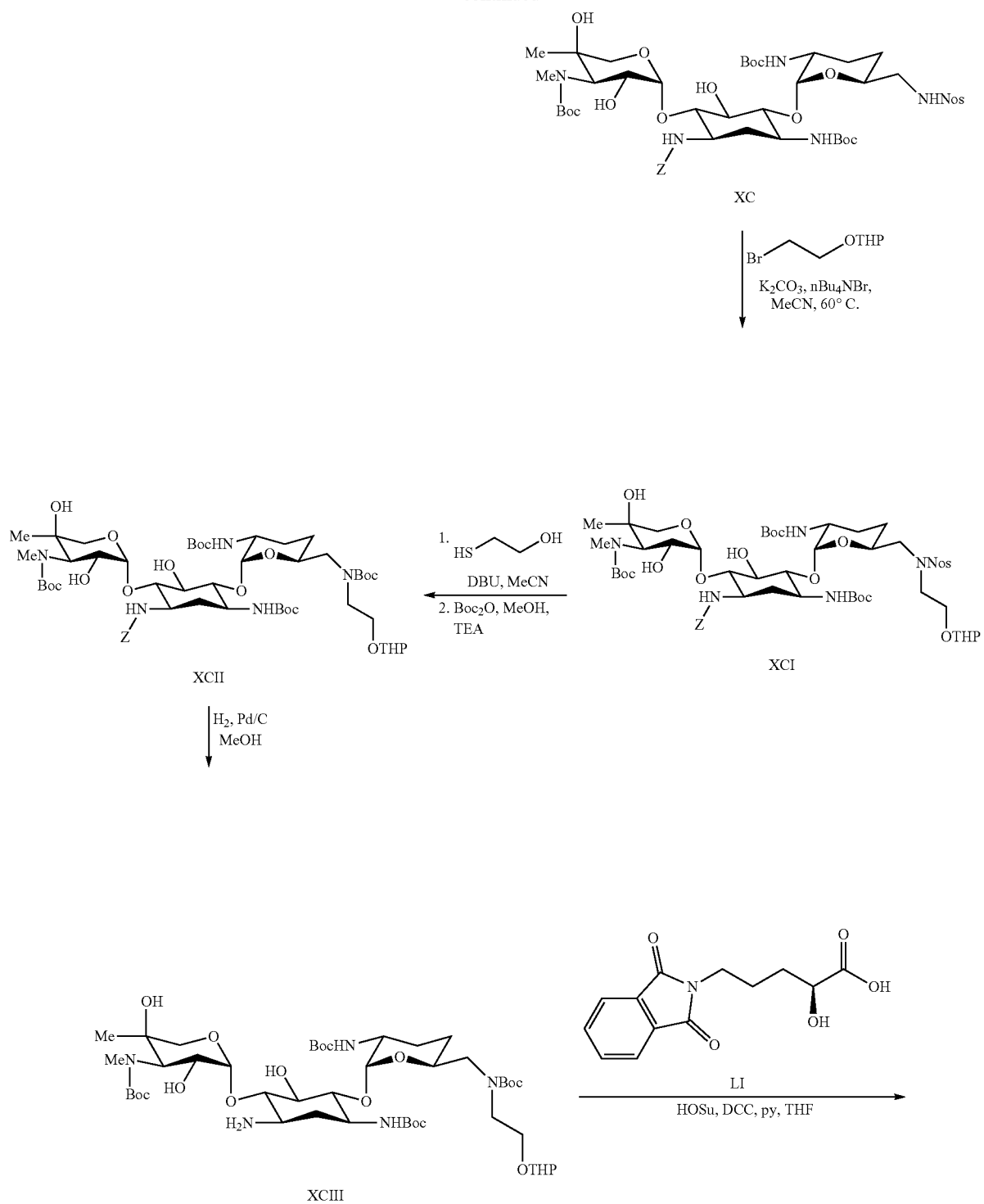

-continued

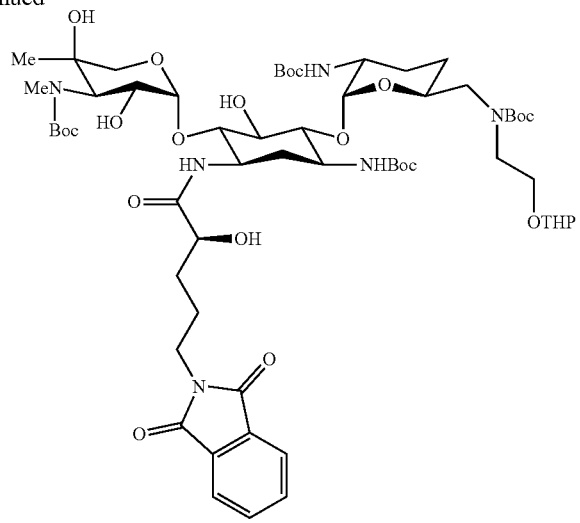

XCIV

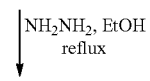
NH$_2$NH$_2$, EtOH
reflux

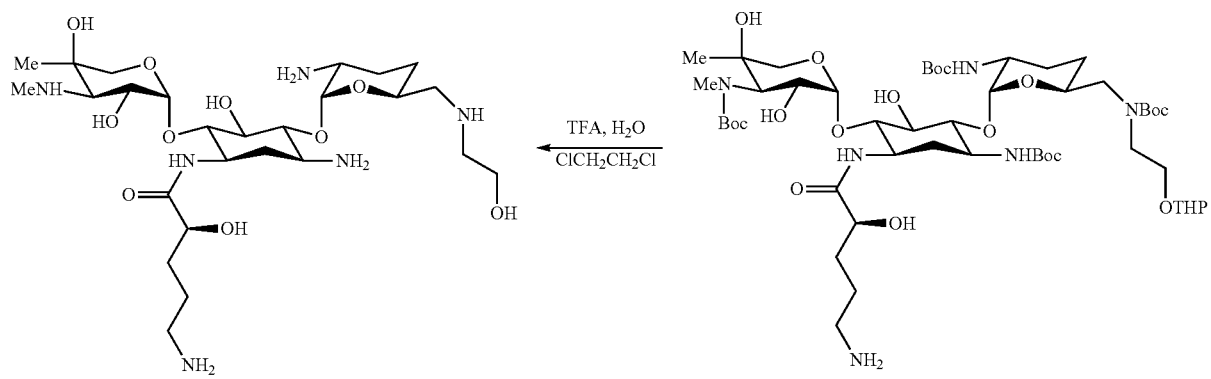

Example 16

Step 1

Procedure can be found in examples 9, step 3.

Step 2-4

Procedures can be found in examples 9, steps 4-5 where compound LXV, HOSu and DCC are replaced by CBz-Su to give compound XC (2.66 g, 58% yield).

Step 5

To a solution of compound XC (3.22 g, 3.0 mmol) in DMF (15 mL) were added K$_2$CO$_3$ (2.05 g, 14.8 mmol) and Et$_4$NI (0.73 g, 2.83 mmol). The mixture was stirred for 20 min at room temperature before adding 2-(2-bromoethoxy)tetrahydro-2H-pyran (3.25 g, 15 mmol). The mixture was stirred at room temperature for 48 h. Water (15 mL) was added and the mixture was extracted with EtOAc (3×15 mL). The organic phase was dried over Na$_2$SO$_4$, filtered and concentrated. The product was purified by column chromatography on silica gel (100% DCM→20:1 DCM/MeOH) to afford benzyl (1R,2S, 3S,4R,5S)-2-((2R,3R,4R,5R)-3,5-dihydroxy-5-methyl-4-(N-methyl-tert-butoxycarbonylamino)tetrahydro-2H-pyran- 2-yloxy)-4-((2R,3R,6S)-3-(tert-butoxycarbonylamino)-6-((2-nitro-N-(2-(tetrahydro-2H-pyran-2-yloxy)ethyl) phenylsulfonamido)methyl)tetrahydro-2H-pyran-2-yloxy)-3-hydroxy-5-tert-butoxycarbonylaminocyclohexylcarbamate XCI contaminated with residual 2-(2-bromoethoxy)tetrahydro-2H-pyran (3.54 g).

Step 6

Procedure can be found in examples 10, step 5. From compound XCI (3.50 g, contaminated with 2-(2-bromoethoxy)tetrahydro-2H-pyran) was obtained benzyl (1R,2S,3S,4R,5S)-2-((2R,3R,4R,5R)-3,5-dihydroxy-5-methyl-4-(N-methyl-tert-butoxy carbonylamino)tetrahydro-2H-pyran-2-yloxy)-3-hydroxy-5-tert-butoxycarbonylamino-4-((2R,3R,6S)-3-tert-butoxycarbonylamino-6-((2-(tetrahydro-2H-pyran-2-yloxy)ethylamino) methyl)tetrahydro-2H-pyran-2-yloxy)cyclohexylcarbamate (1.80 g, 1.78 mmol, 59% yield from XC). ESIMS found for $C_{49}H_{81}N_5O_{17}$ m/z 1012 (M+H).

Step 7

To a solution of benzyl (1R,2S,3S,4R,5S)-2-((2R,3R,4R,5R)-3,5-dihydroxy-5-methyl-4-(N-methyl-tert-butoxy carbonylamino)tetrahydro-2H-pyran-2-yloxy)-3-hydroxy-5-tert-butoxycarbonylamino-4-((2R,3R,6S)-3-tert-butoxycarbonylamino-6-((2-(tetrahydro-2H-pyran-2-yloxy) ethylamino)methyl)tetrahydro-2H-pyran-2-yloxy) cyclohexylcarbamate (1.78 g, 1.76 mmol) in MeOH (7 mL) was added $Et_3N$ (0.27 g, 2.65 mmol), followed by a solution of $Boc_2O$ (0.49 g, 2.24 mmol) in MeOH (1 mL). The mixture was stirred at room temperature for 18 h. The mixture was concentrated to dryness and the residue was dissolved in EtOAc (30 mL), washed with water (10 mL), dried over $Na_2SO_4$, filtered and concentrated. The crude product was purified by column chromatography on silica gel (4:1 EtOAc: hexane) to give benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-3-hydroxy-5-tert-butoxycarbonylamino-4-((2R,3R,6S)-3-tert-butoxycarbonylamino-6-((N-(2-(tetrahydro-2H-pyran-2-yloxy)ethyl)tert-butoxycarbonylamino)methyl)tetrahydro-2H-pyran-2-yloxy)cyclohexylcarbamate XCII (1.70 g, 1.53 mmol, 87% yield). ESIMS found for $C_{54}H_{89}N_5O_{19}$ m/z 1134 (M+Na).

Step 8

To a solution of compound XCII (1.69 g, 1.52 mmol) in MeOH (30 mL) purged with argon was added 10% Pd/C catalyst (0.18 g). The flask was purged with hydrogen and stirred at atmospheric pressure at room temperature for 18 h. The mixture was filtered through Celite, and the filtrate was concentrated to afford tert-butyl (2R,3R,4R,5R)-2-((1S,2R,3R,4S,6R)-6-amino-2-hydroxy-4-tert-butoxycarbonylamino-3-((2R,3R,6S)-3-tert-butoxycarbonylamino-6-((N-(2-(tetrahydro-2H-pyran-2-yloxy)ethyl)tert-butoxycarbonyl amino)methyl)tetrahydro-2H-pyran-2-yloxy)cyclohexyloxy)-3,5-dihydroxy-5-methyltetrahydro-2H-pyran-4-yl (methyl)carbamate XCIII (1.42 g, 1.45 mmol, 95% yield). ESIMS found for $C_{46}H_{83}N_5O_{17}$ m/z 978 (M+H).

Step 9

To a solution of compound XCIII (0.22 g, 0.85 mmol) and N-hydroxysuccinimide (0.10 g, 0.85 mmol) in THF (5 mL) at 0° C. was added DCC (0.17 g, 0.85 mmol). The mixture was allowed to warm to room temperature and was stirred for 1.5 h while a precipitate formed. The solid was removed by filtration, and the clear solution of active ester was added to a solution of (S)-5-(1,3-dioxoisoindolin-2-yl)-2-hydroxypentanoic acid LI (0.48 g, 0.50 mmol) in pyridine (4 mL). The mixture was stirred at room temperature for 18 h and then concentrated to dryness. The residue was dissolved in DCM (30 mL) and was washed with water. The organic phase was dried over $Na_2SO_4$, filtered, and concentrated with a rotary evaporator. The crude product was purified by column chromatography on silica gel (100% EtOAc→9:1 EtOAc/MeOH) to afford tert-butyl (2R,3R,4R,5R)-2-((1S,2S,3R,4S,6R)-6-((S)-5-(1,3-dioxoisoindolin-2-yl)-2-hydroxypentanamido)-2-hydroxy-4-tert-butoxycarbonylamino-3-((2R,3R,6S)-3-tert-butoxycarbonylamino-6-((N-(2-(tetrahydro-2H-pyran-2-yloxy)ethyl)tert-butoxycarbonylamino)methyl) tetrahydro-2H-pyran-2-yloxy)cyclohexyloxy)-3,5-dihydroxy-5-methyltetrahydro-2H-pyran-4-yl(methyl) carbamate XCIV (0.45 g, 0.36 mmol, 73% yield). ESIMS found for $C_{59}H_{94}N_6O_{21}$ m/z 1245 (M+Na).

Step 10

To a solution of compound XCIV (0.17 g, 0.14 mmol) in EtOH (1.0 mL) was added hydrazine (2 drops). The mixture was heated at reflux for 1.5 h during which time a precipitate formed and the mixture turned yellow. The mixture was concentrated to dryness and the residue was dissolved in EtOAc (15 mL) and washed with water. The organic phase was dried over $Na_2SO_4$, filtered and concentrated under reduced pressure. The crude product was purified by column chromatography on silica gel (100% MeOH→10:1 MeOH/$NH_{40}H$) to produce tert-butyl (2R,3R,4R,5R)-2-((1S,2S,3R,4S,6R)-6-((S)-5-amino-2-hydroxypentanamido)-2-hydroxy-4-tert-butoxycarbonylamino-3-((2R,3R,6S)-3-tert-butoxycarbonylamino-6-((N-(2-(tetrahydro-2H-pyran-2-yloxy)ethyl)tert-butoxycarbonyl amino)methyl)tetrahydro-2H-pyran-2-yloxy)cyclohexyloxy)-3,5-dihydroxy-5-methyltetrahydro-2H-pyran-4-yl(methyl)carbamate XCV (0.068 g, 0.06 mmol, 44% yield). ESIMS found for $C_{51}H_{92}N_6O_{19}$ m/z 1293 (M+H).

Step 11

To a solution of compound XCV (0.068 g, 0.062 mmol) in dichloroethane (2 mL) at −20° C. was added TFA (0.7 mL) followed by water (3 drops). The mixture was stirred for 1.5 h and allowed to warm to room temperature. The mixture was concentrated to dryness and the resultant thick oil was treated with diethyl ether (5 mL). The resulting precipitate was removed by filtration, washed with diethyl ether and dried to afford (S)-5-amino-N-((1R,2S,3S,4R,5S)-5-amino-4-((2R,3R,6S)-3-amino-6-((2-hydroxyethylamino) methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxypentanamide as the trifluoroacetate salt (0.073 g, 0.06 mmol, quantitative yield). ESIMS found for $C_{26}H_{52}N_6O_{10}$ m/z 609 (M+H).

Synthesis of (S)—N-((1R,2S,3S,4R,5S)-5-amino-4-((2R,3R,6S)-3-amino-6-((2-hydroxyethyl amino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-3-hydrazinyl-2-hydroxypropanamide 41

An example synthesis of 41 is depicted in Scheme 21 and Example 17.

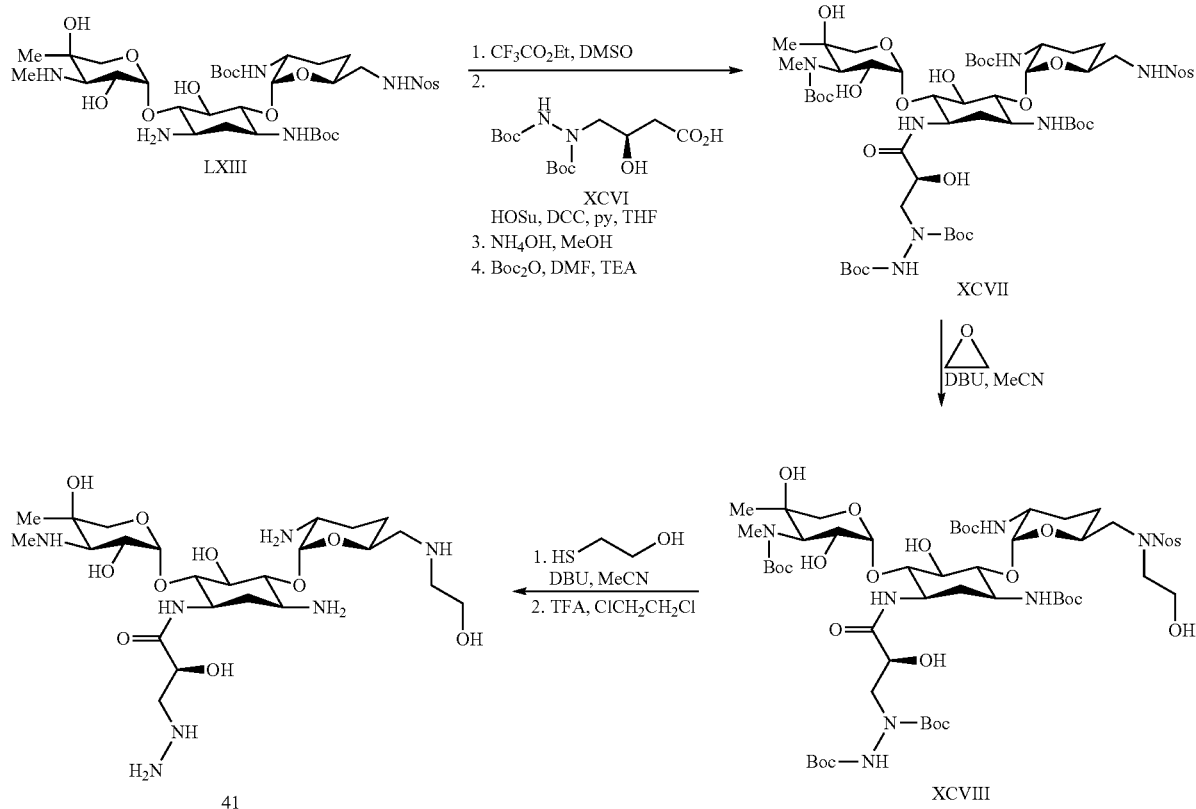

Example 17

Step 1-4

Procedures can be found in examples 9, steps 3-5, with the exception of the final Boc protection of N-3" nitrogen that was done in DMF instead of MeOH. di-tert-butyl 1-((S)-3-((1R,2S,3S,4R,5S)-2-((2R,3R,4R,5R)-4-(tert-butoxycarbonyl(methyl)amino)-3,5-dihydroxy-5-methyltetrahydro-2H-pyran-2-yloxy)-5-(tert-butoxycarbonylamino)-4-((2R,3R,6S)-3-(tert-butoxycarbonylamino)-6-((2-nitrophenylsulfonamido)methyl)tetrahydro-2H-pyran-2-yloxy)-3-hydroxycyclohexylamino)-2-hydroxy-3-oxopropyl)hydrazine-1,2-dicarboxylate XCVII was obtained (1.09 g, 0.88 mmol, 51% yield). ESIMS found for $C_{53}H_{88}N_8O_{23}S$ m/z 1259 (M+Na).

Step 5

To a solution of compound XCVII (0.63 g, 0.51 mmol) in MeCN (1.5 mL) was added DBU (0.031 g, 0.20 mmol) followed by ethylene oxide (4.0 mL). The mixture was stirred at room temperature for 24 hours. After reaction was complete, it was evaporated to dryness and the residue was dissolved in EtOAc (15 mL) and was washed with water. The organic phase was dried over $Na_2SO_4$, filtered and concentrated. The crude product was purified by column chromatography on silica gel (100% EtOAc) to produce di-tert-butyl 1-((S)-3-((1R,2S,3S,4R,5S)-2-((2R,3R,4R,5R)-4-(tert-butoxycarbonyl(methyl)amino)-3,5-dihydroxy-5-methyltetrahydro-2H-pyran- 2-yloxy)-5-(tert-butoxycarbonylamino)-4-((2R,3R,6S)-3-(tert-butoxycarbonylamino)-6-((N-(2-hydroxyethyl)-2-nitrophenyl sulfonamido)methyl)tetrahydro-2H-pyran-2-yloxy)-3-hydroxycyclohexylamino)-2-hydroxy-3-oxopropyl)hydrazine-1,2-dicarboxylate XCVIII (0.20 g, 0.15 mmol, 30% yield). ESIMS found for $C_{55}H_{92}N_8O_{24}S$ m/z 1303 (M+Na).

Step 6-7

Procedures can be found in examples 10, step 5-6. From compound XCVIII (0.19 g, 0.15 mmol) was obtained (S)—N-((1R,2S,3S,4R,5S)-5-amino-4-((2R,3R,6S)-3-amino-6-((2-hydroxyethyl amino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxy cyclohexyl)-3-hydrazinyl-2-hydroxypropanamide 41 as trifluoroacetate salt (0.066 g, 0.056 mmol, 80% yield for 2 steps). ESIMS found for $C_{24}H_{49}N_7O_{10}$ m/z 596 (M+H). HPLC retention time 4.21 min (Method 2).

Synthesis of N-((1R,2S,3S,4R,5S)-5-amino-4-((2R, 3R,6S)-3-amino-6-((2-hydroxyethyl amino)methyl) tetrahydro-2H-pyran-2-yloxy)-2-((2R,3R,4R,5R)-3, 5-dihydroxy-5-methyl-4-(methylamino)tetrahydro-2H-pyran-2-yloxy)-3-hydroxcyclohexyl)-3-hydroxyazetidine-3-carboxamide 43

An example synthesis of 43 is depicted in Scheme 22 and Example 18.

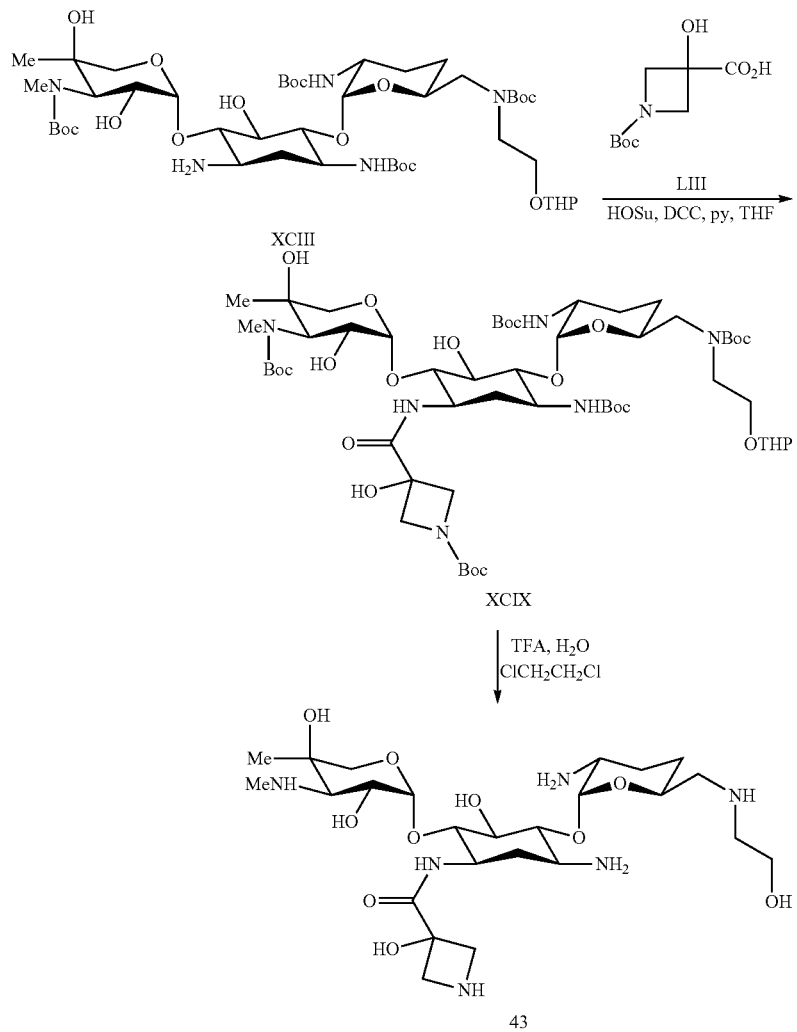

Example 18

Step 1

To a solution of 3-hydroxy-1-(oxoboryl)azetidine-3-carboxylic acid LIII (0.16 g, 0.74 mmol) and N-hydroxysuccinimide (0.11 g, 1.0 mmol) in THF (5 mL) at 0° C. was added DCC (0.21 g, 1.0 mmol). The mixture was allowed to warm to room temperature and stir for 1.5 h, during which time a precipitate formed. The solid was removed by filtration, and the clear solution of active ester was added to a solution of compound XCIII (0.49 g, 0.50 mmol) dissolved in pyridine (10 mL). The mixture was allowed to stir at room temperature for 18 h and then concentrated to dryness. The residue was dissolved in EtOAc (30 mL) and washed with water (30 mL). The organic phase was dried over $Na_2SO_4$, filtered, concentrated and dried under vacuum. The crude product was purified by column chromatography on silica gel (100% EtOAc→10:1 EtOAc/MeOH) to afford tert-butyl 3-((1R,2S, 3S,4R,5S)-4-((2R,3R,6S)-6-((tert-butoxycarbonyl(2-(tetrahydro-2H-pyran-2-yloxy)ethyl)amino)methyl)-3-(tert-butoxycarbonylamino)tetrahydro-2H-pyran-2-yloxy)-2-((2R, 3R,4R,5R)-4-  (tert-butoxycarbonyl(methyl)amino)-3,5-dihydroxy-5-methyltetrahydro-2H-pyran-2-yloxy)-5-(tert-butoxycarbonylamino)-3-hydroxycyclohexylcarbamoyl)-3-hydroxyazetidine-1-carboxylate XCIX (0.19 g, 0.16 mmol, 32% yield). ESIMS found for $C_{55}H_{96}N_6O_{21}$ m/z 1199 (M+Na).

Step 2

To a solution of Compound 17 (0.19 g, 0.16 mmol) in dichloroethane (5 mL) and cooled to −20° C. was added TFA (2 mL) followed by water (3 drops). The mixture was allowed to warm to room temperature and stir for 1.5 h. The mixture was concentrated to dryness and the resultant thick oil was treated with diethyl ether (5 mL). The resulting precipitate was filtered, washed with diethyl ether and dried, affording N-((1R,2S,3S,4R,5S)-5-amino-4-((2R,3R,6S)-3-amino-6-((2-hydroxyethylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-3-hydroxyazetidine-3-carboxamide 43 as trifluoroacetate salt (0.15 g, 0.13 mmol, quantitative yield). ESIMS found for $C_{25}H_{48}N_6O_{11}$ m/z 593 (M+H).

Synthesis of 2-amino-N-((1R,2S,3S,4R,5S)-5-amino-4-((2R,3R,6S)-3-amino-6-(((R)-2,3-dihydroxypropylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)acetamide 44

An example synthesis of 44 is depicted in Scheme 23 and Example 19.

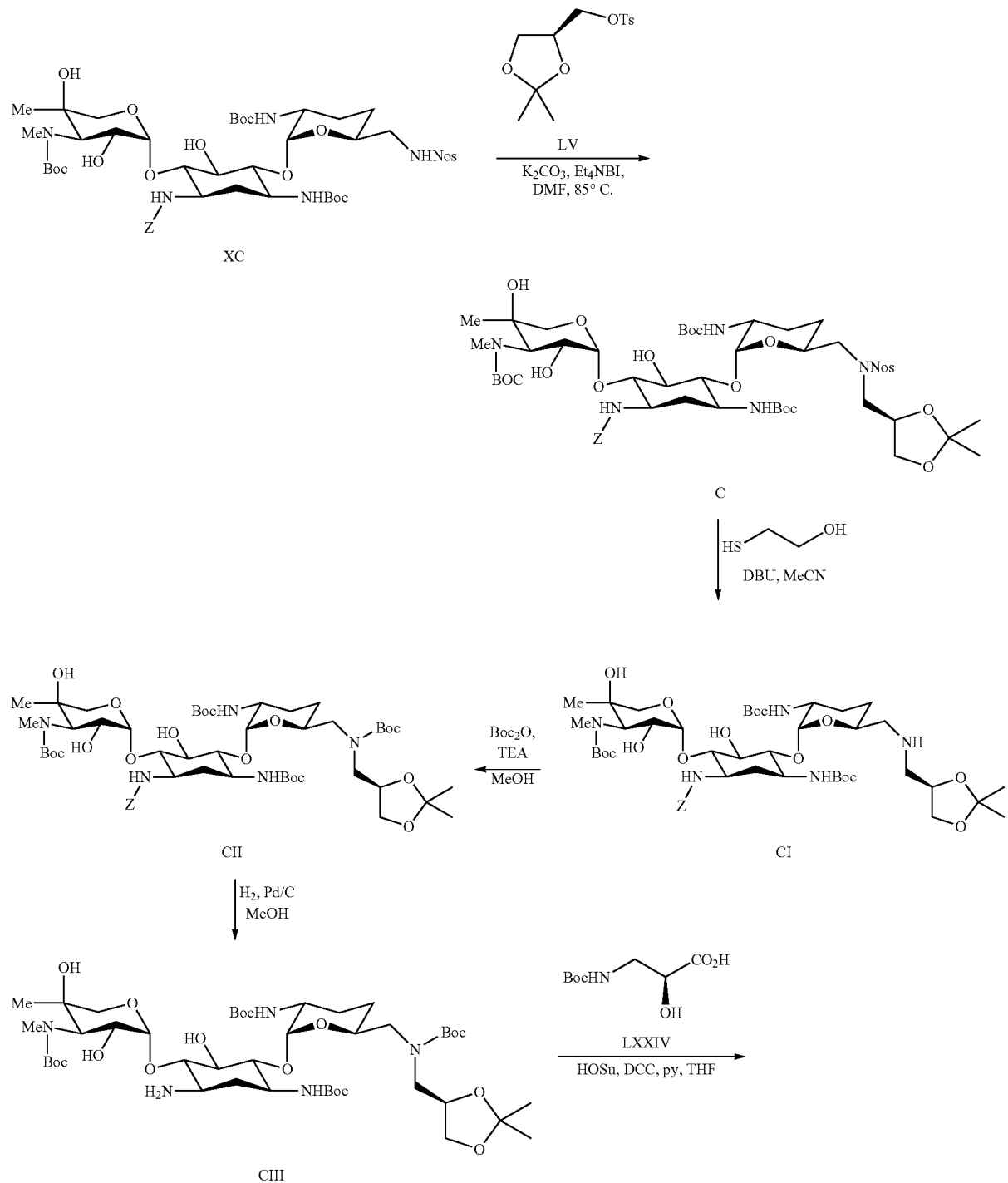

Scheme 23

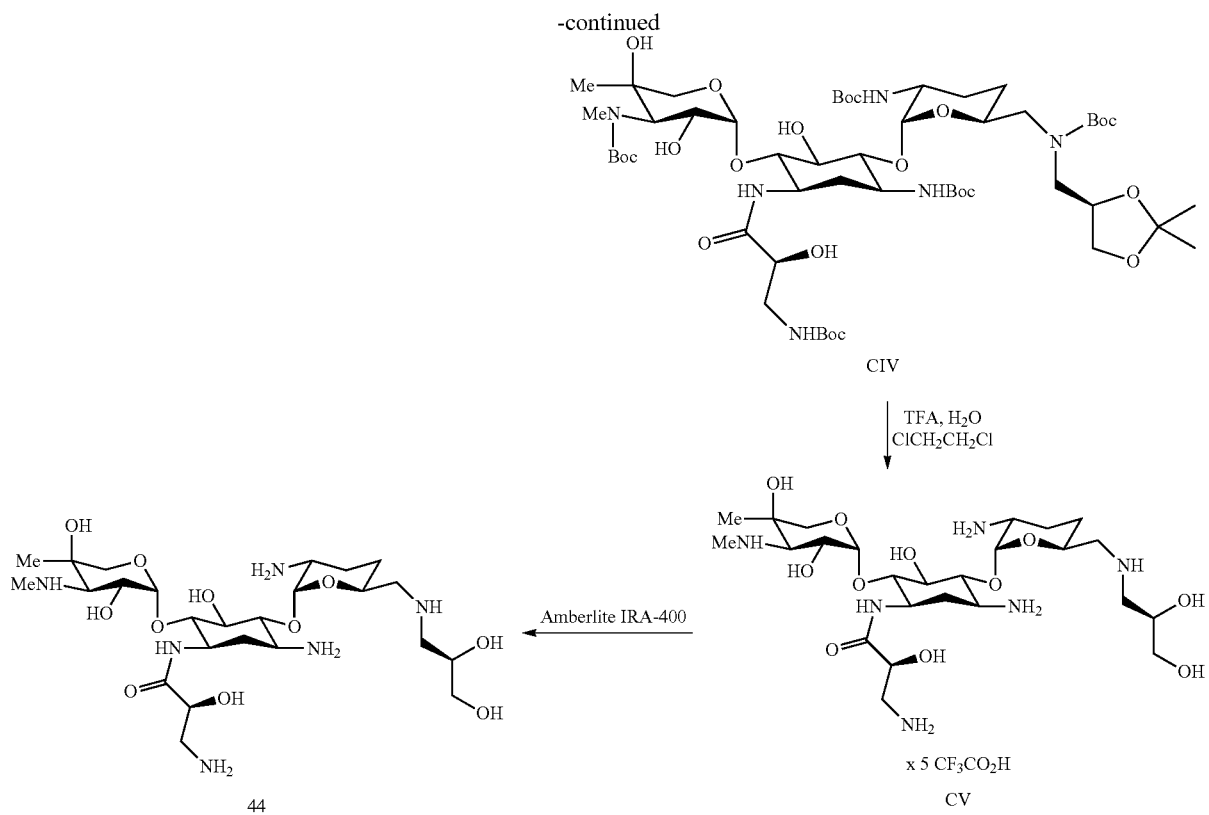

CIV

↓ TFA, H₂O
ClCH₂CH₂Cl

Amberlite IRA-400 ←

44

CV x 5 CF₃CO₂H

Example 19

Step 1

To a solution of compound XC (32.40 g, 0.03 mol) in DMF (400 mL) were added K₂CO₃ (20.7 g, 0.15 mol) and Et₄NI (23.0 g, 0.09 mol). After stirring for 20 min at room temperature, the mixture was treated with (S)-(2,2-dimethyl-1,3-dioxolan-4-yl)methyl 4-methylbenzenesulfonate LV (17.6 g, 0.061 mol). The mixture was heated at 85° C. for 24 h. The solvent was evaporated under reduced pressure. The residue was treated with water (200 mL) and the mixture was extracted with EtOAc (2×200 mL). The organic phase was washed with 5% aqueous NaCl, dried over Na₂SO₄, filtered and concentrated. The crude product was purified by column chromatography on silica gel (100% hexane→1:2 hexane/EtOAc) to yield benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-4-((2R,3R,6S)-6-((N—(((R)-2,2-dimethyl-1,3-dioxolan-4-yl)methyl)-2-nitrophenylsulfonamido)methyl)-3-tert-butoxycarbonylaminotetrahydro-2H-pyran-2-yloxy)-3-hydroxy-5-tert-butoxycarbonyl aminocyclohexylcarbamate C (32.27 g, 0.027 mole, 83% yield).

Step 2

To a solution of compound C (32.0 g, 0.027 mol) in MeCN (400 mL) was added 2-mercaptoethanol (12.8 g, 0.16 mol) followed by DBU (11.9 g, 0.078 mol). The mixture was stirred at room temperature for 4 h before the solvent was evaporated. The residue was partitioned between water (200 mL) and EtOAc (400 mL). The organic phase was washed with water (3×150 mL), dried over Na₂SO₄, filtered and concentrated. The residue was subjected to column chromatography on silica gel (100% EtOAc→9:1 EtOAc/MeOH→1:1 EtOAc/MeOH) to produce benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-4-((2R,3R,6S)-6-(((((R)-2,2-dimethyl-1,3-dioxolan-4-yl)methyl)amino)methyl)-3-tert-butoxycarbonylaminotetrahydro-2H-pyran-2-yloxy)-3-hydroxy-5-tert-butoxycarbonyl aminocyclohexylcarbamate CI (17.5 g, 0.0175 mol, 65% yield). ESIMS found for $C_{48}H_{79}N_5O_{17}$ m/z 998 (M+H).

Step 3

To a solution of compound CI (17.5 g, 0.0175 mol) in MeOH (200 mL) was added Et₃N (2.63 g, 0.026 mol) followed by Boc₂O (5.4 g, 0.026 mol). The mixture was stirred at room temperature for 18 h. The reaction mixture was concentrated to dryness, and the residue was dissolved in EtOAc (100 mL) and washed with water (50 mL). The organic phase was dried over Na₂SO₄, filtered and concentrated. The crude product was purified by column chromatography on silica gel (1:1 EtOAc/hexane) to give benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-4-((2R,3R,6S)-6-((N—(((R)-2,2-dimethyl-1,3-dioxolan-4-yl)methyl)tert-butoxycarbonylamino)methyl)-3-tert-butoxycarbonylaminotetrahydro-2H-pyran-2-yloxy)-3-hydroxy-5-tert-butoxycarbonylaminocyclohexylcarbamate CII (18.4 g, 0.0168 mol, 96% yield). ESIMS found for $C_{53}H_{87}N_5O_{19}$ m/z 1120 (M+H).

Step 4

A solution of compound CII (18.40 g, 16.8 mmol) in MeOH (200 mL) was purged with argon before adding 10%

Pd/C catalyst (2.0 g). The flask was purged with hydrogen and left at ambient pressure at room temperature for 18 h. The mixture was filtered through Celite, and the filtrate was concentrated to dryness to afford tert-butyl (2R,3R,4R,5R)-2-((1S,2R,3R,4S,6R)-6-amino-3-((2R,3R,6S)-6-((N—(((R)-2,2-dimethyl-1,3-dioxolan-4-yl)methyl)tert-butoxycarbonylamino)methyl)-3-tert-butoxycarbonylaminotetrahydro-2H-pyran-2-yloxy)-2-hydroxy-4-tert-butoxycarbonylaminocyclohexyloxy)-3,5-dihydroxy-5-methyltetrahydro-2H-pyran-4-yl(methyl)carbamate CIII (14.95 g, 15.5 mmol, 92% yield). ESIMS found for $C_{45}H_{81}N_5O_{17}$ m/z 964 (M+H).

Step 5

To a solution (S)-3-(tert-butoxycarbonylamino)-2-hydroxypropanoic acid LXXIV (5.20 g, 25.2 mmol) and N-hydroxysuccinimide (3.20 g, 27.7 mmol) in THF (100 mL) at 0° C. was added DCC (5.70 g, 27.7 mmol). The mixture was allowed to warm to room temperature and stir for 1.5 h, during which time a precipitate formed. The solid was removed by filtration, and the clear solution of active ester was added to a solution of compound CIII (14.95 g, 15.5 mmol) in pyridine (100 mL). The mixture was allowed to stir at room temperature for 18 h before concentrating to dryness. The residue was dissolved in EtOAc (100 mL) and washed with water (100 mL). The organic phase was dried over $Na_2SO_4$, filtered, concentrated and dried under vacuum. The crude product was purified by column chromatography on silica gel (1:1 hexane/EtOAc→1:2 hexane/EtOAc→100% EtOAc) to yield tert-butyl (2R,3R,4R,5R)-2-((1S,2S,3R,4S,6R)-3-((2R,3R,6S)-6-((N—(((R)-2,2-dimethyl-1,3-dioxolan-4-yl)methyl)tert-butoxycarbonylamino)methyl)-3-tert-butoxycarbonylaminotetrahydro-2H-pyran-2-yloxy)-2-hydroxy-6-((S)-2-hydroxy-3-tert-butoxycarbonylaminopropanamido)-4-tert-butoxycarbonylaminocyclohexyloxy)-3,5-dihydroxy-5-methyltetrahydro-2H-pyran-4-yl(methyl)carbamate CIV (8.26 g, 7.13 mmol, 42% yield). ESIMS found for $C_{53}H_{94}N_6O_{21}$ m/z 1173 (M+Na).

Step 6

To a solution of compound CIV (8.20 g, 7.13 mmol) in dichloroethane (150 mL) and cooled to −20° C. was added TFA (30 mL) followed by water (4 mL). The mixture was allowed to warm to room temperature and was stirred for 1.5 h. The mixture was concentrated to dryness and the resultant thick oil was treated with diethyl ether (100 mL). The resulting precipitate was filtered, washed with diethyl ether and dried, affording 2-amino-N-((1R,2S,3S,4R,5S)-5-amino-4-((2R,3R,6S)-3-amino-6-(((R)-2,3-dihydroxypropyl amino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)acetamide CV (8.50 g, quantitative yield).

Step 7

Compound CV (8.50 g, 7.13 mmol) was dissolved in deionized water (200 mL) and poured onto a bed of Amberlite IRA 400 resin (OH form) (500 mL). The column was eluted with water, and the basic fractions were collected (c.a. 2000 mL). The volume was reduced to c.a. 150 mL with a rotary evaporator, and the solution was lyophilized to give 44 as hydrated free base (3.95 g, 5.94 mmol, 84% yield). ESIMS found for $C_{25}H_{50}N_6O_{11}$ m/z 611 (M+H).

The following compound is prepared in accordance with the procedure described in the above example 19.

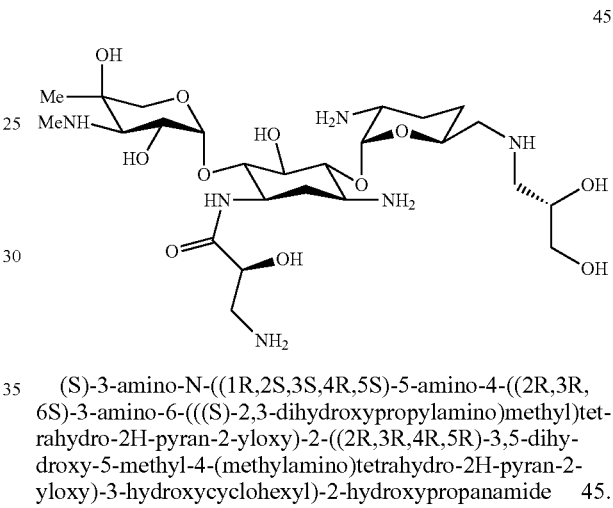

45

(S)-3-amino-N-((1R,2S,3S,4R,5S)-5-amino-4-((2R,3R,6S)-3-amino-6-(((S)-2,3-dihydroxypropylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxypropanamide 45. ESIMS found for $C_{25}H_{50}N_6O_{11}$ m/z 611 (M+H).

Synthesis of (S)-3-amino-N-((1R,2S,3S,4R,5S)-5-amino-4-((2R,3R,6S)-3-amino-6-((2-fluoroethylamino)methyl)tetrahydro-2H-pyran-2-ylxy)-2-((2R,3R,4R,5R)-3,5-dihydroxy-5-methyl-4-(methylamino)tetrahydro-2H-pyran-2-yloxy)-3-hydroxycyclohexyl)-2-hydroxypropanamide 46

An example synthesis of 46 is depicted in Scheme 24 and Example 20.

Scheme 24

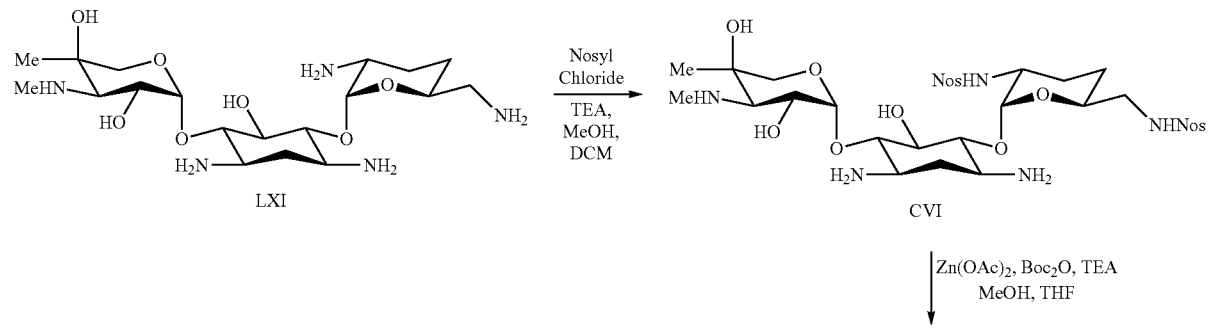

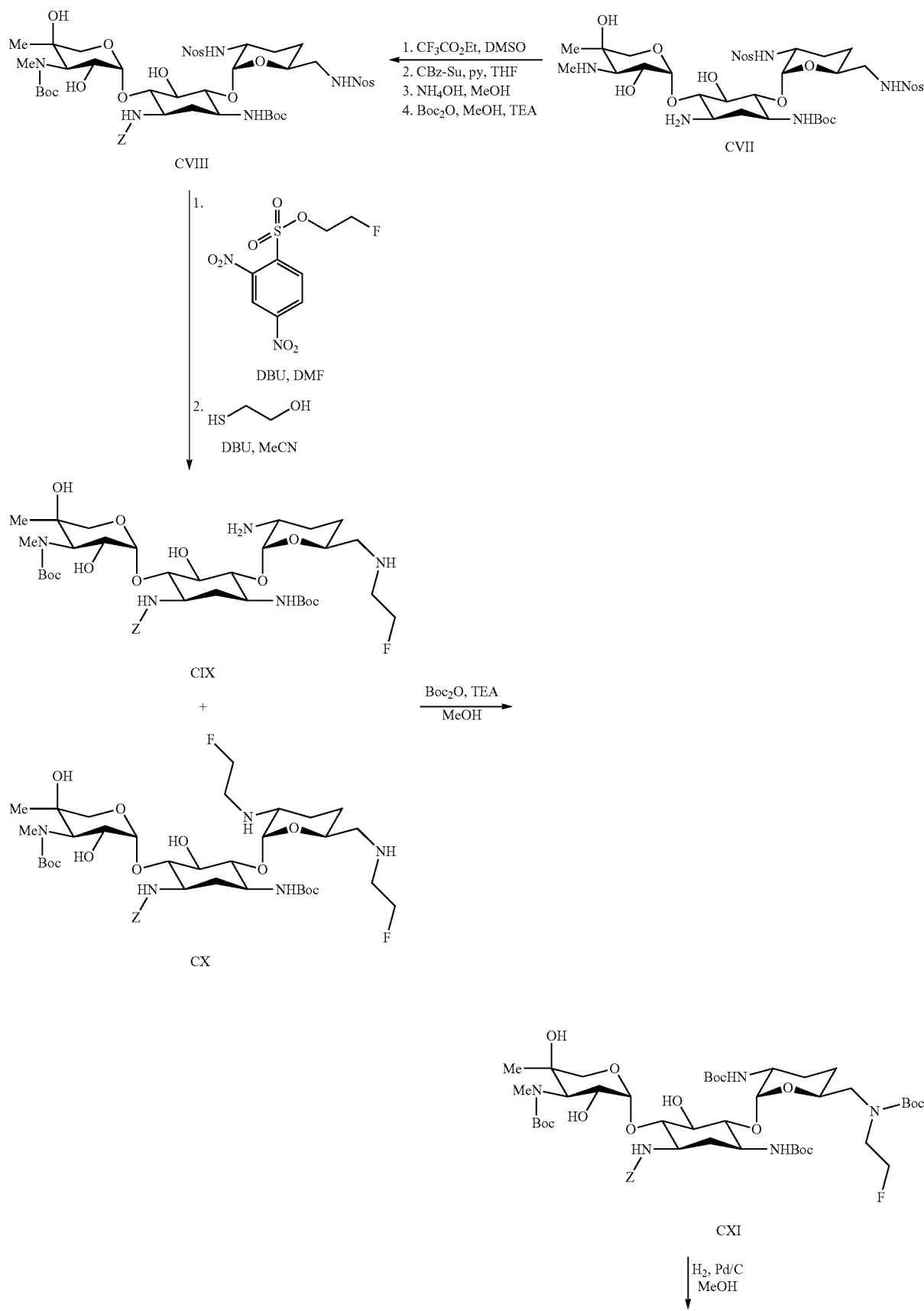

101

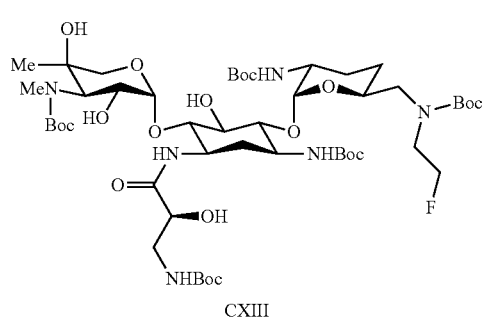

CXIII

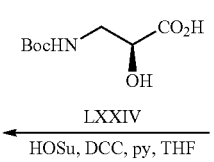

LXXIV

HOSu, DCC, py, THF

102
-continued

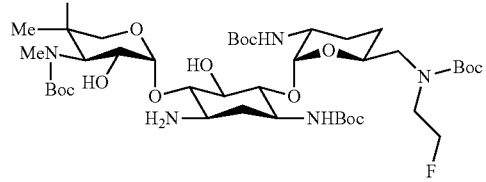

CXII

TFA, H₂O
ClCH₂CH₂Cl

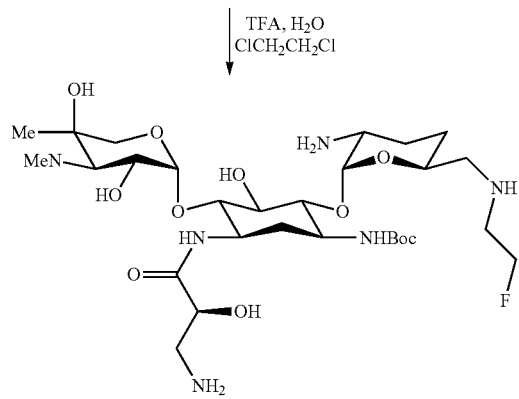

46

Example 20

Step 1

To a solution of gentamycin C1a (LXI) (30.0 g, 90% content, 0.067 mol) in MeOH (300 mL) was added Zn(OAc)₂×2 H₂O (36.7 g, 0.167 mol). The mixture was stirred for 1 h at room temperature before cooling to −60° C. and adding Et₃N (13.43 g, 0.133 mol). A solution of 2-nitrobenzenesulfonyl (nosyl) chloride (29.5 g, 0.133 mol) in DCM (100 mL) was added dropwise. The mixture was allowed to stir at room temperature for 18 h, after which time it was concentrated under reduced pressure. The residue was dissolved in DCM (200 mL) and treated with 10% NH₃OH (200 mL). The mixture was stirred for 1 h. The organic phase was separated, dried over Na₂SO₄ and concentrated. The residue was subjected to column chromatography on silica gel (1:1 DCM/MeOH→10:1 MeOH/Et₃N) to afford N-(((2S,5R,6R)-6-((1R,2S,3S,4R,6S)-4,6-diamino-3-((2R,3R,4R,5R)-3,5-dihydroxy-5-methyl-4-(methylamino)tetrahydro-2H-pyran-2-yloxy)-2-hydroxycyclohexyloxy)-5-(2-nitrophenylsulfonamido)tetrahydro-2H-pyran-2-yl)methyl)-2-nitrobenzenesulfonamide CVI (8.66 g, 0.010 mol, 16% yield). ESIMS found for $C_{31}H_{45}N_7O_{15}S_2$ m/z 820 (M+H).

Step 2

To a solution of compound CVI (16.11 g, 19.67 mmol) in MeOH (350 mL) at room temperature was added Zn(OAc)₂×2 H₂O (10.8 g, 49.17 mmol). The mixture was stirred for 1 h, after which time a solution of Boc₂O (4.71 g, 21.69 mmol) and Et₃N (2.18 g, 21.63 mmol) in THF (50 mL) was added dropwise. The mixture was allowed to stir at room temperature for 18 h. The mixture was concentrated under reduced pressure. The residue was dissolved in DCM (250 mL), treated with 10% NH₄OH (100 mL) and stirred for 0.5 h. The organic phase was separated and washed with 10% NH₄OH (4×100 mL) and water (100 mL). The organic phase was dried over Na₂SO₄, filtered and concentrated to dryness under reduced pressure. The residue was dissolved in hot EtOAc (50 mL) and treated with hexane until it became cloudy (c.a.15 mL). The mixture was cooled in an ice bath, and the solid was filtered, washed with hexane and dried to give tert-butyl (1S,2R,3R,4S,5R)-5-amino-4-((2R,3R,4R,5R)-3,5-dihydroxy-5-methyl-4-(methylamino)tetrahydro-2H-pyran-2-yloxy)-3-hydroxy-2-((2R,3R,6S)-3-(2-nitrophenylsulfonamido)-6-((2-nitrophenyl sulfonamido)methyl) tetrahydro-2H-pyran-2-yloxy)cyclohexylcarbamate CVII (11.05 g, 12.02 mmol, 67% yield). ESIMS found for $C_{36}H_{53}N_7O_{17}S_2$ m/z 920 (M+H).

Step 3-6

Procedures can be found in examples 16, step 1-4. From compound CVII (11.00 g, 12.00 mmol) was obtained benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-3-hydroxy-5-tert-butoxycarbonylamino-4-((2R,3R,6S)-3-(2-nitrophenylsulfonamido)-6-((2-nitrophenylsulfonamido)methyl)tetrahydro-2H-pyran-2-yloxy)cyclohexylcarbamate CVIII (8.92 g, 7.73 mmol, 64% yield for 4 steps). ESIMS found for $C_{49}H_{67}N_7O_{21}S_2$ m/z 1176 (M+Na).

Step 7-8

To a solution of compound CVIII (1.16 g, 1.0 mmol) in DMF (4 mL) was added 2-fluoroethyl 2,4-dinitrobenzenesulfonate LVII (0.89 g, 3.0 mmol) followed by DBU (0.34 g, 2.2 mmol), at which time a red color developed. The mixture was heated at 45° C. for 48 h. After 1 day, the ratio of compounds CIX:CX was 2:1, and did not change upon further heating. Water (10 mL) was added to the reaction mixture and the mixture was extracted with EtOAc (3×15 mL). The combined organic phases were dried over $Na_2SO_4$, filtered and concentrated to dryness. The residue was dissolved in MeCN (50 mL) and 2-mercaptoethanol (1.54 g, 20 mmol) was added followed by DBU (1.9 g, 12.5 mmol). The mixture was stirred at room temperature for 4 h and the solvent was evaporated. The residue was partitioned between water (40 mL) and EtOAc (40 mL). The organic phase was washed with water (3×15 mL), dried over $Na_2SO_4$, filtered and concentrated. The residue was chromatographed on silica gel (100% EtOAc→1:1 EtOAc/MeOH→10:1 MeOH/$NH_4OH$) to yield benzyl (1R,2S,3S,4R,5S)-4-((2R,3R,6S)-3-amino-6-((2-fluoroethylamino)methyl)tetrahydro-2H-pyran-2-yloxy)-2-((2R,3R,4R,5R)-3,5-dihydroxy-5-methyl-4-(N-methyl-tert-butoxycarbonylamino)tetrahydro-2H-pyran-2-yloxy)-3-hydroxy-5-tert-butoxycarbonylamino cyclohexylcarbamate CIX (0.34 g, 0.41 mmol, 41% yield) and benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-4-((2R,3R,6S)-3-(2-fluoroethylamino)-6-((2-fluoroethylamino)methyl)tetrahydro-2H-pyran-2-yloxy)-3-hydroxy-5-tert-butoxycarbonylaminocyclohexylcarbamate CX (0.17 g, 0.20 mmol, 20% yield).

Step 9

Procedures can be found in examples 16, step 7. From compound CIX (0.34 g, 0.41 mmol) was obtained benzyl (1R,2S,3S,4R,5S)-2-((2R,3R,4R,5R)-3,5-dihydroxy-5-methyl-4-(N-methyl-tert-butoxycarbonylamino)tetrahydro-2H-pyran-2-yloxy)-4-((2R,3R,6S)-6-((N-(2-fluoroethyl)tert-butoxycarbonylamino)methyl)-3-tert-butoxycarbonylaminotetrahydro-2H-pyran-2-yloxy)-3-hydroxy-5-tert-butoxycarbonylamino cyclohexylcarbamate CXI (0.34 g, 0.33 mmol, 80% yield). ESIMS found for $C_{49}H_{80}N_5O_{17}F$ m/z 1052 (M+Na).

Step 10

Procedures can be found in examples 16, step 8. From compound CXI (0.34 g, 0.33 mmol) was obtained tert-butyl (2R,3R,4R,5R)-2-((1S,2R,3R,4S,6R)-6-amino-3-((2R,3R,6S)-6-((N-(2-fluoroethyl)tert-butoxycarbonylamino)methyl)-3-tert-butoxy carbonylaminotetrahydro-2H-pyran-2-yloxy)-2-hydroxy-4-tert-butoxycarbonylamino cyclohexyloxy)-3,5-dihydroxy-5-methyltetrahydro-2H-pyran-4-yl(methyl)carbamate CXII (0.27 g, 0.30 mmol, 90% yield). ESIMS found for $C_{41}H_{74}N_5O_{15}F$ m/z 896 (M+H).

Step 11

Procedures can be found in examples 19, step 5. From compound CXII (0.26 g, 0.46 mmol) was obtained tert-butyl (2R,3R,4R,5R)-2-((1S,2S,3R,4S,6R)-3-((2R,3R,6S)-6-((N-(2-fluoroethyl)tert-butoxycarbonylamino)methyl)-3-tert-butoxycarbonylaminotetrahydro-2H-pyran-2-yloxy)-2-hydroxy-6-((S)-2-hydroxy-3-tert-butoxycarbonylaminopropanamido)-4-tert-butoxycarbonylaminocyclohexyloxy)-3,5-dihydroxy-5-methyltetrahydro-2H-pyran-4-yl(methyl)carbamate CXIII (0.23 g, 0.21 mmol, 74% yield). ESIMS found for $C_{49}H_{87}N_6O_{19}F$ m/z 1105 (M+Na).

Step 12

Procedures can be found in examples 19, step 6. From compound CXIII (0.23 g, 0.21 mmol) was obtained (S)-3-amino-N-((1R,2S,3S,4R,5S)-5-amino-4-((2R,3R,6S)-3-amino-6-((2-fluoroethylamino)methyl)tetrahydro-2H-pyran-2-yloxy)-2-((2R,3R,4R,5R)-3,5-dihydroxy-5-methyl-4-(methylamino)tetrahydro-2H-pyran-2-yloxy)-3-hydroxycyclohexyl)-2-hydroxypropanamide 46 (0.22 g, 0.19 mmol, 91% yield). ESIMS found for $C_{24}H_{47}N_6O_9F$ m/z 583 (M+H).

Illustrative compounds of Formula (I) are shown in TABLE 1. Preferred structures are shown with defined configurations at selected stereocenters but the shown stereochemistries are not meant to be limiting and all possible stereoisomers of the shown structures are encompassed in the present invention. Compounds of any absolute and relative configurations at the stereocenters as well as mixtures of enantiomers and diastereoisomers of any given structure are also encompassed in the present invention.

TABLE 1

| Example | Structure |
|---------|-----------|
| 1 | 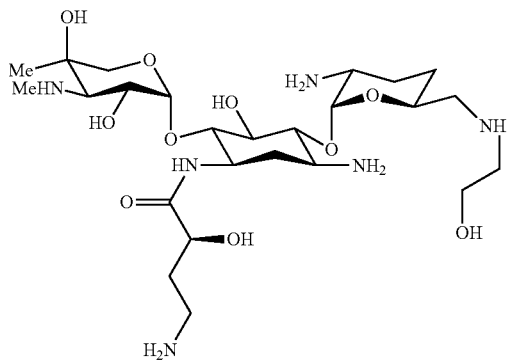 |

TABLE 1-continued

| Example | Structure |
|---|---|
| 2 | 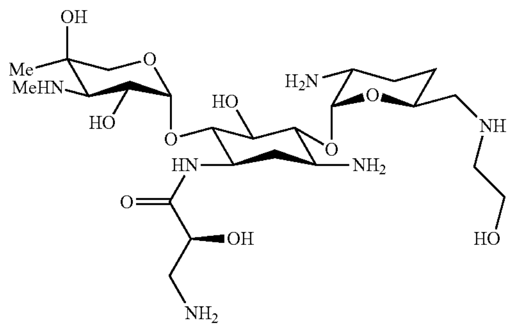 |
| 3 | 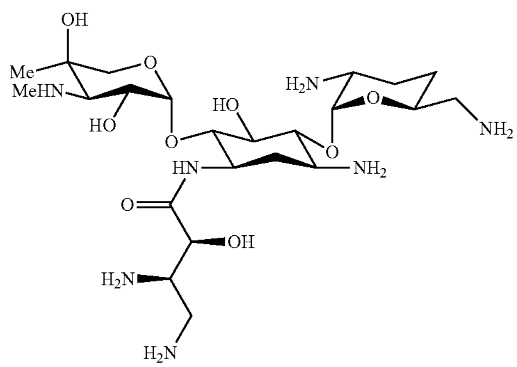 |
| 4 | 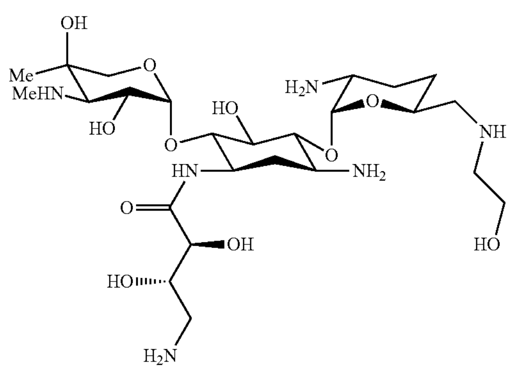 |
| 5 | 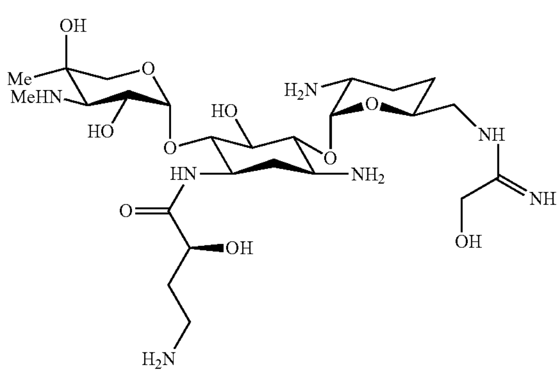 |

TABLE 1-continued
| Example | Structure |
|---|---|
| 6 | 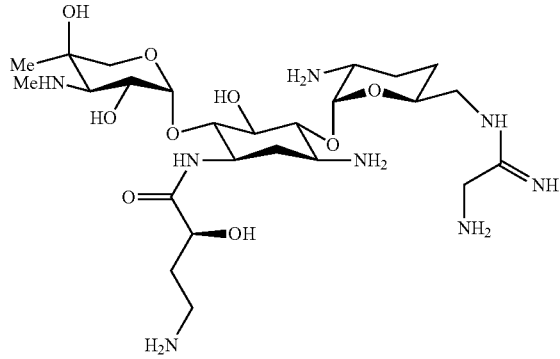 |
| 7 | 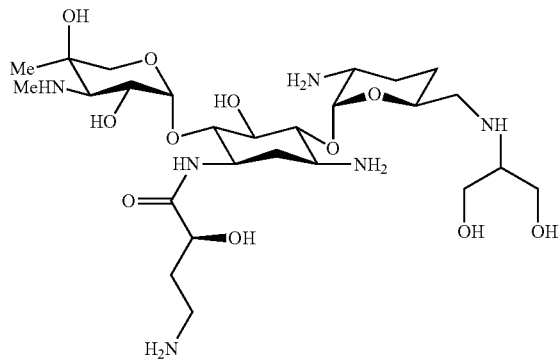 |
| 8 | 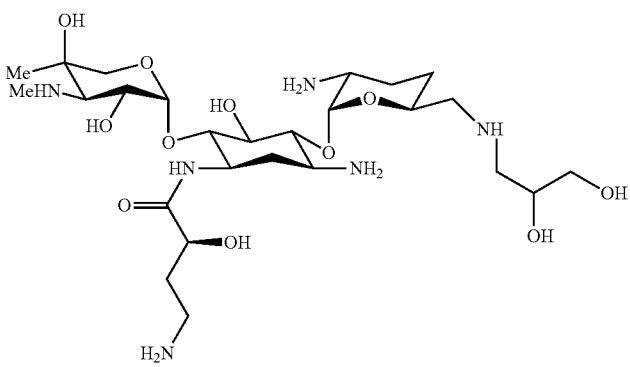 |
| 9 | 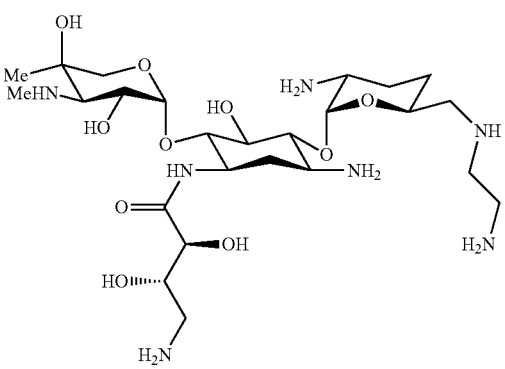 |

TABLE 1-continued

| Example | Structure |
|---|---|
| 10 | (chemical structure) |
| 11 | (chemical structure) |
| 12 | (chemical structure) |
| 13 | (chemical structure) |

TABLE 1-continued

| Example | Structure |
|---|---|
| 14 | (structure) |
| 15 | (structure) |
| 16 | (structure) |
| 17 | (structure) |

TABLE 1-continued

| Example | Structure |
|---------|-----------|
| 18 | 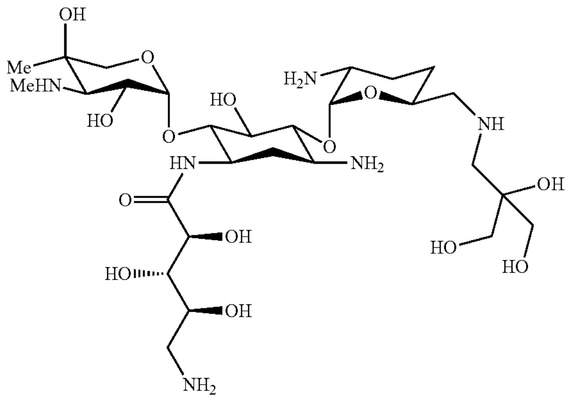 |
| 19 | 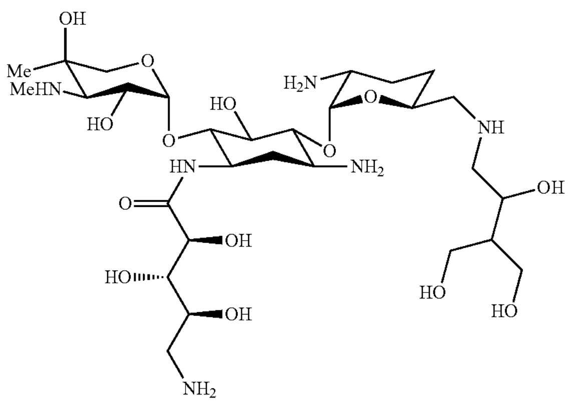 |
| 20 | 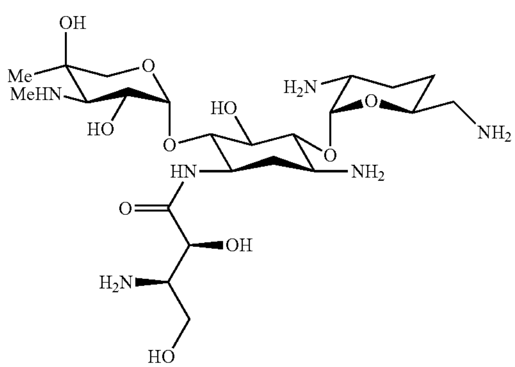 |
| 21 | 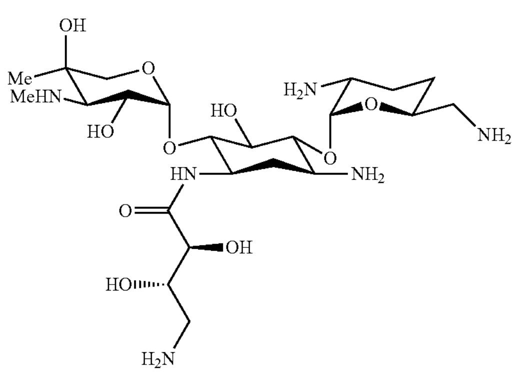 |

TABLE 1-continued

| Example | Structure |
|---|---|
| 22 | 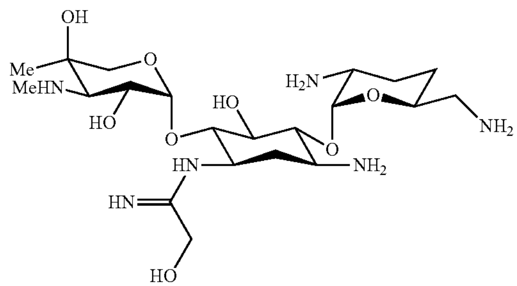 |
| 23 | 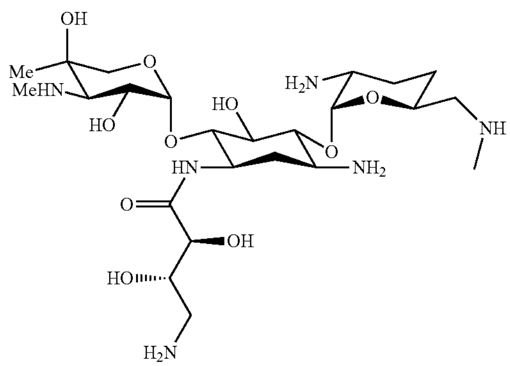 |
| 24 | 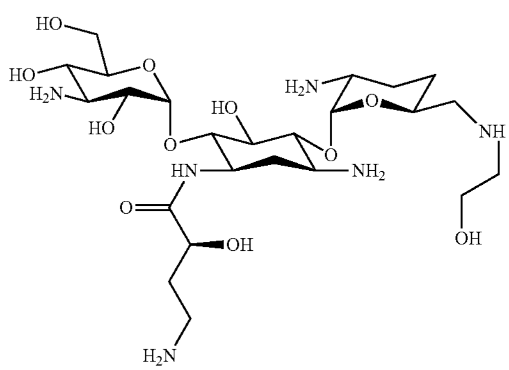 |
| 25 | 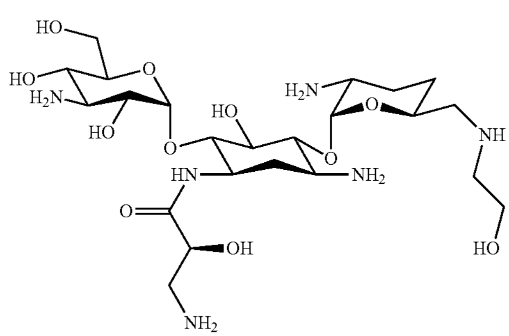 |

TABLE 1-continued
| Example | Structure |
|---|---|
| 26 | 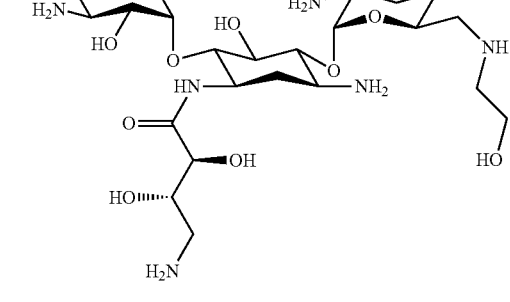 |
| 27 | 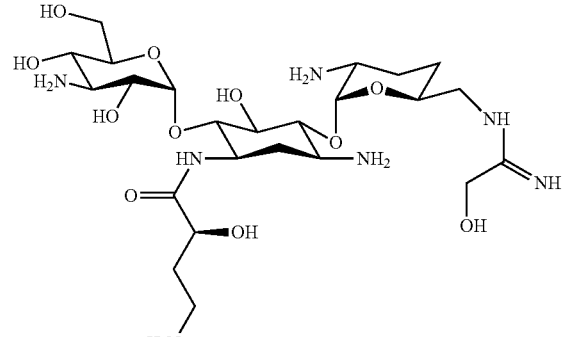 |
| 28 | 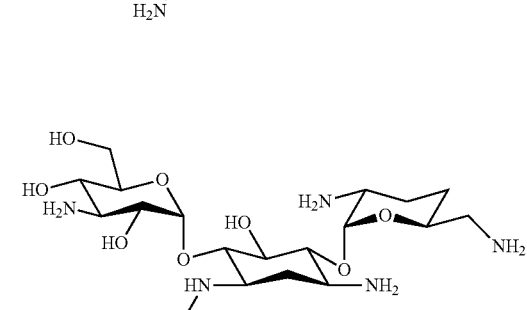 |
| 29 | 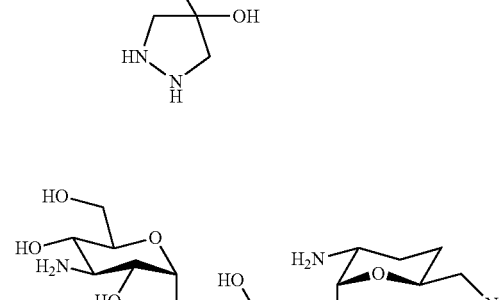 |

TABLE 1-continued
| Example | Structure |
|---|---|
| 30 | 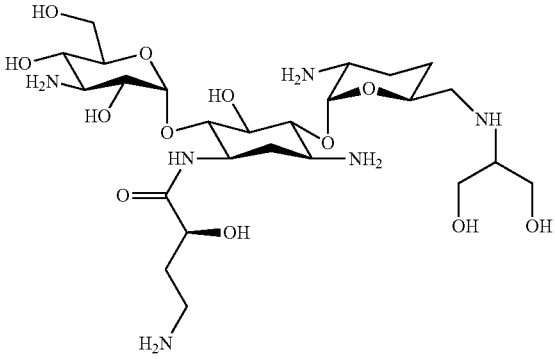 |
| 31 | 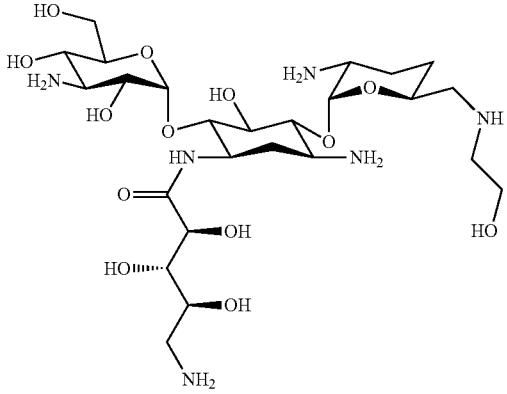 |
| 32 | 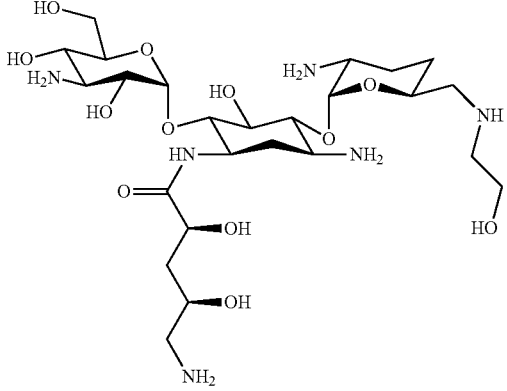 |
| 33 | 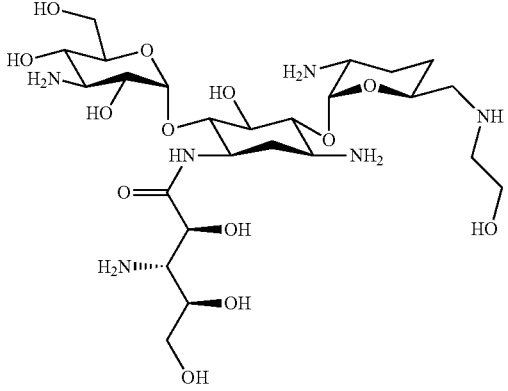 |

TABLE 1-continued

| Example | Structure |
|---|---|
| 34 | 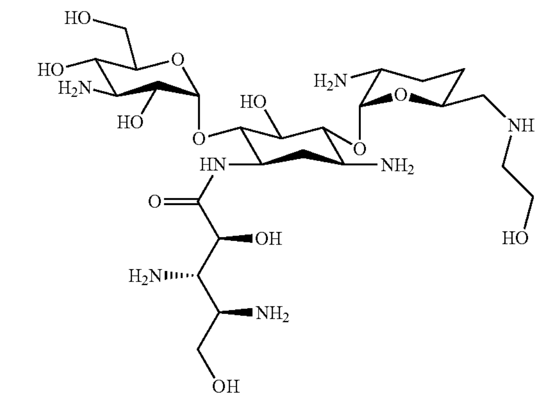 |
| 35 | 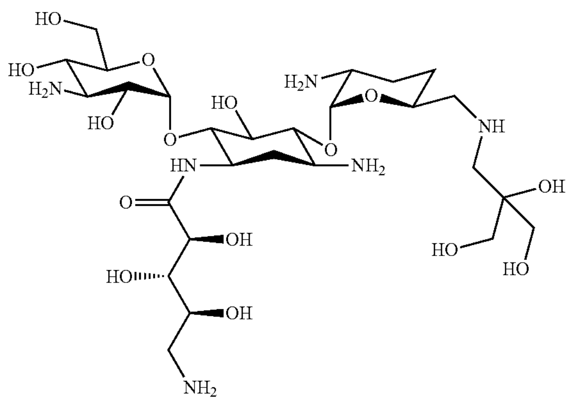 |
| 36 | 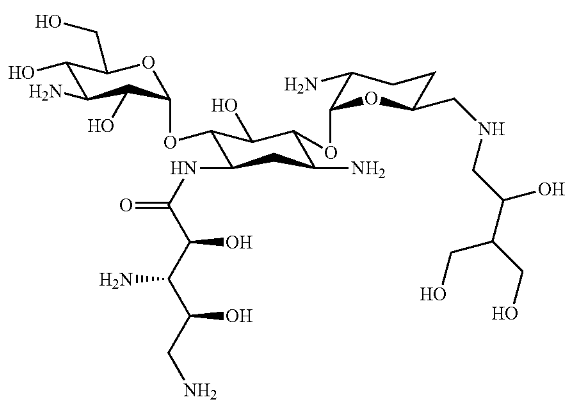 |
| 37 | 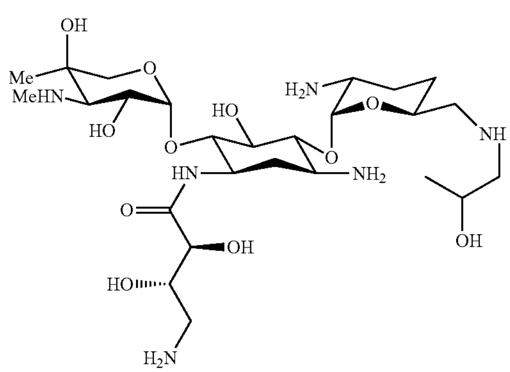 |

TABLE 1-continued

| Example | Structure |
|---|---|
| 38 | 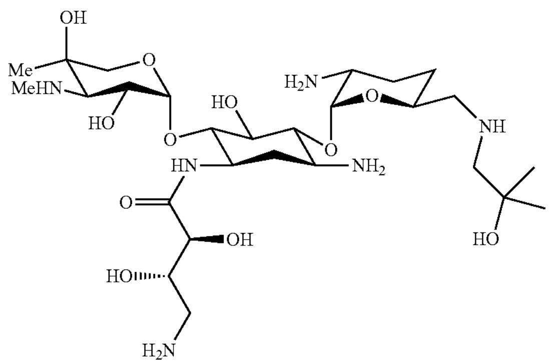 |
| 39 | 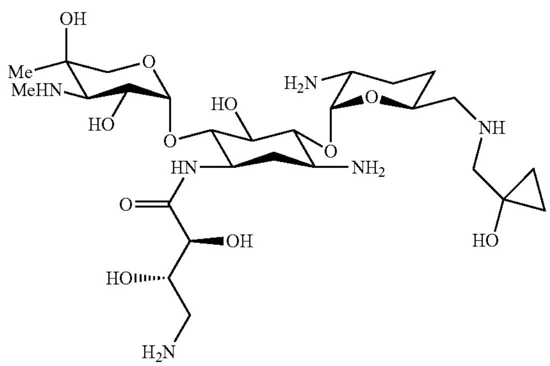 |
| 40 | 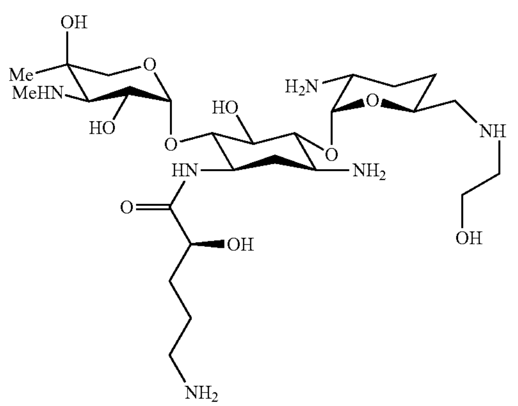 |
| 41 | 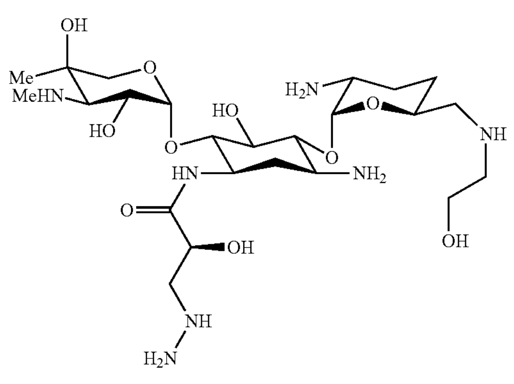 |

TABLE 1-continued

| Example | Structure |
|---------|-----------|
| 42 | 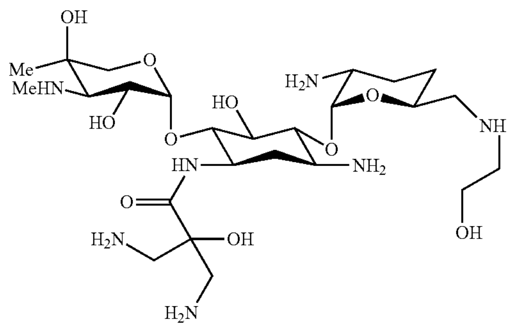 |
| 43 | 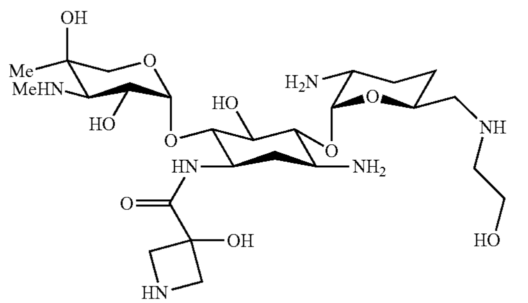 |
| 44 | 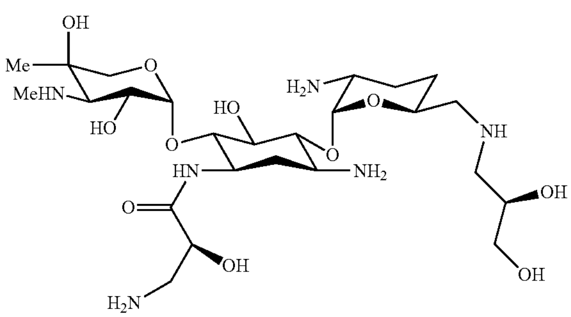 |
| 45 | 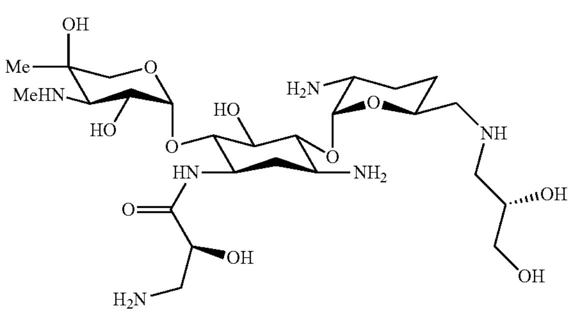 |
| 46 | 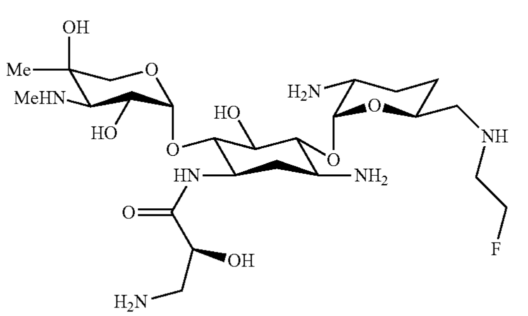 |

TABLE 1-continued

| Example | Structure |
|---------|-----------|
| 47 | 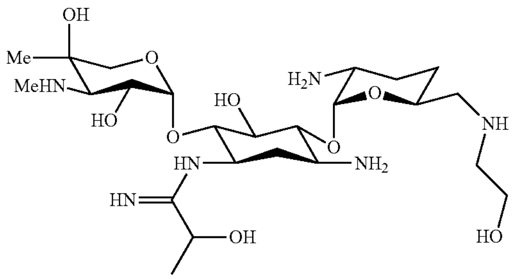 |
| 48 | 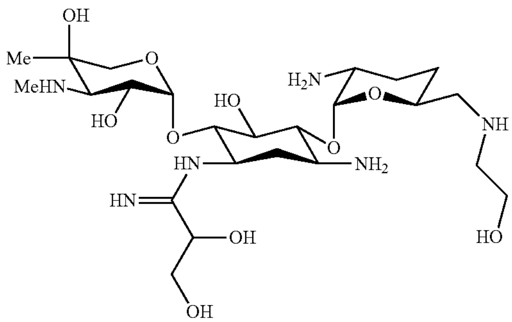 |
| 49 | 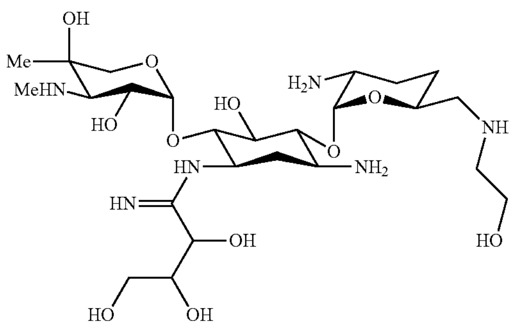 |
| 50 | 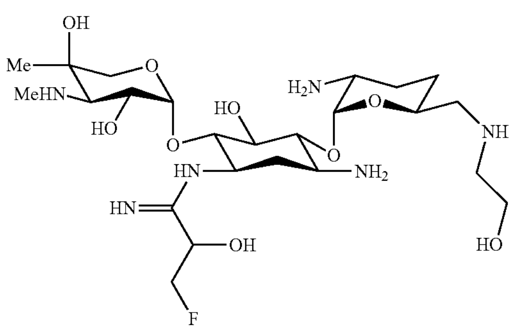 |
| 51 | 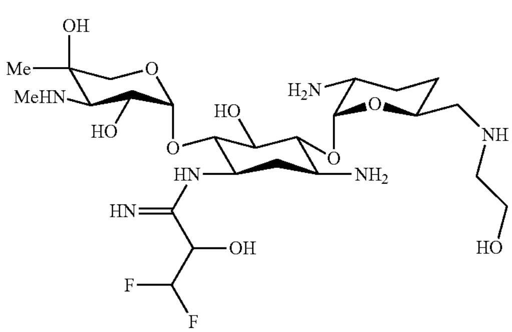 |

TABLE 1-continued

| Example | Structure |
|---|---|
| 52 | (chemical structure) |
| 53 | (chemical structure) |
| 54 | (chemical structure) |
| 55 | (chemical structure) |
| 56 | (chemical structure) |

TABLE 1-continued

| Example | Structure |
|---|---|
| 57 | 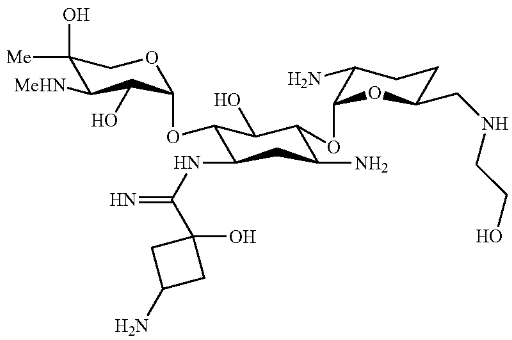 |
| 58 | 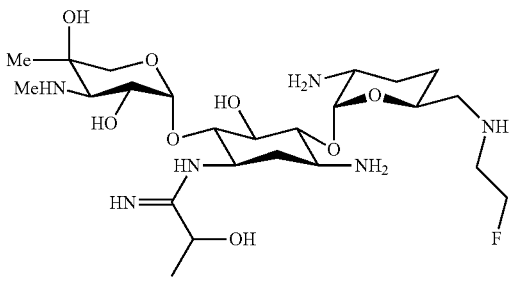 |
| 59 | 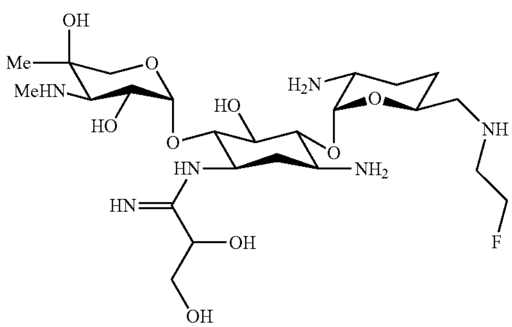 |
| 60 | 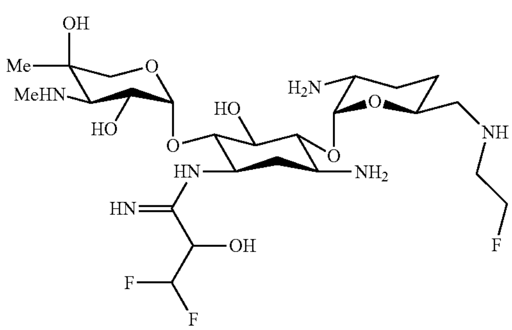 |
| 61 | 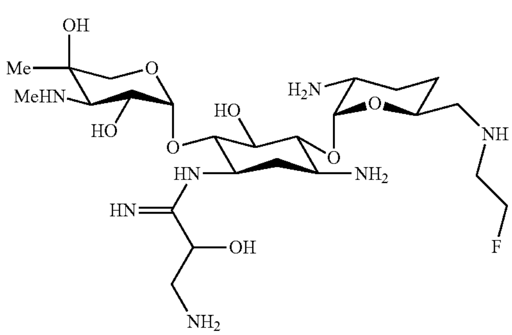 |

TABLE 1-continued

| Example | Structure |
|---|---|
| 62 | 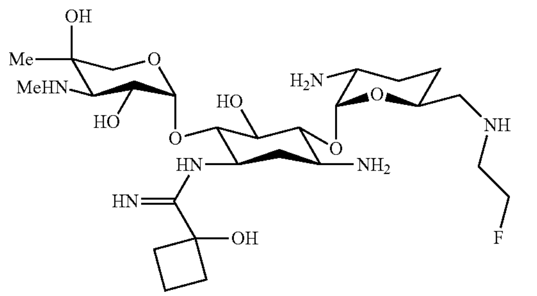 |
| 63 | 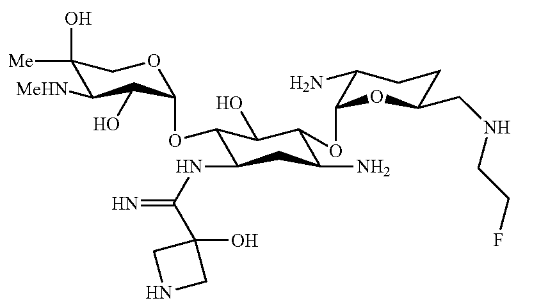 |
| 64 | 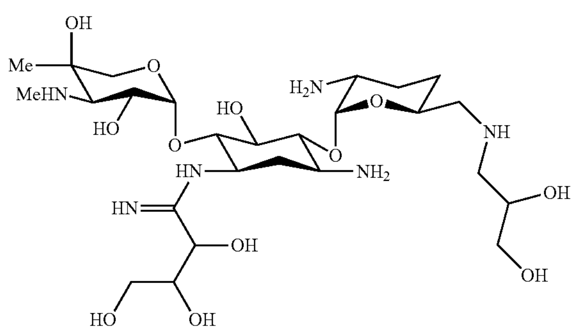 |
| 65 | 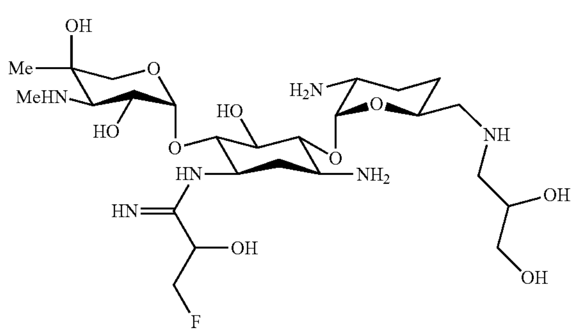 |

TABLE 1-continued
| Example | Structure |
|---|---|
| 66 | 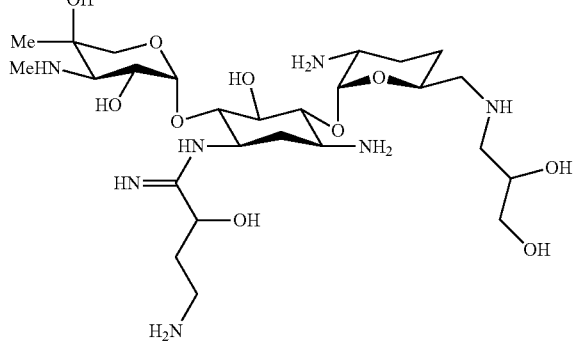 |
| 67 | 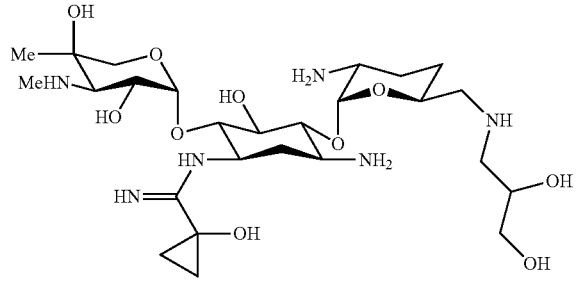 |
| 68 | 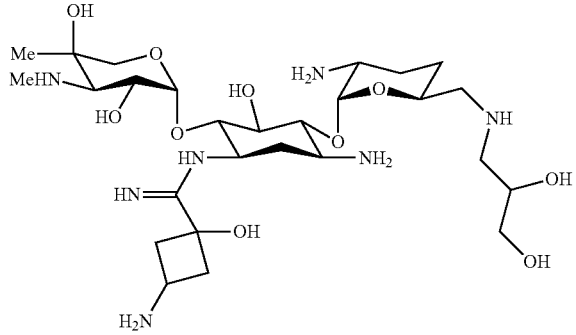 |
| 69 | 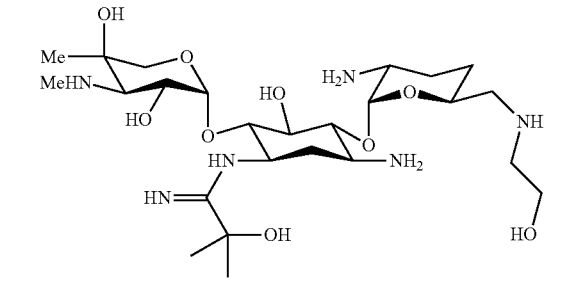 |
| 70 | 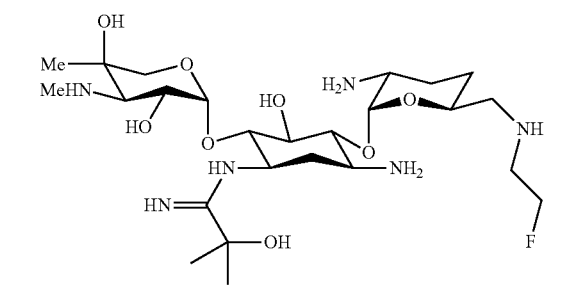 |

TABLE 1-continued

| Example | Structure |
|---|---|
| 71 | 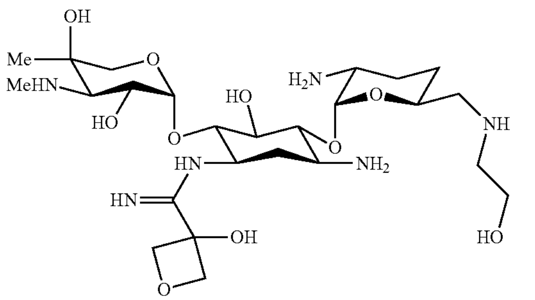 |
| 72 | 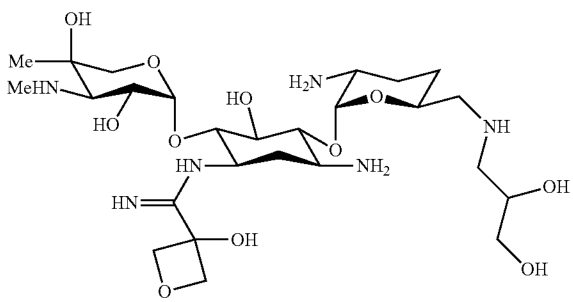 |
| 73 | 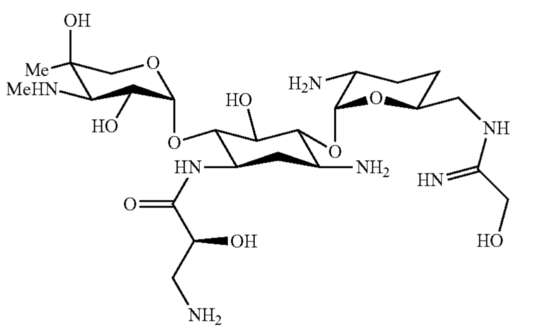 |
| 74 | 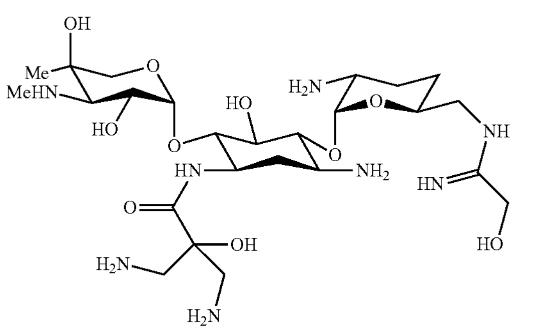 |
| 75 | 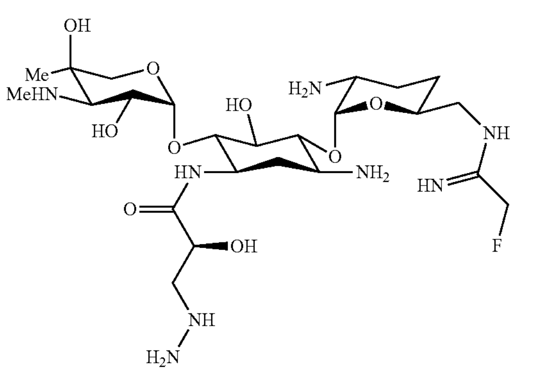 |

TABLE 1-continued

| Example | Structure |
|---|---|
| 76 | 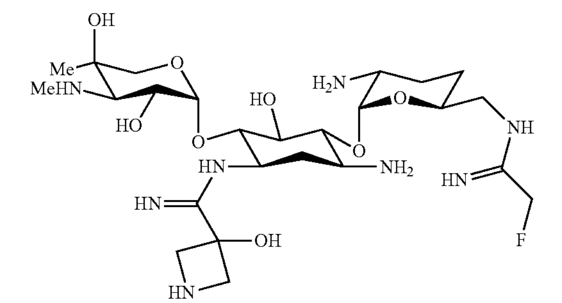 |
| 77 | 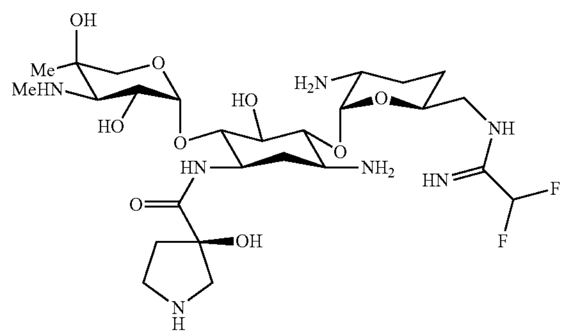 |
| 78 | 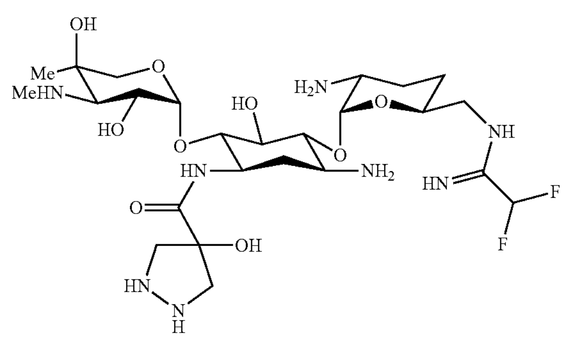 |
| 79 | 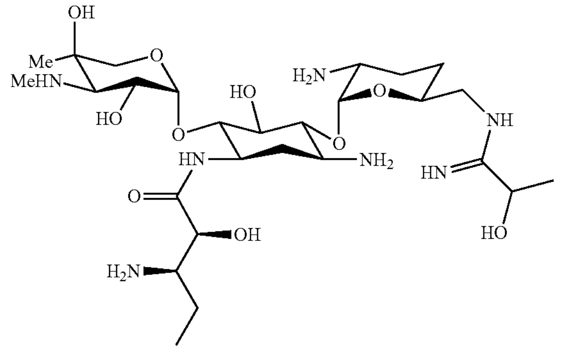 |

TABLE 1-continued

| Example | Structure |
|---|---|
| 80 | 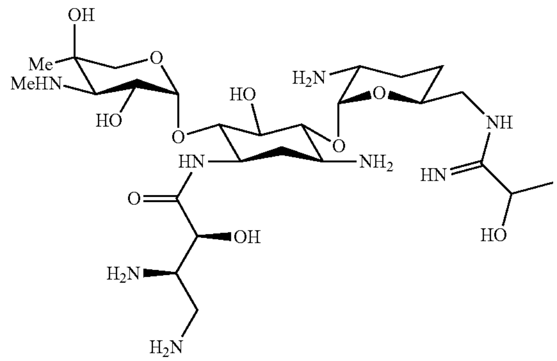 |
| 81 | 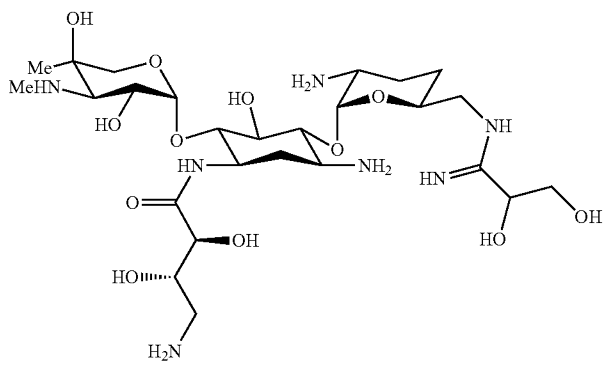 |
| 82 | 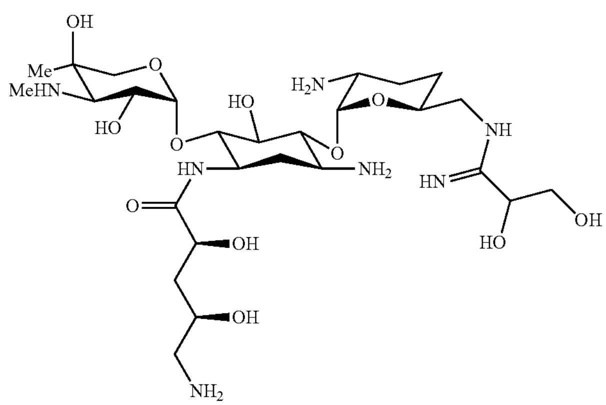 |
| 83 | 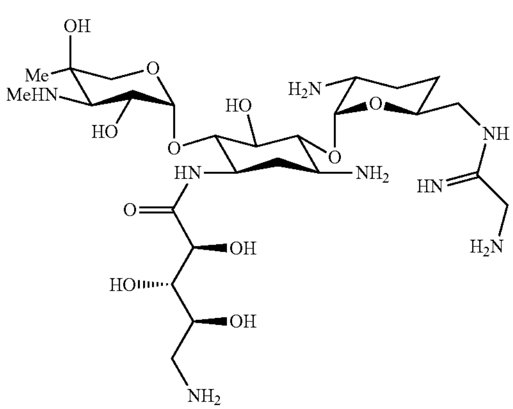 |

TABLE 1-continued

| Example | Structure |
|---|---|
| 84 | 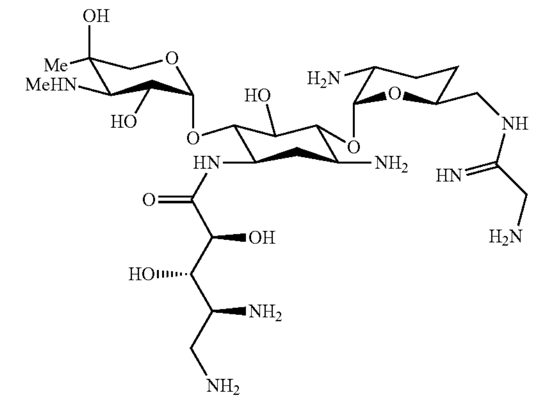 |
| 85 | 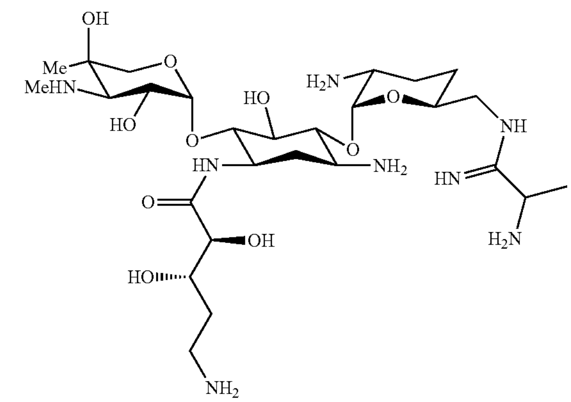 |
| 86 | 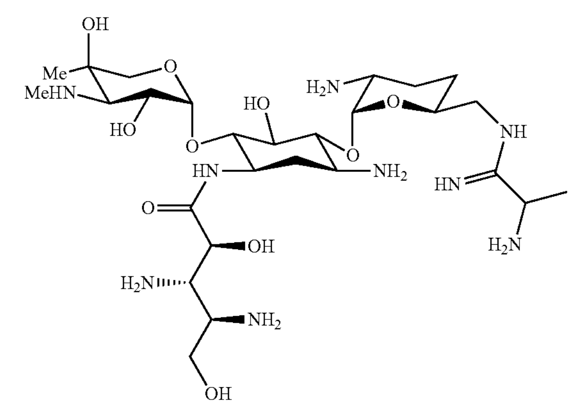 |
| 87 | 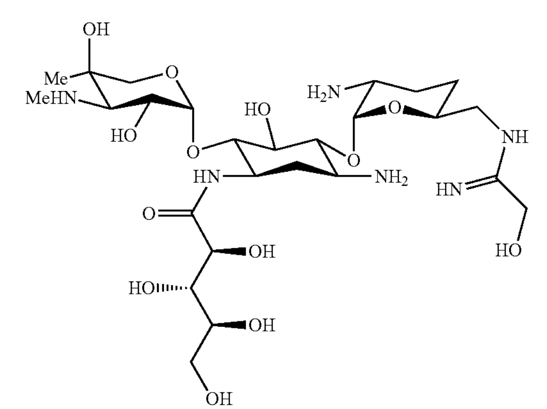 |

TABLE 1-continued

| Example | Structure |
|---|---|
| 88 | 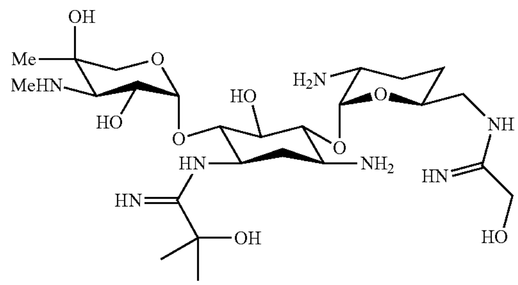 |
| 89 | 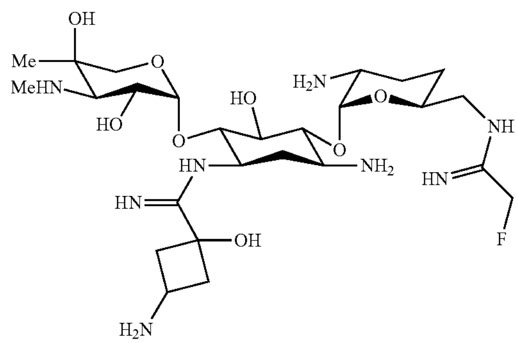 |
| 90 | 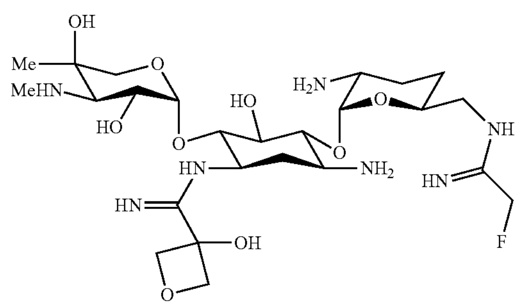 |
| 91 | 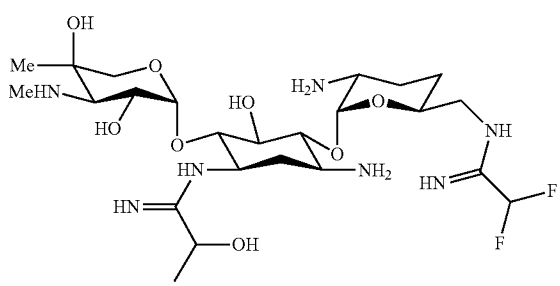 |
| 92 | 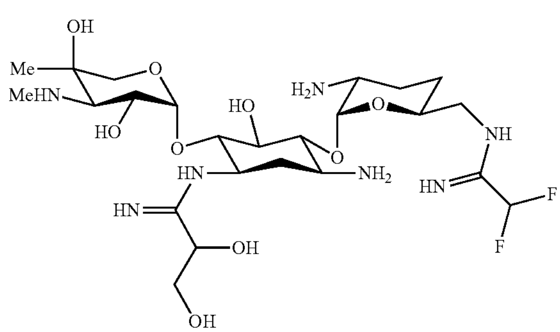 |

TABLE 1-continued

| Example | Structure |
| --- | --- |
| 93 | 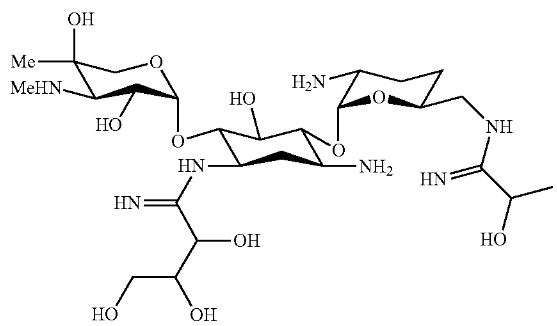 |
| 94 | 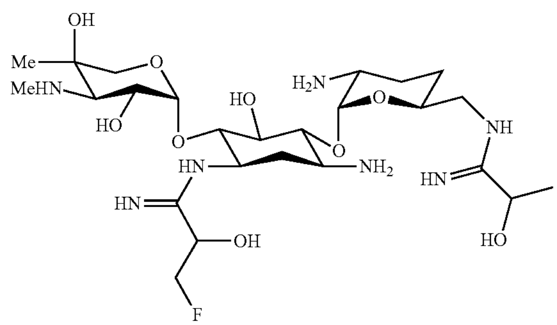 |
| 95 | 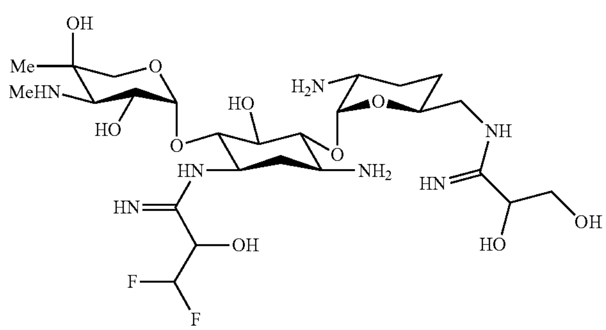 |
| 96 | 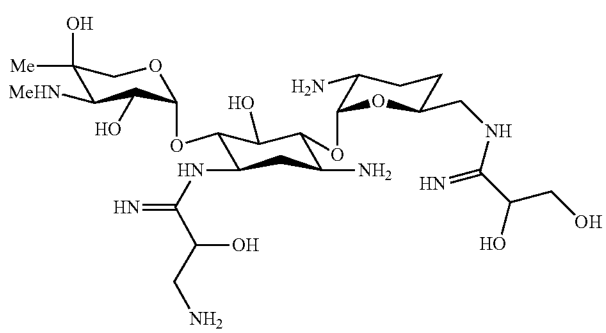 |

TABLE 1-continued

| Example | Structure |
|---|---|
| 97 | (chemical structure) |
| 98 | (chemical structure) |
| 99 | (chemical structure) |
| 100 | (chemical structure) |
| 101 | (chemical structure) |

TABLE 1-continued

| Example | Structure |
|---|---|
| 102 | 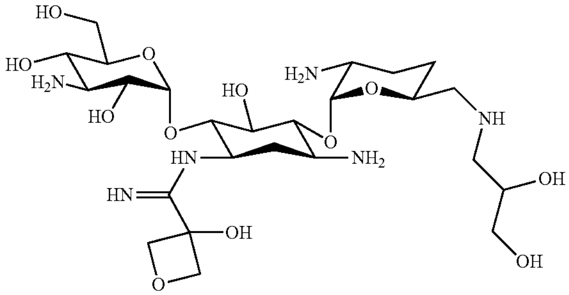 |
| 103 | 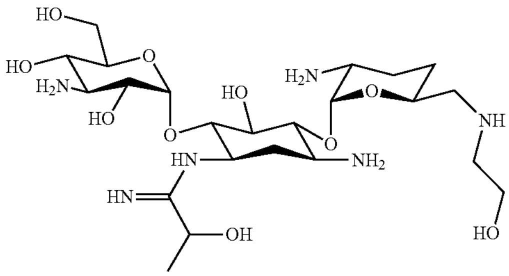 |
| 104 | 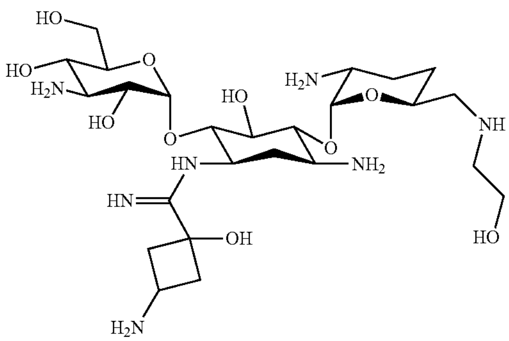 |
| 105 | 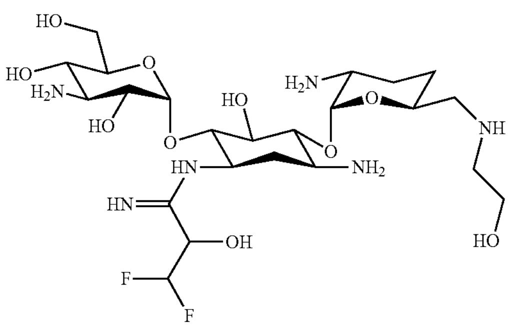 |
| 106 | 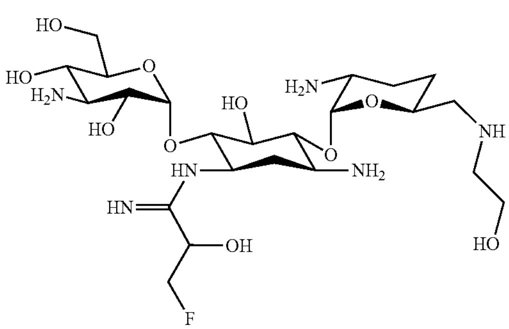 |

TABLE 1-continued

| Example | Structure |
|---------|-----------|
| 107 | 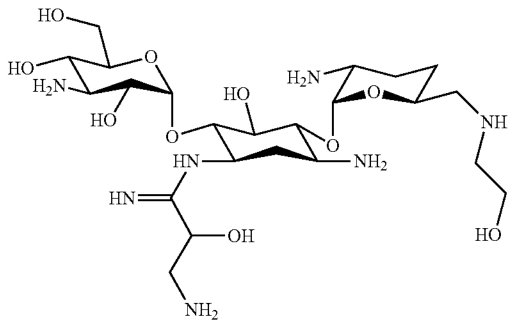 |
| 108 | 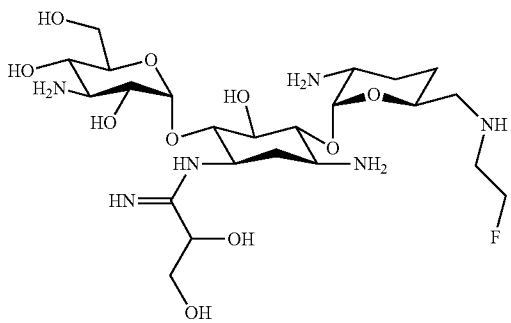 |
| 109 | 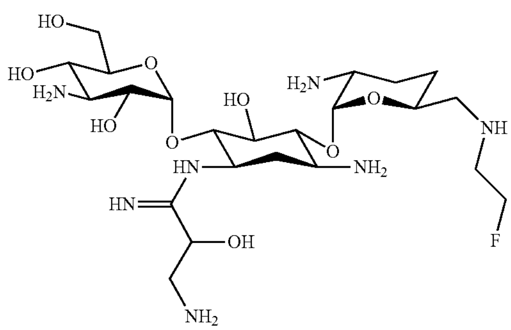 |
| 110 | 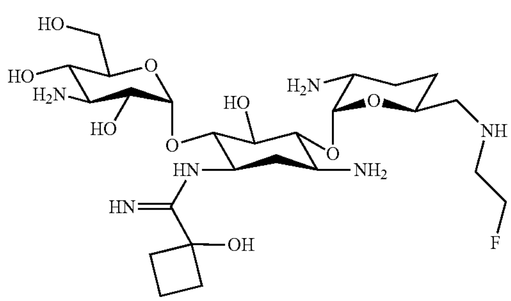 |
| 111 | 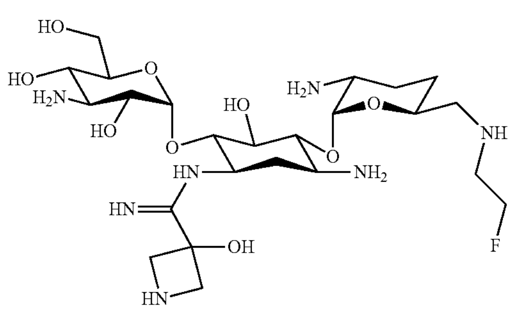 |

TABLE 1-continued

| Example | Structure |
|---|---|
| 112 | (structure) |
| 113 | (structure) |
| 114 | (structure) |
| 115 | (structure) |
| 116 | (structure) |

TABLE 1-continued

| Example | Structure |
| --- | --- |
| 117 | 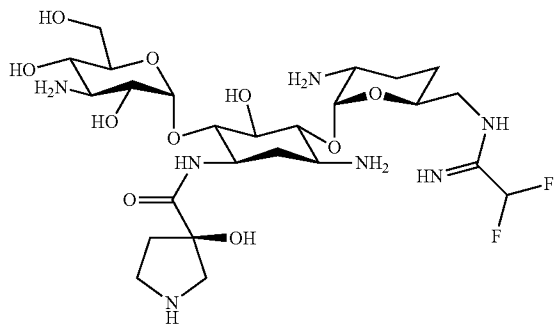 |
| 118 | 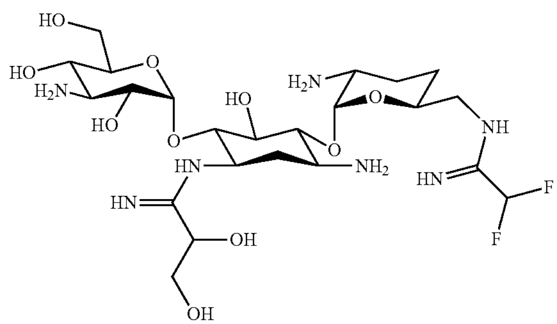 |
| 119 | 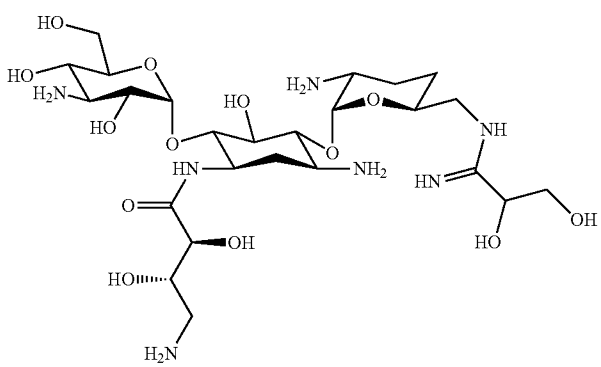 |
| 120 | 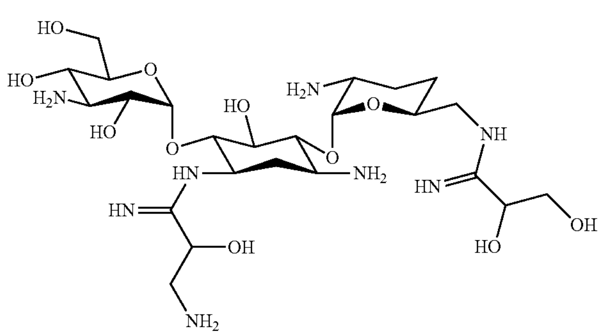 |

TABLE 1-continued
| Example | Structure |
|---|---|
| 121 | 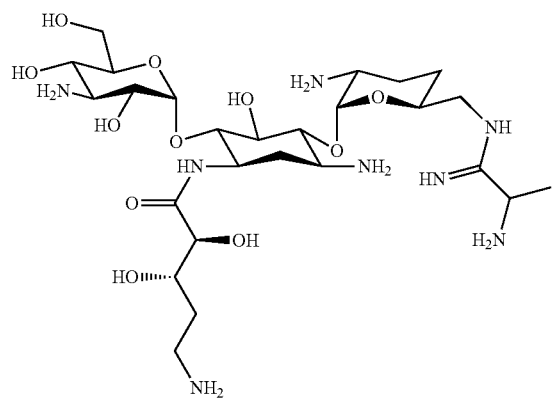 |
| 122 | 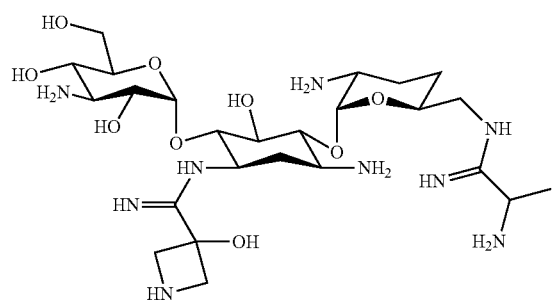 |
| 123 | 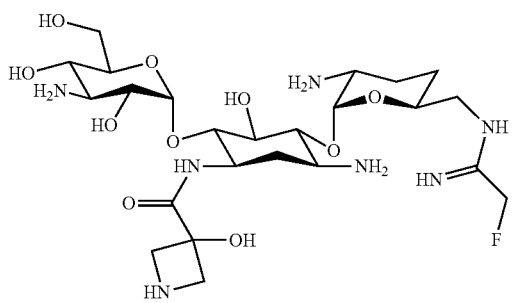 |
| 124 | 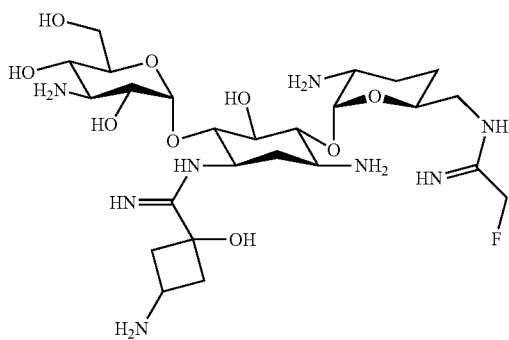 |

TABLE 1-continued
| Example | Structure |
|---|---|
| 125 | 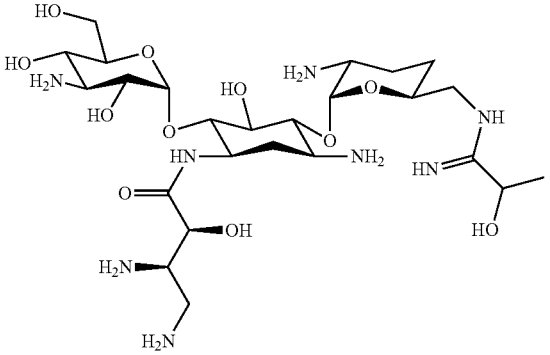 |
| 126 | 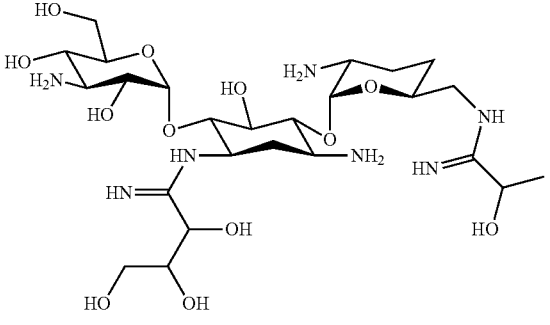 |
| 127 | 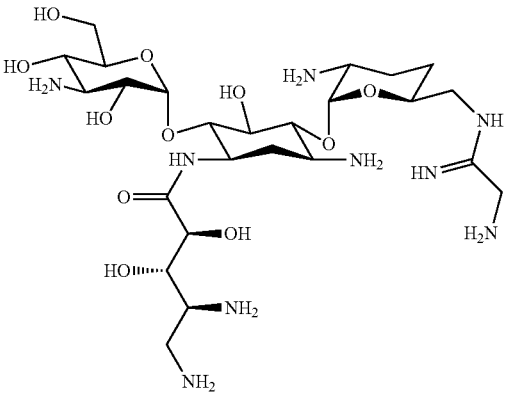 |
| 128 | 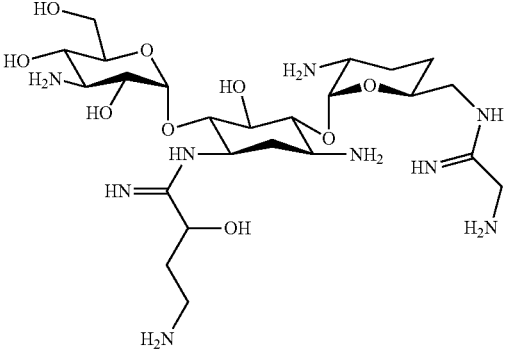 |

TABLE 1-continued
| Example | Structure |
|---|---|
| 129 | 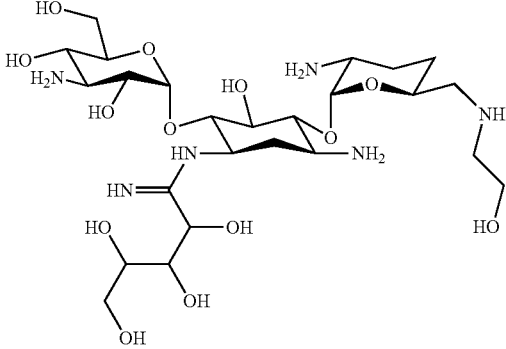 |
| 130 | 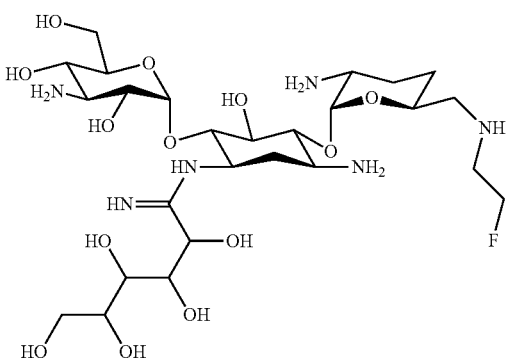 |
| 131 | 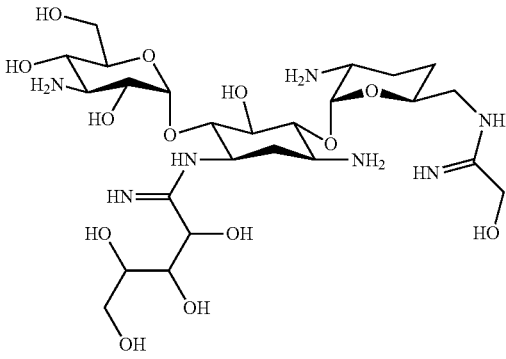 |
| 132 | 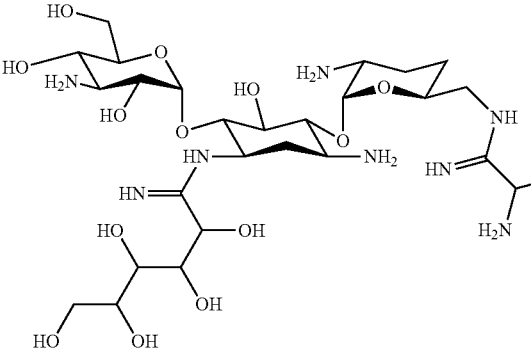 |

TABLE 1-continued
| Example | Structure |
|---|---|
| 133 | 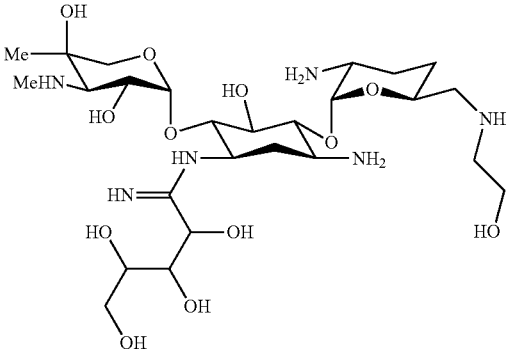 |
| 134 | 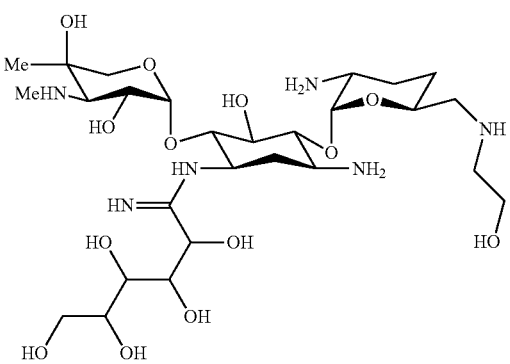 |
| 135 | 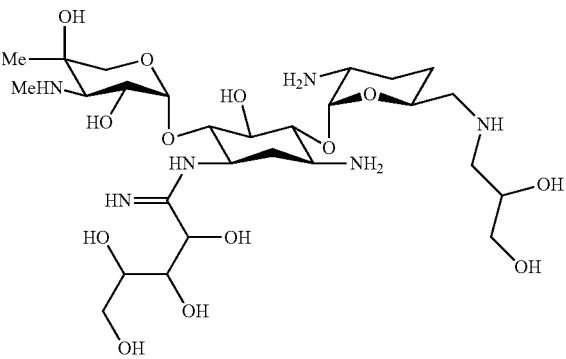 |
| 136 | 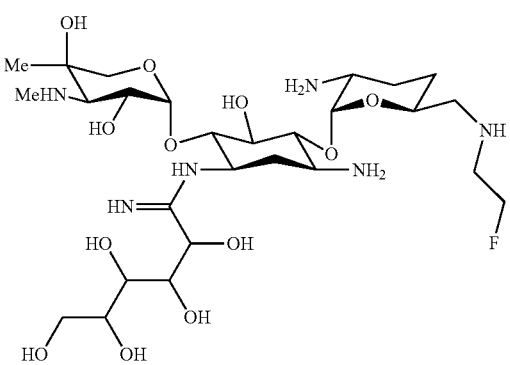 |

TABLE 1-continued
| Example | Structure |
|---|---|
| 137 | 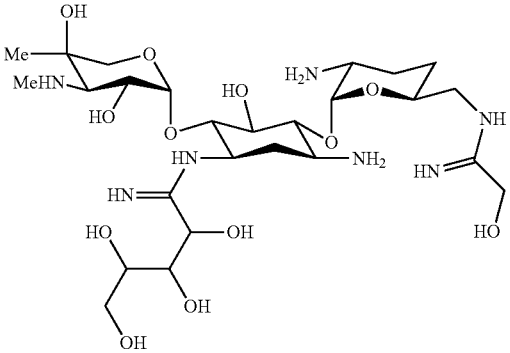 |
| 138 | 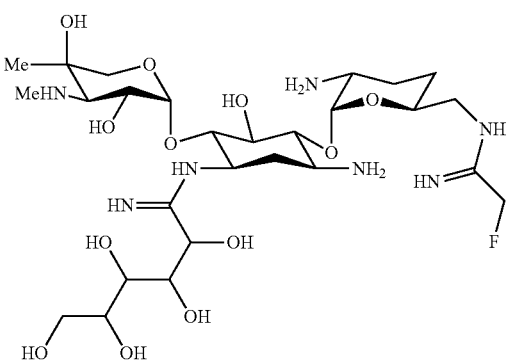 |
| 139 | 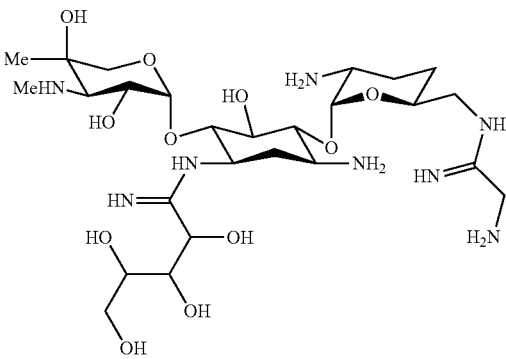 |
| 140 | 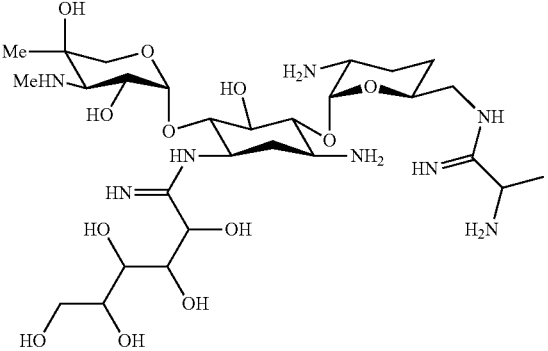 |

Example 21

Comparative Microbiological Activity of the Test Compounds Against QC Strains To compare microbiological activity of the test compounds, minimum inhibitory concentrations (MIC.s) were determined. Antibiotic MICs were obtained using the broth microdilution method according to Clinical and Laboratory Standards Institute (CLSI) approved guidelines (Methods for dilution antimicrobial susceptibility tests for bacteria that grow aerobically; approved standard—7th ed. CLSI document M7-A7. Clinical and Laboratory Standards Institute, Wayne, Pa., incorporated herein by reference in its entirety). Antibiotics were dissolved as specified by CLSI (Performance standards for antimicrobial susceptibility testing; Seventeenth informational supplement. CLSI document M100-S17. Clinical and Laboratory Standards Institute, Wayne, Pa., incorporated herein by reference in its entirety), and were serially diluted 2-fold in cation adjusted Mueller Hinton Broth (CaMHB) at 2× concentration. Bacterial inoculums were prepared in CaMHB by suspension of a colony from an agar plate that was prepared the previous day to obtain a final concentration of $5\times10^5$ CFU/ml. The plates were incubated for 18 hours at 35° C. The MIC was defined as the lowest concentration of test compounds that resulted in no visible bacteria growth. MIC.s were determined by reading the turbidity of plate wells using a SpectraMax Plus384 plate reader (Molecular Devices, Sunnyvale, Calif., USA) at 600 nm and were confirmed by visual inspection.

Compounds were evaluated using a panel of strains that did not possess known aminoglycoside resistance mechanisms. This panel contained ATCC strains of *Escherichia coli* (ATCC 25922), *Staphylococcus aureus* (ATCC 29213), *Klebsiella pneumonia* (ATCC 43816), *Pseudomonas aeruginosa* (ATCC 27853) and *Acinetobacter baumannii* (ATCC 19606). These strains are routinely used as a reference to provide the quality control for antibiotic ranges. Results are summarized in TABLE 2.

TABLE 2

| | Compound MIC on Bacterial Strains (µg/ml) | | | | |
|---|---|---|---|---|---|
| Compound | E. coli ATCC 25922 | S. aureus ATCC 29213 | K. pneumonia ATCC 43816 | P. aeruginosa ATCC 27853 | A. baumannii ATCC 19606 |
| Amikacin | B | B | A | B | B |
| Gentamicin | A | A | A | A | C |
| Netilmicin | A | A | A | B | C |
| Tobramycin | A | A | A | A | B |
| 1 | A | A | A | B | C |
| 2 | A | A | A | B | C |
| 3 | A | A | A | A | C |
| 8 | A | A | A | B | C |
| 20 | B | B | A | B | C |
| 21 | A | A | A | A | C |
| 22 | B | A | A | A | C |
| 23 | A | A | A | B | C |
| 40 | B | B | A | C | C |
| 41 | B | B | B | C | C |
| 43 | A | A | A | B | C |
| 44 | A | A | A | B | C |
| 45 | A | B | A | B | C |
| 46 | A | A | A | B | C |

A = MIC of 1 µg/ml or less.
B = MIC of greater than 1 µg/ml to 8 µg/ml.
C = MIC of greater than 8 µg/ml

Example 22

Activity of the Test Compounds Against Strains with Known Resistance Mechanisms Activity of the test compounds was determined using QC strains and strains with known aminoglycoside resistance mechanisms (TABLE 3). This specific panel contained strains expressing enzymes that covalently modify N2", N3 and N3' positions. As expected none of the compounds were susceptible to modifications by aminoglycoside phosphotransferases at N3' (like gentamicin C1a, all of the tested compounds lack an OH group at t N3'). Several gentamicin C1a derivatives with novel N1 substitutions were resistant to modifications by N2" and N3 modifying enzymes.

The panel also contained a strain expressing ribosomal RNA methylase, RmtB. RmtB was previously shown to confer high level resistance to 2-deoxystreptamine-based aminoglycosides. While RmtB conferred 32- to >64-fold increased resistance to all commercial aminoglycosides and the majority of novel derivatives, RmtB conferred only 8-fold resistance to compound 28.

TABLE 3

Compound MIC on Bacterial Strains (μg/ml)

| Compound | ECM6000 ATCC 25922 | ECM6010 ant(2")-I | ECM6009 aac(3)-II | ECM6003 rmtB | EC1002 aph(3')-IV | ECM6011 aph(3')-I | ECM6006 aph(3')-III |
|---|---|---|---|---|---|---|---|
| Amikacin | B | B | A | C | C | B | B |
| Gentamicin | A | C | C | C | B | B | B |
| Netilmicin | A | A | C | C | A | A | A |
| Tobramycin | A | C | C | C | A | B | B |
| Gentamicin C1a | A | C | C | C | A | B | B |
| Micronomicin | A | C | C | C | A | B | B |
| 1 | A | A | A | C | A | A | B |
| 2 | A | A | A | C | B | A | A |
| 4 | B | B | A | C | B | A | B |
| 8 | A | A | A | C | A | A | B |
| 20 | B | B | A | C | B | B | B |
| 21 | B | A | A | B | B | B | B |
| 22 | B | C | C | C | B | B | B |
| 23 | B | B | B | B | B | B | B |
| 40 | B | A | A | C | B | A | B |
| 41 | B | B | C | C | B | B | C |
| 43 | A | A | B | C | B | A | A |
| 44 | A | A | A | C | A | A | A |
| 45 | A | A | A | C | B | A | A |
| 46 | A | A | A | C | A | A | A |

A = MIC of 1 μg/ml or less.
B = MIC of greater than 1 μg/ml to 8 μg/ml.
C = MIC of greater than 8 μg/ml.

Example 23

Activity of the Test Compounds Against Strains Expressing N6' Modifying Enzymes

Activity of the test compounds was determined against a panel of strains expressing various acetyltransferases capable of modifying the N6' position (TABLE 4 and TABLE 5). While methyl modification at N6' provided resistance to some AAC6' enzymes (aac6'-Ib from *P. aeruginosa*), more bulky modifications were required to confer resistance to AAC6' enzymes from *E. coli* and *A. baumannii*. In general, di-substituted derivatives showed the highest resistance towards N6' modifying enzymes.

TABLE 4

Compound MIC on Bacterial Strains (μg/ml)

| | Escherichia coli | | | Acinetobacter baumannii | |
|---|---|---|---|---|---|
| Compound | ECM6000 ATCC 25922 | EC1001 acc(6')-Ib | ECM6007 aac(6') + aph(2") | ACM1005 ATCC 19004 | ACM1006 acc(6')-Ib |
| Amikacin | B | C | A | A | B |
| Gentamicin | A | B | B | A | B |
| Netilmicin | A | C | A | B | C |
| Tobramycin | A | C | C | A | C |
| Gentamicin C1a | A | C | B | A | C |
| Micronomicin | A | C | B | A | C |
| 1 | A | A | A | A | A |
| 2 | A | A | A | B | B |
| 3 | B | C | A | B | B |
| 8 | A | A | A | B | B |
| 21 | B | C | A | B | B |
| 22 | B | C | B | B | C |
| 23 | B | B | A | B | B |
| 40 | B | B | A | B | B |
| 41 | B | C | B | ND | ND |
| 43 | A | B | A | B | A |
| 44 | A | A | A | B | B |
| 45 | A | B | A | B | B |
| 46 | A | B | A | B | B |

A = MIC of 1 μg/ml or less.
B = MIC of greater than 1 μg/ml to 8 μg/ml.
C = MIC of greater than 8 μg/ml.
ND = not determined

TABLE 5

| | Compound MIC on Bacterial Strains (µg/ml) | | | | |
|---|---|---|---|---|---|
| | Pseudomonas aeruginosa | | | Staphylococcus aureus | |
| Compound | PAM3034 ATCC 27853 | PAM3072 aac(6')-II | PAM3073 aac(6')-I | SAM1000 ATCC 29213 | Sa 287 aac(6') + aph(2'') |
| Amikacin | B | B | C | B | C |
| Gentamicin | A | C | B | A | C |
| Netilmicin | B | C | C | A | ND |
| Tobramycin | A | C | C | A | C |
| Gentamicin C1a | A | C | B | A | C |
| Amikacin | B | C | B | A | C |
| 1 | B | C | B | A | B |
| 2 | B | C | B | A | A |
| 4 | B | C | B | B | B |
| 8 | B | C | B | A | ND |
| 20 | B | C | C | B | ND |
| 21 | B | C | B | A | B |
| 22 | B | C | B | A | ND |
| 23 | B | C | B | B | B |
| 40 | C | C | B | B | ND |
| 41 | C | C | C | B | ND |
| 43 | B | C | B | A | ND |
| 44 | B | C | B | A | ND |
| 45 | B | C | B | B | ND |
| 46 | B | C | B | A | ND |

A = MIC of 1 µg/ml or less.
B = MIC of greater than 1 µg/ml to 8 µg/ml.
C = MIC of greater than 8 µg/ml.
ND = not determined.

Example 24

Nephrotoxicity of Test Compounds in Rats

The nephrotoxicity of test compounds was determined in rats after 7 and 14 days of once daily subcutaneous doses; results are summarized in TABLE 6.

TABLE 6

| Compound | Dose (mg/kg/day) | Histopathology Results | |
|---|---|---|---|
| | | After 7 days of Dosing | After 14 days of Dosing |
| Gentamicin C1a | 300 | Severe Nephrosis | 4/4 Died |
| Gentamicin C1a | 100 | No Change | Mild to Moderate Nephrosis |
| Gentamicin C1a | 30 | No Change | Minimal Nephrosis |
| 1 | 100 | Severe Nephrosis | 4/4 Died |
| 1 | 30 | Mild Nephrosis | Moderate to Severe Nephrosis |
| 1 | 10 | No Change | No Change |
| 2 | 100 | Mild Tubular Eosinophila | No Deaths; Moderate to Severe Nephrosis |
| 2 | 30 | Minimal Tubular Eosinophilia; 3/4 Rats | Minimal to Mild Dilatation |
| 2 | 10 | Minimal Tubular Eosinophilia; 1/4 Rats | No change |
| 44 | 60 | No change | Minimal Hyaline-droplet degeneration |
| 44 | 30 | No change | No change |

Example 25

Activity of the Test Compounds 44 and 45 Against Representative Strains of Various Bacteria Table 7 shows MICs of 44 and 45 for representative strains of various bacteria, and Table 8 shows MICs of 44 and 45 vs. strains expressing various aminoglycoside modifying enzymes. The data indicate that 44 is frequently 2- to 4-fold more active than 45.

TABLE 7

| Organism | Strain | Alternative name/Description | 44 | 45 |
|---|---|---|---|---|
| Acinetobacter baumannii | ACM1003 | ATCC 19606 | C | C |
| Acinetobacter baumannii | ACM1005 | ATCC 19004 | B | B |
| Citrobacter freundii | CFM1000 | ATCC 8090 | A | A |
| Enterobacter aerogenes | EAM1000 | ATCC 13048 | A | B |
| Enterobacter cloacae | ECLM1000 | ATCC 13047 | A | A |
| Escherichia coli | ECM6025 | ATCC 25922 | A | A |
| Klebsiella pneumoniae | KPM1001 | ATCC 43816 | A | A |
| Pseudomonas aeruginosa | PAM3034 | ATCC 27853 | B | B |
| Staphylococcus aureus | SAM1000 | ATCC 29213 | A | B |
| Staphylococcus aureus | SAM1001 | ATCC 25923 | A | A |
| Pseudomonas aeruginosa | PAM2900 | PAM2859/pXY | C | C |
| Pseudomonas aeruginosa | PAM2859 | multiple pumps deleted | A | A |

A = MIC of 1 µg/ml or less.
B = MIC of greater than 1 µg/ml to 8 µg/ml.
C = MIC of greater than 8 µg/ml.
D = not determined.

TABLE 8

| Organism | Strain | Gene for AME | 44 | 45 |
|---|---|---|---|---|
| Acinetobacter baumannii | ACM1006 | aac(6')-Ib | B | B |
| Acinetobacter baumannii | ACM1008 | aac(3)-Ia | B | B |
| Acinetobacter spp. | AB1051 | aph(3')VI | B | B |
| Escherichia coli | EC1001 | aac(6')-Ib | A | B |
| Escherichia coli | EC1003 | aac(3)I | A | A |
| Escherichia coli | ECM6003 | rmtB | C | C |
| Escherichia coli | ECM6004 | aac(2') | A | A |
| Escherichia coli | ECM6005 | aac(3)-II, aph(3')-II | A | A |
| Escherichia coli | ECM6006 | aph(3')-III | B | B |
| Escherichia coli | ECM6007 | aac(6') + aph(2'') | A | A |
| Escherichia coli | ECM6008 | aac(3)-I, ant(3'') | A | B |
| Escherichia coli | ECM6009 | aac(3)-II, aph(3') | A | A |
| Escherichia coli | ECM6010 | ant(2'') | A | A |
| Escherichia coli | ECM6011 | aph(3')-I | A | A |
| Escherichia coli | ECM6012 | armA | C | C |
| Providencia stuartii | PSM1000 | aac(2') | C | C |
| Pseudomonas aeruginosa | pa1060 | ant(2'') | A | B |
| Pseudomonas aeruginosa | pa1061 | aac(6') (no efflux) | A | A |
| Pseudomonas aeruginosa | pa1062 | aac(3)-I | C | C |
| Pseudomonas aeruginosa | PAM3072 | aac(6')-II or III | C | C |
| Pseudomonas aeruginosa | PAM3073 | aac(6')-I, wt efflux | B | B |

A = MIC of 1 µg/ml or less.
B = MIC of greater than 1 µg/ml to 8 µg/ml.
C = MIC of greater than 8 µg/ml.
ND = not determined.

Example 26

Activity of the Test Compounds 44 and 45 Against Various Species of Enterobacteriacea Table 9 summarizes results of testing 44 and 45 against 143 clinical isolates of various species of Enterobacteriacea. The results confirm the superior activity of 44.

TABLE 9

|  | 44 | 45 |
|---|---|---|
| $MIC_{50}$* | 0.5 | 1 |
| $MIC_{90}$ | 2 | 2 |

*MIC50 and MIC90 represent MIC of 50% and 90% population, respectively.

Table 10 shows the distribution of strains based on the ratio of MICs of 45 vs. 44. A ratio of 1 means that both compounds have the same activity; a ratio of 0.5 means that 45 is 2-fold more potent than 44; and a ratio of ≥2 means that 44 is at least 2-fold more potent than 45. While 45 was more potent than 44 in less than 2% of strains, 44 was more potent than 45 in nearly 75% of strains of Enterobacteriacae.

TABLE 10

| MIC ratio | Amount of strains | Percent of Strains |
|---|---|---|
| 0.5 | 3 | 1.8 |
| 1 | 40 | 23.8 |
| ≥2 | 125 | 74.4 |

Example 27

Acute Toxicity of 44 Versus 45 in Mice

The acute toxicity of 44 was compared to that of 45 in mice. Ascending doses of each compound were administered to mice (n=3) IV through the tail vein. Animals were observed for 24 hours after dosing. Acute toxicity was reported as the minimal lethal dose, or MLD, defined as the lowest dose of a compound that is lethal for at least one mouse. The MLD for 45 was 100 mg/kg while for 44 it was >125 mg/kg (i.e., not lethal at the highest dose tested, 125 mg/kg), indicating that 44 is less acutely toxic than 45.

Example 28

Aminoglycoside Cytotoxicity in HK-2 Cells

Human kidney cortex proximal tubule cells (HK-2) were purchased from ATCC and maintained according to manufacturer's recommendations in Keratinocyte Serum-Free Media (SFM; Invitrogen), with 0.05 mg/ml bovine pituitary extract and 5 ng/ml of Epidermal growth factor.

Solutions of aminoglycosides at a concentration of 50 mg/mL (both control and novel test compounds) were prepared in sterile deionized water. Before treatment of cells, the concentrated drug solutions were diluted to the appropriate concentration in Keratinocyte SFM {20, 10, 5, 2.5, 1.25, 0.6, 0.3, and 0 mM}. Pentamidine was used as a positive control.

HK-2 cells were seeded at $2.5*10^4$ cells/well density in 96-well plates in Keratinocyte SFM and placed in a 37° C. tissue culture $CO_2$ incubator. One day after seeding, the cell media was aspirated and replaced with 0.1 ml of diluted drug solution in cell medium prepared as described above. Each treatment was performed in duplicate. Plates were incubated in a $CO_2$ incubator at 37 C for 48 hours. Drug solutions were aspirated and replaced with 0.1 ml of 5% Alamar Blue (Abd Serotec) cell proliferation reagent in Keratinocyte SFM. Plates were read on a Molecular Devices Gemini EM fluorometer pre-warmed at 37° C. at em=544 nm, ex=590 nm. Plates were read at 0 and 4 hrs, and were incubated at 37° C.

in a CO₂ incubator in between reads. The fluorescence signal at the 0 h timepoint was subtracted from that at 4 h to account for background fluorescence.

The cytotoxicity data were reported as the amount of drug producing a 50% decrease in Alamar Blue signal relative to the no drug treatment control. The results are presented in Table 11.

TABLE 11

| Compound | IC$_{50}$ @ 24 hrs (mM) |
|---|---|
| Gentamicin | >20 |
| Arbekacin | >20 |
| Compound 44 | >20 |
| Compound 45 | 10 |
| Pentamidine | 64 mg/ml |

Compound 44 was essentially non-cytotoxic, similar to gentamicin and arbekacin. Compound 45 was at least 2-fold more cytotoxic than compound 44.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:
1. A compound having the structure of formula I:

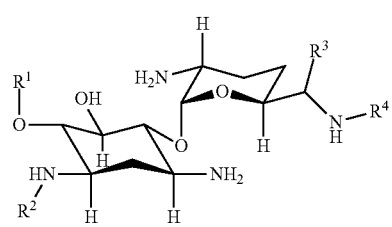

or a pharmaceutically acceptable salt thereof,
wherein:
R$^1$ is

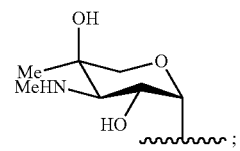

R$^2$ is selected from the group consisting of —(CR$^5$R$^6$)$_n$R$^7$, —C(=X)NR$^{10}$(CR$^5$R$^6$)$_n$R$^7$ and —C(=X)(CR$^5$R$^6$)$_n$R$^7$;

R$^3$ is selected from the group consisting of H and Me;

R$^4$ is selected from the group consisting of unsubstituted carbocyclyl, substituted or unsubstituted heterocyclyl, —(CR$^5$R$^6$)$_n$R$^7$ and —C(=NR$^8$)(CR$^5$R$^6$)$_n$R$^7$, with the proviso that R$^4$ is not Me;

each R$^5$ is independently selected from the group consisting of H, F, amino, aminoC$_{1-6}$alkyl, OH, —C$_{1-6}$alkylOR$^{12}$ and C$_{1-6}$alkyl;

each R$^6$ is independently selected from the group consisting of H, F, aminoC$_{1-6}$ alkyl, —C$_{1-6}$ alkylOR$^{12}$ and C$_{1-6}$alkyl, provided that each CR$^5$R$^6$ unit does not comprise two OH, two NH$_2$, one OH and one NH$_2$, one F and one NH$_2$, or one F and one OH;

each R$^7$ is selected from the group consisting of H, OR$^{12}$, NR$^9$R$^{10}$ and —NHC(=NR$^8$)R$^{14}$;

alternatively R$^5$ and R$^7$ or R$^6$ and R$^7$ are taken together with the atom or atoms to which they are attached to form a four, five or six membered substituted or unsubstituted heterocyclyl ring;

alternatively R$^5$ and R$^6$ are taken together with the atom or atoms to which they are attached to form a three, four, five or six membered substituted or unsubstituted carbocyclyl or a substituted or unsubstituted heterocyclyl ring;

each R$^8$ is independently selected from the group consisting of H, OR$^{12}$, CN and C$_{1-6}$ alkyl;

with the proviso that at least one of R$^5$, R$^6$, R$^7$ and R$^8$ is not H;

each R$^9$ is independently selected from the group consisting of H and —(CR$^5$R$^6$)$_n$R$^{13}$;

each R$^{10}$ is independently selected from the group consisting of H and —(CR$^5$R$^6$)$_m$R$^{13}$;

each R$^{12}$ is independently selected from the group consisting of H, C$_{1-6}$ alkyl, C$_{2-6}$ alkylOH and C$_{2-6}$ alkylamino;

each R$^{13}$ is independently selected from the group consisting of OH and NH$_2$;

each $R^{14}$ is independently selected from the group consisting of H and $NR^9R^{10}$;

each X is independently selected from O and $NR^8$;

each m is independently an integer from 0 to 5; and each n is independently an integer from 1 to 5.

2. The compound of claim 1 wherein $R^2$ is $-(CR^5R^6)_nR^7$.

3. The compound of claim 1, wherein $R^2$ is $-C(=X)(CR^5R^6)_nR^7$.

4. The compound of claim 3 wherein X is O.

5. The compound of claim 3 wherein X is NH.

6. The compound of claim 1, wherein $R^2$ is $-C(=X)NR^{10}(CR^5R^6)_nR^7$.

7. The compound of claim 6, wherein X is O; n is an integer from 2 to 3; $R^{10}$ is $-(CR^5R^6)_mR^{13}$; m is 0; and $R^{13}$ is OH.

8. The compound of claim 2, wherein $R^7$ is OH.

9. The compound of claim 2, wherein $R^7$ is $NH_2$.

10. The compound of claim 2, wherein $R^7$ is $-NHNH_2$.

11. The compound of claim 2, wherein $R^7$ is $-NHC(=NH)NH_2$.

12. The compound of claim 2, wherein $R^2$ is selected from the group consisting of:

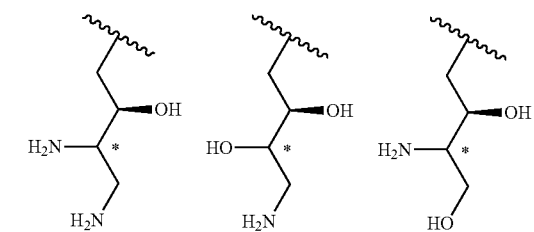
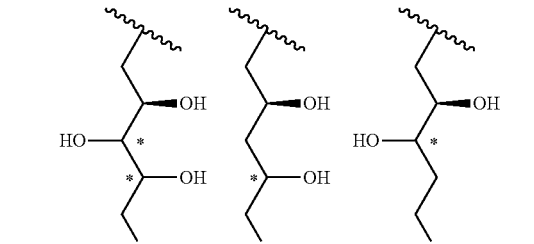
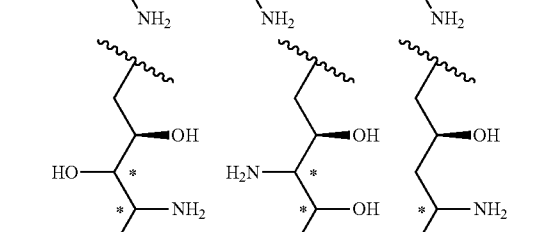
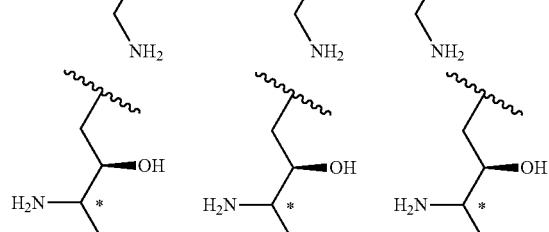

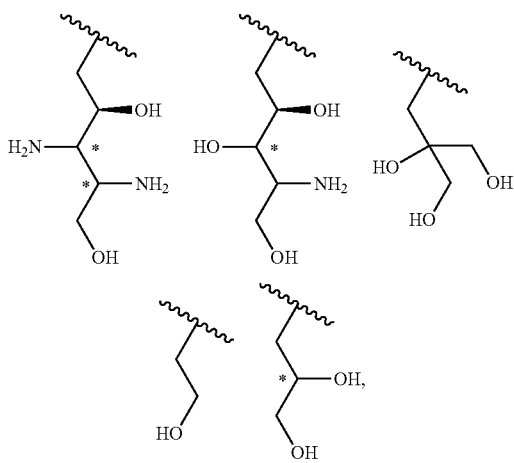

wherein * is a stereogenic center of R or S configuration.

13. The compound of claim 3, wherein $R^2$ is selected from the group consisting of:

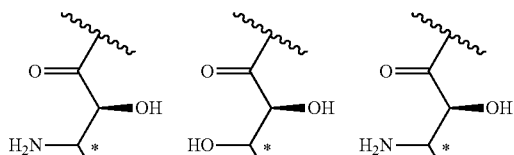
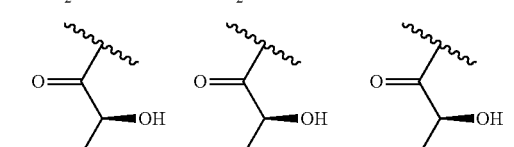
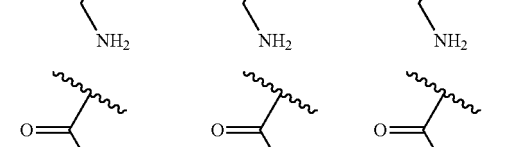
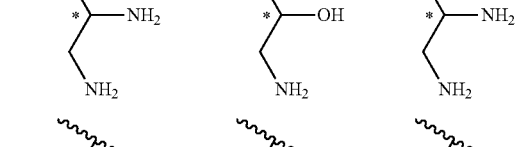
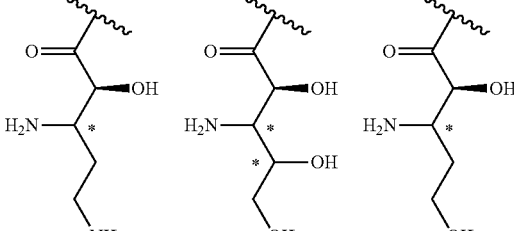

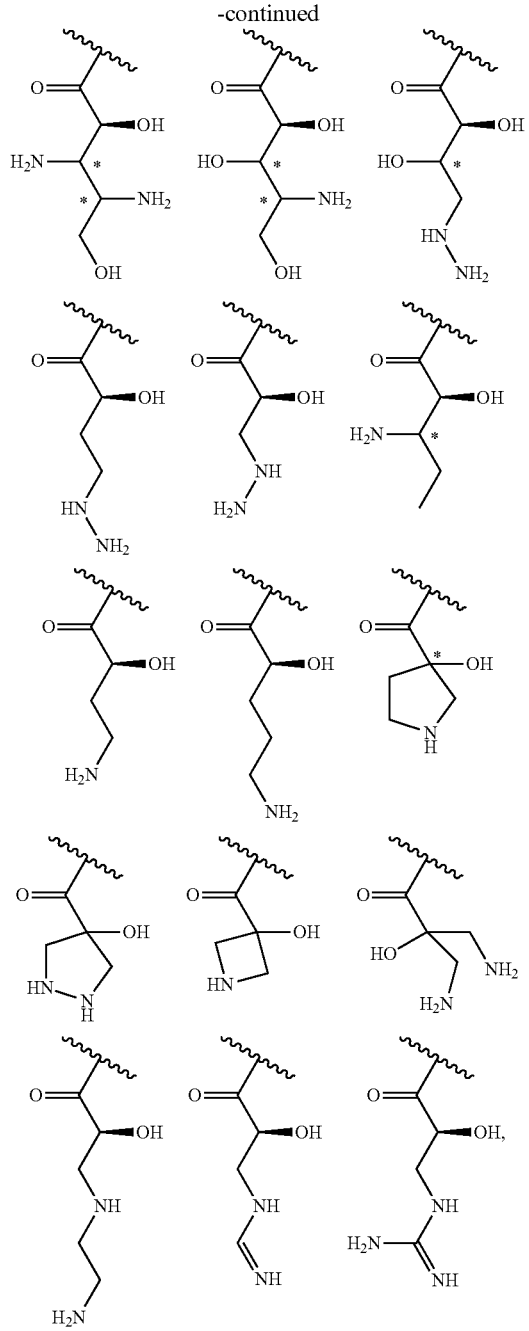
wherein * is a stereogenic center of R or S configuration.
14. The compound of claim 3, wherein $R^2$ is selected from the group consisting of:
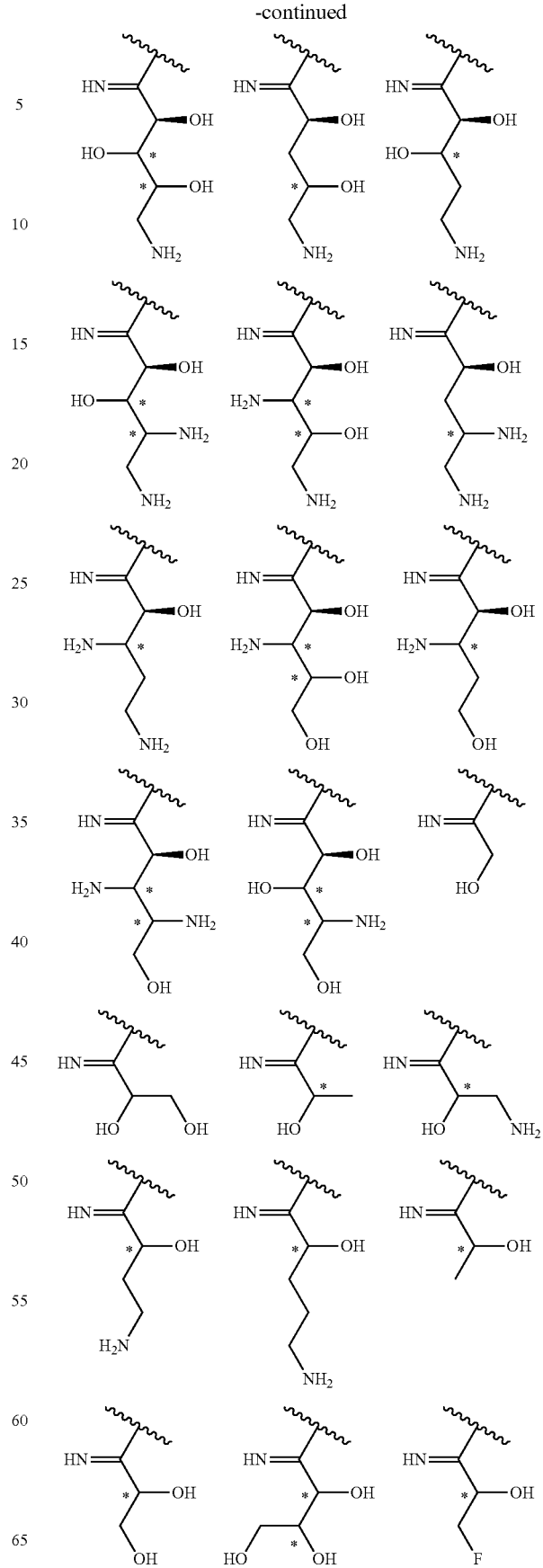
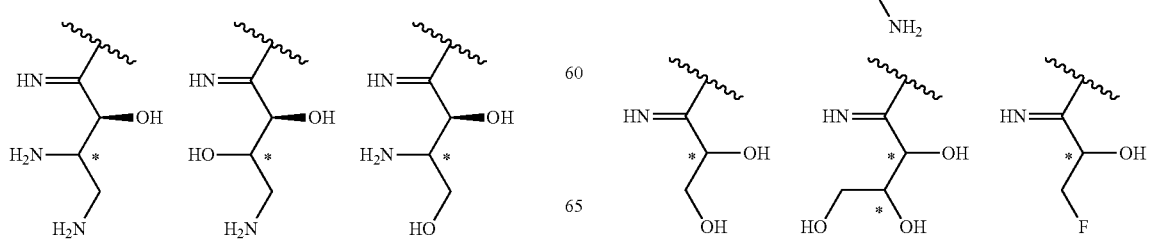

-continued

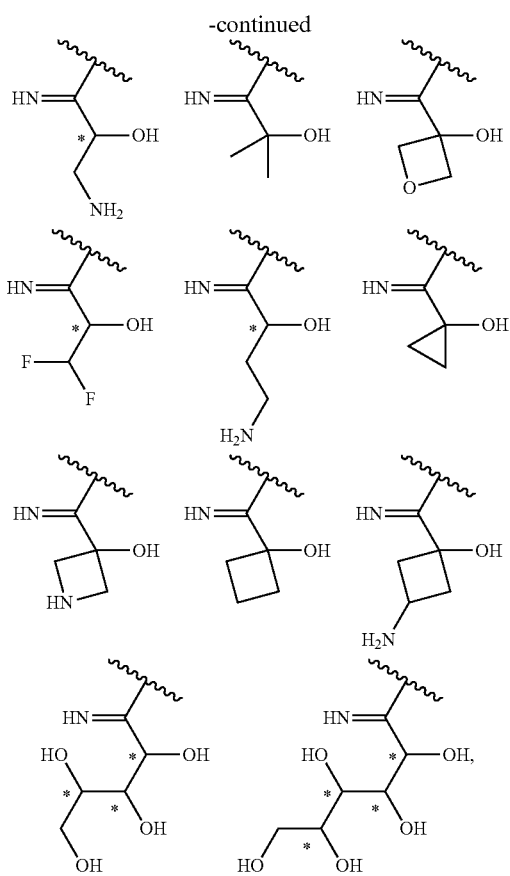

wherein * is a stereogenic center of R or S configuration.

15. The compound of claim 6, wherein $R^2$ is selected from the group consisting of:

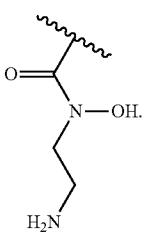 [SMILES: *C(=O)N(O)CCN]

16. The compound of claim 1, wherein $R^3$ is H.

17. The compound of claim 1, wherein $R^4$ is $-(CR^5R^6)_nR^7$.

18. The compound of claim 17, wherein n is an integer from 2 to 3 and $R^7$ is OH.

19. The compound of claim 17, wherein $R^4$ is selected from the group consisting of:

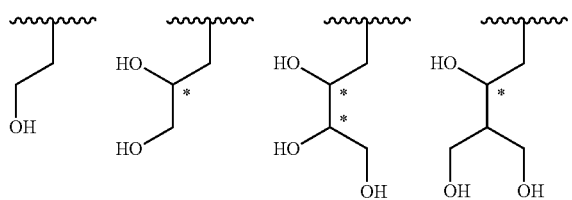

-continued

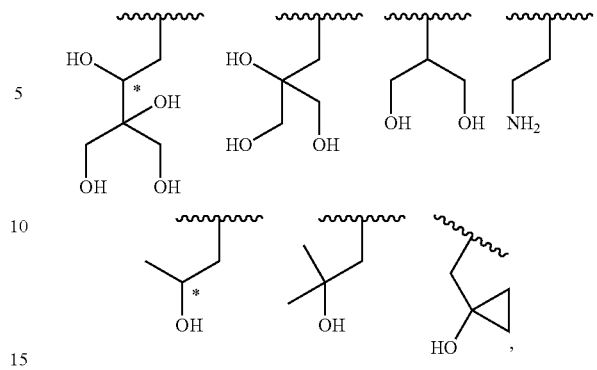

wherein * is a stereogenic center of R or S configuration.

20. The compound of claim 1, wherein $R^4$ is $-C(=NR^8)(CR^5R^6)_nR^7$.

21. The compound of claim 20, wherein $R^8$ is H; n is an integer from 1 to 3 and $R^7$ is selected from the group consisting of OH and $NH_2$.

22. The compound of claim 20, wherein $R^4$ is selected from the group consisting of:

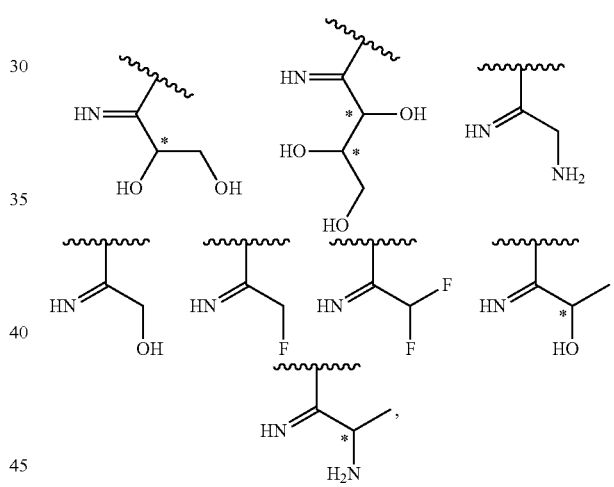

wherein * is a stereogenic center of R or S configuration.

23. The compound of claim 1, having a structure selected from the group consisting of:

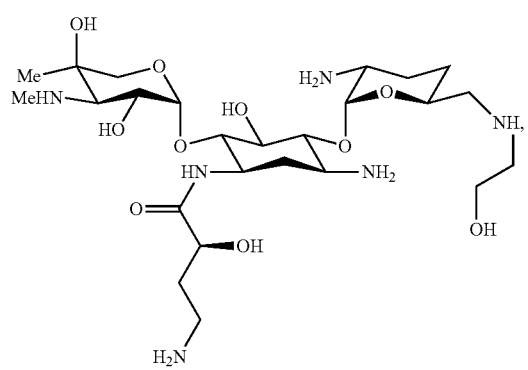

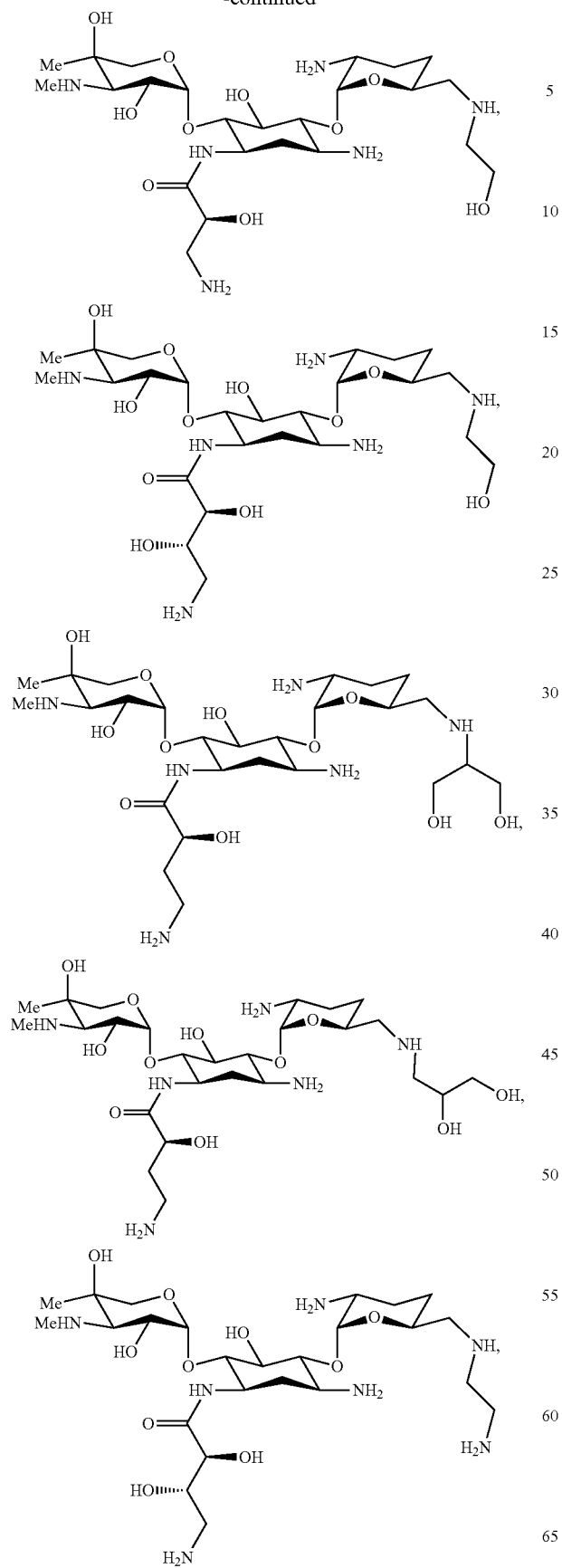
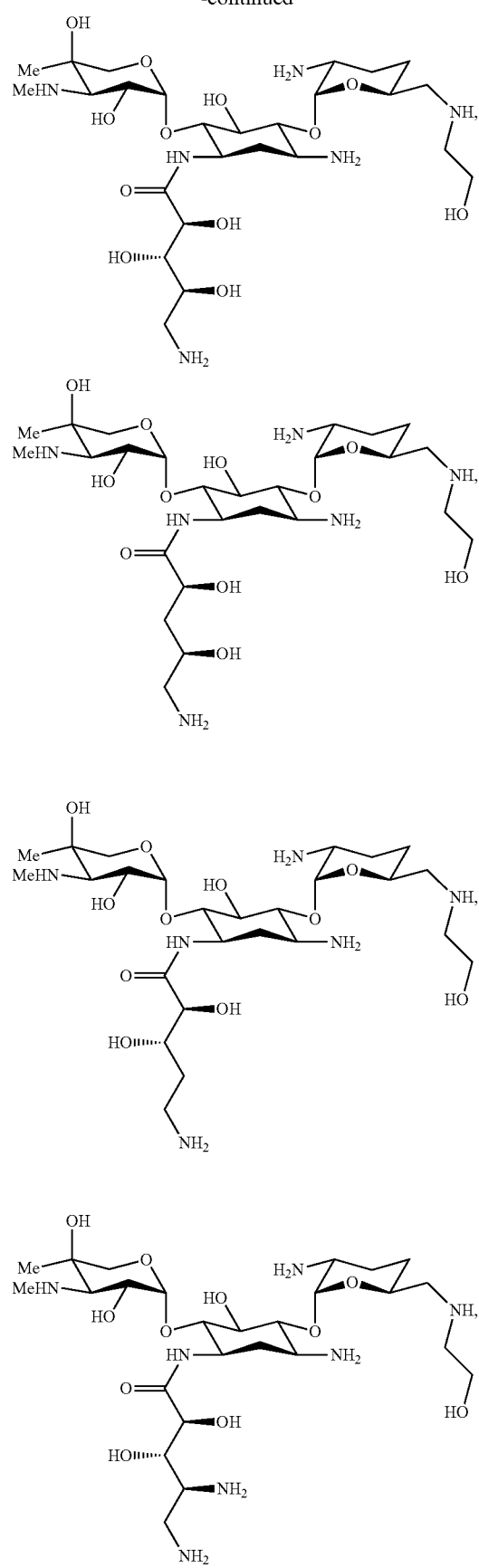

187
-continued
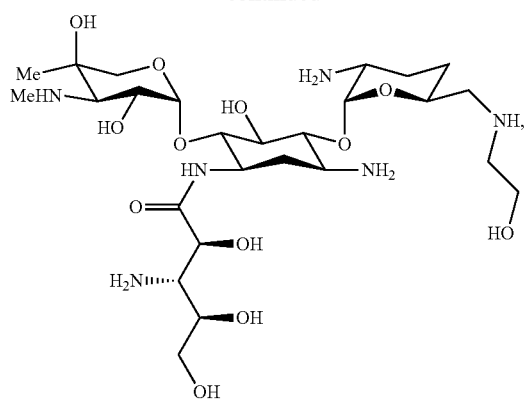
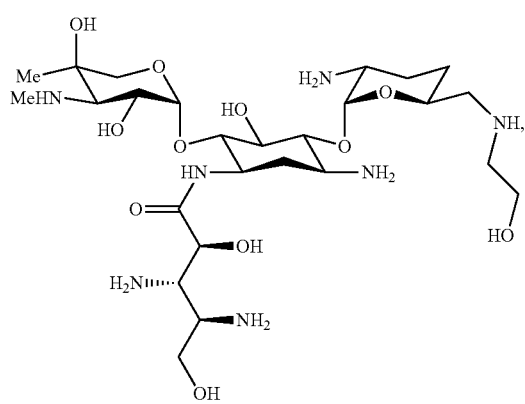
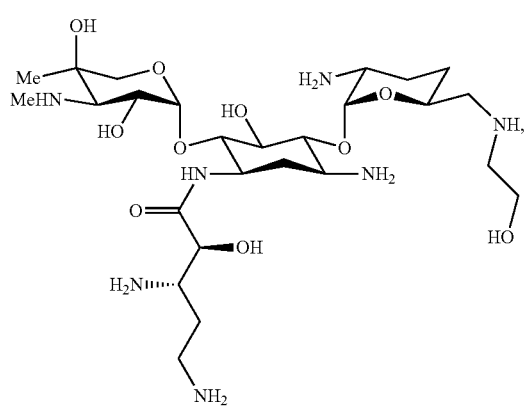
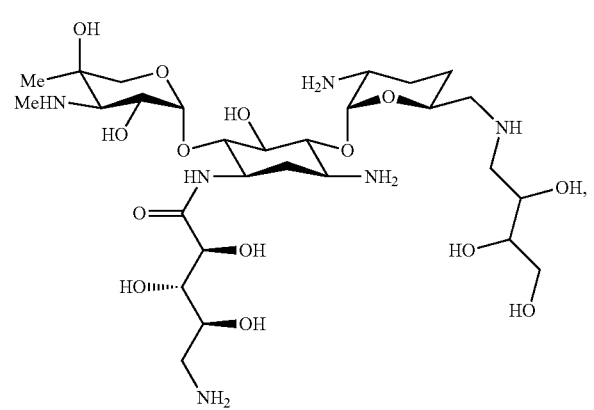
188
-continued
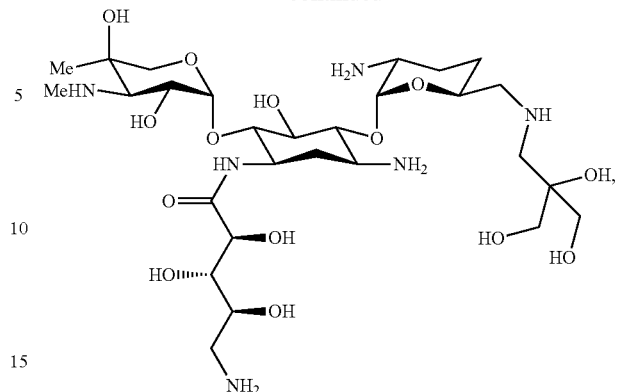
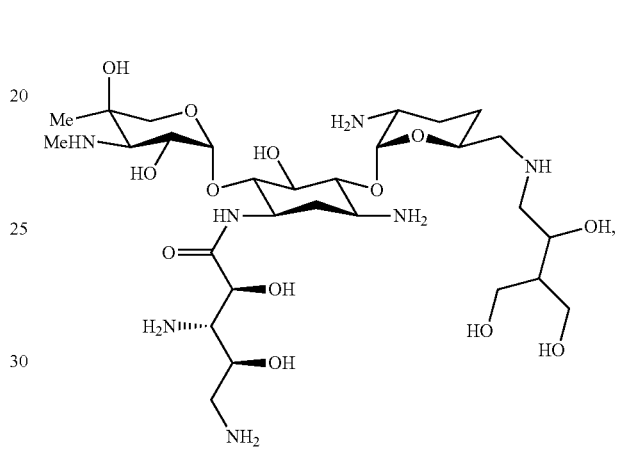
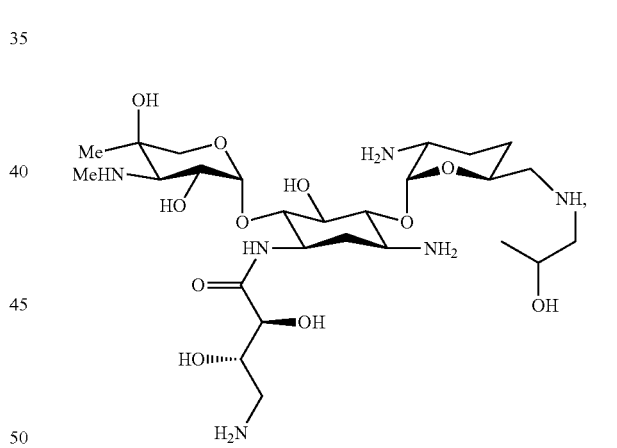
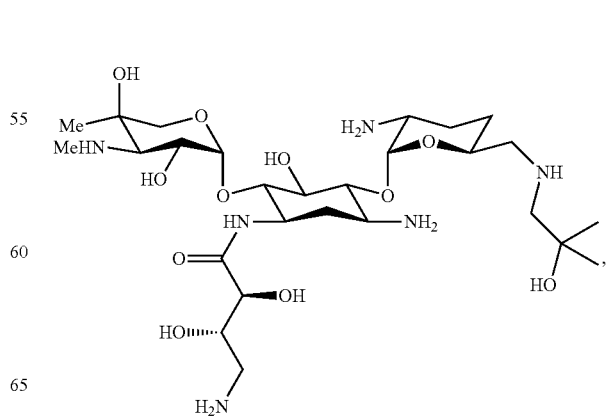

189
-continued
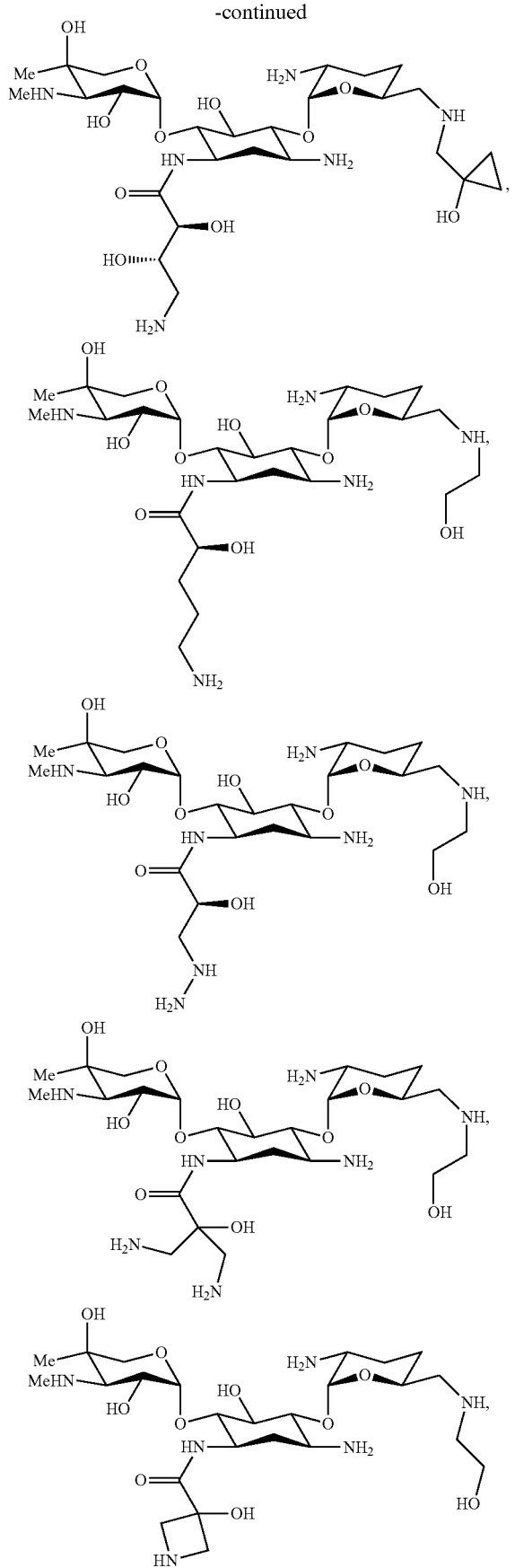
190
-continued
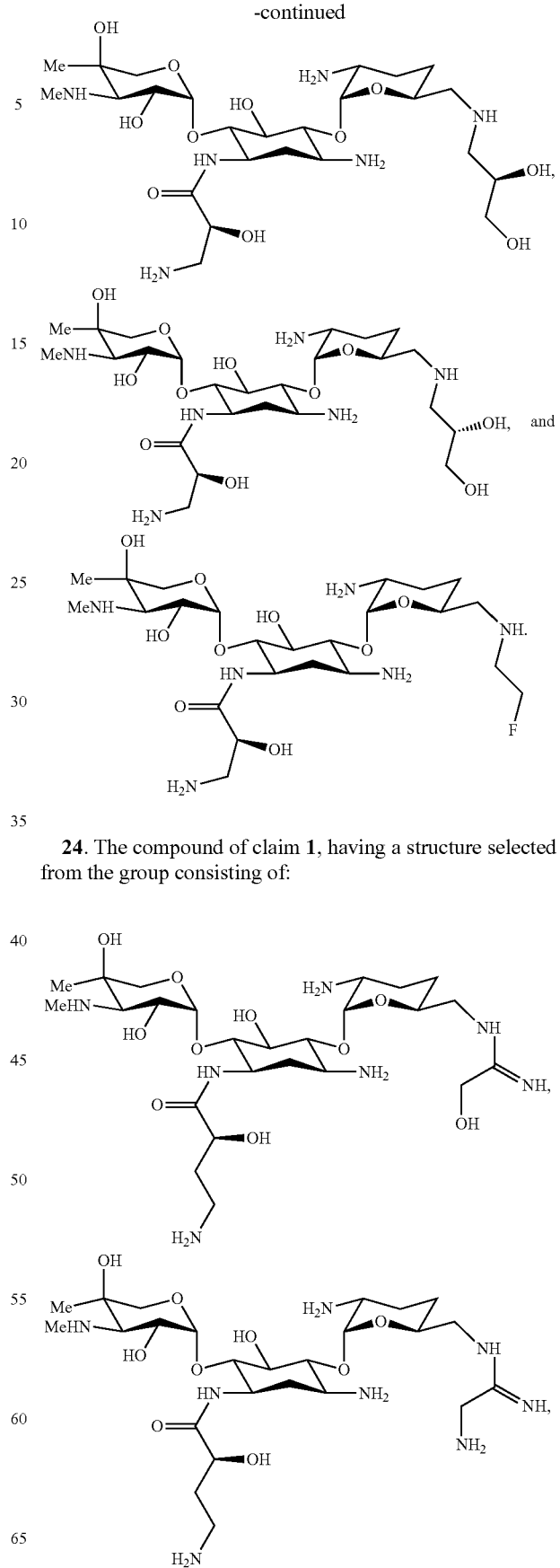
24. The compound of claim 1, having a structure selected from the group consisting of:

191
-continued
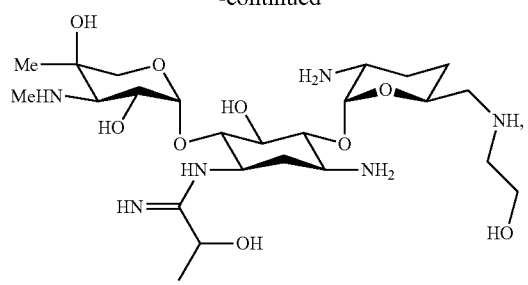
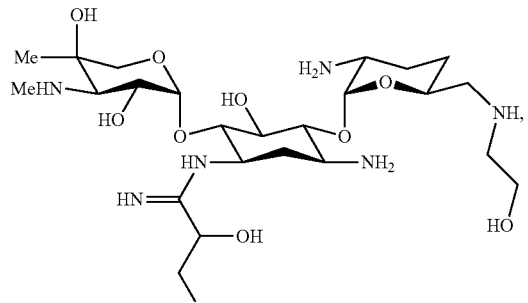
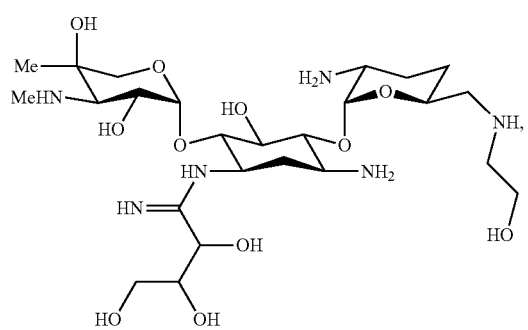
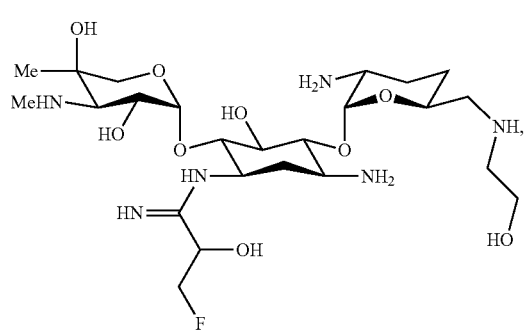
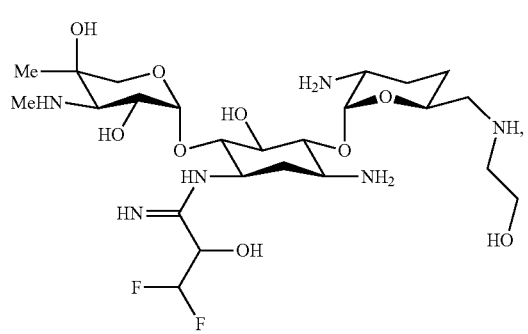
192
-continued
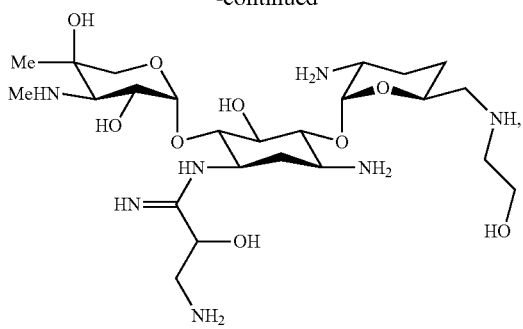
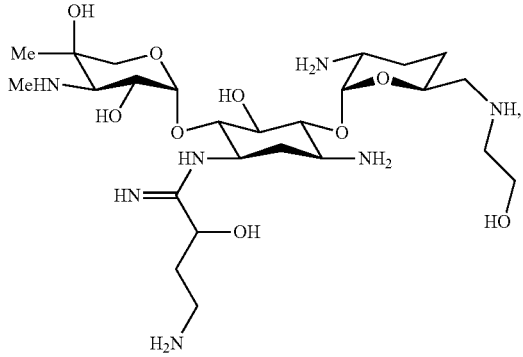
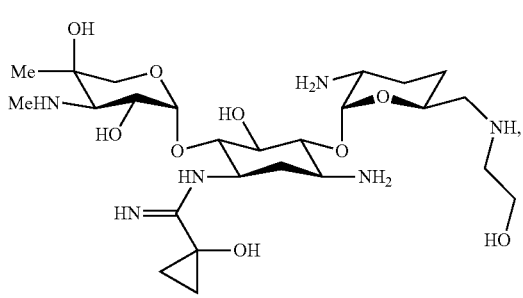
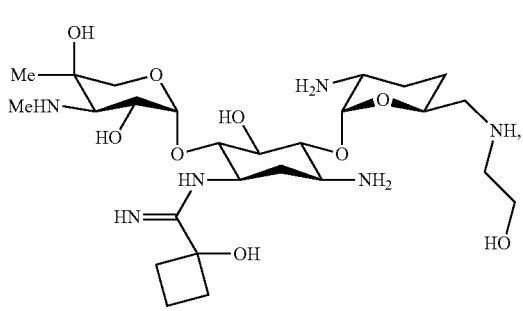
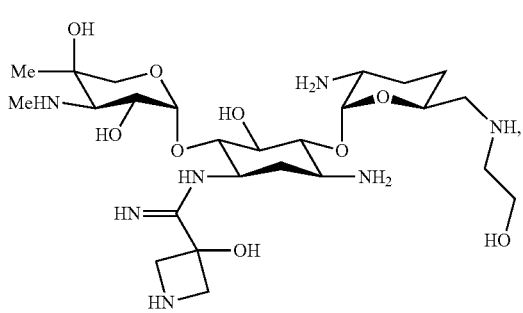

193
-continued
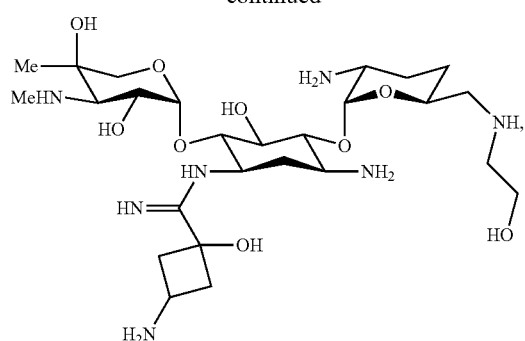
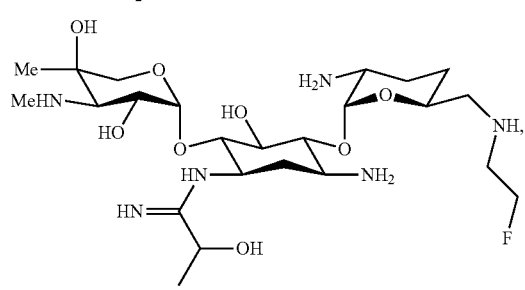
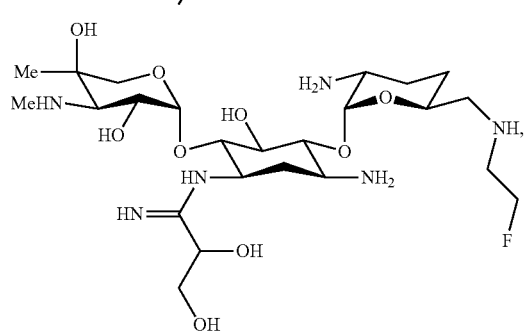
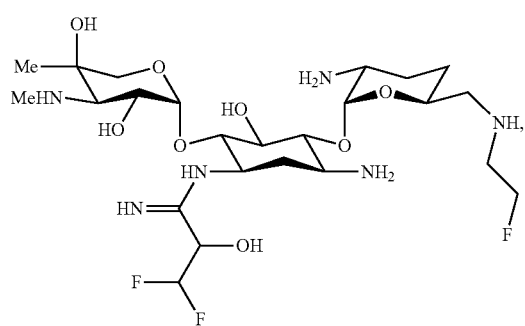
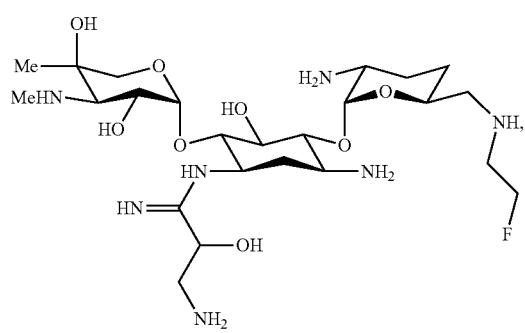
194
-continued
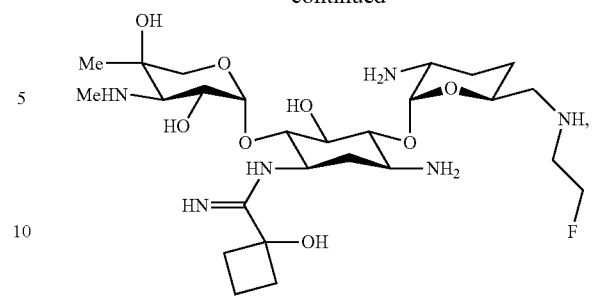
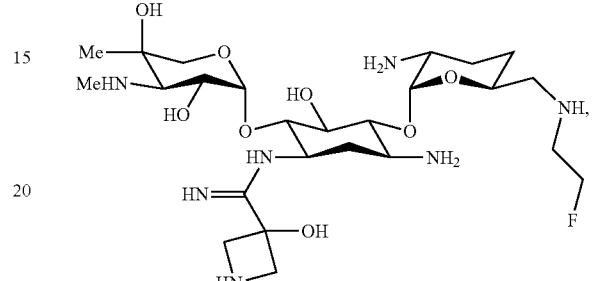
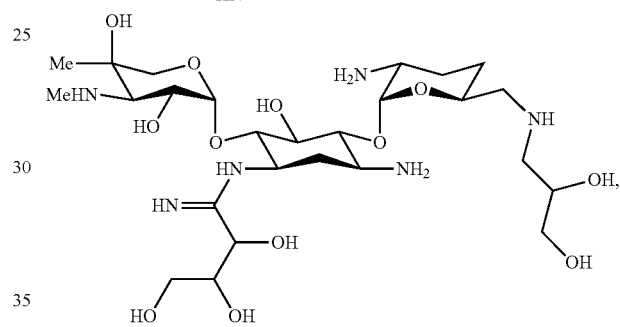
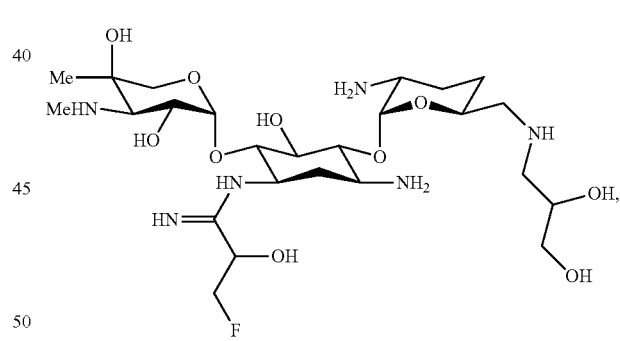
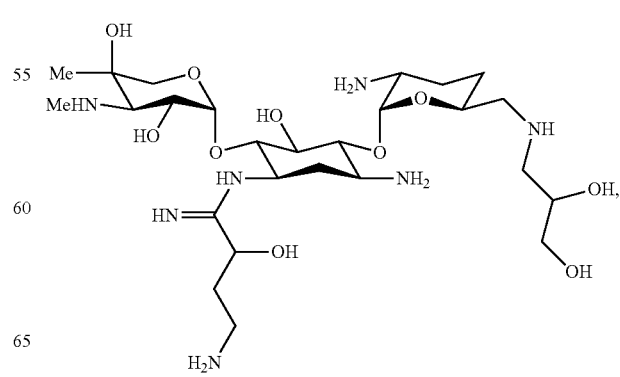

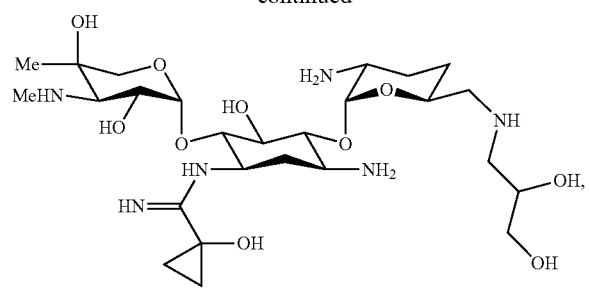
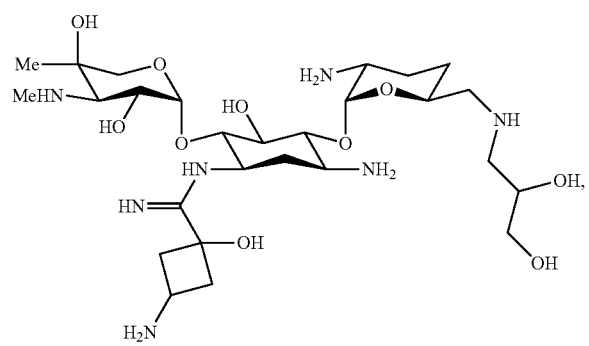
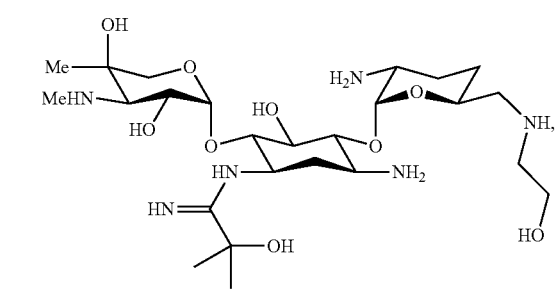
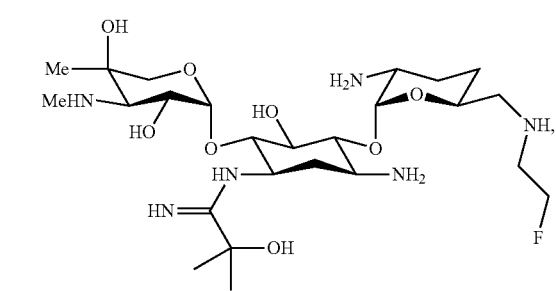
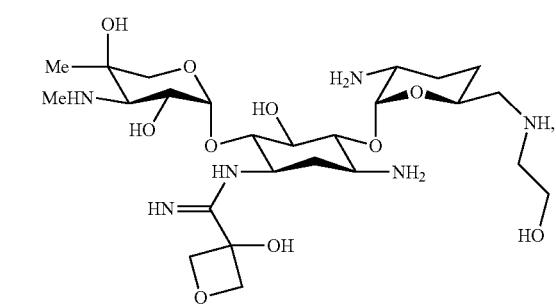
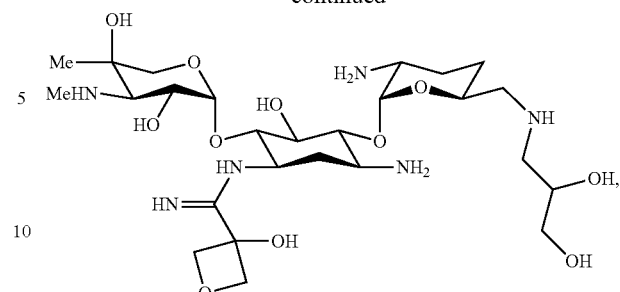
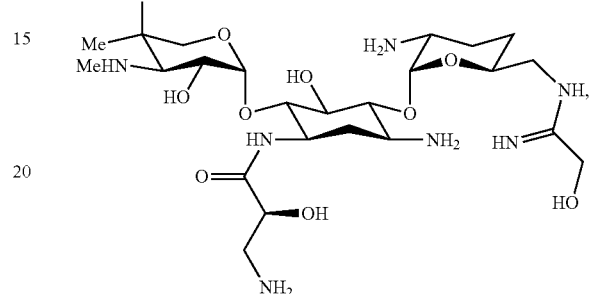
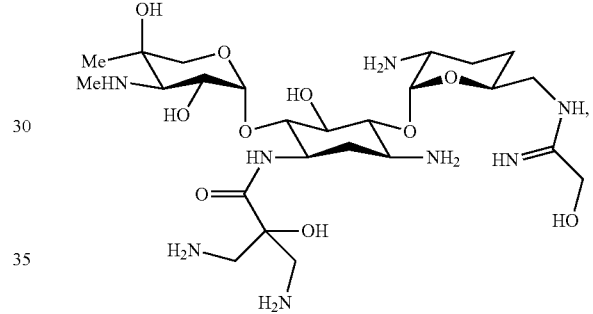
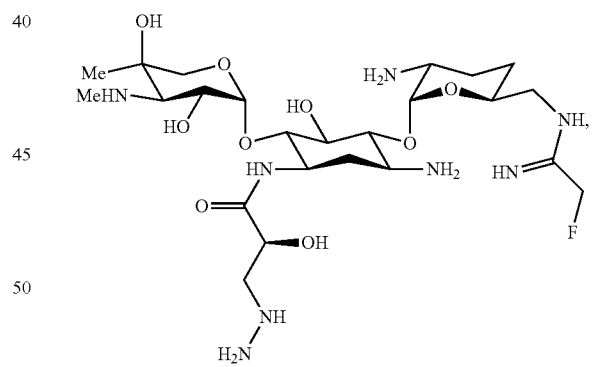
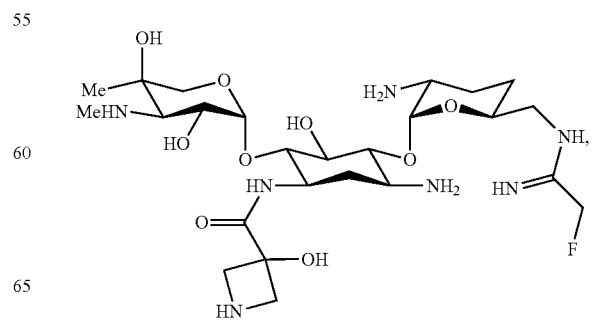

197
-continued
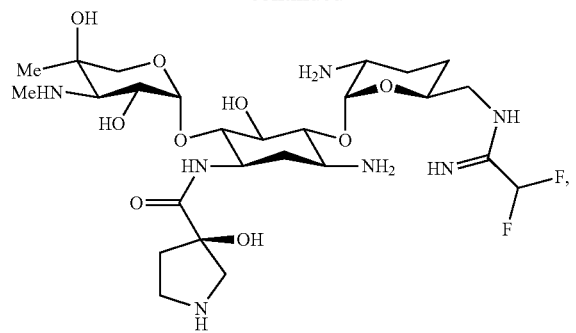
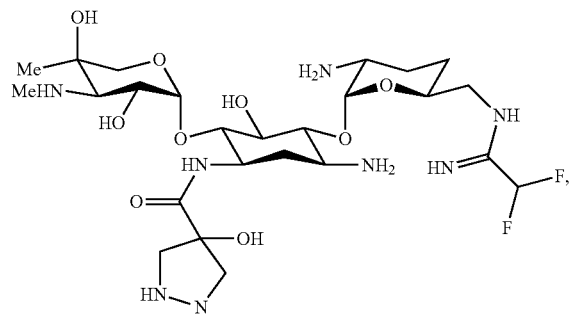
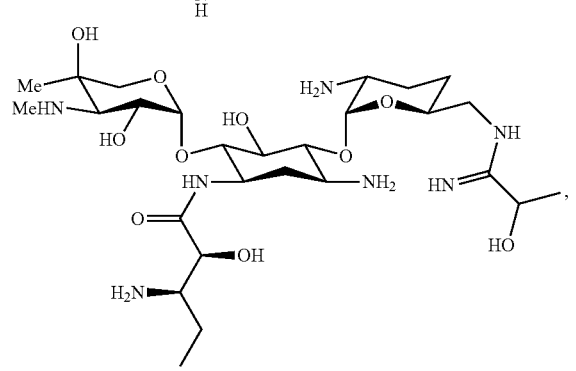
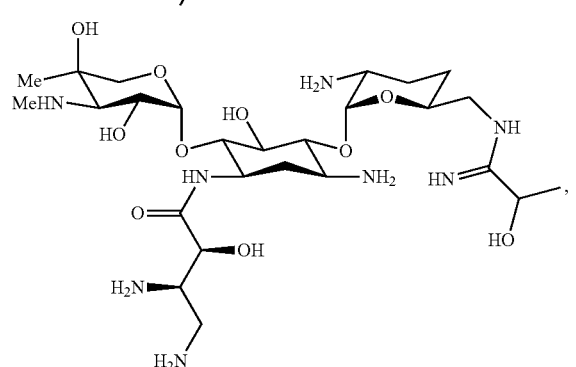
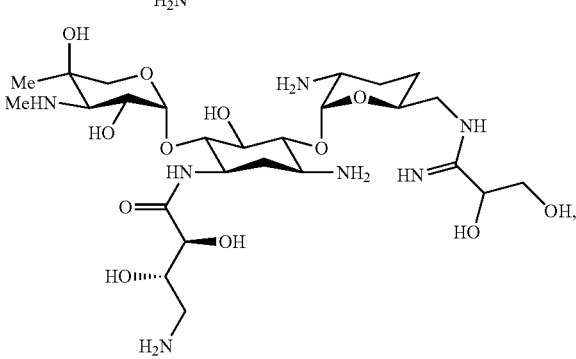
198
-continued
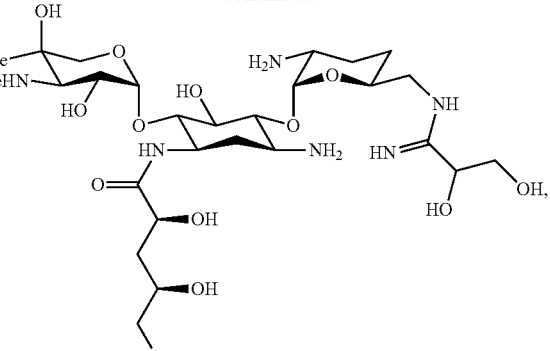
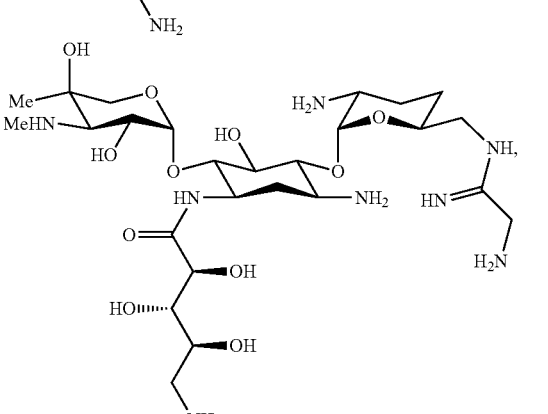
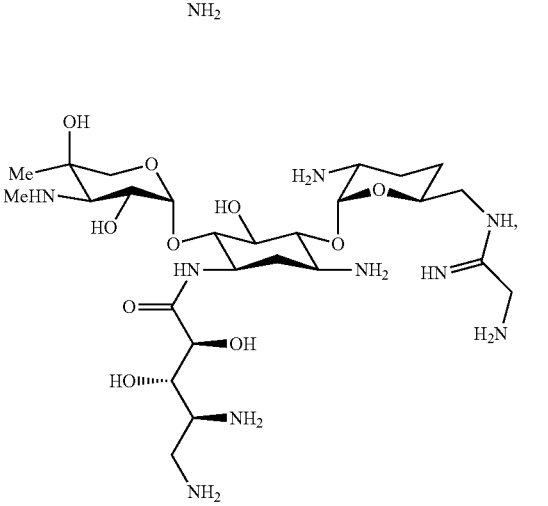
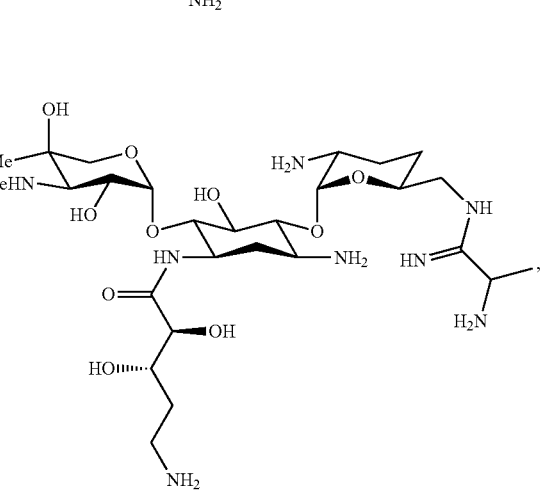

199
-continued
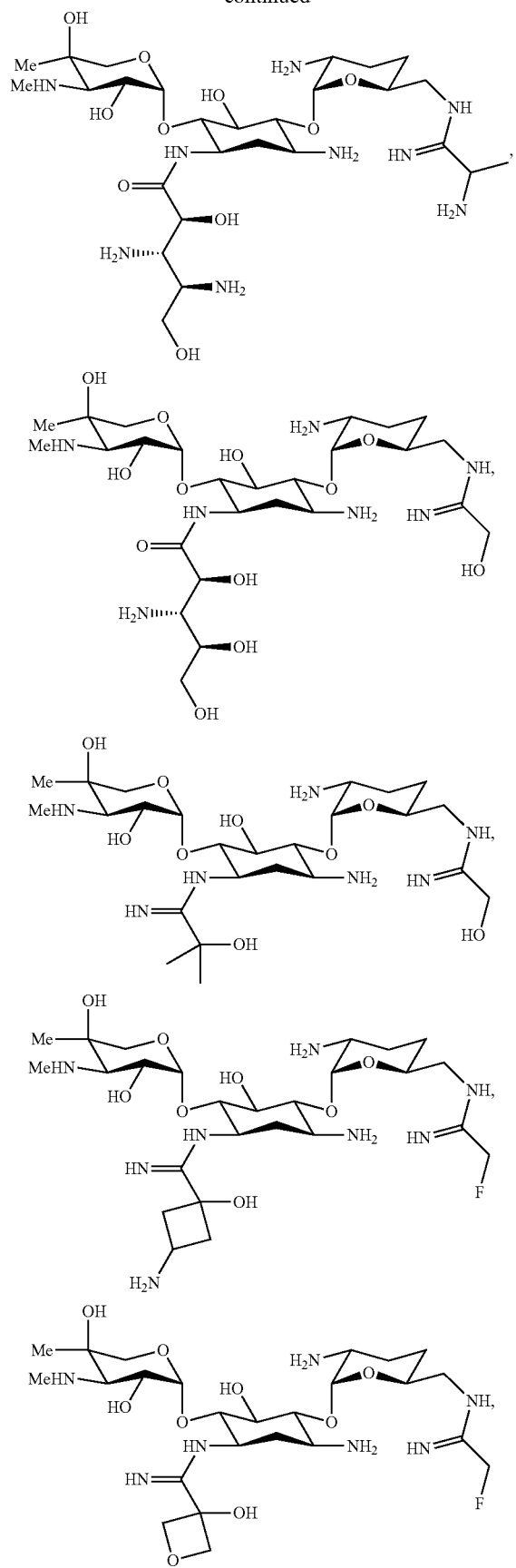
200
-continued
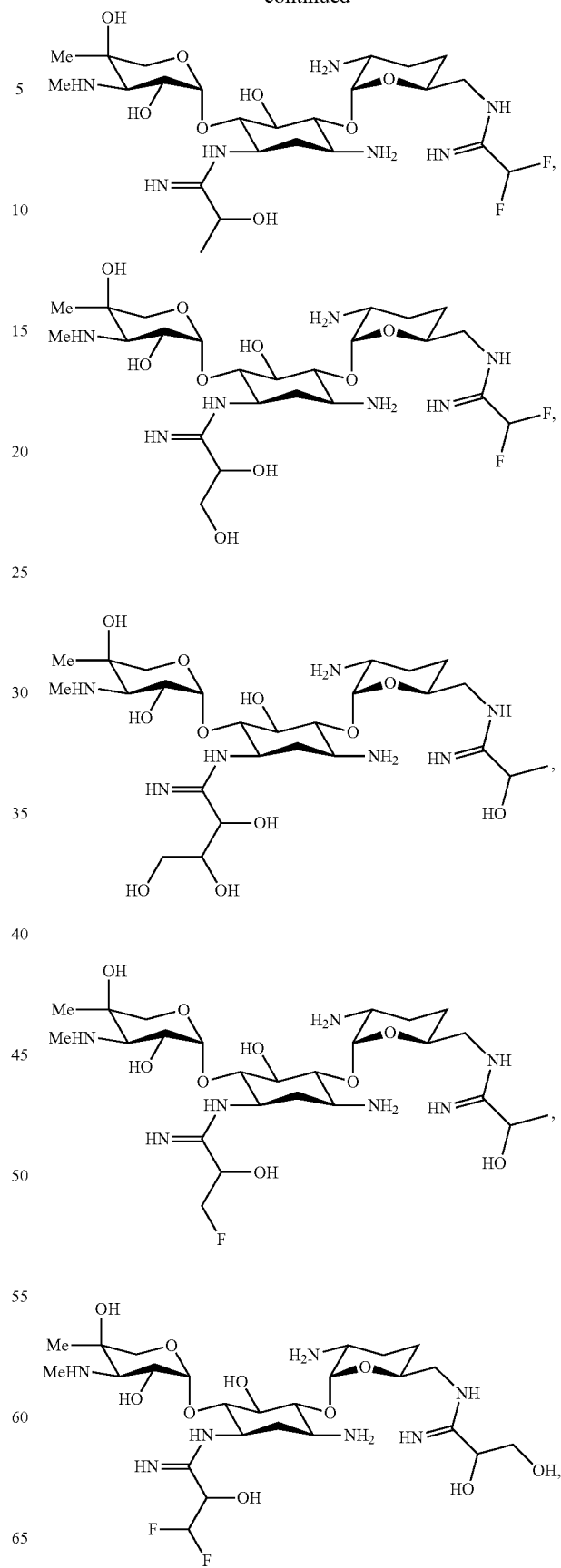

201
-continued
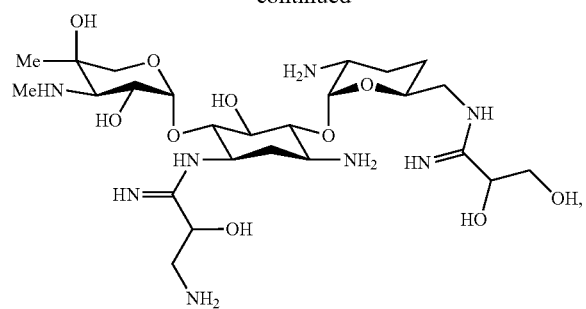
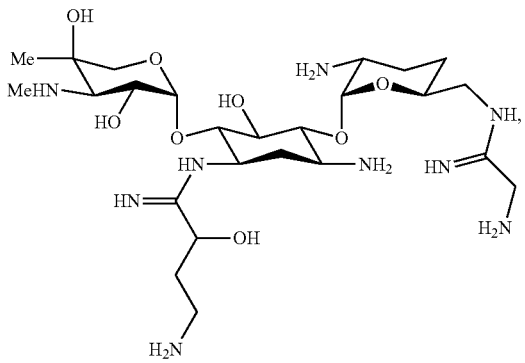
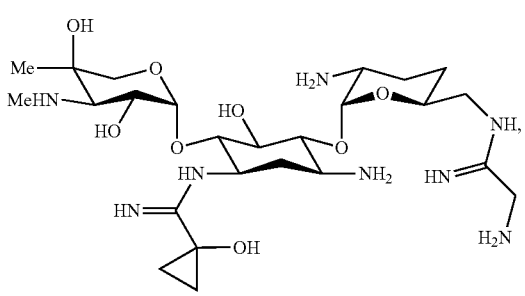
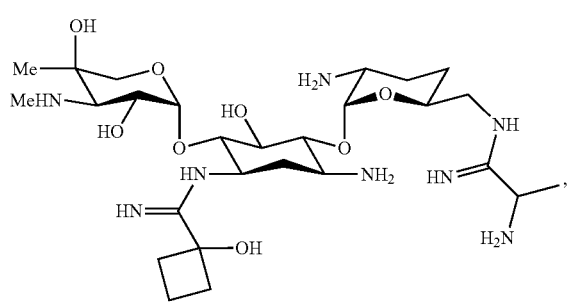
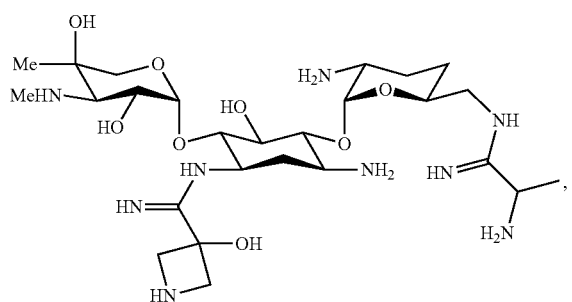
202
-continued
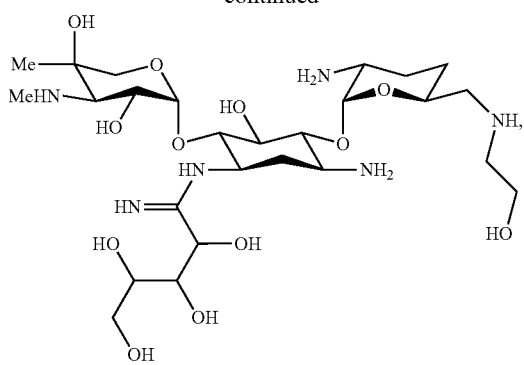
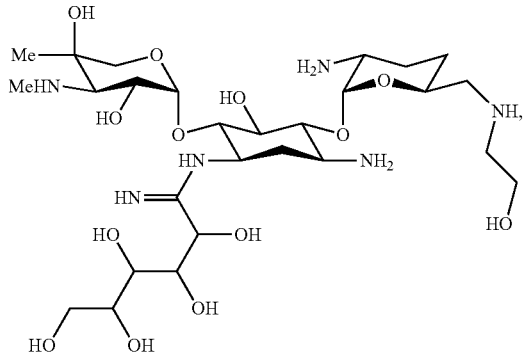
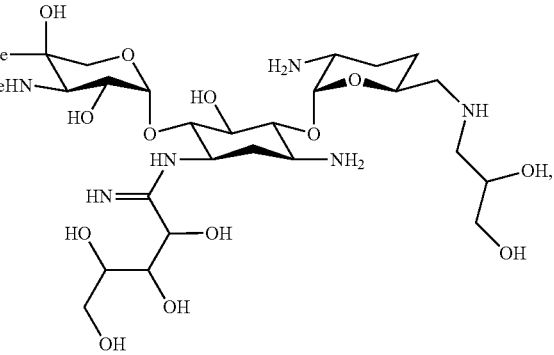
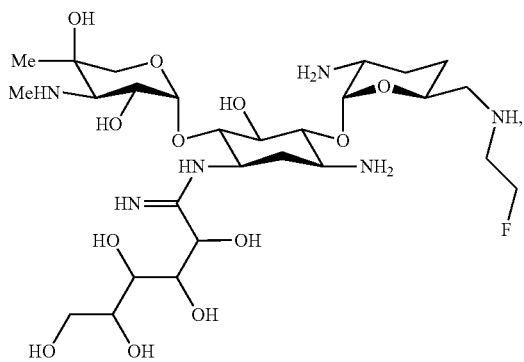

-continued

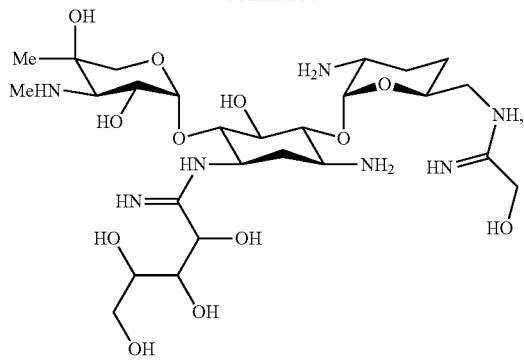

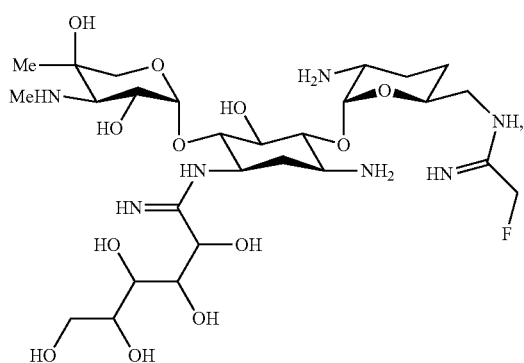

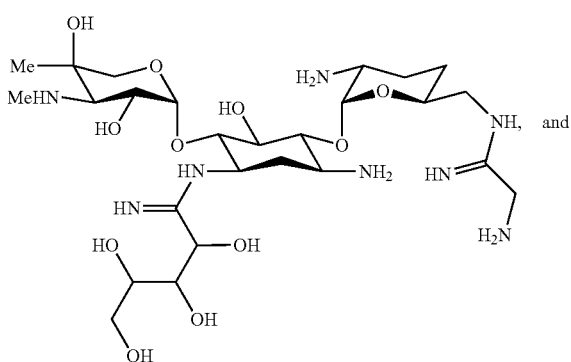

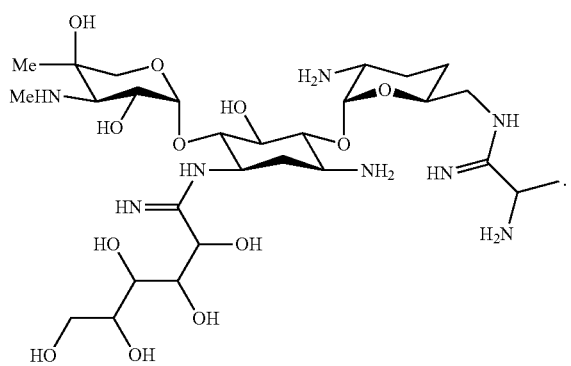

25. A compound having the structure of

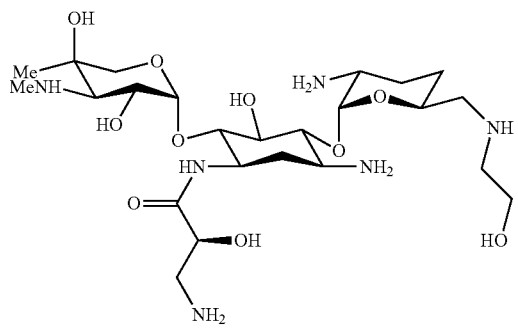

or a pharmaceutically acceptable salt thereof.

26. A compound having the structure of

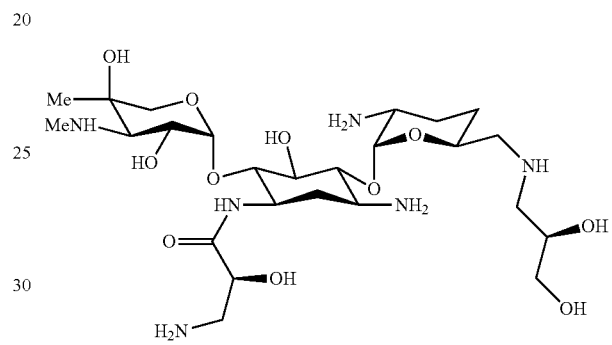

or a pharmaceutically acceptable salt thereof.

27. A pharmaceutical composition comprising a therapeutically effective amount of a compound according to claim 1 and a pharmaceutically acceptable excipient.

28. A method of therapeutically treating a bacterial infection, comprising administering to a subject in need thereof, a compound according to claim 1.

29. The method of claim 28, wherein the subject is a mammal.

30. The method of claim 29, wherein the mammal is a human.

31. The method of claim 28, wherein the bacterial infection comprises infection with a bacteria selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophila, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter* jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, and Staphylococcus saccharolyticus.

32. The method of claim 28, wherein the bacterial infection comprises infection with a bacteria selected from the group consisting of Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii, and Bacteroides splanchnicus.

* * * * *

UNITED STATES PATENT AND TRADEMARK OFFICE
CERTIFICATE OF CORRECTION

PATENT NO. : 8,906,868 B2  
APPLICATION NO. : 13/697302  
DATED : December 9, 2014  
INVENTOR(S) : Tomasz W. Glinka et al.

Page 1 of 2

It is certified that error appears in the above-identified patent and that said Letters Patent is hereby corrected as shown below:

Title Page,

In column 2 (page 1, item 56) at line 2, Under Other Publications, change "Chern" to --Chem.--.

In column 2 (page 1, item 56) at line 10, Under Other Publications, change "Chern." to --Chem.--.

In column 2 (page 1, item 56) at line 43, Under Other Publications, change "gentamincin" to --gentamicin--.

In the Specification,

In column 4 at line 40, Change "hydrophilia," to --hydrophila,--.

In column 4 at line 63, Change "ovalus," to --ovatus,--.

In column 5 at line 26, Change "ovalus," to --ovatus,--.

In column 6 at line 58, Change "H;" to --H.--.

In column 7 at line 33 (approx.), Change "$(CR^6R^6)_nR^7$." to --$(CR^5R^6)_nR^7$.--.

In column 7 at line 35 (approx.), Change "—$(CR^5R6)_mR^{13}$;" to -- —$(CR^5R^6)_mR^{13}$;--.

In column 29 at line 15, Change "$R_{11}$," to --$R^{11}$--.

In column 30 at line 10, Change "Nephrotoxicity" to --Nephrotoxicity:--.

In column 30 at line 11, Change "1447-52.," to --1447-52,--.

In column 30 at line 19, Change "Antibiotics" to --Antibiotics:--.

In column 31 at line 20, Change "pyrridyl," to --pyridyl,--.

In column 31 at line 21, Change "pyrollyl," to --pyrrolyl,--.

In column 31 at line 34, Change "$RNR^8CO$—" to --RNR'CO— --.

In column 31 at line 35, Change "alkaminocarbonyl-)" to --alkaminocarbonyl)--.

In column 31 at line 36, Change "alkyl carbonylamino-)" to --alkylcarbonylamino)--.

Signed and Sealed this  
Twenty-fifth Day of August, 2015

Michelle K. Lee  
*Director of the United States Patent and Trademark Office*

CERTIFICATE OF CORRECTION (continued)
U.S. Pat. No. 8,906,868 B2

In column 31 at line 38, Change "alkoxycarbonyl-)" to --alkoxycarbonyl)--.

In column 31 at line 39, Change "alkylcarbonyloxy-)." to --alkylcarbonyloxy).--.

In column 37 at lines 21-22, Change "croscarmelose;" to --croscarmellose;--.

In column 39 at line 13, Change "fluoroquinolnes," to --fluoroquinolones,--.

In column 39 at line 20, Change "gancyclovir," to --ganciclovir,--.

In column 39 at line 27, Change "antiinflammatory" to --anti-inflammatory--.

In column 39 at line 41, Change "Nisseria," to --Neisseria,--.

In column 39 at line 41, Change "Baccillus," to --Bacillus,--.

In column 39 at line 48, Change "hydrophilia," to --hydrophila,--.

In column 40 at line 3, Change "ovalus," to -- ovarus,--.

In column 57 at line 6, Change "diazamidecane" to --diazatridecane--.

In column 60 at line 53, Change "1ls" to --1 is--.

In column 77 at line 39, Change "vyloxy)" to --yloxy)--.

In column 80 at line 46, Change "vlxy)" to --yloxy)--.

In column 82 at line 49, Change "1" to --5--.

In column 88 at line 40, Change "$NH_{40}H)$" to --$NH_4OH$)--.

In column 88 at line 65, After "hydroxypentanamide" insert --40--.

In column 89 at line 6, Change "hvdrazinyl" to --hydrazinyl--.

In column 89 at line 58, Change "methy)" to --methyl)--.

In column 91 at line 5, Change "hydroxcyclohexyl" to --hydroxycyclohexyl--.

In column 98 at line 44, Change "ylxy)" to --yloxy)--.

In column 170 at line 5, Change "$5\times10^5$CFU/ml." to --$5\times10^5$ CFU/ml.--.

In columns 169-170 at line 3 (below Table 2), Change "µg/ml" to --µg/ml.--.

In columns 171-172 at line 4 (below Table 4), Change "determined" to --determined.--.

In columns 173-174 at line 12 (Table 6), Change "Eosinophila" to --Eosinophilia--.

In column 175 at line 30, Change "D =" to --ND =--.

In column 175 at line 62 (approx.), Change "Enterobacteriacea" to --Enterobacteriaceae--.

In column 175 at line 66, Change "Enterobacteriacea." to --Enterobacteriaceae.--.

In column 176 at line 15, Change "Enterobacteriacae." to --Enterobacteriaceae.--.

In column 176 at line 62, Change "37 C" to --37 °C.--.

In the Claims,

In column 204 at line 51, In Claim 31, change "hydrophilia," to --hydrophila,--.

In column 205 at line 7, In Claim 31, change "ovalus," to --ovatus,--.

In column 206 at line 17, In Claim 32, change "ovalus," to --ovatus,--.